(12) United States Patent
Bolton et al.

(10) Patent No.: US 11,578,098 B2
(45) Date of Patent: Feb. 14, 2023

(54) ON-COLUMN VIRAL INACTIVATION METHODS

(71) Applicant: BIOVERATIV THERAPEUTICS INC., Waltham, MA (US)

(72) Inventors: Glen Bolton, Boston, MA (US); Keith Selvitelli, Sutton, MA (US)

(73) Assignee: BIOVERATIV THERAPEUTICS INC., Waltham, MA (US)

( * ) Notice: Subject to any disclaimer, the term of this patent is extended or adjusted under 35 U.S.C. 154(b) by 425 days.

(21) Appl. No.: 16/793,676

(22) Filed: Feb. 18, 2020

(65) Prior Publication Data
US 2020/0283474 A1 Sep. 10, 2020

Related U.S. Application Data

(63) Continuation of application No. 15/024,988, filed as application No. PCT/US2014/057524 on Sep. 25, 2014, now Pat. No. 10,611,794.
(Continued)

(51) Int. Cl.
| | |
|---|---|
| *A61L 2/00* | (2006.01) |
| *A61K 38/00* | (2006.01) |
| *A61K 35/16* | (2015.01) |
| *A61K 35/14* | (2015.01) |
| *C07K 1/22* | (2006.01) |
| *C07K 16/06* | (2006.01) |
| *C07K 1/16* | (2006.01) |
| *C07K 14/755* | (2006.01) |

(52) U.S. Cl.
CPC .............. *C07K 1/22* (2013.01); *A61L 2/0088* (2013.01); *C07K 1/165* (2013.01); *C07K 14/755* (2013.01); *C07K 16/065* (2013.01); *A61L 2202/21* (2013.01); *C07K 2319/30* (2013.01)

(58) Field of Classification Search
CPC .. B08B 9/027; B08B 3/08; A61L 2/18; A61K 35/16; C07K 1/22; C12N 9/6437
USPC ....... 422/1, 28; 514/1.4, 15.3; 530/380, 205, 530/435; 424/530
See application file for complete search history.

(56) References Cited

U.S. PATENT DOCUMENTS

| | | |
|---|---|---|
| 4,683,195 A | 7/1987 | Mullis et al. |
| 4,965,199 A | 10/1990 | Capon et al. |

(Continued)

FOREIGN PATENT DOCUMENTS

| | | |
|---|---|---|
| EP | 0506757 B2 | 10/2005 |
| EP | 3048899 A2 | 12/2016 |

(Continued)

OTHER PUBLICATIONS

U.S. Appl. No. 15/024,988 2016/0347788 U.S. Pat. No. 10,611,794, filed Mar. 25, 2016 Dec. 1, 2016 Apr. 7, 2020, Glen Bolton.
(Continued)

*Primary Examiner* — Monzer R Chorbaji
(74) *Attorney, Agent, or Firm* — Lathrop GPM LLP; James H. Velema, Esq.

(57) ABSTRACT

The present invention is directed to a method of inactivating virus that is present during production of a polypeptide of interest. In particular, the present invention is directed to a method of on-column virus inactivation using a low pH and high salt wash solution that effectively inactivates viruses with minimum recovery loss of the polypeptide.

20 Claims, 15 Drawing Sheets

Figure 1:
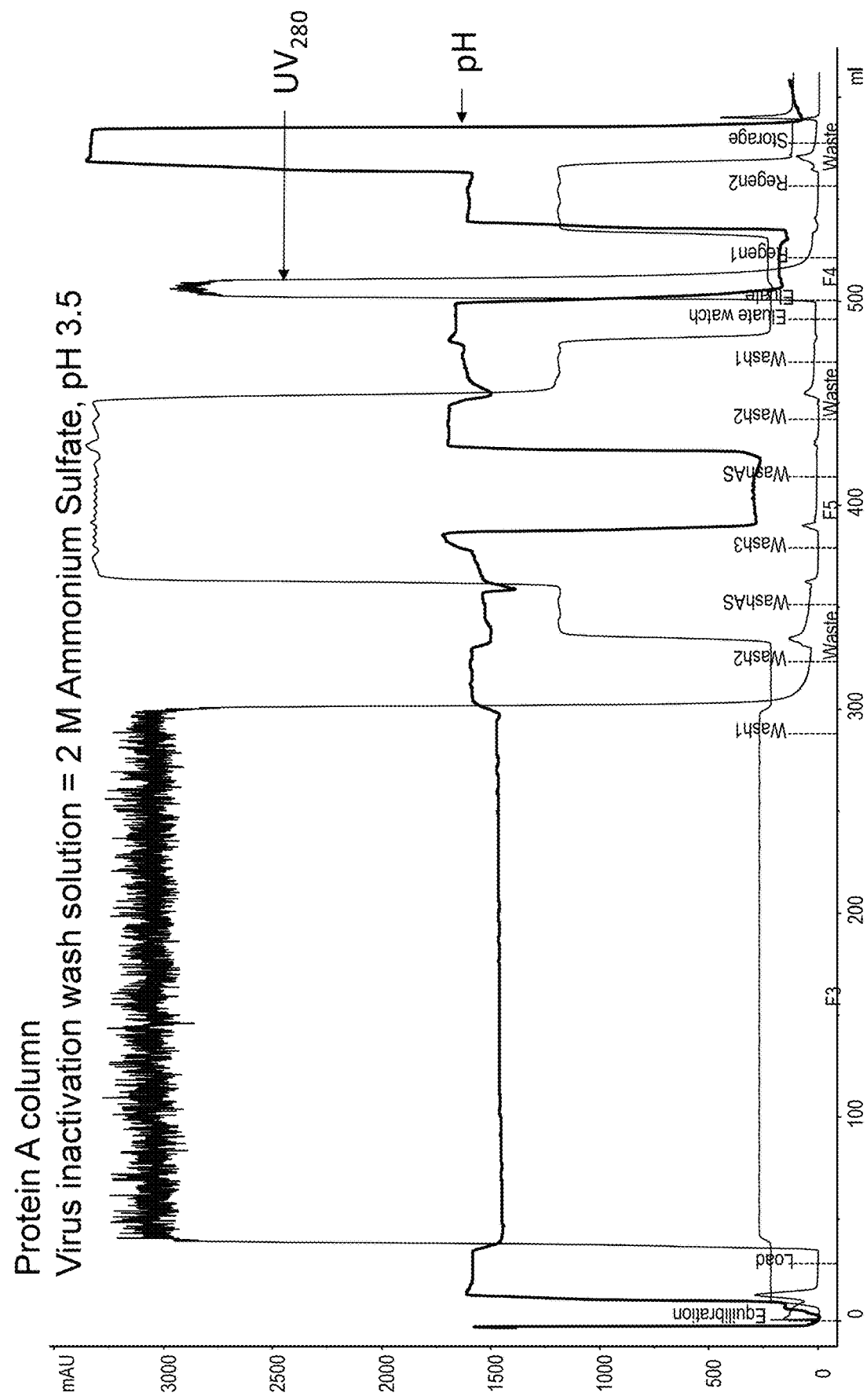

Specification includes a Sequence Listing.

Related U.S. Application Data

(60) Provisional application No. 62/028,657, filed on Jul. 24, 2014, provisional application No. 61/882,488, filed on Sep. 25, 2013.

(56) References Cited

U.S. PATENT DOCUMENTS

| | | | |
|---|---|---|---|
| 5,223,409 A | 6/1993 | Ladner et al. | |
| 5,429,746 A | 7/1995 | Shadle et al. | |
| 5,585,089 A | 12/1996 | Queen et al. | |
| 5,643,575 A | 7/1997 | Martinez et al. | |
| 5,648,260 A | 7/1997 | Winter et al. | |
| 5,658,727 A | 8/1997 | Barbas et al. | |
| 5,667,988 A | 9/1997 | Barbas et al. | |
| 5,693,761 A | 12/1997 | Queen et al. | |
| 5,693,762 A | 12/1997 | Queen et al. | |
| 5,739,277 A | 4/1998 | Presta et al. | |
| 5,834,250 A | 11/1998 | Wells et al. | |
| 5,846,951 A | 12/1998 | Gregoriadis | |
| 5,859,205 A | 1/1999 | Adair et al. | |
| 5,869,046 A | 2/1999 | Presta et al. | |
| 5,885,793 A | 3/1999 | Griffiths et al. | |
| 6,030,613 A | 2/2000 | Blumberg et al. | |
| 6,086,875 A | 7/2000 | Blumberg et al. | |
| 6,096,871 A | 8/2000 | Presta et al. | |
| 6,121,022 A | 9/2000 | Presta et al. | |
| 6,194,551 B1 | 2/2001 | Idusogie et al. | |
| 6,242,195 B1 | 6/2001 | Idusogie et al. | |
| 6,251,632 B1 | 6/2001 | Lillicrap et al. | |
| 6,277,375 B1 | 8/2001 | Ward | |
| 6,407,213 B1 | 6/2002 | Carter et al. | |
| 6,485,726 B1 | 11/2002 | Blumberg et al. | |
| 6,528,624 B1 | 3/2003 | Idusogie et al. | |
| 6,538,124 B1 | 3/2003 | Idusogie et al. | |
| 6,696,245 B2 | 2/2004 | Winter et al. | |
| 6,737,056 B1 | 5/2004 | Presta | |
| 6,821,505 B2 | 11/2004 | Ward | |
| 6,998,253 B1 | 2/2006 | Presta et al. | |
| 7,083,784 B2 | 8/2006 | Dall'Acqua et al. | |
| 7,317,091 B2 | 1/2008 | Lazar et al. | |
| 7,404,956 B2 | 7/2008 | Peters et al. | |
| 8,329,182 B2 | 12/2012 | Peters et al. | |
| 10,611,794 B2 * | 4/2020 | Bolton | C07K 16/065 |
| 2003/0069395 A1 | 4/2003 | Sato et al. | |
| 2003/0235536 A1 | 12/2003 | Blumberg et al. | |
| 2005/0079574 A1 | 4/2005 | Bond | |
| 2007/0191597 A1 | 8/2007 | Sanjay et al. | |
| 2007/0237765 A1 | 9/2007 | Lazar et al. | |
| 2007/0237766 A1 | 9/2007 | Lazar et al. | |
| 2007/0237767 A1 | 9/2007 | Lazar et al. | |
| 2007/0243188 A1 | 9/2007 | Lazar et al. | |
| 2007/0248603 A1 | 9/2007 | Lazar et al. | |
| 2007/0231329 A1 | 10/2007 | Lazar et al. | |
| 2007/0286859 A1 | 12/2007 | Lazar et al. | |
| 2008/0004206 A1 | 1/2008 | Rosen et al. | |
| 2008/0057056 A1 | 5/2008 | Lazar et al. | |
| 2008/0153751 A1 | 6/2008 | Rosen et al. | |
| 2008/0161243 A1 | 7/2008 | Rosen et al. | |
| 2008/0194481 A1 | 8/2008 | Rosen et al. | |
| 2008/0261877 A1 | 10/2008 | Ballance et al. | |
| 2009/0247735 A1 | 10/2009 | Gagnon | |
| 2010/0292130 A1 | 11/2010 | Skerra et al. | |
| 2011/0046060 A1 * | 2/2011 | Schellenberger | C07K 14/001 530/381 |
| 2011/0190194 A1 * | 8/2011 | Lim | A61P 43/00 530/380 |
| 2012/0015424 A1 | 1/2012 | Selvitelli et al. | |
| 2013/0108629 A1 | 5/2013 | Dumont et al. | |
| 2013/0202595 A1 | 8/2013 | Pierce et al. | |
| 2016/0347788 A1 | 12/2016 | Bolton et al. | |

FOREIGN PATENT DOCUMENTS

| | | | |
|---|---|---|---|
| EP | | 3903599 A1 | 11/2021 |
| WO | WO 1988007089 A1 | | 9/1988 |
| WO | WO 1990002809 A1 | | 3/1990 |
| WO | WO 1991017271 A1 | | 11/1991 |
| WO | WO 1992001047 A1 | | 1/1992 |
| WO | WO 1992009690 A2 | | 6/1992 |
| WO | WO 1992015679 A1 | | 9/1992 |
| WO | WO 1992018619 A1 | | 10/1992 |
| WO | WO 1992020791 A1 | | 11/1992 |
| WO | WO 1993001288 A1 | | 1/1993 |
| WO | WO 1996014339 A1 | | 5/1996 |
| WO | WO 1998005787 A1 | | 2/1998 |
| WO | WO 1998023289 A1 | | 6/1998 |
| WO | WO 1999051642 A1 | | 10/1999 |
| WO | WO 1999058572 A1 | | 11/1999 |
| WO | WO 2000009560 A2 | | 2/2000 |
| WO | WO 2000032767 A1 | | 6/2000 |
| WO | WO 2000042072 A2 | | 7/2000 |
| WO | WO 2001087922 A2 | | 11/2001 |
| WO | WO 2002044215 A2 | | 6/2002 |
| WO | WO 2002060919 A2 | | 8/2002 |
| WO | WO 2003020764 A2 | | 3/2003 |
| WO | WO 2003074569 A2 | | 9/2003 |
| WO | WO 2003077834 A2 | | 9/2003 |
| WO | WO 2002040544 A3 | | 10/2003 |
| WO | WO 2004016750 A2 | | 2/2004 |
| WO | WO 2004029207 A2 | | 4/2004 |
| WO | WO 2004035752 A2 | | 4/2004 |
| WO | WO 2004/044859 A1 | | 5/2004 |
| WO | WO 2004063351 A2 | | 7/2004 |
| WO | WO 2004074455 A2 | | 9/2004 |
| WO | WO 2004099249 A2 | | 11/2004 |
| WO | WO 2004101740 A2 | | 11/2004 |
| WO | WO 2005040217 A2 | | 5/2005 |
| WO | WO 2005070963 A1 | | 8/2005 |
| WO | WO 2005077981 A2 | | 8/2005 |
| WO | WO 2005092925 A2 | | 10/2005 |
| WO | WO 2005123780 A2 | | 12/2005 |
| WO | WO 2006019447 A1 | | 2/2006 |
| WO | WO 2006047350 A2 | | 5/2006 |
| WO | WO 2006074199 A1 | | 7/2006 |
| WO | WO 2006085967 A2 | | 8/2006 |
| WO | WO 2007021494 A2 | | 2/2007 |
| WO | WO 2007149406 A2 | | 12/2007 |
| WO | WO 2008033413 A2 | | 3/2008 |
| WO | WO 2008118507 A2 | | 10/2008 |
| WO | WO 2008155134 A1 | | 12/2008 |
| WO | WO 2009051717 A2 | | 4/2009 |
| WO | WO 2009058322 A1 | | 5/2009 |
| WO | WO 2009130198 A2 | | 10/2009 |
| WO | WO 2009137254 A2 | | 11/2009 |
| WO | WO 2009140015 A2 | | 11/2009 |
| WO | WO 2009145695 A1 | | 12/2009 |
| WO | WO 2009154695 A1 | | 12/2009 |
| WO | WO 2011069164 A2 | | 6/2011 |
| WO | WO 2012006623 A1 | | 1/2012 |
| WO | WO 2012006624 A2 | | 1/2012 |
| WO | WO 2012006633 A1 | | 1/2012 |
| WO | WO 2012006635 A1 | | 1/2012 |
| WO | WO 2012014183 A1 | | 2/2012 |
| WO | WO 2013106787 A1 | | 7/2013 |
| WO | WO 2013123457 A1 | | 8/2013 |
| WO | WO 2015048330 A2 | | 4/2015 |
| WO | WO 2015048330 A3 | | 10/2015 |

OTHER PUBLICATIONS

U.S. Appl. No. 16/793,676 2020/0283474, filed Feb. 18, 2020 Sep. 10, 2020, Glen Bolton.

Brorson et al., (May 2003) "Bracketed Generic Inactivation of Rodent Retroviruses by Low pH Treatment for Monoclonal Antibodies and Recombinant Proteins", Biotechnol Bioeng. 5;82(3) pp. 321/329. doi: 10.1002/bit.10574.

Burmeister, et al. (Nov. 24, 1994) "Crystal Structure of The Complex of Rat Neonatal Fc Receptor With Fc," Nature, vol. 372, pp. 379-383.

Caliceti, et al. (Jul. 1999) "Biopharmaceutical properties of uricase conjugated to neutral and amphiphilic polymers." Bioconjugate chemistry, vol. 10, No. 4, pp. 638/46.

(56) References Cited

OTHER PUBLICATIONS

Cameron, et al. (Feb. 1998) "The canine factor VIII cDNA and 5' flanking sequence." Thrombosis and haemostasis, vol. 79, No. 2, pp. 317/22.
Capon, et al. (Feb. 1989) "Designing CD4 immunoadhesins for AIDS therapy." Nature, vol. 337, No. 6207, pp. 525/31.
Cutler, et al. (Mar. 2002) "The identification and classification of 41 novel mutations in the factor VIII gene (F8C)." Human mutation, vol. 19, No. 3, pp. 274/8.
Davies et al. (Jun. 1996) "Single antibody domains as small recognition units: design and in vitro antigen selection of camelized, human VH domains with improved protein stability." Protein engineering, vol. 9, No. 6 pp. 531/7.
De Vries, et al. (Feb. 21, 1992) "The fms/like tyrosine kinase, a receptor for vascular endothelial growth factor." Science (New York, N.Y.) vol. 255, No. 5047, pp. 989/91.
Dennis, et al. (Sep. 20, 2002) "Albumin binding as a general strategy for improving the pharmacokinetics of proteins." The Journal of biological chemistry, vol. 277, No. 38, pp. 35035/43.
Extended European Search Report received for European Patent Application No. 14849291.1, dated Jul. 4, 2017, 12 pages.
GenBank, "*Homo sapiens* Transferrin (TF), mRNA," Accession No. NM001063.3 published on May 25, 2014, accessed at http://www.ncbi.nlm.nih.gov/nuccore/NM_001063, accessed on Sep. 24, 2014, 5 pages.
GenBank, "*Homo sapiens* Transferrin (TF), mRNA," Accession No. XM002793 published on May 13, 2002, accessed at https://www.ncbi.nlm.nih.gov/nuccore/XM_002793.7?report=genbank, accessed on Sep. 24, 2014, 2 pages.
GenBank, "*Homo sapiens* Transferrin (TF), mRNA," Accession No. XM039847 published on Jul. 16, 2001, accessed at http://www.ncbi.nlm.nih.gov/nuccore/XM_039847.1?report=genbank, accessed on Sep. 24, 2014, 2 pages.
GenBank, "*Homo sapiens* Transferrin (TF), mRNA," Accession No. XM039845 published Jul. 16, 2001, accessed at https://www.ncbi.nlm.nih.gov/nuccore/XM_039845.1?report=genbank, accessed on Sep. 24, 2014, 2 pages.
GenBank, "Human Transferrin mRNA, Complete cds," Accession No. M12530.1, published on Jan. 14, 1995, accessed at http://www.ncbi.nlm.nih.gov/nuccore/M1253014, accessed on Jan. 15, 2015, 2 pages.
GenBank, "Transferrin [human, liver, mRNA, 2347 nt]," Accession No. S95936.1, published on May 7, 1993, accessed at http://www.ncbi.nlm.nih.gov/nuccore/595936, accessed on Sep. 24, 2014, 2 pages.
GenBank, "transferrin precursor [*Homo sapiens*]" Accession AAA61140.1, accessed at http://www.ncbi.nlm.nih.gov/protein/AAA61140, Mar. 29, 2016, 3 pages.
Graham, et al. (Jul. 1, 1997) "Characteristics of a human cell line transformed by DNA from human adenovirus type 5." The Journal of general virology, vol. 36, No. 1, pp. 59/74.
International Search Report and Written Opinion received for PCT Patent Application No. PCT/US2014/057524, dated Mar. 23, 2015, 13 pages.
Josić, et al. (Jul. 4, 1997) "Issues in the development of medical products based on human plasma." Journal of chromatography. B, Biomedical sciences and applications, vol. 694, No. 2, pp. 253/69.
Juo Pei/Show (2002), The Concise Dictionary of Biomedicine and Molecular Biology, 2nd Edition, CRC Press, United States.
König et al. (Sep. 1, 1998) "Use of an albumin/binding domain for the selective immobilisation of recombinant capture antibody fragments on ELISA plates." Journal of immunological methods, vol. 218, Nos. 1/2, pp. 73/83.
Liu et al., (Sep./Oct. 2010) "Recovery and purification process development for monoclonal antibody production", MAbs. 2(5) pp. 480-499. doi: 10.4161/mabs.2.5.12645.
Mather, et al. (Jun. 1982) "Culture of testicular cells in hormone/supplemented serum/free medium." Annals of the New York Academy of Sciences, vol. 383, pp. 44/68.
Mather (Sep. 1980) "Establishment and characterization of two distinct mouse testicular epithelial cell lines." Biology of reproduction, vol. 23, No. 1, pp. 243/52.
"Montage Spin Columns with PROSEP/G media." 3 pages (Jul. 6, 2011).
Milstein et al. (Oct. 1983) "Hybrid hybridomas and their use in immunohistochemistry." Nature, vol. 305, No. 5934 pp. 537/40.
Morpurgo, et al. (Jan. 1996) "Covalent modification of mushroom tyrosinase with different amphiphic polymers for pharmaceutical and biocatalysis applications." Applied biochemistry and biotechnology, vol. 56, No. 1, pp. 59/72.
Morrison (1985) "Transfectomas provide novel chimeric antibodies." Science (New York, N.Y.), vol. 229 Number 4719, pp. 1202/7.
Mustonen et al. (May 2, 1995) "Endothelial receptor tyrosine kinases involved in angiogenesis." The Journal of cell biology, vol. 129, No. 4, pp. 895/8.
Oi et al., (May/Jun. 1986). "Chimeric Antibodies," BioTechniques, vol. 4, pp. 214/221.
Persson, et al. (Nov. 2001) "Rational design of coagulation factor VIIa variants with substantially increased intrinsic activity." Proceedings of the National Academy of Sciences of the United States of America, vol. 98, No. 24, pp. 13583/8.
Persson, et al. (Jun. 1, 2001) "Substitution of valine for leucine 305 in factor VIIa increases the intrinsic enzymatic activity." The Journal of biological chemistry, vol. 276, No. 31, pp. 29195/9.
Petrovan et al. (Nov. 14, 2001) "Residue Met (156) contributes to the labile enzyme conformation of coagulation factor VIIa." The Journal of biological chemistry, vol. 276, No. 9, pp. 6616/20.
Roberts et al. (Oct. 2007) "Virus inactivation by protein denaturants used in affinity chromatography." Biologicals: journal of the International Association of Biological Standardization, vol. 35, No. 4, pp. 343/7.
Roth, et al. (1993) Expression of polysialic acid in human tumors and its significance for tumor growth. In: Roth J, Rutishauser U, Troy FA II (eds) Polysialic acid: from microbes to man. Birkhäuser, Basel Boston Berlin, pp. 335-348.
Sambrook et al. (1989) Molecular cloning. A laboratory manual. 3rd edition, Cold Spring Harbor Laboratory Press, Cold Spring Harbor, New York.
Sato, et al. (Jul. 6, 1995) "Distinct roles of the receptor tyrosine kinases Tie/1 and Tie/2 in blood vessel formation." Nature, vol. 376, No. 6535, pp. 70/4.
Schlapschy, et al. (Jun. 1, 2007) "Fusion of a recombinant antibody fragment with a homo/amino/acid polymer: effects on biophysical properties and prolonged plasma half/life." Protein engineering, design & selection: PEDS, vol. 20, No. 6, pp. 273/84.
Shibuya, et al. (Apr. 1, 1990) "Nucleotide sequence and expression of a novel human receptor/type tyrosine kinase gene (flt) closely related to the fms family." Oncogene, vol. 5, No. 4, pp. 519/24.
Smith (Jun. 14, 1985) "Filamentous fusion phage: novel expression vectors that display cloned antigens on the virion surface." Science (New York, N.Y.), vol. 228, No. 4705, pp. 1315/7.
Soejima, et al. (May 1, 2001) "Factor VIIa modified in the 170 loop shows enhanced catalytic activity but does not change the zymogen/like property." The Journal of biological chemistry, vol. 276, No. 20, pp. 17229/35.
Soejima, et al. (Dec. 13, 2002) "The 99 and 170 loop/modified factor VIIa mutants show enhanced catalytic activity without tissue factor." The Journal of biological chemistry, vol. 277, No. 50, pp. 49027/35.
Sommermeyer, et al. (1987) "Klinisch verwendete Hydroxyethylstärke: Physikalisch/chemische Charakterisierung." Krankenhauspharmazie, vol. 8, pp. 271/278.
Stadler, et al. (Dec. 1, 2006) "Characterisation of a novel high/purity, double virus inactivated von Willebrand Factor and Factor VIII concentrate (Wilate)." Biologicals: journal of the International Association of Biological Standardization, vol. 34, No. 4, pp. 281/8.
Story, et al. (Dec. 1, 1994) "A major histocompatibility complex class I/like Fc receptor cloned from human placenta: possible role in transfer of immunoglobulin G from mother to fetus." The Journal of experimental medicine, vol. 180, No. 6 pp. 2377/81.

(56) References Cited

OTHER PUBLICATIONS

Terman, et al. (Sep. 1, 1991) "Identification of a new endothelial cell growth factor receptor tyrosine kinase." *Oncogene*, vol. 6, No. 9, pp. 1677/83.
Ullrich et al. (Apr. 20, 1990) "Signal transduction by receptors with tyrosine kinase activity." *Cell* vol. 61, No. 2, pp. 203/12.
Urlaub et al. (Jul. 1980) "Isolation of Chinese hamster cell mutants deficient in dihydrofolate reductase activity." *Proceedings of the National Academy of Sciences of the United States of America*, vol. 77, No. 7, pp. 4216/20.
Vorobjev, et al. (Nov./Dec. 1999) "Oligonucleotide conjugated to linear and branched high molecular weight polyethylene glycol as substrates for RNase H." *Nucleosides & nucleotides*, vol. 18, No. 11/12 pp. 2745/50.
Weidler, et al. (May 1991) "Pharmakokinetische Merkmale als Kriterien für den klinischen Einsatz von Hydroxyethylstärke" [Pharmacokinetic parameters as criteria for clinical use of hydroxyethyl starch preparations]. *Arzneimittel/Forschung*, vol. 41, No. 5, pp. 494/8.
Yarden et al. (Jul. 1988) "Growth factor receptor tyrosine kinases." *Annual review of biochemistry*, vol. 57 pp. 443/78.
Zhang, et al. (Jan. 2014) "Quality by design approach for viral clearance by protein a chromatography." *Biotechnology and bioengineering*, vol. 111, No. 1, pp. 95/103.
Extended European Search Report for European Patent Application No. 21161387.2, dated Sep. 23, 2021.

\* cited by examiner

```

SEQUENCE LISTING

<160> NUMBER OF SEQ ID NOS: 23

<210> SEQ ID NO 1
<211> LENGTH: 5052
<212> TYPE: DNA
<213> ORGANISM: Artificial Sequence
<220> FEATURE:
<223> OTHER INFORMATION: B-Domain Deleted FVIII-Fc Chain
<220> FEATURE:
<221> NAME/KEY: sig_peptide
<222> LOCATION: (1)..(57)
<223> OTHER INFORMATION: FVIII signal peptide
<220> FEATURE:
<221> NAME/KEY: misc_feature
<222> LOCATION: (4372)..(5053)
<223> OTHER INFORMATION: Fc region

<400> SEQUENCE: 1

```
atgcaaatag agctctccac ctgcttcttt ctgtgccttt tgcgattctg ctttagtgcc     60
accagaagat actacctggg tgcagtggaa ctgtcatggg actatatgca aagtgatctc    120
ggtgagctgc ctgtggacgc aagatttcct cctagagtgc aaaatctttt ccattcaac    180 acctcagtcg tgtacaaaaa gactctgttt gtagaattca cggatcacct tttcaacatc    240
gctaagccaa ggccaccctg gatgggtctg ctaggtccta ccatccaggc tgaggtttat    300
gatacagtgg tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagccata catatgtctg gcaggtcctg    480
aaagagaatg gtccaatggc ctctgaccca ctgtgcctta cctactcata tctttctcat    540
gtggacctgg taaagactt gaattcaggc ctcattggag ccctactagt atgtagagaa    600
gggagtctgg ccaaggaaaa gacacagacc ttgcacaaat ttatactact ttttgctgta    660
```

```
tttgatgaag ggaaaagttg gcactcagaa acaaagaact ccttgatgca ggatagggat      720
gctgcatctg ctcgggcctg gcctaaaatg cacacagtca atggttatgt aaacaggtct      780
ctgccaggtc tgattggatg ccacaggaaa tcagtctatt ggcatgtgat tggaatgggc      840
accactcctg aagtgcactc aatattcctc gaaggtcaca catttcttgt gaggaaccat      900
cgccaggcgt ccttggaaat ctcgccaata actttcctta ctgctcaaac actcttgatg      960
gaccttggac agtttctact gttttgtcat atctcttccc accaacatga tggcatggaa     1020
gcttatgtca agtagacag ctgtccagag aaccccaac tacgaatgaa aaataatgaa     1080
gaagcggaag actatgatga tgatcttact gattctgaaa tggatgtggt caggtttgat     1140
gatgacaact ctccttcctt tatccaaatt cgctcagttg ccaagaagca tcctaaaact     1200
tgggtacatt acattgctgc tgaagaggag gactgggact atgctccctt agtcctcgcc     1260
cccgatgaca gaagttataa aagtcaatat ttgaacaatg cccctcagcg gattggtagg     1320
aagtacaaaa aagtccgatt tatggcatac acagatgaaa cctttaagac tcgtgaagct     1380
attcagcatg aatcaggaat cttgggacct ttactttatg gggaagttgg agacacactg     1440
ttgattatat ttaagaatca agcaagcaga ccatataaca tctaccctca cggaatcact     1500
gatgtccgtc ctttgtattc aaggagatta ccaaaaggtg taaaacattt gaaggatttt     1560
ccaattctgc caggagaaat attcaaatat aaatggacag tgactgtaga agatgggcca     1620
actaaatcag atcctcggtg cctgacccgc tattactcta gtttcgttaa tatggagaga     1680
gatctagctt caggactcat tggccctctc ctcatctgct acaaagaatc tgtagatcaa     1740
agaggaaacc agataatgtc agacaagagg aatgtcatcc tgttttctgt atttgatgag     1800
aaccgaagct ggtacctcac agagaatata caacgctttc tccccaatcc agctggagtg     1860
cagcttgagg atccagagtt ccaagcctcc aacatcatgc acagcatcaa tggctatgtt     1920
tttgatagtt tgcagttgtc agtttgtttg catgaggtgg catactggta cattctaagc     1980
attggagcac agactgactt cctttctgtc ttcttctctg atataccttt caaacacaaa     2040
atggtctatg aagacacact caccctattc ccattctcag gagaaactgt cttcatgtcg     2100
atggaaaacc caggtctatg gattctgggg tgccacaact cagactttcg gaacagaggc     2160
atgaccgcct tactgaaggt ttctagttgt gacaagaaca ctggtgatta ttacgaggac     2220
agttatgaag atatttcagc atacttgctg agtaaaaaca atgccattga accaagaagc     2280
ttctctcaaa acccaccagt cttgaaacgc catcaacggg aaataactcg tactactctt     2340
cagtcagatc aagaggaaat tgactatgat gataccatat cagttgaaat gaagaaggaa     2400
gattttgaca tttatgatga ggatgaaaat cagagcccc gcagctttca aagaaaaca     2460 cgacactatt ttattgctgc agtggagagg ctctgggatt atgggatgag tagctcccca     2520
catgttctaa gaaacagggc tcagagtggc agtgtccctc agttcaagaa agttgttttc     2580
caggaattta ctgatggctc ctttactcag cccttatacc gtggagaact aaatgaacat     2640
ttgggactcc tggggccata tataagagca gaagttgaag ataatatcat ggtaactttc     2700
agaaatcagg cctctcgtcc ctattccttc tattctagcc ttatttctta tgaggaagat     2760
cagaggcaag gagcagaacc tagaaaaaac tttgtcaagc ctaatgaaac caaaacttac     2820
ttttggaaag tgcaacatca tatggcaccc actaaagatg agtttgactg caaagcctgg     2880
gcttatttct ctgatgttga cctggaaaaa gatgtgcact caggcctgat tggacccctt     2940
ctggtctgcc acactaacac actgaaccct gctcatggga gacaagtgac agtacaggaa     3000
```

| tttgctctgt | ttttcaccat | ctttgatgag | accaaaagct | ggtacttcac | tgaaaatatg | 3060 |
| gaaagaaact | gcagggctcc | ctgcaatatc | cagatggaag | atcccacttt | taaagagaat | 3120 |
| tatcgcttcc | atgcaatcaa | tggctacata | atggatacac | tacctggctt | agtaatggct | 3180 |
| caggatcaaa | ggattcgatg | gtatctgctc | agcatgggca | gcaatgaaaa | catccattct | 3240 |
| attcatttca | gtggacatgt | gttcactgta | cgaaaaaaag | aggagtataa | aatggcactg | 3300 |
| tacaatctct | atccaggtgt | ttttgagaca | gtggaaatgt | taccatccaa | agctggaatt | 3360 |
| tggcgggtgg | aatgccttat | tggcgagcat | ctacatgctg | ggatgagcac | acttttctg | 3420 |
| gtgtacagca | ataagtgtca | gactcccctg | ggaatggctt | ctggacacat | agagatttt | 3480 |
| cagattacag | cttcaggaca | atatggacag | tgggcccaa | agctggccag | acttcattat | 3540 |
| tccggatcaa | tcaatgcctg | gagcaccaag | gagcccttt | cttggatcaa | ggtggatctg | 3600 |
| ttggcaccaa | tgattattca | cggcatcaag | acccagggtg | cccgtcagaa | gttctccagc | 3660 |
| ctctacatct | ctcagtttat | catcatgtat | agtcttgatg | gaagaagtg | gcagacttat | 3720 |
| cgaggaaatt | ccactggaac | cttaatggtc | ttctttggca | atgtggattc | atctgggata | 3780 |
| aaacacaata | ttttttaaccc | tccaattatt | gctcgataca | tccgtttgca | cccaactcat | 3840 |
| tatagcattc | gcagcactct | tcgcatggag | ttgatgggct | gtgatttaaa | tagttgcagc | 3900 |
| atgccattgg | gaatggagag | taaagcaata | tcagatgcac | agattactgc | ttcatcctac | 3960 |
| tttaccaata | tgtttgccac | tggtctcct | tcaaaagctc | gacttcacct | ccaagggagg | 4020 |
| agtaatgcct | ggagacctca | ggtgaataat | ccaaaagagt | ggctgcaagt | ggacttccag | 4080 |
| aagacaatga | aagtcacagg | agtaactact | cagggagtaa | aatctctgct | taccagcatg | 4140 |
| tatgtgaagg | agttcctcat | ctccagcagt | caagatggcc | atcagtggac | tctcttttt | 4200 |
| cagaatggca | aagtaaaggt | ttttcaggga | aatcaagact | ccttcacacc | tgtggtgaac | 4260 |
| tctctagacc | caccgttact | gactcgctac | cttcgaattc | accccagag | ttgggtgcac | 4320 |
| cagattgccc | tgaggatgga | ggttctgggc | tgcgaggcac | aggacctcta | cgacaaaact | 4380 |
| cacacatgcc | caccgtgccc | agctccagaa | ctcctgggcg | gaccgtcagt | cttcctcttc | 4440 |
| cccccaaaac | ccaaggacac | cctcatgatc | tcccggaccc | ctgaggtcac | atgcgtggtg | 4500 |
| gtggacgtga | gccacgaaga | ccctgaggtc | aagttcaact | ggtacgtgga | cggcgtggag | 4560 |
| gtgcataatg | ccaagacaaa | gccgcgggag | gagcagtaca | acagcacgta | ccgtgtggtc | 4620 |
| agcgtcctca | ccgtcctgca | ccaggactgg | ctgaatggca | aggagtacaa | gtgcaaggtc | 4680 |
| tccaacaaag | ccctcccagc | ccccatcgag | aaaaccatct | ccaaagccaa | agggcagccc | 4740 |
| cgagaaccac | aggtgtacac | cctgccccca | tcccgggatg | agctgaccaa | gaaccaggtc | 4800 |
| agcctgacct | gcctggtcaa | aggcttctat | cccagcgaca | tcgccgtgga | gtgggagagc | 4860 |
| aatgggcagc | cggagaacaa | ctacaagacc | acgcctcccg | tgttggactc | cgacggctcc | 4920 |
| ttcttcctct | acagcaagct | caccgtggac | aagagcaggt | ggcagcaggg | gaacgtcttc | 4980 |
| tcatgctccg | tgatgcatga | ggctctgcac | aaccactaca | cgcagaagag | cctctccctg | 5040 |
| tctccgggta | aa | | | | | 5052 |

<210> SEQ ID NO 2
<211> LENGTH: 1684
<212> TYPE: PRT
<213> ORGANISM: Artificial Sequence
<220> FEATURE:
<223> OTHER INFORMATION: B domain deleted FVIII-Fc chain
<220> FEATURE:
<221> NAME/KEY: SIGNAL

```
<222> LOCATION: (1)..(19)
<223> OTHER INFORMATION: signal sequence
<220> FEATURE:
<221> NAME/KEY: MISC_FEATURE
<222> LOCATION: (20)..(759)
<223> OTHER INFORMATION: HC sequence
<220> FEATURE:
<221> NAME/KEY: MISC_FEATURE
<222> LOCATION: (760)..(773)
<223> OTHER INFORMATION: remaining B Domain sequence
<220> FEATURE:
<221> NAME/KEY: MISC_FEATURE
<222> LOCATION: (1458)..(1684)
<223> OTHER INFORMATION: Fc sequence

<400> SEQUENCE: 2

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335
```

```
Asp Gly Met Glu Ala Tyr Val Lys Val Asp Ser Cys Pro Glu Pro
            340                 345                 350

Gln Leu Arg Met Lys Asn Asn Glu Ala Glu Asp Tyr Asp Asp Asp
            355                 360                 365

Leu Thr Asp Ser Glu Met Asp Val Val Arg Phe Asp Asp Asn Ser
            370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
            450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
            530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
            690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750
```

```
Asn Asn Ala Ile Glu Pro Arg Ser Phe Ser Gln Asn Pro Val Leu
        755                 760                 765

Lys Arg His Gln Arg Glu Ile Thr Arg Thr Thr Leu Gln Ser Asp Gln
770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
            805                 810                 815

Gln Lys Lys Thr Arg His Tyr Phe Ile Ala Ala Val Glu Arg Leu Trp
            820                 825                 830

Asp Tyr Gly Met Ser Ser Pro His Val Leu Arg Asn Arg Ala Gln
            835                 840                 845

Ser Gly Ser Val Pro Gln Phe Lys Lys Val Val Phe Gln Glu Phe Thr
850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
            915                 920                 925

Lys Asn Phe Val Lys Pro Asn Glu Thr Lys Thr Tyr Phe Trp Lys Val
            930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
            965                 970                 975

Ile Gly Pro Leu Leu Val Cys His Thr Asn Thr Leu Asn Pro Ala His
            980                 985                 990

Gly Arg Gln Val Thr Val Gln Glu Phe Ala Leu Phe Phe Thr Ile Phe
            995                 1000                1005

Asp Glu Thr Lys Ser Trp Tyr Phe Thr Glu Asn Met Glu Arg Asn
    1010                1015                1020

Cys Arg Ala Pro Cys Asn Ile Gln Met Glu Asp Pro Thr Phe Lys
    1025                1030                1035

Glu Asn Tyr Arg Phe His Ala Ile Asn Gly Tyr Ile Met Asp Thr
    1040                1045                1050

Leu Pro Gly Leu Val Met Ala Gln Asp Gln Arg Ile Arg Trp Tyr
    1055                1060                1065

Leu Leu Ser Met Gly Ser Asn Glu Asn Ile His Ser Ile His Phe
    1070                1075                1080

Ser Gly His Val Phe Thr Val Arg Lys Lys Glu Glu Tyr Lys Met
    1085                1090                1095

Ala Leu Tyr Asn Leu Tyr Pro Gly Val Phe Glu Thr Val Glu Met
    1100                1105                1110

Leu Pro Ser Lys Ala Gly Ile Trp Arg Val Glu Cys Leu Ile Gly
    1115                1120                1125

Glu His Leu His Ala Gly Met Ser Thr Leu Phe Leu Val Tyr Ser
    1130                1135                1140

Asn Lys Cys Gln Thr Pro Leu Gly Met Ala Ser Gly His Ile Arg
    1145                1150                1155

Asp Phe Gln Ile Thr Ala Ser Gly Gln Tyr Gly Gln Trp Ala Pro
```

-continued

```
            1160                1165                1170
Lys Leu Ala Arg Leu His Tyr Ser Gly Ser Ile Asn Ala Trp Ser
            1175                1180                1185
Thr Lys Glu Pro Phe Ser Trp Ile Lys Val Asp Leu Leu Ala Pro
            1190                1195                1200
Met Ile Ile His Gly Ile Lys Thr Gln Gly Ala Arg Gln Lys Phe
            1205                1210                1215
Ser Ser Leu Tyr Ile Ser Gln Phe Ile Ile Met Tyr Ser Leu Asp
            1220                1225                1230
Gly Lys Lys Trp Gln Thr Tyr Arg Gly Asn Ser Thr Gly Thr Leu
            1235                1240                1245
Met Val Phe Phe Gly Asn Val Asp Ser Ser Gly Ile Lys His Asn
            1250                1255                1260
Ile Phe Asn Pro Pro Ile Ile Ala Arg Tyr Ile Arg Leu His Pro
            1265                1270                1275
Thr His Tyr Ser Ile Arg Ser Thr Leu Arg Met Glu Leu Met Gly
            1280                1285                1290
Cys Asp Leu Asn Ser Cys Ser Met Pro Leu Gly Met Glu Ser Lys
            1295                1300                1305
Ala Ile Ser Asp Ala Gln Ile Thr Ala Ser Ser Tyr Phe Thr Asn
            1310                1315                1320
Met Phe Ala Thr Trp Ser Pro Ser Lys Ala Arg Leu His Leu Gln
            1325                1330                1335
Gly Arg Ser Asn Ala Trp Arg Pro Gln Val Asn Asn Pro Lys Glu
            1340                1345                1350
Trp Leu Gln Val Asp Phe Gln Lys Thr Met Lys Val Thr Gly Val
            1355                1360                1365
Thr Thr Gln Gly Val Lys Ser Leu Leu Thr Ser Met Tyr Val Lys
            1370                1375                1380
Glu Phe Leu Ile Ser Ser Ser Gln Asp Gly His Gln Trp Thr Leu
            1385                1390                1395
Phe Phe Gln Asn Gly Lys Val Lys Val Phe Gln Gly Asn Gln Asp
            1400                1405                1410
Ser Phe Thr Pro Val Val Asn Ser Leu Asp Pro Pro Leu Leu Thr
            1415                1420                1425
Arg Tyr Leu Arg Ile His Pro Gln Ser Trp Val His Gln Ile Ala
            1430                1435                1440
Leu Arg Met Glu Val Leu Gly Cys Glu Ala Gln Asp Leu Tyr Asp
            1445                1450                1455
Lys Thr His Thr Cys Pro Pro Cys Pro Ala Pro Glu Leu Leu Gly
            1460                1465                1470
Gly Pro Ser Val Phe Leu Phe Pro Pro Lys Pro Lys Asp Thr Leu
            1475                1480                1485
Met Ile Ser Arg Thr Pro Glu Val Thr Cys Val Val Val Asp Val
            1490                1495                1500
Ser His Glu Asp Pro Glu Val Lys Phe Asn Trp Tyr Val Asp Gly
            1505                1510                1515
Val Glu Val His Asn Ala Lys Thr Lys Pro Arg Glu Glu Gln Tyr
            1520                1525                1530
Asn Ser Thr Tyr Arg Val Val Ser Val Leu Thr Val Leu His Gln
            1535                1540                1545
Asp Trp Leu Asn Gly Lys Glu Tyr Lys Cys Lys Val Ser Asn Lys
            1550                1555                1560
```

```
Ala Leu Pro Ala Pro Ile Glu Lys Thr Ile Ser Lys Ala Lys Gly
        1565                1570                1575

Gln Pro Arg Glu Pro Gln Val Tyr Thr Leu Pro Pro Ser Arg Asp
    1580                1585                1590

Glu Leu Thr Lys Asn Gln Val Ser Leu Thr Cys Leu Val Lys Gly
    1595                1600                1605

Phe Tyr Pro Ser Asp Ile Ala Val Glu Trp Glu Ser Asn Gly Gln
    1610                1615                1620

Pro Glu Asn Asn Tyr Lys Thr Thr Pro Pro Val Leu Asp Ser Asp
    1625                1630                1635

Gly Ser Phe Phe Leu Tyr Ser Lys Leu Thr Val Asp Lys Ser Arg
    1640                1645                1650

Trp Gln Gln Gly Asn Val Phe Ser Cys Ser Val Met His Glu Ala
    1655                1660                1665

Leu His Asn His Tyr Thr Gln Lys Ser Leu Ser Leu Ser Pro Gly
    1670                1675                1680

Lys

<210> SEQ ID NO 3
<211> LENGTH: 741
<212> TYPE: DNA
<213> ORGANISM: Artificial Sequence
<220> FEATURE:
<223> OTHER INFORMATION: Fc DNA sequence
<220> FEATURE:
<221> NAME/KEY: sig_peptide
<222> LOCATION: (1)..(60)
<223> OTHER INFORMATION: mouse Ig kappa signal peptide

<400> SEQUENCE: 3
atggagacag acacactcct gctatgggta ctgctgctct gggttccagg ttccactggt      60
gacaaaactc acacatgccc accgtgccca gcacctgaac tcctgggagg accgtcagtc     120
ttcctcttcc ccccaaaacc caaggacacc ctcatgatct cccggacccc tgaggtcaca     180
tgcgtggtgg tggacgtgag ccacgaagac cctgaggtca agttcaactg gtacgtggac     240
ggcgtggagg tgcataatgc caagacaaag ccgcgggagg agcagtacaa cagcacgtac     300
cgtgtggtca gcgtcctcac cgtcctgcac caggactggc tgaatggcaa ggagtacaag     360
tgcaaggtct ccaacaaagc cctcccagcc cccatcgaga aaaccatctc caaagccaaa     420
gggcagcccc gagaaccaca ggtgtacacc ctgcccccat cccgcgatga gctgaccaag     480
aaccaggtca gcctgacctg cctggtcaaa ggcttctatc cagcgacat cgccgtggag      540 tgggagagca atgggcagcc ggagaacaac tacaagacca cgcctcccgt gttggactcc     600
gacggctcct tcttcctcta cagcaagctc accgtggaca agagcaggtg gcagcagggg     660
aacgtcttct catgctccgt gatgcatgag gctctgcaca accactacac gcagaagagc     720
ctctccctgt ctccgggtaa a                                               741

<210> SEQ ID NO 4
<211> LENGTH: 247
<212> TYPE: PRT
<213> ORGANISM: Artificial Sequence
<220> FEATURE:
<223> OTHER INFORMATION: B domain deleted FVIII-Fc chain
<220> FEATURE:
<221> NAME/KEY: SIGNAL
<222> LOCATION: (1)..(19)
<223> OTHER INFORMATION: mouse Ig kappa signal peptide
```

<400> SEQUENCE: 4

```
Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys
                245
```

```
<210> SEQ ID NO 5
<211> LENGTH: 7734
<212> TYPE: DNA
<213> ORGANISM: Artificial Sequence
<220> FEATURE:
<223> OTHER INFORMATION: Full Length FVIII-Fc DNA Sequence
<220> FEATURE:
<221> NAME/KEY: sig_peptide
<222> LOCATION: (1)..(57)
<223> OTHER INFORMATION: FVIII signal peptide
<220> FEATURE:
<221> NAME/KEY: misc_feature
<222> LOCATION: (7054)..(7734)
<223> OTHER INFORMATION: Fc region
```

<400> SEQUENCE: 5

| | |
|---|---|
| atgcaaatag agctctccac ctgcttcttt ctgtgccttt tgcgattctg ctttagtgcc | 60 |
| accagaagat actacctggg tgcagtggaa ctgtcatggg actatatgca aagtgatctc | 120 |
| ggtgagctgc ctgtggacgc aagatttcct cctagagtgc aaaatctttt ccattcaac | 180 |
| acctcagtcg tgtacaaaaa gactctgttt gtagaattca cggatcacct tttcaacatc | 240 |
| gctaagccaa ggccaccctg gatgggtctg ctaggtccta ccatccaggc tgaggtttat | 300 |
| gatacagtgg tcattacact taagaacatg gcttcccatc ctgtcagtct tcatgctgtt | 360 |

```
ggtgtatcct actggaaagc ttctgaggga gctgaatatg atgatcagac cagtcaaagg      420
gagaaagaag atgataaagt cttccctggt ggaagccata catatgtctg gcaggtcctg      480
aaagagaatg gtccaatggc ctctgaccca ctgtgcctta cctactcata tctttctcat      540
gtggacctgg taaaagactt gaattcaggc ctcattggag ccctactagt atgtagagaa      600
gggagtctgg ccaaggaaaa gacacagacc ttgcacaaat ttatactact ttttgctgta      660
tttgatgaag ggaaaagttg gcactcagaa acaaagaact ccttgatgca ggatagggat      720
gctgcatctg ctcgggcctg gcctaaaatg cacacagtca atggttatgt aaacaggtct      780
ctgccaggtc tgattggatg ccacaggaaa tcagtctatt ggcatgtgat tggaatgggc      840
accactcctg aagtgcactc aatattcctc gaaggtcaca catttcttgt gaggaaccat      900
cgccaggcgt ccttggaaat ctcgccaata actttcctta ctgctcaaac actcttgatg      960
gaccttggac agtttctact gttttgtcat atctcttccc accaacatga tggcatggaa     1020
gcttatgtca aagtagacag ctgtccagag gaacccaac tacgaatgaa aaataatgaa      1080
gaagcggaag actatgatga tgatcttact gattctgaaa tggatgtggt caggtttgat     1140
gatgacaact ctccttcctt tatccaaatt cgctcagttg ccaagaagca tcctaaaact     1200
tgggtacatt acattgctgc tgaagaggag gactgggact atgctccctt agtcctcgcc     1260
cccgatgaca gaagttataa aagtcaatat ttgaacaatg ccctcagcg gattggtagg      1320 aagtacaaaa aagtccgatt tatggcatac acagatgaaa cctttaagac tcgtgaagct     1380
attcagcatg aatcaggaat cttgggacct ttactttatg gggaagttgg agacacactg     1440
ttgattatat ttaagaatca agcaagcaga ccatataaca tctaccctca cggaatcact     1500
gatgtccgtc ctttgtattc aaggagatta ccaaaaggtg taaaacattt gaaggatttt     1560
ccaattctgc caggagaaat attcaaatat aaatggacag tgactgtaga agatgggcca     1620
actaaatcag atcctcggtg cctgacccgc tattactcta gtttcgttaa tatggagaga     1680
gatctagctt caggactcat tggccctctc ctcatctgct acaaagaatc tgtagatcaa     1740
agaggaaacc agataatgtc agacaagagg aatgtcatcc tgttttctgt atttgatgag     1800
aaccgaagct ggtacctcac agagaatata caacgctttc tccccaatcc agctggagtg     1860
cagcttgagg atccagagtt ccaagcctcc aacatcatgc acagcatcaa tggctatgtt     1920
tttgatagtt tgcagttgtc agtttgtttg catgaggtgg catactggta cattctaagc     1980
attggagcac agactgactt cctttctgtc ttcttctctg gatataccct caaacacaaa     2040
atggtctatg aagacacact caccctattc ccattctcag agaaactgt cttcatgtcg      2100 atggaaaaacc caggtctatg gattctgggg tgccacaact cagactttcg aacagaggc      2160 atgaccgcct tactgaaggt ttctagttgt gacaagaaca ctggtgatta ttacgaggac     2220
agttatgaag atatttcagc atacttgctg agtaaaaaca tgccattga ccaagaagc      2280 ttctcccaga attcaagaca ccctagcact aggcaaaagc aatttaatgc caccacaatt     2340
ccagaaaatg acatagagaa gactgaccct tggtttgcac acagaacacc tatgcctaaa     2400
atacaaaatg tctcctctag tgatttgttg atgctcttgc gacagagtcc tactccacat     2460
gggctatcct tatctgatct ccaagaagcc aaatatgaga cttttctga tgatccatca      2520 cctggagcaa tagacagtaa taacagcctg tctgaaatga cacacttcag gccacagctc     2580
catcacagtg gggacatggt atttacccct gagtcaggcc tccaattaag attaaatgag     2640
aaactgggga caactgcagc aacagagttg aagaaacttg atttcaaagt ttctagtaca     2700
```

```
tcaaataatc tgatttcaac aattccatca gacaatttgg cagcaggtac tgataataca    2760
agttccttag gacccccaag tatgccagtt cattatgata gtcaattaga taccactcta    2820
tttggcaaaa agtcatctcc ccttactgag tctggtggac ctctgagctt gagtgaagaa    2880
aataatgatt caaagttgtt agaatcaggt ttaatgaata gccaagaaag ttcatgggga    2940
aaaaatgtat cgtcaacaga gagtggtagg ttatttaaag ggaaagagc tcatggacct     3000 gctttgttga ctaaagataa tgccttattc aaagttagca tctctttgtt aaagacaaac    3060
aaaacttcca ataattcagc aactaataga aagactcaca ttgatggccc atcattatta    3120
attgagaata gtccatcagt ctggcaaaat atattagaaa gtgacactga gtttaaaaaa    3180
gtgacacctt tgattcatga cagaatgctt atggacaaaa atgctacagc tttgaggcta    3240
aatcatatgt caaataaaac tacttcatca aaaacatgg aaatggtcca acagaaaaaa     3300
gagggcccca ttccaccaga tgcacaaaat ccagatatgt cgttctttaa gatgctattc    3360
ttgccagaat cagcaaggtg gatacaaagg actcatggaa agaactctct gaactctggg    3420
caaggcccca gtccaaagca attagtatcc ttaggaccag aaaaatctgt ggaaggtcag    3480
aatttcttgt ctgagaaaaa caaagtggta gtaggaaagg gtgaatttac aaaggacgta    3540
ggactcaaag agatggtttt tccaagcagc agaaacctat ttcttactaa cttggataat    3600
ttacatgaaa ataatacaca caatcaagaa aaaaaaattc aggaagaaat agaaagaag     3660 gaaacattaa tccaagagaa tgtagttttg cctcagatac atacagtgac tggcactaag    3720
aatttcatga agaacctttt cttactgagc actaggcaaa atgtagaagg ttcatatgac    3780
ggggcatatg ctccagtact tcaagatttt aggtcattaa atgattcaac aaatagaaca    3840
aagaaacaca cagctcattt ctcaaaaaaa ggggaggaag aaaacttgga aggcttggga    3900
aatcaaacca agcaaattgt agagaaatat gcatgcacca caaggatatc tcctaataca    3960
agccagcaga attttgtcac gcaacgtagt aagagagctt tgaaacaatt cagactccca    4020
ctagaagaaa cagaacttga aaaaaggata attgtggatg acacctcaac ccagtggtcc    4080
aaaaacatga acatttgac cccgagcacc ctcacacaga tagactacaa tgagaaggag     4140
aaaggggcca ttactcagtc tcccttatca gattgcctta cgaggagtca tagcatccct    4200
caagcaaata gatctccatt acccattgca aaggtatcat catttccatc tattagacct    4260
atatatctga ccagggtcct attccaagac aactcttctc atcttccagc agcatcttat    4320
agaaagaaag attctggggt ccaagaaagc agtcatttct acaaggagc caaaaaaaat     4380 aacctttctt tagccattct aaccttggag atgactggtg atcaaagaga ggttggctcc    4440
ctggggacaa gtgccacaaa ttcagtcaca tacaagaaag ttgagaacac tgttctcccg    4500
aaaccagact tgcccaaaac atctggcaaa gttgaattgc ttccaaaagt tcacatttat    4560
cagaaggacc tattccctac ggaaactagc aatgggtctc ctggccatct ggatctcgtg    4620
gaagggagcc ttcttcaggg aacagaggga gcgattaagt ggaatgaagc aaacagacct    4680
ggaaaagttc cctttctgag agtagcaaca gaaagctctg caaagactcc ctccaagcta    4740
ttggatcctc ttgcttggga taaccactat ggtactcaga taccaaaaga agagtggaaa    4800
tcccaagaga agtcaccaga aaaacagct tttaagaaaa aggataccat tttgtccctg     4860
aacgcttgtg aaagcaatca tgcaatagca gcaataaatg agggacaaaa taagcccgaa    4920
atagaagtca cctgggcaaa gcaaggtagg actgaaaggc tgtgctctca aacccacca    4980 gtcttgaaac gccatcaacg ggaaataact cgtactactc ttcagtcaga tcaagaggaa    5040
attgactatg atgataccat atcagttgaa atgaagaagg aagattttga catttatgat    5100
```

```
gaggatgaaa atcagagccc ccgcagcttt caaaagaaaa cacgacacta ttttattgct    5160
gcagtggaga ggctctggga ttatgggatg agtagctccc cacatgttct aagaaacagg    5220
gctcagagtg gcagtgtccc tcagttcaag aaagttgttt tccaggaatt tactgatggc    5280
tcctttactc agcccttata ccgtggagaa ctaaatgaac atttgggact cctggggcca    5340
tatataagag cagaagttga agataatatc atggtaactt tcagaaatca ggcctctcgt    5400
ccctattcct tctattctag ccttatttct tatgaggaag atcagaggca aggagcagaa    5460
cctagaaaaa actttgtcaa gcctaatgaa accaaaactt acttttggaa agtgcaacat    5520
catatggcac ccactaaaga tgagtttgac tgcaaagcct gggcttattt ctctgatgtt    5580
gacctggaaa aagatgtgca ctcaggcctg attggacccc ttctggtctg ccacactaac    5640
acactgaacc ctgctcatgg gagacaagtg acagtacagg aatttgctct gttttttcacc    5700 atctttgatg agaccaaaag ctggtacttc actgaaaata tggaaagaaa ctgcagggct    5760
ccctgcaata tccagatgga agatcccact tttaaagaga attatcgctt ccatgcaatc    5820
aatggctaca taatggatac actacctggc ttagtaatgg ctcaggatca aaggattcga    5880
tggtatctgc tcagcatggg cagcaatgaa aacatccatt ctattcattt cagtggacat    5940
gtgttcactg tacgaaaaaa agaggagtat aaaatggcac tgtacaatct ctatccaggt    6000 gttttgaga cagtggaaat gttaccatcc aaagctggaa tttggcgggt ggaatgcctt    6060
attggcgagc atctacatgc tgggatgagc acacttttc tggtgtacag caataagtgt    6120
cagactcccc tggaatggc ttctggacac attagagatt ttcagattac agcttcagga    6180
caatatggac agtgggcccc aaagctggcc agacttcatt attccggatc aatcaatgcc    6240
tggagcacca aggagccctt ttcttggatc aaggtggatc tgttggcacc aatgattatt    6300
cacggcatca agacccaggg tgcccgtcag aagttctcca gcctctacat ctctcagttt    6360
atcatcatgt atagtcttga tgggaagaag tggcagactt atcgaggaaa ttccactgga    6420
accttaatgg tcttcttttgg caatgtggat tcatctggga taaaacacaa tatttttaac    6480
cctccaatta ttgctcgata catccgtttg cacccaactc attatagcat tcgcagcact    6540
cttcgcatgg agttgatggg ctgtgattta aatagttgca gcatgccatt gggaatggag    6600
agtaaagcaa tatcagatgc acagattact gcttcatcct actttaccaa tatgtttgcc    6660
acctggtctc cttcaaaagc tcgacttcac ctccaaggga ggagtaatgc ctggagacct    6720
caggtgaata tccaaaaga gtggctgcaa gtggacttcc agaagacaat gaaagtcaca    6780
ggagtaacta ctcagggagt aaaatctctg cttaccagca tgtatgtgaa ggagttcctc    6840
atctccagca gtcaagatgg ccatcagtgg actctctttt ttcagaatgg caaagtaaag    6900 gttttcagg gaaatcaaga ctccttcaca cctgtggtga actctctaga cccaccgtta    6960
ctgactcgct accttcgaat tcaccccag agttgggtgc accagattgc cctgaggatg    7020
gaggttctgg gctgcgaggc acaggacctc tacgacaaaa ctcacacatg cccaccgtgc    7080
ccagctccag aactcctggg cggaccgtca gtcttcctct tccccccaaa acccaaggac    7140
accctcatga tctcccggac ccctgaggtc acatgcgtgg tggtggacgt gagccacgaa    7200
gaccctgagg tcaagttcaa ctggtacgtg gacggcgtgg aggtgcataa tgccaagaca    7260
aagccgcggg aggagcagta caacagcacg taccgtgtgg tcagcgtcct caccgtcctg    7320
caccaggact ggctgaatgg caaggagtac aagtgcaagg tctccaacaa agccctccca    7380
gcccccatcg agaaaaccat ctccaaagcc aaagggcagc cccgagaacc acaggtgtac    7440
```

-continued

```
accctgcccc catcccggga tgagctgacc aagaaccagg tcagcctgac ctgcctggtc    7500
aaaggcttct atcccagcga catcgccgtg gagtgggaga gcaatgggca gccggagaac    7560
aactacaaga ccacgcctcc cgtgttggac tccgacggct ccttcttcct ctacagcaag    7620
ctcaccgtgg acaagagcag gtggcagcag gggaacgtct tctcatgctc cgtgatgcat    7680
gaggctctgc acaaccacta cacgcagaag agcctctccc tgtctccggg taaa          7734
```

<210> SEQ ID NO 6
<211> LENGTH: 2578
<212> TYPE: PRT
<213> ORGANISM: Artificial Sequence
<220> FEATURE:
<223> OTHER INFORMATION: Full length FVIIIFc chain
<220> FEATURE:
<221> NAME/KEY: SIGNAL
<222> LOCATION: (1)..(19)
<223> OTHER INFORMATION: FVIII signal peptide
<220> FEATURE:
<221> NAME/KEY: MISC_FEATURE
<222> LOCATION: (20)..(759)
<223> OTHER INFORMATION: HC sequence
<220> FEATURE:
<221> NAME/KEY: MISC_FEATURE
<222> LOCATION: (760)..(1667)
<223> OTHER INFORMATION: B Domain sequence
<220> FEATURE:
<221> NAME/KEY: MISC_FEATURE
<222> LOCATION: (2351)..(2578)
<223> OTHER INFORMATION: Fc sequence

<400> SEQUENCE: 6

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
```

```
                 225                 230                 235                 240
Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
                260                 265                 270

Tyr Trp His Val Ile Gly Met Gly Thr Thr Pro Glu Val His Ser Ile
                275                 280                 285

Phe Leu Glu Gly His Thr Phe Leu Val Arg Asn His Arg Gln Ala Ser
                290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
                340                 345                 350

Gln Leu Arg Met Lys Asn Asn Glu Glu Ala Glu Asp Tyr Asp Asp Asp
                355                 360                 365

Leu Thr Asp Ser Glu Met Asp Val Val Arg Phe Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Lys Val Arg Phe Met
                435                 440                 445

Ala Tyr Thr Asp Glu Thr Phe Lys Thr Arg Glu Ala Ile Gln His Glu
                450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
                515                 520                 525

Lys Tyr Lys Trp Thr Val Thr Val Glu Asp Gly Pro Thr Lys Ser Asp
                530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
                595                 600                 605

Asn Ile Gln Arg Phe Leu Pro Asn Pro Ala Gly Val Gln Leu Glu Asp
                610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655
```

```
Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Gln Lys Gln Phe Asn Ala Thr Thr Ile Pro Glu Asn Asp
    770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
        835                 840                 845

Ser Leu Ser Glu Met Thr His Phe Arg Pro Gln Leu His His Ser Gly
    850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
        915                 920                 925

Pro Val His Tyr Asp Ser Gln Leu Asp Thr Thr Leu Phe Gly Lys Lys
    930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala
        995                 1000                1005

Leu Phe Lys Val Ser Ile Ser Leu Leu Lys Thr Asn Lys Thr Ser
    1010                1015                1020

Asn Asn Ser Ala Thr Asn Arg Lys Thr His Ile Asp Gly Pro Ser
    1025                1030                1035

Leu Leu Ile Glu Asn Ser Pro Ser Val Trp Gln Asn Ile Leu Glu
    1040                1045                1050

Ser Asp Thr Glu Phe Lys Lys Val Thr Pro Leu Ile His Asp Arg
    1055                1060                1065
```

```
Met Leu Met Asp Lys Asn Ala Thr Ala Leu Arg Leu Asn His Met
    1070                1075                1080

Ser Asn Lys Thr Thr Ser Ser Lys Asn Met Glu Met Val Gln Gln
    1085                1090                1095

Lys Lys Glu Gly Pro Ile Pro Pro Asp Ala Gln Asn Pro Asp Met
    1100                1105                1110

Ser Phe Phe Lys Met Leu Phe Leu Pro Glu Ser Ala Arg Trp Ile
    1115                1120                1125

Gln Arg Thr His Gly Lys Asn Ser Leu Asn Ser Gly Gln Gly Pro
    1130                1135                1140

Ser Pro Lys Gln Leu Val Ser Leu Gly Pro Glu Lys Ser Val Glu
    1145                1150                1155

Gly Gln Asn Phe Leu Ser Glu Lys Asn Lys Val Val Val Gly Lys
    1160                1165                1170

Gly Glu Phe Thr Lys Asp Val Gly Leu Lys Glu Met Val Phe Pro
    1175                1180                1185

Ser Ser Arg Asn Leu Phe Leu Thr Asn Leu Asp Asn Leu His Glu
    1190                1195                1200

Asn Asn Thr His Asn Gln Glu Lys Lys Ile Gln Glu Glu Ile Glu
    1205                1210                1215

Lys Lys Glu Thr Leu Ile Gln Glu Asn Val Val Leu Pro Gln Ile
    1220                1225                1230

His Thr Val Thr Gly Thr Lys Asn Phe Met Lys Asn Leu Phe Leu
    1235                1240                1245

Leu Ser Thr Arg Gln Asn Val Glu Gly Ser Tyr Asp Gly Ala Tyr
    1250                1255                1260

Ala Pro Val Leu Gln Asp Phe Arg Ser Leu Asn Asp Ser Thr Asn
    1265                1270                1275

Arg Thr Lys Lys His Thr Ala His Phe Ser Lys Lys Gly Glu Glu
    1280                1285                1290

Glu Asn Leu Glu Gly Leu Gly Asn Gln Thr Lys Gln Ile Val Glu
    1295                1300                1305

Lys Tyr Ala Cys Thr Thr Arg Ile Ser Pro Asn Thr Ser Gln Gln
    1310                1315                1320

Asn Phe Val Thr Gln Arg Ser Lys Arg Ala Leu Lys Gln Phe Arg
    1325                1330                1335

Leu Pro Leu Glu Glu Thr Glu Leu Glu Lys Arg Ile Ile Val Asp
    1340                1345                1350

Asp Thr Ser Thr Gln Trp Ser Lys Asn Met Lys His Leu Thr Pro
    1355                1360                1365

Ser Thr Leu Thr Gln Ile Asp Tyr Asn Glu Lys Glu Lys Gly Ala
    1370                1375                1380

Ile Thr Gln Ser Pro Leu Ser Asp Cys Leu Thr Arg Ser His Ser
    1385                1390                1395

Ile Pro Gln Ala Asn Arg Ser Pro Leu Pro Ile Ala Lys Val Ser
    1400                1405                1410

Ser Phe Pro Ser Ile Arg Pro Ile Tyr Leu Thr Arg Val Leu Phe
    1415                1420                1425

Gln Asp Asn Ser Ser His Leu Pro Ala Ala Ser Tyr Arg Lys Lys
    1430                1435                1440

Asp Ser Gly Val Gln Glu Ser Ser His Phe Leu Gln Gly Ala Lys
    1445                1450                1455

Lys Asn Asn Leu Ser Leu Ala Ile Leu Thr Leu Glu Met Thr Gly
```

```
             1460                1465                1470
Asp Gln Arg Glu Val Gly Ser Leu Gly Thr Ser Ala Thr Asn Ser
    1475                1480                1485
Val Thr Tyr Lys Lys Val Glu Asn Thr Val Leu Pro Lys Pro Asp
    1490                1495                1500
Leu Pro Lys Thr Ser Gly Lys Val Glu Leu Leu Pro Lys Val His
    1505                1510                1515
Ile Tyr Gln Lys Asp Leu Phe Pro Thr Glu Thr Ser Asn Gly Ser
    1520                1525                1530
Pro Gly His Leu Asp Leu Val Glu Gly Ser Leu Leu Gln Gly Thr
    1535                1540                1545
Glu Gly Ala Ile Lys Trp Asn Glu Ala Asn Arg Pro Gly Lys Val
    1550                1555                1560
Pro Phe Leu Arg Val Ala Thr Glu Ser Ser Ala Lys Thr Pro Ser
    1565                1570                1575
Lys Leu Leu Asp Pro Leu Ala Trp Asp Asn His Tyr Gly Thr Gln
    1580                1585                1590
Ile Pro Lys Glu Glu Trp Lys Ser Gln Glu Lys Ser Pro Glu Lys
    1595                1600                1605
Thr Ala Phe Lys Lys Lys Asp Thr Ile Leu Ser Leu Asn Ala Cys
    1610                1615                1620
Glu Ser Asn His Ala Ile Ala Ile Asn Glu Gly Gln Asn Lys
    1625                1630                1635
Pro Glu Ile Glu Val Thr Trp Ala Lys Gln Gly Arg Thr Glu Arg
    1640                1645                1650
Leu Cys Ser Gln Asn Pro Pro Val Leu Lys Arg His Gln Arg Glu
    1655                1660                1665
Ile Thr Arg Thr Thr Leu Gln Ser Asp Gln Glu Glu Ile Asp Tyr
    1670                1675                1680
Asp Asp Thr Ile Ser Val Glu Met Lys Lys Glu Asp Phe Asp Ile
    1685                1690                1695
Tyr Asp Glu Asp Glu Asn Gln Ser Pro Arg Ser Phe Gln Lys Lys
    1700                1705                1710
Thr Arg His Tyr Phe Ile Ala Ala Val Glu Arg Leu Trp Asp Tyr
    1715                1720                1725
Gly Met Ser Ser Ser Pro His Val Leu Arg Asn Arg Ala Gln Ser
    1730                1735                1740
Gly Ser Val Pro Gln Phe Lys Lys Val Val Phe Gln Glu Phe Thr
    1745                1750                1755
Asp Gly Ser Phe Thr Gln Pro Leu Tyr Arg Gly Glu Leu Asn Glu
    1760                1765                1770
His Leu Gly Leu Leu Gly Pro Tyr Ile Arg Ala Glu Val Glu Asp
    1775                1780                1785
Asn Ile Met Val Thr Phe Arg Asn Gln Ala Ser Arg Pro Tyr Ser
    1790                1795                1800
Phe Tyr Ser Ser Leu Ile Ser Tyr Glu Glu Asp Gln Arg Gln Gly
    1805                1810                1815
Ala Glu Pro Arg Lys Asn Phe Val Lys Pro Asn Glu Thr Lys Thr
    1820                1825                1830
Tyr Phe Trp Lys Val Gln His His Met Ala Pro Thr Lys Asp Glu
    1835                1840                1845
Phe Asp Cys Lys Ala Trp Ala Tyr Phe Ser Asp Val Asp Leu Glu
    1850                1855                1860
```

```
Lys Asp Val His Ser Gly Leu Ile Gly Pro Leu Leu Val Cys His
    1865                1870                1875

Thr Asn Thr Leu Asn Pro Ala His Gly Arg Gln Val Thr Val Gln
    1880                1885                1890

Glu Phe Ala Leu Phe Phe Thr Ile Phe Asp Glu Thr Lys Ser Trp
    1895                1900                1905

Tyr Phe Thr Glu Asn Met Glu Arg Asn Cys Arg Ala Pro Cys Asn
    1910                1915                1920

Ile Gln Met Glu Asp Pro Thr Phe Lys Glu Asn Tyr Arg Phe His
    1925                1930                1935

Ala Ile Asn Gly Tyr Ile Met Asp Thr Leu Pro Gly Leu Val Met
    1940                1945                1950

Ala Gln Asp Gln Arg Ile Arg Trp Tyr Leu Leu Ser Met Gly Ser
    1955                1960                1965

Asn Glu Asn Ile His Ser Ile His Phe Ser Gly His Val Phe Thr
    1970                1975                1980

Val Arg Lys Lys Glu Glu Tyr Lys Met Ala Leu Tyr Asn Leu Tyr
    1985                1990                1995

Pro Gly Val Phe Glu Thr Val Glu Met Leu Pro Ser Lys Ala Gly
    2000                2005                2010

Ile Trp Arg Val Glu Cys Leu Ile Gly Glu His Leu His Ala Gly
    2015                2020                2025

Met Ser Thr Leu Phe Leu Val Tyr Ser Asn Lys Cys Gln Thr Pro
    2030                2035                2040

Leu Gly Met Ala Ser Gly His Ile Arg Asp Phe Gln Ile Thr Ala
    2045                2050                2055

Ser Gly Gln Tyr Gly Gln Trp Ala Pro Lys Leu Ala Arg Leu His
    2060                2065                2070

Tyr Ser Gly Ser Ile Asn Ala Trp Ser Thr Lys Glu Pro Phe Ser
    2075                2080                2085

Trp Ile Lys Val Asp Leu Leu Ala Pro Met Ile Ile His Gly Ile
    2090                2095                2100

Lys Thr Gln Gly Ala Arg Gln Lys Phe Ser Ser Leu Tyr Ile Ser
    2105                2110                2115

Gln Phe Ile Ile Met Tyr Ser Leu Asp Gly Lys Lys Trp Gln Thr
    2120                2125                2130

Tyr Arg Gly Asn Ser Thr Gly Thr Leu Met Val Phe Phe Gly Asn
    2135                2140                2145

Val Asp Ser Ser Gly Ile Lys His Asn Ile Phe Asn Pro Pro Ile
    2150                2155                2160

Ile Ala Arg Tyr Ile Arg Leu His Pro Thr His Tyr Ser Ile Arg
    2165                2170                2175

Ser Thr Leu Arg Met Glu Leu Met Gly Cys Asp Leu Asn Ser Cys
    2180                2185                2190

Ser Met Pro Leu Gly Met Glu Ser Lys Ala Ile Ser Asp Ala Gln
    2195                2200                2205

Ile Thr Ala Ser Ser Tyr Phe Thr Asn Met Phe Ala Thr Trp Ser
    2210                2215                2220

Pro Ser Lys Ala Arg Leu His Leu Gln Gly Arg Ser Asn Ala Trp
    2225                2230                2235

Arg Pro Gln Val Asn Asn Pro Lys Glu Trp Leu Gln Val Asp Phe
    2240                2245                2250
```

```
Gln Lys Thr Met Lys Val Thr Gly Val Thr Gln Gly Val Lys
2255             2260             2265

Ser Leu Leu Thr Ser Met Tyr Val Lys Glu Phe Leu Ile Ser Ser
2270             2275             2280

Ser Gln Asp Gly His Gln Trp Thr Leu Phe Phe Gln Asn Gly Lys
2285             2290             2295

Val Lys Val Phe Gln Gly Asn Gln Asp Ser Phe Thr Pro Val Val
2300             2305             2310

Asn Ser Leu Asp Pro Pro Leu Leu Thr Arg Tyr Leu Arg Ile His
2315             2320             2325

Pro Gln Ser Trp Val His Gln Ile Ala Leu Arg Met Glu Val Leu
2330             2335             2340

Gly Cys Glu Ala Gln Asp Leu Tyr Asp Lys Thr His Thr Cys Pro
2345             2350             2355

Pro Cys Pro Ala Pro Glu Leu Leu Gly Gly Pro Ser Val Phe Leu
2360             2365             2370

Phe Pro Pro Lys Pro Lys Asp Thr Leu Met Ile Ser Arg Thr Pro
2375             2380             2385

Glu Val Thr Cys Val Val Val Asp Val Ser His Glu Asp Pro Glu
2390             2395             2400

Val Lys Phe Asn Trp Tyr Val Asp Gly Val Glu Val His Asn Ala
2405             2410             2415

Lys Thr Lys Pro Arg Glu Glu Gln Tyr Asn Ser Thr Tyr Arg Val
2420             2425             2430

Val Ser Val Leu Thr Val Leu His Gln Asp Trp Leu Asn Gly Lys
2435             2440             2445

Glu Tyr Lys Cys Lys Val Ser Asn Lys Ala Leu Pro Ala Pro Ile
2450             2455             2460

Glu Lys Thr Ile Ser Lys Ala Lys Gly Gln Pro Arg Glu Pro Gln
2465             2470             2475

Val Tyr Thr Leu Pro Pro Ser Arg Asp Glu Leu Thr Lys Asn Gln
2480             2485             2490

Val Ser Leu Thr Cys Leu Val Lys Gly Phe Tyr Pro Ser Asp Ile
2495             2500             2505

Ala Val Glu Trp Glu Ser Asn Gly Gln Pro Glu Asn Asn Tyr Lys
2510             2515             2520

Thr Thr Pro Pro Val Leu Asp Ser Asp Gly Ser Phe Phe Leu Tyr
2525             2530             2535

Ser Lys Leu Thr Val Asp Lys Ser Arg Trp Gln Gln Gly Asn Val
2540             2545             2550

Phe Ser Cys Ser Val Met His Glu Ala Leu His Asn His Tyr Thr
2555             2560             2565

Gln Lys Ser Leu Ser Leu Ser Pro Gly Lys
2570             2575

<210> SEQ ID NO 7
<211> LENGTH: 2958
<212> TYPE: DNA
<213> ORGANISM: Artificial Sequence
<220> FEATURE:
<223> OTHER INFORMATION: FVIII Heavy Chain (HC)-Fc DNA sequence (no
      linker between HC and Fc)
<220> FEATURE:
<221> NAME/KEY: sig_peptide
<222> LOCATION: (1)..(57)
<223> OTHER INFORMATION: signal peptide
<220> FEATURE:
```

<221> NAME/KEY: misc_feature
<222> LOCATION: (2278)..(2958)
<223> OTHER INFORMATION: Fc region

<400> SEQUENCE: 7

| | | | | | |
|---|---|---|---|---|---|
| atgcaaatag | agctctccac | ctgcttcttt | ctgtgccttt | tgcgattctg | ctttagtgcc | 60 |
| accagaagat | actacctggg | tgcagtggaa | ctgtcatggg | actatatgca | aagtgatctc | 120 |
| ggtgagctgc | ctgtggacgc | aagatttcct | cctagagtgc | caaaatcttt | tccattcaac | 180 |
| acctcagtcg | tgtacaaaaa | gactctgttt | gtagaattca | cggatcacct | tttcaacatc | 240 |
| gctaagccaa | ggccaccctg | gatgggtctg | ctaggtccta | ccatccaggc | tgaggtttat | 300 |
| gatacagtgg | tcattacact | taagaacatg | gcttcccatc | ctgtcagtct | tcatgctgtt | 360 |
| ggtgtatcct | actggaaagc | ttctgaggga | gctgaatatg | atgatcagac | cagtcaaagg | 420 |
| gagaaagaag | atgataaagt | cttccctggt | ggaagccata | catatgtctg | gcaggtcctg | 480 |
| aaagagaatg | gtccaatggc | ctctgaccca | ctgtgcctta | cctactcata | tctttctcat | 540 |
| gtggacctgg | taaaagactt | gaattcaggc | ctcattggag | ccctactagt | atgtagagaa | 600 |
| gggagtctgg | ccaaggaaaa | gacacagacc | ttgcacaaat | ttatactact | ttttgctgta | 660 |
| tttgatgaag | ggaaaagttg | gcactcagaa | acaaagaact | ccttgatgca | ggataggggat | 720 |
| gctgcatctg | ctcgggcctg | gcctaaaatg | cacacagtca | atggttatgt | aaacaggtct | 780 |
| ctgccaggtc | tgattggatg | ccacaggaaa | tcagtctatt | ggcatgtgat | tggaatgggc | 840 |
| accactcctg | aagtgcactc | aatattcctc | gaaggtcaca | catttcttgt | gaggaaccat | 900 |
| cgccaggcgt | ccttggaaat | ctcgccaata | actttcctta | ctgctcaaac | actcttgatg | 960 |
| gaccttggac | agtttctact | gttttgtcat | atctcttccc | accaacatga | tggcatggaa | 1020 |
| gcttatgtca | aagtagacag | ctgtccagag | gaaccccaac | tacgaatgaa | aaataatgaa | 1080 |
| gaagcggaag | actatgatga | tgatcttact | gattctgaaa | tggatgtggt | caggtttgat | 1140 |
| gatgacaact | ctccttcctt | tatccaaatt | cgctcagttg | ccaagaagca | tcctaaaaact | 1200 |
| tgggtacatt | acattgctgc | tgaagaggag | gactgggact | atgctccctt | agtcctcgcc | 1260 |
| cccgatgaca | gaagttataa | aagtcaatat | ttgaacaatg | gccctcagcg | gattggtagg | 1320 |
| aagtacaaaa | aagtccgatt | tatggcatac | acagatgaaa | cctttaagac | tcgtgaagct | 1380 |
| attcagcatg | aatcaggaat | cttgggacct | ttactttatg | gggaagttgg | agacacactg | 1440 |
| ttgattatat | ttaagaatca | agcaagcaga | ccatataaca | tctaccctca | cggaatcact | 1500 |
| gatgtccgtc | ctttgtattc | aaggagatta | ccaaaaggtg | taaaacattt | gaaggatttt | 1560 |
| ccaattctgc | caggagaaat | attcaaatat | aaatggacag | tgactgtaga | agatgggcca | 1620 |
| actaaatcag | atcctcggtg | cctgacccgc | tattactcta | gtttcgttaa | tatggagaga | 1680 |
| gatctagcct | caggactcat | tggccctctc | ctcatctgct | acaaagaatc | tgtagatcaa | 1740 |
| agaggaaacc | agataatgtc | agacaagagg | aatgtcatcc | tgttttctgt | atttgatgag | 1800 |
| aaccgaagct | ggtacctcac | agagaatata | caacgctttc | tccccaatcc | agctggagtg | 1860 |
| cagcttgagg | atccagagtt | ccaagcctcc | aacatcatgc | acagcatcaa | tggctatgtt | 1920 |
| tttgatagtt | tgcagttgtc | agtttgtttg | catgaggtgg | catactggta | cattctaagc | 1980 |
| attggagcac | agactgactt | cctttctgtc | ttcttctctg | atataccttt | caaacacaaa | 2040 |
| atggtctatg | aagacacact | caccctattc | ccattctcag | agaaactgt | cttcatgtcg | 2100 |
| atggaaaacc | caggtctatg | gattctgggg | tgccacaact | cagactttcg | aacagaggc | 2160 |
| atgaccgcct | tactgaaggt | ttctagttgt | gacaagaaca | ctggtgatta | ttacgaggac | 2220 |

-continued

```
agttatgaag atatttcagc atacttgctg agtaaaaaca atgccattga accaagagac      2280
aaaactcaca catgcccacc gtgcccagct ccagaactcc tgggcggacc gtcagtcttc      2340
ctcttccccc caaaacccaa ggacaccctc atgatctccc ggacccctga ggtcacatgc      2400
gtggtggtgg acgtgagcca cgaagaccct gaggtcaagt tcaactggta cgtggacggc      2460
gtggaggtgc ataatgccaa gacaaagccg cgggaggagc agtacaacag cacgtaccgt      2520
gtggtcagcg tcctcaccgt cctgcaccag gactggctga atggcaagga gtacaagtgc      2580
aaggtctcca acaaagccct cccagccccc atcgagaaaa ccatctccaa agccaaaggg      2640
cagccccgag aaccacaggt gtacaccctg cccccatccc gggatgagct gaccaagaac      2700
caggtcagcc tgacctgcct ggtcaaaggc ttctatccca gcgacatcgc cgtggagtgg      2760
gagagcaatg ggcagccgga gaacaactac aagaccacgc ctcccgtgtt ggactccgac      2820
ggctccttct tcctctacag caagctcacc gtggacaaga gcaggtggca gcaggggaac      2880
gtcttctcat gctccgtgat gcatgaggct ctgcacaacc actacacgca gaagagcctc      2940
tccctgtctc cgggtaaa                                                   2958
```

<210> SEQ ID NO 8
<211> LENGTH: 986
<212> TYPE: PRT
<213> ORGANISM: Artificial Sequence
<220> FEATURE:
<223> OTHER INFORMATION: HC-Fc
<220> FEATURE:
<221> NAME/KEY: SIGNAL
<222> LOCATION: (1)..(19)
<223> OTHER INFORMATION: signal peptide
<220> FEATURE:
<221> NAME/KEY: MISC_FEATURE
<222> LOCATION: (760)..(986)
<223> OTHER INFORMATION: Fc sequence

<400> SEQUENCE: 8

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
```

```
            180                 185                 190
Gly Ala Leu Leu Val Cys Arg Glu Gly Ser Leu Ala Lys Glu Lys Thr
            195                 200                 205
Gln Thr Leu His Lys Phe Ile Leu Leu Phe Ala Val Phe Asp Glu Gly
            210                 215                 220
Lys Ser Trp His Ser Glu Thr Lys Asn Ser Leu Met Gln Asp Arg Asp
225                 230                 235                 240
Ala Ala Ser Ala Arg Ala Trp Pro Lys Met His Thr Val Asn Gly Tyr
                245                 250                 255
Val Asn Arg Ser Leu Pro Gly Leu Ile Gly Cys His Arg Lys Ser Val
                260                 265                 270
Tyr Trp His Val Ile Gly Met Gly Thr Thr Pro Glu Val His Ser Ile
            275                 280                 285
Phe Leu Glu Gly His Thr Phe Leu Val Arg Asn His Arg Gln Ala Ser
            290                 295                 300
Leu Glu Ile Ser Pro Ile Thr Phe Leu Thr Ala Gln Thr Leu Leu Met
305                 310                 315                 320
Asp Leu Gly Gln Phe Leu Leu Phe Cys His Ile Ser Ser His Gln His
                325                 330                 335
Asp Gly Met Glu Ala Tyr Val Lys Val Asp Ser Cys Pro Glu Glu Pro
                340                 345                 350
Gln Leu Arg Met Lys Asn Asn Glu Glu Ala Glu Asp Tyr Asp Asp Asp
            355                 360                 365
Leu Thr Asp Ser Glu Met Asp Val Val Arg Phe Asp Asp Asp Asn Ser
            370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Glu Asp Trp Asp Tyr Ala Pro
                405                 410                 415
Leu Val Leu Ala Pro Asp Asp Arg Ser Tyr Lys Ser Gln Tyr Leu Asn
                420                 425                 430
Asn Gly Pro Gln Arg Ile Gly Arg Lys Tyr Lys Lys Val Arg Phe Met
            435                 440                 445
Ala Tyr Thr Asp Glu Thr Phe Lys Thr Arg Glu Ala Ile Gln His Glu
            450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
                500                 505                 510
Gly Val Lys His Leu Lys Asp Phe Pro Ile Leu Pro Gly Glu Ile Phe
            515                 520                 525
Lys Tyr Lys Trp Thr Val Thr Val Glu Asp Gly Pro Thr Lys Ser Asp
            530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Ile Met Ser Asp Lys Arg Asn Val
                580                 585                 590
Ile Leu Phe Ser Val Phe Asp Glu Asn Arg Ser Trp Tyr Leu Thr Glu
            595                 600                 605
```

Asn Ile Gln Arg Phe Leu Pro Asn Pro Ala Gly Val Gln Leu Glu Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Asp Lys Thr His Thr Cys Pro Pro Cys
        755                 760                 765

Pro Ala Pro Glu Leu Leu Gly Gly Pro Ser Val Phe Leu Phe Pro Pro
770                 775                 780

Lys Pro Lys Asp Thr Leu Met Ile Ser Arg Thr Pro Glu Val Thr Cys
785                 790                 795                 800

Val Val Val Asp Val Ser His Glu Asp Pro Glu Val Lys Phe Asn Trp
                805                 810                 815

Tyr Val Asp Gly Val Glu Val His Asn Ala Lys Thr Lys Pro Arg Glu
            820                 825                 830

Glu Gln Tyr Asn Ser Thr Tyr Arg Val Val Ser Val Leu Thr Val Leu
        835                 840                 845

His Gln Asp Trp Leu Asn Gly Lys Glu Tyr Lys Cys Lys Val Ser Asn
850                 855                 860

Lys Ala Leu Pro Ala Pro Ile Glu Lys Thr Ile Ser Lys Ala Lys Gly
865                 870                 875                 880

Gln Pro Arg Glu Pro Gln Val Tyr Thr Leu Pro Pro Ser Arg Asp Glu
                885                 890                 895

Leu Thr Lys Asn Gln Val Ser Leu Thr Cys Leu Val Lys Gly Phe Tyr
            900                 905                 910

Pro Ser Asp Ile Ala Val Glu Trp Glu Ser Asn Gly Gln Pro Glu Asn
        915                 920                 925

Asn Tyr Lys Thr Thr Pro Pro Val Leu Asp Ser Asp Gly Ser Phe Phe
930                 935                 940

Leu Tyr Ser Lys Leu Thr Val Asp Lys Ser Arg Trp Gln Gln Gly Asn
945                 950                 955                 960

Val Phe Ser Cys Ser Val Met His Glu Ala Leu His Asn His Tyr Thr
                965                 970                 975

Gln Lys Ser Leu Ser Leu Ser Pro Gly Lys
            980                 985

<210> SEQ ID NO 9
<211> LENGTH: 2973
<212> TYPE: DNA
<213> ORGANISM: Artificial Sequence
<220> FEATURE:

<223> OTHER INFORMATION: FVIII Heavy Chain (HC)-Fc DNA sequence (5 amino
      acid linker between HC and Fc)
<220> FEATURE:
<221> NAME/KEY: sig_peptide
<222> LOCATION: (1)..(58)
<223> OTHER INFORMATION: signal peptide
<220> FEATURE:
<221> NAME/KEY: misc_feature
<222> LOCATION: (2278)..(2292)
<223> OTHER INFORMATION: 5 amino acid linker
<220> FEATURE:
<221> NAME/KEY: misc_feature
<222> LOCATION: (2293)..(2973)
<223> OTHER INFORMATION: Fc region

<400> SEQUENCE: 9

```
atgcaaatag agctctccac ctgcttcttt ctgtgccttt tgcgattctg ctttagtgcc     60
accagaagat actacctggg tgcagtggaa ctgtcatggg actatatgca aagtgatctc    120
ggtgagctgc ctgtggacgc aagatttcct cctagagtgc aaaatctttt ccattcaac     180
acctcagtcg tgtacaaaaa gactctgttt gtagaattca cggatcacct tttcaacatc    240
gctaagccaa ggccacccctg gatgggtctg ctaggtccta ccatccaggc tgaggtttat   300
gatacagtgt tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagccata catatgtctg gcaggtcctg    480
aaagagaatg gtccaatggc ctctgaccca ctgtgcctta cctactcata tctttctcat    540
gtggacctgg taaaagactt gaattcaggc ctcattggag ccctactagt atgtagagaa    600
gggagtctgg ccaaggaaaa gacacagacc ttgcacaaat ttatactact ttttgctgta    660
tttgatgaag ggaaaagttg gcactcagaa acaaagaact ccttgatgca ggataggat    720
gctgcatctg ctcgggcctg cctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca agtagacag ctgtccagag gaaccccaac tacgaatgaa aaataatgaa    1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca aagttataa aagtcaatat ttgaacaatg gccctcagcg gattggtagg    1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaacatttt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc tcatctgct acaaagaatc tgtagatcaa    1740
agaggaaacc agataatgtc agacaagagg aatgtcatcc tgtttctgt atttgatgag   1800
aaccgaagct ggtacctcac agagaatata caacgctttc tccccaatcc agctggagtg   1860
```

```
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg gatataccct caaacacaaa    2040
atggtctatg aagacacact caccctattc ccattctcag gagaaactgt cttcatgtcg    2100
atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctcccaga tgacaaaaac tcacacatgc ccaccgtgcc cagctccaga actcctgggc    2340
ggaccgtcag tcttcctctt ccccccaaaa cccaaggaca cctcatgat ctcccggacc    2400 cctgaggtca catgcgtggt ggtggacgtg agccacgaag accctgaggt caagttcaac    2460
tggtacgtgg acggcgtgga ggtgcataat gccaagacaa agccgcggga ggagcagtac    2520
aacagcacgt accgtgtggt cagcgtcctc accgtcctgc accaggactg gctgaatggc    2580
aaggagtaca agtgcaaggt ctccaacaaa gccctcccag cccccatcga gaaaaccatc    2640
tccaaagcca agggcagccc cgagaaccag gtgtaca ccctgccccc atcccgggat    2700
gagctgacca agaaccaggt cagcctgacc tgcctggtca aaggcttcta tcccagcgac    2760
atcgccgtgg agtgggagag caatgggcag ccggagaaca actacaagac cacgcctccc    2820
gtgttggact ccgacggctc cttcttcctc tacagcaagc tcaccgtgga caagagcagg    2880
tggcagcagg ggaacgtctt ctcatgctcc gtgatgcatg aggctctgca caaccactac    2940
acgcagaaga gcctctccct gtctccgggt aaa                               2973
```

<210> SEQ ID NO 10
<211> LENGTH: 991
<212> TYPE: PRT
<213> ORGANISM: Artificial Sequence
<220> FEATURE:
<223> OTHER INFORMATION: HC+5-Fc
<220> FEATURE:
<221> NAME/KEY: SIGNAL
<222> LOCATION: (1)..(19)
<223> OTHER INFORMATION: signal sequence
<220> FEATURE:
<221> NAME/KEY: MISC_FEATURE
<222> LOCATION: (760)..(764)
<223> OTHER INFORMATION: 5 amino acide linker sequence from the B domain
      of FVIII
<220> FEATURE:
<221> NAME/KEY: MISC_FEATURE
<222> LOCATION: (765)..(991)
<223> OTHER INFORMATION: Fc sequence

<400> SEQUENCE: 10

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95
```

-continued

```
Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
```

```
               515                 520                 525
Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Asp Lys Thr His
            755                 760                 765

Thr Cys Pro Pro Cys Pro Ala Pro Glu Leu Leu Gly Gly Pro Ser Val
770                 775                 780

Phe Leu Phe Pro Pro Lys Pro Lys Asp Thr Leu Met Ile Ser Arg Thr
785                 790                 795                 800

Pro Glu Val Thr Cys Val Val Val Asp Val Ser His Glu Asp Pro Glu
                805                 810                 815

Val Lys Phe Asn Trp Tyr Val Asp Gly Val Glu Val His Asn Ala Lys
                820                 825                 830

Thr Lys Pro Arg Glu Glu Gln Tyr Asn Ser Thr Tyr Arg Val Val Ser
            835                 840                 845

Val Leu Thr Val Leu His Gln Asp Trp Leu Asn Gly Lys Glu Tyr Lys
            850                 855                 860

Cys Lys Val Ser Asn Lys Ala Leu Pro Ala Pro Ile Glu Lys Thr Ile
865                 870                 875                 880

Ser Lys Ala Lys Gly Gln Pro Arg Glu Pro Gln Val Tyr Thr Leu Pro
                885                 890                 895

Pro Ser Arg Asp Glu Leu Thr Lys Asn Gln Val Ser Leu Thr Cys Leu
                900                 905                 910

Val Lys Gly Phe Tyr Pro Ser Asp Ile Ala Val Glu Trp Glu Ser Asn
            915                 920                 925

Gly Gln Pro Glu Asn Asn Tyr Lys Thr Thr Pro Pro Val Leu Asp Ser
        930                 935                 940
```

```
Asp Gly Ser Phe Phe Leu Tyr Ser Lys Leu Thr Val Asp Lys Ser Arg
945                 950                 955                 960

Trp Gln Gln Gly Asn Val Phe Ser Cys Ser Val Met His Glu Ala Leu
                965                 970                 975

His Asn His Tyr Thr Gln Lys Ser Leu Ser Leu Ser Pro Gly Lys
            980                 985                 990

<210> SEQ ID NO 11
<211> LENGTH: 2793
<212> TYPE: DNA
<213> ORGANISM: Artificial Sequence
<220> FEATURE:
<223> OTHER INFORMATION: FVIII Light Chain (LC)-Fc DNA sequence
<220> FEATURE:
<221> NAME/KEY: sig_peptide
<222> LOCATION: (1)..(60)
<223> OTHER INFORMATION: signal peptide
<220> FEATURE:
<221> NAME/KEY: misc_feature
<222> LOCATION: (2113)..(2793)
<223> OTHER INFORMATION: Fc region

<400> SEQUENCE: 11
atggagacag acacactcct gctatgggta ctgctgctct gggttccagg ttccactggt      60
gaaataactc gtactactct tcagtcagat caagaggaaa ttgactatga tgataccata     120
tcagttgaaa tgaagaagga agattttgac atttatgatg aggatgaaaa tcagagcccc     180
cgcagctttc aaaagaaaac acgacactat tttattgctg cagtggagag gctctgggat     240
tatgggatga gtagctcccc acatgttcta gaaacagggc tcagagtggc agtgtccct     300 cagttcaaga agttgttttt ccaggaattt actgatggct cctttactca gcccttatac     360
cgtggagaac taaatgaaca tttgggactc ctggggccat atataagagc agaagttgaa     420
gataatatca tggtaacttt cagaaatcag gcctctcgtc cctattcctt ctattctagc     480
cttatttctt atgaggaaga tcagaggcaa ggagcagaac tagaaaaaaa ctttgtcaag     540
cctaatgaaa ccaaaactta cttttggaaa gtgcaacatc atatggcacc cactaaagat     600
gagtttgact gcaaagcctg gcttatttc tctgatgttg acctggaaaa agatgtgcac     660
tcaggcctga ttgacccct ctggtctgc cacactaaca cactgaaccc tgctcatggg     720
agacaagtga cagtacagga atttgctctg tttttcacca tctttgatga gaccaaaagc     780
tggtacttca ctgaaaatat ggaaagaaac tgcagggctc cctgcaatat ccagatggaa     840
gatcccactt ttaaagagaa ttatcgcttc catgcaatca atggctacat aatggataca     900
ctacctggct agtaatggc tcaggatcaa aggattcgat ggtatctgct cagcatgggc     960
agcaatgaaa acatccattc tattcatttc agtggacatg tgttcactgt acgaaaaaaa    1020
gaggagtata aaatggcact gtacaatctc tatccaggtg ttttttgagac agtggaaatg    1080 ttaccatcca aagctggaat ttggcgggtg gaatgcctta ttggcgagca tctacatgct    1140
gggatgagca cttttttct ggtgtacagc aataagtgtc agactcccct gggaatggct    1200
tctggacaca ttagagattt tcagattaca gcttcaggac aatatggaca gtgggcccca    1260
aagctggcca gacttcatta ttccggatca atcaatgcct ggagcaccaa ggagcccttt    1320
tcttggatca aggtggatct gttggcacca atgattattc acggcatcaa gacccagggt    1380
gcccgtcaga agttctccag cctctacatc tctcagttta tcatcatgta tagtcttgat    1440
gggaagaagt ggcagactta tcgaggaaat tccactggaa ccttaatggt cttctttggc    1500
aatgtggatt catctgggat aaaacacaat attttttaacc ctccaattat tgctcgatac    1560
```

```
atccgtttgc acccaactca ttatagcatt cgcagcactc ttcgcatgga gttgatgggc    1620
tgtgatttaa atagttgcag catgccattg ggaatggaga gtaaagcaat atcagatgca    1680
cagattactg cttcatccta ctttaccaat atgtttgcca cctggtctcc ttcaaaagct    1740
cgacttcacc tccaagggag gagtaatgcc tggagacctc aggtgaataa tccaaaagag    1800
tggctgcaag tggacttcca gaagacaatg aaagtcacag gagtaactac tcagggagta    1860
aaatctctgc ttaccagcat gtatgtgaag gagttcctca tctccagcag tcaagatggc    1920
catcagtgga ctctcttttt tcagaatggc aaagtaaagg tttttcaggg aaatcaagac    1980
tccttcacac ctgtggtgaa ctctctagac ccaccgttac tgactcgcta ccttcgaatt    2040
cacccccaga gttgggtgca ccagattgcc ctgaggatgg aggttctggg ctgcgaggca    2100
caggacctct acgacaaaac tcacacatgc ccaccgtgcc cagctccaga actcctgggc    2160
ggaccgtcag tcttcctctt ccccccaaaa cccaaggaca ccctcatgat ctcccggacc    2220
cctgaggtca catgcgtggt ggtggacgtg agccacgaag accctgaggt caagttcaac    2280
tggtacgtgg acggcgtgga ggtgcataat gccaagacaa agccgcggga ggagcagtac    2340
aacagcacgt accgtgtggt cagcgtcctc accgtcctgc accaggactg gctgaatggc    2400
aaggagtaca agtgcaaggt ctccaacaaa gccctcccag cccccatcga gaaaaccatc    2460
tccaaagcca agggcagccc cgagaaccag gtgtacaccc tgcccccc atccgggat     2520 gagctgacca agaaccaggt cagcctgacc tgcctggtca aaggcttcta tcccagcgac    2580
atcgccgtgg agtgggagag caatgggcag ccggagaaca actacaagac cacgcctccc    2640
gtgttggact ccgacggctc cttcttcctc tacagcaagc tcaccgtgga caagagcagg    2700
tggcagcagg ggaacgtctt ctcatgctcc gtgatgcatg aggctctgca caaccactac    2760
acgcagaaga gcctctccct gtctccgggt aaa    2793
```

<210> SEQ ID NO 12
<211> LENGTH: 931
<212> TYPE: PRT
<213> ORGANISM: Artificial Sequence
<220> FEATURE:
<223> OTHER INFORMATION: LC-Fc6His
<220> FEATURE:
<221> NAME/KEY: SIGNAL
<222> LOCATION: (1)..(20)
<223> OTHER INFORMATION: signal peptide
<220> FEATURE:
<221> NAME/KEY: MISC_FEATURE
<222> LOCATION: (705)..(931)
<223> OTHER INFORMATION: Fc sequence

<400> SEQUENCE: 12

```
Met Glu Thr Asp Thr Leu Leu Leu Trp Val Leu Leu Leu Trp Val Pro
1               5                   10                  15

Gly Ser Thr Gly Glu Ile Thr Arg Thr Thr Leu Gln Ser Asp Gln Glu
            20                  25                  30

Glu Ile Asp Tyr Asp Asp Thr Ile Ser Val Glu Met Lys Lys Glu Asp
        35                  40                  45

Phe Asp Ile Tyr Asp Glu Asp Glu Asn Gln Ser Pro Arg Ser Phe Gln
    50                  55                  60

Lys Lys Thr Arg His Tyr Phe Ile Ala Ala Val Glu Arg Leu Trp Asp
65                  70                  75                  80

Tyr Gly Met Ser Ser Ser Pro His Val Leu Arg Asn Arg Ala Gln Ser
                85                  90                  95
```

```
Gly Ser Val Pro Gln Phe Lys Lys Val Val Phe Gln Glu Phe Thr Asp
            100                 105                 110

Gly Ser Phe Thr Gln Pro Leu Tyr Arg Gly Glu Leu Asn Glu His Leu
        115                 120                 125

Gly Leu Leu Gly Pro Tyr Ile Arg Ala Glu Val Glu Asp Asn Ile Met
    130                 135                 140

Val Thr Phe Arg Asn Gln Ala Ser Arg Pro Tyr Ser Phe Tyr Ser Ser
145                 150                 155                 160

Leu Ile Ser Tyr Glu Glu Asp Gln Arg Gln Gly Ala Glu Pro Arg Lys
                165                 170                 175

Asn Phe Val Lys Pro Asn Glu Thr Lys Thr Tyr Phe Trp Lys Val Gln
            180                 185                 190

His His Met Ala Pro Thr Lys Asp Glu Phe Asp Cys Lys Ala Trp Ala
        195                 200                 205

Tyr Phe Ser Asp Val Asp Leu Glu Lys Asp Val His Ser Gly Leu Ile
    210                 215                 220

Gly Pro Leu Leu Val Cys His Thr Asn Thr Leu Asn Pro Ala His Gly
225                 230                 235                 240

Arg Gln Val Thr Val Gln Glu Phe Ala Leu Phe Phe Thr Ile Phe Asp
                245                 250                 255

Glu Thr Lys Ser Trp Tyr Phe Thr Glu Asn Met Glu Arg Asn Cys Arg
            260                 265                 270

Ala Pro Cys Asn Ile Gln Met Glu Asp Pro Thr Phe Lys Glu Asn Tyr
        275                 280                 285

Arg Phe His Ala Ile Asn Gly Tyr Ile Met Asp Thr Leu Pro Gly Leu
    290                 295                 300

Val Met Ala Gln Asp Gln Arg Ile Arg Trp Tyr Leu Leu Ser Met Gly
305                 310                 315                 320

Ser Asn Glu Asn Ile His Ser Ile His Phe Ser Gly His Val Phe Thr
                325                 330                 335

Val Arg Lys Lys Glu Glu Tyr Lys Met Ala Leu Tyr Asn Leu Tyr Pro
            340                 345                 350

Gly Val Phe Glu Thr Val Glu Met Leu Pro Ser Lys Ala Gly Ile Trp
        355                 360                 365

Arg Val Glu Cys Leu Ile Gly Glu His Leu His Ala Gly Met Ser Thr
    370                 375                 380

Leu Phe Leu Val Tyr Ser Asn Lys Cys Gln Thr Pro Leu Gly Met Ala
385                 390                 395                 400

Ser Gly His Ile Arg Asp Phe Gln Ile Thr Ala Ser Gly Gln Tyr Gly
                405                 410                 415

Gln Trp Ala Pro Lys Leu Ala Arg Leu His Tyr Ser Gly Ser Ile Asn
            420                 425                 430

Ala Trp Ser Thr Lys Glu Pro Phe Ser Trp Ile Lys Val Asp Leu Leu
        435                 440                 445

Ala Pro Met Ile Ile His Gly Ile Lys Thr Gln Gly Ala Arg Gln Lys
    450                 455                 460

Phe Ser Ser Leu Tyr Ile Ser Gln Phe Ile Ile Met Tyr Ser Leu Asp
465                 470                 475                 480

Gly Lys Lys Trp Gln Thr Tyr Arg Gly Asn Ser Thr Gly Thr Leu Met
                485                 490                 495

Val Phe Phe Gly Asn Val Asp Ser Ser Gly Ile Lys His Asn Ile Phe
            500                 505                 510

Asn Pro Pro Ile Ile Ala Arg Tyr Ile Arg Leu His Pro Thr His Tyr
```

```
            515                 520                 525
Ser Ile Arg Ser Thr Leu Arg Met Glu Leu Met Gly Cys Asp Leu Asn
530                 535                 540

Ser Cys Ser Met Pro Leu Gly Met Glu Ser Lys Ala Ile Ser Asp Ala
545                 550                 555                 560

Gln Ile Thr Ala Ser Ser Tyr Phe Thr Asn Met Phe Ala Thr Trp Ser
                565                 570                 575

Pro Ser Lys Ala Arg Leu His Leu Gln Gly Arg Ser Asn Ala Trp Arg
                580                 585                 590

Pro Gln Val Asn Asn Pro Lys Glu Trp Leu Gln Val Asp Phe Gln Lys
                595                 600                 605

Thr Met Lys Val Thr Gly Val Thr Thr Gln Gly Val Lys Ser Leu Leu
        610                 615                 620

Thr Ser Met Tyr Val Lys Glu Phe Leu Ile Ser Ser Ser Gln Asp Gly
625                 630                 635                 640

His Gln Trp Thr Leu Phe Phe Gln Asn Gly Lys Val Lys Val Phe Gln
                645                 650                 655

Gly Asn Gln Asp Ser Phe Thr Pro Val Val Asn Ser Leu Asp Pro Pro
            660                 665                 670

Leu Leu Thr Arg Tyr Leu Arg Ile His Pro Gln Ser Trp Val His Gln
                675                 680                 685

Ile Ala Leu Arg Met Glu Val Leu Gly Cys Glu Ala Gln Asp Leu Tyr
        690                 695                 700

Asp Lys Thr His Thr Cys Pro Pro Cys Pro Ala Pro Glu Leu Leu Gly
705                 710                 715                 720

Gly Pro Ser Val Phe Leu Phe Pro Pro Lys Pro Lys Asp Thr Leu Met
                725                 730                 735

Ile Ser Arg Thr Pro Glu Val Thr Cys Val Val Val Asp Val Ser His
                740                 745                 750

Glu Asp Pro Glu Val Lys Phe Asn Trp Tyr Val Asp Gly Val Glu Val
                755                 760                 765

His Asn Ala Lys Thr Lys Pro Arg Glu Glu Gln Tyr Asn Ser Thr Tyr
            770                 775                 780

Arg Val Val Ser Val Leu Thr Val Leu His Gln Asp Trp Leu Asn Gly
785                 790                 795                 800

Lys Glu Tyr Lys Cys Lys Val Ser Asn Lys Ala Leu Pro Ala Pro Ile
                805                 810                 815

Glu Lys Thr Ile Ser Lys Ala Lys Gly Gln Pro Arg Glu Pro Gln Val
                820                 825                 830

Tyr Thr Leu Pro Pro Ser Arg Asp Glu Leu Thr Lys Asn Gln Val Ser
            835                 840                 845

Leu Thr Cys Leu Val Lys Gly Phe Tyr Pro Ser Asp Ile Ala Val Glu
        850                 855                 860

Trp Glu Ser Asn Gly Gln Pro Glu Asn Asn Tyr Lys Thr Thr Pro Pro
865                 870                 875                 880

Val Leu Asp Ser Asp Gly Ser Phe Phe Leu Tyr Ser Lys Leu Thr Val
                885                 890                 895

Asp Lys Ser Arg Trp Gln Gln Gly Asn Val Phe Ser Cys Ser Val Met
                900                 905                 910

His Glu Ala Leu His Asn His Tyr Thr Gln Lys Ser Leu Ser Leu Ser
            915                 920                 925

Pro Gly Lys
        930
```

<210> SEQ ID NO 13
<211> LENGTH: 7583
<212> TYPE: DNA
<213> ORGANISM: Artificial Sequence
<220> FEATURE:
<223> OTHER INFORMATION: FIX-Fc Chain DNA sequence
<220> FEATURE:
<221> NAME/KEY: sig_peptide
<222> LOCATION: (690)..(777)
<223> OTHER INFORMATION: FIX signal peptide
<220> FEATURE:
<221> NAME/KEY: Intron
<222> LOCATION: (778)..(1076)
<223> OTHER INFORMATION: FIX mini intron
<220> FEATURE:
<221> NAME/KEY: misc_feature
<222> LOCATION: (1077)..(2371)
<223> OTHER INFORMATION: FIX sequence
<220> FEATURE:
<221> NAME/KEY: misc_feature
<222> LOCATION: (2372)..(3050)
<223> OTHER INFORMATION: Fc region

<400> SEQUENCE: 13

```
gcgcgcgttg acattgatta ttgactagtt attaatagta atcaattacg gggtcattag      60
ttcatagccc atatatggag ttccgcgtta cataacttac ggtaaatggc ccgcctggct     120
gaccgcccaa cgacccccgc ccattgacgt caataatgac gtatgttccc atagtaacgc     180
caatagggac tttccattga cgtcaatggg tggagtattt acggtaaact gcccacttgg     240
cagtacatca agtgtatcat atgccaagta cgccccctat tgacgtcaat gacggtaaat     300
ggcccgcctg gcattatgcc cagtacatga ccttatggga ctttcctact tggcagtaca     360
tctacgtatt agtcatcgct attaccatgg tgatgcggtt ttggcagtac atcaatgggc     420
gtggatagcg gtttgactca cggggatttc caagtctcca ccccattgac gtcaatggga     480
gtttgttttg gcaccaaaat caacgggact ttccaaaatg tcgtaacaac tccgccccat     540
tgacgcaaat gggcggtagg cgtgtacggt gggaggtcta tataagcaga gctctctggc     600
taactagaga acccactgct tactggctta tcgaaattaa tacgactcac tatagggaga     660
cccaagcttc gcgacgtacg gccgccacca tgcagcgcgt gaacatgatc atggcagaat     720
caccaggcct catcaccatc tgccttttag gatatctact cagtgctgaa tgtacaggtt     780
tgtttccttt tttaaaatac attgagtatg cttgcctttt agatatagaa atatctgatg     840
ctgtcttctt cactaaattt tgattacatg atttgacagc aatattgaag agtctaacag     900
ccagcacgca ggttggtaag tactgtggga acatcacaga ttttggctcc atgccctaaa     960
gagaaattgg ctttcagatt atttggatta aaacaaaga ctttcttaag agatgtaaaa    1020
ttttcatgat gttttctttt ttgctaaaac taaagaatta ttcttttaca tttcagtttt    1080
tcttgatcat gaaaacgcca acaaaattct gaatcggcca agagggtata attcaggtaa    1140
attggaagag tttgttcaag ggaatctaga gagagaatgt atggaagaaa agtgtagttt    1200
tgaagaagca cgagaagttt ttgaaaacac tgaaagaaca actgaatttt ggaagcagta    1260
tgttgatgga gatcagtgtg agtccaatcc atgtttaaat ggcggcagtt gcaaggatga    1320
cattaattcc tatgaatgtt ggtgtccctt tggatttgaa ggaaagaact gtgaattaga    1380
tgtaacatgt aacattaaga atggcagatg cgagcagttt tgtaaaaata gtgctgataa    1440
caaggtggtt tgctcctgta ctgagggata tcgacttgca gaaaaccaga agtcctgtga    1500
accagcagtg ccatttccat gtggaagagt ttctgtttca caaacttcta agctcacccg    1560
```

```
tgctgagact gttttcctg atgtggacta tgtaaattct actgaagctg aaaccatttt    1620
ggataacatc actcaaagca cccaatcatt taatgacttc actcggttg ttggtggaga    1680 agatgccaaa ccaggtcaat tcccttggca ggttgttttg aatggtaaag ttgatgcatt    1740
ctgtggaggc tctatcgtta tgaaaaatg gattgtaact gctgcccact gtgttgaaac    1800
tggtgttaaa attacagttg tcgcaggtga acataatatt gaggagacag aacatacaga    1860
gcaaaagcga aatgtgattc gaattattcc tcaccacaac tacaatgcag ctattaataa    1920
gtacaaccat gacattgccc ttctggaact ggacgaaccc ttagtgctaa acagctacgt    1980
tacacctatt tgcattgctg acaaggaata cacgaacatc ttcctcaaat ttggatctgg    2040
ctatgtaagt ggctggggaa gagtcttcca caaagggaga tcagctttag ttcttcagta    2100
ccttagagtt ccacttgttg accgagccac atgtcttcga tctacaaagt tcaccatcta    2160
taacaacatg ttctgtgctg gcttccatga aggaggtaga gattcatgtc aaggagatag    2220 tggggaccc catgttactg aagtggaagg gaccagtttc ttaactggaa ttattagctg    2280
gggtgaagag tgtgcaatga aaggcaaata tggaatatat accaaggtgt cccggtatgt    2340
caactggatt aaggaaaaaa caaagctcac tgacaaaact cacacatgcc accgtgccc    2400 agctccggaa ctcctgggcg gaccgtcagt cttcctcttc cccccaaaac ccaaggacac    2460
cctcatgatc tcccggaccc ctgaggtcac atgcgtggtg gtggacgtga gccacgaaga    2520
ccctgaggtc aagttcaact ggtacgtgga cggcgtggag gtgcataatg ccaagacaaa    2580
gccgcgggag gagcagtaca acagcacgta ccgtgtggtc agcgtcctca ccgtcctgca    2640
ccaggactgg ctgaatggca aggagtacaa gtgcaaggtc tccaacaaag ccctcccagc    2700
ccccatcgag aaaaccatct ccaaagccaa agggcagccc cgagaaccac aggtgtacac    2760 cctgcccca tcccgggatg agctgaccaa gaaccaggtc agcctgacct gcctggtcaa    2820
aggcttctat cccagcgaca tcgccgtgga gtgggagagc aatgggcagc cggagaacaa    2880
ctacaagacc acgcctcccg tgttggactc cgacggctcc ttcttcctct acagcaagct    2940
caccgtggac aagagcaggt ggcagcaggg gaacgtcttc tcatgctccg tgatgcatga    3000
ggctctgcac aaccactaca cgcagaagag cctctccctg tctccgggta atgagaatt    3060 cagacatgat aagatacatt gatgagttg acaaaccac aactagaatg cagtgaaaaa    3120
aatgctttat ttgtgaaatt tgtgatgcta ttgctttatt tgtaaccatt ataagctgca    3180
ataaacaagt tgggtgggc aagaactcc agcatgagat cccgcgctg gaggatcatc    3240 cagccggcgt cccggaaaac gattccgaag cccaaccttt catagaaggc ggcggtggaa    3300
tcgaaatctc gtagcacgtg tcagtcctgc tcctcggcca cgaagtgcac gcagttgccg    3360
gccgggtcgc gcagggcgaa ctcccgcccc cacggctgct cgccgatctc ggtcatggcc    3420
ggcccggagg cgtcccggaa gttcgtggac acgacctccg accactcggc gtacagctcg    3480
tccaggccgc gcacccacac ccaggccagg gtgttgtccg gcaccacctg gtcctggacc    3540
gcgctgatga cagggtcac gtcgtcccgg accacccgg cgaagtcgtc ctccacgaag    3600
tcccgggaga acccgagccg gtcggtccag aactcgaccg ctccggcgac gtcgcgcgcg    3660
gtgagcaccg gaacggcact ggtcaacttg gccatggttt agttcctcac cttgtcgtat    3720
tatactatgc cgatatacta tgccgatgat taattgtcaa cacgtgctga tcagatccga    3780
aaatggatat acaagctccc gggagctttt tgcaaaagcc taggcctcca aaaaagcctc    3840
ctcactactt ctggaatagc tcagaggcag aggcggcctc ggcctctgca taaataaaaa    3900
aaattagtca gccatggggc ggagaatggg cggaactggg cggagttagg ggcgggatgg    3960
```

```
gcggagttag gggcgggact atggttgctg actaattgag atgcatgctt tgcatacttc   4020
tgcctgctgg ggagcctggg gactttccac acctggttgc tgactaattg agatgcatgc   4080
tttgcatact tctgcctgct ggggagcctg gggactttcc acaccctcgt cgagctagct   4140
tcgtgaggct ccggtgcccg tcagtgggca gagcgcacat cgcccacagt ccccgagaag   4200
ttggggggag gggtcggcaa ttgaaccggt gcctagagaa ggtggcgcgg ggtaaactgg   4260
gaaagtgatg tcgtgtactg gctccgcctt tttcccgagg gtgggggaga accgtatata   4320
agtgcagtag tcgccgtgaa cgttcttttt cgcaacgggt ttgccgccag aacacaggta   4380
agtgccgtgt gtggttcccg cgggcctggc tctcttacgg gttatggccc ttgcgtgcct   4440
tgaattactt ccacctggct ccagtacgtg attcttgatc ccgagctgga gccaggggcg   4500
ggccttgcgc tttaggagcc ccttcgcctc gtgcttgagt tgaggcctgg cctgggcgct   4560
ggggccgccg cgtgcgaatc tggtggcacc ttcgcgcctg tctcgctgct ttcgataagt   4620
ctctagccat ttaaaatttt tgatgacctg ctgcgacgct ttttttctgg caagatagtc   4680
ttgtaaatgc gggccaggat ctgcacactg gtatttcggt ttttggggcc gcgggcggcg   4740
acggggcccg tgcgtcccag cgcacatgtt cggcgaggcg gggcctgcga gcgcggccac   4800
cgagaatcgg acggggtag tctcaagctg gccggcctgc tctggtgcct ggcctcgcgc   4860
cgccgtgtat cgccccgccc tgggcggcaa ggctggcccg gtcggcacca gttgcgtgag   4920
cggaaagatg gccgcttccc ggccctgctc caggggctc aaaatggagg acgcggcgct   4980
cgggagagcg ggcgggtgag tcacccacac aaaggaaagg ggcctttccg tcctcagccg   5040
tcgcttcatg tgactccacg gagtaccggg cgccgtccag gcacctcgat tagttctgga   5100
gcttttggag tacgtcgtct ttaggttggg gggaggggtt ttatgcgatg gagtttcccc   5160
acactgagtg ggtggagact gaagttaggc cagcttggca cttgatgtaa ttctccttgg   5220
aatttgccct ttttgagttt ggatcttggt tcattctcaa gcctcagaca gtggttcaaa   5280 gttttttttct tccatttcag gtgtcgtgaa cacgtggtcg cggccgcgcc gccaccatgg   5340
agacagacac actcctgcta tgggtactgc tgctctgggt tccaggttcc actggtgaca   5400
aaactcacac atgcccaccg tgcccagcac ctgaactcct gggaggaccg tcagtcttcc   5460
tcttcccccc aaaacccaag gacaccctca tgatctcccg gacccctgag gtcacatgcg   5520
tggtggtgga cgtgagccac gaagaccctg aggtcaagtt caactggtac gtggacggcg   5580
tggaggtgca taatgccaag acaaagccgc gggaggagca gtacaacagc acgtaccgtg   5640
tggtcagcgt cctcaccgtc ctgcaccagg actggctgaa tggcaaggag tacaagtgca   5700
aggtctccaa caaagccctc ccagccccca tcgagaaaac catctccaaa gccaagggc    5760 agccccgaga accacaggtg tacaccctgc cccatcccg cgatgagctg accaagaacc    5820
aggtcagcct gacctgcctg gtcaaaggct tctatcccag cgacatcgcc gtggagtggg   5880
agagcaatgg gcagccggag aacaactaca agaccacgcc tcccgtgttg gactccgacg   5940
gctccttctt cctctacagc aagctcaccg tggacaagag caggtggcag caggggaacg   6000
tcttctcatg ctccgtgatg catgaggctc tgcacaacca ctacacgcag aagagcctct   6060
ccctgtctcc gggtaaatga ctcgagagat ctggccggct gggcccgttt cgaaggtaag   6120
cctatcccta accctctcct cggtctcgat tctacgcgta ccggtcatca tcaccatcac   6180
cattgagttt aaacccgctg atcagcctcg actgtgcctt ctagttgcca gccatctgtt   6240
gtttgcccct ccccgtgcc ttccttgacc ctggaaggtg ccactcccac tgtcctttcc    6300
```

-continued

| | | | |
|---|---|---|---|
| taataaaatg aggaaattgc atcgcattgt ctgagtaggt gtcattctat tctgggggt | 6360 | | |
| ggggtggggc aggacagcaa ggggaggat tgggaagaca atagcaggca tgctggggat | 6420 | | |
| gcggtgggct ctatggcttc tgaggcggaa agaaccagtg gcggtaatac ggttatccac | 6480 | | |
| agaatcaggg gataacgcag gaaagaacat gtgagcaaaa ggccagcaaa aggccaggaa | 6540 | | |
| ccgtaaaaag gccgcgttgc tggcgttttt ccataggctc cgcccccctg acgagcatca | 6600 | | |
| caaaatcga cgctcaagtc agaggtggcg aaacccgaca ggactataaa gataccaggc | 6660 | | |
| gtttccccct agaagctccc tcgtgcgctc tcctgttccg accctgccgc ttaccggata | 6720 | | |
| cctgtccgcc tttctccctt cgggaagcgt ggcgctttct catagctcac gctgtaggta | 6780 | | |
| tctcagttcg gtgtaggtcg ttcgctccaa gctgggctgt gtgcacgaac cccccgttca | 6840 | | |
| gcccgaccgc tgcgccttat ccggtaacta tcgtcttgag tccaacccgg taagacacga | 6900 | | |
| cttatcgcca ctggcagcag ccactggtaa caggattagc agagcgaggt atgtaggcgg | 6960 | | |
| tgctacagag ttcttgaagt ggtggcctaa ctacggctac actagaagaa cagtatttgg | 7020 | | |
| tatctgcgct ctgctgaagc cagttacctt cggaaaaaga gttggtagct cttgatccgg | 7080 | | |
| caaacaaacc accgctggta gcggtggttt ttttgtttgc aagcagcaga ttacgcgcag | 7140 | | |
| aaaaaaagga tctcaagaag atcctttgat cttttctacg gggtctgacg ctcagtggaa | 7200 | | |
| cgaaaactca cgttaaggga ttttggtcat gacattaacc tataaaaata ggcgtatcac | 7260 | | |
| gaggcccttt cgtctcgcgc gtttcggtga tgacggtgaa aacctctgac acatgcagct | 7320 | | |
| cccggagacg gtcacagctt gtctgtaagc ggatgccggg agcagacaag cccgtcaggg | 7380 | | |
| cgcgtcagcg ggtgttggcg ggtgtcgggg ctggcttaac tatgcggcat cagagcagat | 7440 | | |
| tgtactgaga gtgcaccata tatgcggtgt gaaataccgc acagatgcgt aaggagaaaa | 7500 | | |
| taccgcatca ggcgccattc gccattcagg ctgcgcaact gttgggaagg gcgatcggtg | 7560 | | |
| cgggcctctt cgctattacg cca | 7583 | | |

<210> SEQ ID NO 14
<211> LENGTH: 688
<212> TYPE: PRT
<213> ORGANISM: Artificial Sequence
<220> FEATURE:
<223> OTHER INFORMATION: FIX-Fc chain
<220> FEATURE:
<221> NAME/KEY: SIGNAL
<222> LOCATION: (1)..(46)
<223> OTHER INFORMATION: amino acid signal sequence
<220> FEATURE:
<221> NAME/KEY: MISC_FEATURE
<222> LOCATION: (462)..(688)
<223> OTHER INFORMATION: Fc part of FIX-Fc

<400> SEQUENCE: 14

Met Gln Arg Val Asn Met Ile Met Ala Glu Ser Pro Ser Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

```
Cys Glu Ser Asn Pro Cys Leu Asn Gly Gly Ser Cys Lys Asp Ile
            100                 105                 110

Asn Ser Tyr Glu Cys Trp Cys Pro Phe Gly Phe Glu Gly Lys Asn Cys
            115                 120                 125

Glu Leu Asp Val Thr Cys Asn Ile Lys Asn Gly Arg Cys Glu Gln Phe
            130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
            195                 200                 205

Thr Ile Leu Asp Asn Ile Thr Gln Ser Thr Gln Ser Phe Asn Asp Phe
            210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
            275                 280                 285

His Thr Glu Gln Lys Arg Asn Val Ile Arg Ile Ile Pro His His Asn
            290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
            355                 360                 365

Leu Gln Tyr Leu Arg Val Pro Leu Val Asp Arg Ala Thr Cys Leu Arg
            370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
            405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
            435                 440                 445

Arg Tyr Val Asn Trp Ile Lys Glu Lys Thr Lys Leu Thr Asp Lys Thr
450                 455                 460

His Thr Cys Pro Pro Cys Pro Ala Pro Glu Leu Leu Gly Gly Pro Ser
465                 470                 475                 480

Val Phe Leu Phe Pro Pro Lys Pro Lys Asp Thr Leu Met Ile Ser Arg
                485                 490                 495

Thr Pro Glu Val Thr Cys Val Val Val Asp Val Ser His Glu Asp Pro
            500                 505                 510
```

```
Glu Val Lys Phe Asn Trp Tyr Val Asp Gly Val Glu Val His Asn Ala
            515                 520                 525

Lys Thr Lys Pro Arg Glu Glu Gln Tyr Asn Ser Thr Tyr Arg Val Val
        530                 535                 540

Ser Val Leu Thr Val Leu His Gln Asp Trp Leu Asn Gly Lys Glu Tyr
545                 550                 555                 560

Lys Cys Lys Val Ser Asn Lys Ala Leu Pro Ala Pro Ile Glu Lys Thr
                565                 570                 575

Ile Ser Lys Ala Lys Gly Gln Pro Arg Glu Pro Gln Val Tyr Thr Leu
            580                 585                 590

Pro Pro Ser Arg Asp Glu Leu Thr Lys Asn Gln Val Ser Leu Thr Cys
        595                 600                 605

Leu Val Lys Gly Phe Tyr Pro Ser Asp Ile Ala Val Glu Trp Glu Ser
610                 615                 620

Asn Gly Gln Pro Glu Asn Asn Tyr Lys Thr Thr Pro Pro Val Leu Asp
625                 630                 635                 640

Ser Asp Gly Ser Phe Phe Leu Tyr Ser Lys Leu Thr Val Asp Lys Ser
                645                 650                 655

Arg Trp Gln Gln Gly Asn Val Phe Ser Cys Ser Val Met His Glu Ala
            660                 665                 670

Leu His Asn His Tyr Thr Gln Lys Ser Leu Ser Leu Ser Pro Gly Lys
        675                 680                 685

<210> SEQ ID NO 15
<211> LENGTH: 2082
<212> TYPE: DNA
<213> ORGANISM: Artificial Sequence
<220> FEATURE:
<223> OTHER INFORMATION: Full Length FVII-Fc DNA Sequence
<220> FEATURE:
<221> NAME/KEY: sig_peptide
<222> LOCATION: (1)..(180)
<223> OTHER INFORMATION: FVIII signal peptide
<220> FEATURE:
<221> NAME/KEY: sig_peptide
<222> LOCATION: (1)..(180)
<223> OTHER INFORMATION: FVII signal peptide
<220> FEATURE:
<221> NAME/KEY: misc_feature
<222> LOCATION: (1402)..(2082)
<223> OTHER INFORMATION: Fc region

<400> SEQUENCE: 15
atggtctccc aggccctcag gctcctctgc cttctgcttg ggcttcaggg ctgcctggct      60
gcaggcgggg tcgctaaggc ctcaggagga gaaacacggg acatgccgtg gaagccgggg    120
cctcacagag tcttcgtaac ccaggaggaa gcccacggcg tcctgcaccg gcgccggcgc    180
gccaacgcgt tcctggagga gctgcggccg ggctccctgg agagggagtg caaggaggag    240
cagtgctcct cgaggaggc ccgggagatc ttcaaggacg cggagaggac gaagctgttc    300
tggatttctt acagtgatgg ggaccagtgt gcctcaagtc catgccagaa tgggggctcc    360
tgcaaggacc agctccagtc ctatatctgc ttctgcctcc ctgccttcga gggccggaac    420
tgtgagacgc acaaggatga ccagctgatc tgtgtgaacg agaacggcgg ctgtgagcag    480
tactgcagtg accacacggg caccaagcgc tcctgtcggt gccacgaggg gtactctctg    540
ctggcagacg gggtgtcctg cacacccaca gttgaatatc catgtggaaa aataccatt    600 ctagaaaaaa gaaatgccag caaaccccaa ggccgaattg tgggggcaa ggtgtgcccc    660 aaagggggagt gtccatggca ggtcctgttg ttggtgaatg gagctcagtt gtgtggggg    720
```

| | |
|---|---|
| accctgatca acaccatctg ggtggtctcc gcggcccact gtttcgacaa aatcaagaac | 780 |
| tggaggaacc tgatcgcggt gctgggcgag cacgacctca gcgagcacga cggggatgag | 840 |
| cagagccggc gggtggcgca ggtcatcatc cccagcacgt acgtcccggg caccaccaac | 900 |
| cacgacatcg cgctgctccg cctgcaccag cccgtggtcc tcactgacca tgtggtgccc | 960 |
| ctctgcctgc ccgaacggac gttctctgag aggacgctgg ccttcgtgcg cttctcattg | 1020 |
| gtcagcggct ggggccagct gctggaccgt ggcgccacgg ccctggagct catggtcctc | 1080 |
| aacgtgcccc ggctgatgac ccaggactgc ctgcagcagt cacggaaggt gggagactcc | 1140 |
| ccaaatatca cggagtacat gttctgtgcc ggctactcgg atggcagcaa ggactcctgc | 1200 |
| aagggggaca gtggaggccc acatgccacc cactaccggg gcacgtggta cctgacgggc | 1260 |
| atcgtcagct ggggccaggg ctgcgcaacc gtgggccact ttgggggtgta caccagggtc | 1320 |
| tcccagtaca tcgagtggct gcaaaagctc atgcgctcag agccacgccc aggagtcctc | 1380 |
| ctgcgagccc catttcccta ggacaaaact cacacatgcc caccgtgccc agctccagaa | 1440 |
| ctcctgggcg gaccgtcagt cttcctcttc cccccaaaac ccaaggacac cctcatgatc | 1500 |
| tcccggaccc ctgaggtcac atgcgtggtg gtggacgtga gccacgaaga ccctgaggtc | 1560 |
| aagttcaact ggtacgtgga cggcgtggag gtgcataatg ccaagacaaa gccgcgggag | 1620 |
| gagcagtaca acagcacgta ccgtgtggtc agcgtcctca ccgtcctgca ccaggactgg | 1680 |
| ctgaatggca aggagtacaa gtgcaaggtc tccaacaaag ccctcccagc ccccatcgag | 1740 |
| aaaaccatct ccaaagccaa agggcagccc cgagaaccac aggtgtacac cctgccccca | 1800 |
| tcccgggatg agctgaccaa gaaccaggtc agcctgacct gcctggtcaa aggcttctat | 1860 |
| cccagcgaca tcgccgtgga gtgggagagc aatgggcagc cggagaacaa ctacaagacc | 1920 |
| acgcctcccg tgttggactc cgacggctcc ttcttcctct acagcaagct caccgtggac | 1980 |
| aagagcaggt ggcagcaggg gaacgtcttc tcatgctccg tgatgcatga ggctctgcac | 2040 |
| aaccactaca cgcagaagag cctctccctg tctccgggta aa | 2082 |

```
<210> SEQ ID NO 16
<211> LENGTH: 693
<212> TYPE: PRT
<213> ORGANISM: Artificial Sequence
<220> FEATURE:
<223> OTHER INFORMATION: FVII-Fc chain
<220> FEATURE:
<221> NAME/KEY: SIGNAL
<222> LOCATION: (1)..(60)
<223> OTHER INFORMATION: signal sequence
<220> FEATURE:
<221> NAME/KEY: MISC_FEATURE
<222> LOCATION: (467)..(693)
<223> OTHER INFORMATION: Fc region

<400> SEQUENCE: 16
```

Met Val Ser Gln Ala Leu Arg Leu Leu Cys Leu Leu Leu Gly Leu Gln
1               5                   10                  15

Gly Cys Leu Ala Ala Gly Gly Val Ala Lys Ala Ser Gly Gly Glu Thr
            20                  25                  30

Arg Asp Met Pro Trp Lys Pro Gly Pro His Arg Val Phe Val Thr Gln
        35                  40                  45

Glu Glu Ala His Gly Val Leu His Arg Arg Arg Ala Asn Ala Phe
    50                  55                  60

Leu Glu Glu Leu Arg Pro Gly Ser Leu Glu Arg Glu Cys Lys Glu Glu
65                  70                  75                  80

-continued

Gln Cys Ser Phe Glu Glu Ala Arg Glu Ile Phe Lys Asp Ala Glu Arg
                85                  90                  95

Thr Lys Leu Phe Trp Ile Ser Tyr Ser Asp Gly Asp Gln Cys Ala Ser
            100                 105                 110

Ser Pro Cys Gln Asn Gly Gly Ser Cys Lys Asp Gln Leu Gln Ser Tyr
        115                 120                 125

Ile Cys Phe Cys Leu Pro Ala Phe Glu Gly Arg Asn Cys Glu Thr His
    130                 135                 140

Lys Asp Asp Gln Leu Ile Cys Val Asn Glu Asn Gly Gly Cys Glu Gln
145                 150                 155                 160

Tyr Cys Ser Asp His Thr Gly Thr Lys Arg Ser Cys Arg Cys His Glu
                165                 170                 175

Gly Tyr Ser Leu Leu Ala Asp Gly Val Ser Cys Thr Pro Thr Val Glu
            180                 185                 190

Tyr Pro Cys Gly Lys Ile Pro Ile Leu Glu Lys Arg Asn Ala Ser Lys
        195                 200                 205

Pro Gln Gly Arg Ile Val Gly Gly Lys Val Cys Pro Lys Gly Glu Cys
    210                 215                 220

Pro Trp Gln Val Leu Leu Leu Val Asn Gly Ala Gln Leu Cys Gly Gly
225                 230                 235                 240

Thr Leu Ile Asn Thr Ile Trp Val Val Ser Ala Ala His Cys Phe Asp
                245                 250                 255

Lys Ile Lys Asn Trp Arg Asn Leu Ile Ala Val Leu Gly Glu His Asp
            260                 265                 270

Leu Ser Glu His Asp Gly Asp Glu Gln Ser Arg Arg Val Ala Gln Val
        275                 280                 285

Ile Ile Pro Ser Thr Tyr Val Pro Gly Thr Thr Asn His Asp Ile Ala
    290                 295                 300

Leu Leu Arg Leu His Gln Pro Val Val Leu Thr Asp His Val Val Pro
305                 310                 315                 320

Leu Cys Leu Pro Glu Arg Thr Phe Ser Glu Arg Thr Leu Ala Phe Val
                325                 330                 335

Arg Phe Ser Leu Val Ser Gly Trp Gly Gln Leu Leu Asp Arg Gly Ala
            340                 345                 350

Thr Ala Leu Glu Leu Met Val Leu Asn Val Pro Arg Leu Met Thr Gln
        355                 360                 365

Asp Cys Leu Gln Gln Ser Arg Lys Val Gly Asp Ser Pro Asn Ile Thr
    370                 375                 380

Glu Tyr Met Phe Cys Ala Gly Tyr Ser Asp Gly Ser Lys Asp Ser Cys
385                 390                 395                 400

Lys Gly Asp Ser Gly Gly Pro His Ala Thr His Tyr Arg Gly Thr Trp
                405                 410                 415

Tyr Leu Thr Gly Ile Val Ser Trp Gly Gln Gly Cys Ala Thr Val Gly
            420                 425                 430

His Phe Gly Val Tyr Thr Arg Val Ser Gln Tyr Ile Glu Trp Leu Gln
        435                 440                 445

Lys Leu Met Arg Ser Glu Pro Arg Pro Gly Val Leu Leu Arg Ala Pro
    450                 455                 460

Phe Pro Asp Lys Thr His Thr Cys Pro Pro Cys Pro Ala Pro Glu Leu
465                 470                 475                 480

Leu Gly Gly Pro Ser Val Phe Leu Phe Pro Pro Lys Pro Lys Asp Thr
                485                 490                 495

Leu Met Ile Ser Arg Thr Pro Glu Val Thr Cys Val Val Val Asp Val

```
                    500                 505                 510
Ser His Glu Asp Pro Glu Val Lys Phe Asn Trp Tyr Val Asp Gly Val
            515                 520                 525

Glu Val His Asn Ala Lys Thr Lys Pro Arg Glu Glu Gln Tyr Asn Ser
        530                 535                 540

Thr Tyr Arg Val Val Ser Val Leu Thr Val Leu His Gln Asp Trp Leu
545                 550                 555                 560

Asn Gly Lys Glu Tyr Lys Cys Lys Val Ser Asn Lys Ala Leu Pro Ala
            565                 570                 575

Pro Ile Glu Lys Thr Ile Ser Lys Ala Lys Gly Gln Pro Arg Glu Pro
        580                 585                 590

Gln Val Tyr Thr Leu Pro Pro Ser Arg Asp Glu Leu Thr Lys Asn Gln
            595                 600                 605

Val Ser Leu Thr Cys Leu Val Lys Gly Phe Tyr Pro Ser Asp Ile Ala
        610                 615                 620

Val Glu Trp Glu Ser Asn Gly Gln Pro Glu Asn Asn Tyr Lys Thr Thr
625                 630                 635                 640

Pro Pro Val Leu Asp Ser Asp Gly Ser Phe Phe Leu Tyr Ser Lys Leu
            645                 650                 655

Thr Val Asp Lys Ser Arg Trp Gln Gln Gly Asn Val Phe Ser Cys Ser
        660                 665                 670

Val Met His Glu Ala Leu His Asn His Tyr Thr Gln Lys Ser Leu Ser
            675                 680                 685

Leu Ser Pro Gly Lys
        690

<210> SEQ ID NO 17
<211> LENGTH: 20
<212> TYPE: PRT
<213> ORGANISM: Artificial Sequence
<220> FEATURE:
<223> OTHER INFORMATION: PAS sequence

<400> SEQUENCE: 17

Ala Ser Pro Ala Ala Pro Ala Pro Ala Ser Pro Ala Ala Pro Ala Pro
1               5                   10                  15

Ser Ala Pro Ala
            20

<210> SEQ ID NO 18
<211> LENGTH: 20
<212> TYPE: PRT
<213> ORGANISM: Artificial Sequence
<220> FEATURE:
<223> OTHER INFORMATION: PAS sequence

<400> SEQUENCE: 18

Ala Ala Pro Ala Ser Pro Ala Pro Ala Ala Pro Ser Ala Pro Ala Pro
1               5                   10                  15

Ala Ala Pro Ser
            20

<210> SEQ ID NO 19
<211> LENGTH: 20
<212> TYPE: PRT
<213> ORGANISM: Artificial Sequence
<220> FEATURE:
<223> OTHER INFORMATION: PAS sequence

<400> SEQUENCE: 19
```

```
Ala Pro Ser Ser Pro Ser Pro Ser Ala Pro Ser Ser Pro Ser Pro Ala
1               5                   10                  15

Ser Pro Ser Ser
            20

<210> SEQ ID NO 20
<211> LENGTH: 19
<212> TYPE: PRT
<213> ORGANISM: Artificial Sequence
<220> FEATURE:
<223> OTHER INFORMATION: PAS sequence

<400> SEQUENCE: 20

Ala Pro Ser Ser Pro Ser Pro Ser Ala Pro Ser Ser Pro Ser Pro Ala
1               5                   10                  15

Ser Pro Ser

<210> SEQ ID NO 21
<211> LENGTH: 20
<212> TYPE: PRT
<213> ORGANISM: Artificial Sequence
<220> FEATURE:
<223> OTHER INFORMATION: PAS sequence

<400> SEQUENCE: 21

Ser Ser Pro Ser Ala Pro Ser Pro Ser Ser Pro Ala Ser Pro Ser Pro
1               5                   10                  15

Ser Ser Pro Ala
            20

<210> SEQ ID NO 22
<211> LENGTH: 24
<212> TYPE: PRT
<213> ORGANISM: Artificial Sequence
<220> FEATURE:
<223> OTHER INFORMATION: PAS sequence

<400> SEQUENCE: 22

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 23
<211> LENGTH: 20
<212> TYPE: PRT
<213> ORGANISM: Artificial Sequence
<220> FEATURE:
<223> OTHER INFORMATION: PAS sequence

<400> SEQUENCE: 23

Ala Ser Ala Ala Ala Pro Ala Ala Ser Ala Ala Ala Ser Ala Ala Pro
1               5                   10                  15

Ser Ala Ala Ala
            20
```

ON-COLUMN VIRAL INACTIVATION METHODS

RELATED APPLICATIONS

This application is a continuation of U.S. patent application Ser. No. 15/024,988, filed Mar. 25, 2016, which is a 35 U.S.C. § 371 filing of International Patent Application No. PCT/US2014/057524, filed Sep. 25, 2014, which claims priority to U.S. Provisional Patent Application Ser. No. 62/028,657, filed Jul. 24, 2014; and 61/882,488, filed Sep. 25, 2013, the entire disclosures of which are hereby incorporated herein by reference.

BACKGROUND OF THE INVENTION

Field of the Invention

The present invention is directed to a method of inactivating virus that is present during production of a polypeptide of interest. In particular, the present invention is directed to a method of on-column virus inactivation using a low pH and high salt wash solution that effectively inactivates viruses with minimum recovery loss of the polypeptide.

Background Art

With the advent of recombinant protein technology, a protein of interest can be produced using cultured cell lines engineered to express the protein. The use of the desired recombinant protein for pharmaceutical applications is however generally contingent on the ability to reliably recover adequate levels of the protein from impurities such as host cell proteins, cell culture additives, and viruses. Various chromatography methods have been employed to remove the impurities and to recover the protein.

A number of methods for inactivating viruses based on different mechanisms are known in the art. Each method however has its own disadvantages, and may not be suitable or optimal for some protein products. For example, when low pH is used to inactivate viruses, it has the potential to precipitate proteins, cause aggregation of the product, and/or alter the conformation of certain proteins which can lead to product loss. In addition, during the protein purification process, the low pH virus inactivation step is typically performed after the protein of interest has been eluted from the chromatography column and held in a tank or vessel, especially if significant product loss may be caused by low pH wash. Adding an extra step in a tank or vessel to inactivate virus is a cause for inconvenience.

Therefore, there are needs to develop on-column viral inactivation steps that can effectively inactivate viruses and at the same time can improve the product yield in a convenient manner.

BRIEF SUMMARY OF THE INVENTION

The present invention pertains to a method of inactivating virus that is present during production of a polypeptide of interest, comprising: (a) binding the polypeptide to a chromatography matrix, and (b) performing a virus inactivation step by washing the polypeptide-bound chromatography matrix with a wash solution at a pH of lower than about 4.0, wherein the wash solution comprises a sufficient concentration of salt to substantially reduce elution of the polypeptide during the virus inactivation step.

In certain embodiments, the chromatography matrix is an affinity chromatography matrix. In certain embodiments, the affinity chromatography matrix is a Protein A column. In certain embodiments, the Protein A column is selected from the group consisting of MABSELECT™, MABSELECT™ SuRe, MABSELECT™ SuRe LX, ESHMUNO® A, AMSPHERE™ JWT203, TOYOPEARL®) AF-rProtein A-650F, PROSEP®-vA Ultra, PROSEP® Ultra Plus, and PROSEP®-vA High Capacity, and any combination thereof. In some embodiments, the Protein A ligand is immobilized on a matrix selected from the group consisting of dextran based matrix, agarose based matrix, polystyrene based matrix, hydrophilic polyvinyl ethyl based matrix, rigid polymethacrylate based matrix, porous polymer based matrix, controlled pore glass based matrix, and any combination thereof.

In certain embodiments, the chromatography matrix is a mixed-mode chromatography matrix. In certain embodiments, the chromatography matrix is a mixed-mode anion-exchange chromatography matrix. In certain embodiments, the mixed-mode chromatography matrix is selected from the group consisting of CAPTO™ Adhere, CAPTO™ MMC, ESHMUNO® HCX, CAPTO™ MMC ImpRes, CAPTO™ Blue, NUVIA™ cPrime, BLUE SEPHAROSE® Fast Flow, CAPTO™ Adhere ImpRes, CHT™ Ceramic Hydroxyapatite, CFT™ Ceramic. Fluoroapatite, and any combinations thereof. In some embodiments, the mixed-mode chromatography matrix is selected from the group consisting of dextran based matrix, agarose based matrix, polystyrene based matrix, polyvinyl ethyl hydrophilic polymer based matrix, macroporous highly crosslinked polymer based matrix, hydroxyapatite (($Ca_5(PO_4)_3OH$)2) based matrix, fluoroapatite (($Ca_5(PO_4)_3F$)2) based matrix, and any combinations thereof.

In certain embodiments, the polypeptide of interest is a CH2/CH3-containing polypeptide. In certain embodiments, the CH2/CH3-containing polypeptide is an antibody or an antibody fragment. In one embodiment, the antibody is a monoclonal antibody.

In certain embodiments, the polypeptide of interest comprises a clotting factor. In certain embodiments, the polypeptide of interest is FIX-Fc, FVIII-Fc, or FVII-Fc. In certain embodiments, the polypeptide is a monomer-dimer hybrid. In certain embodiments, the polypeptide further comprises a heterologous moiety. In one embodiment, the heterologous moiety is selected from the group consisting of albumin, albumin-binding polypeptide. Fc, PAS, the C-terminal peptide (CTP) of the β subunit of human chorionic gonadotropin, polyethylene glycol (PEG), hydroxyethyl starch (HES), albumin-binding small molecules, and any combinations thereof.

In certain embodiments, the polypeptide of interest is recombinantly produced in a cell culture. In certain embodiments, the cell culture is a human cell culture. In one embodiment, the human cell culture is Human Embryonic Kidney (HEK) 293 cell.

In certain embodiments, the polypeptide of interest is harvested after recombinant production in the cell culture. In certain embodiments, the polypeptide is bound to the chromatography matrix at a pH from about 6.0 to about 8.0.

In certain embodiments, the elution of the polypeptide during the virus inactivation step is reduced to less than 30%. In certain embodiments, the elution of the polypeptide during the virus inactivation step is reduced to less than 25%, less than 20%, less than 15%, less than 10%, or less than 5%.

In certain embodiments, the pH of the wash solution is about 2.5 to about 4.0. In other embodiments, the pH of the wash solution is about 2.5 to about 3.0, about 3.0 to about 3.5, or about 3.5 to about 4.0. In certain embodiments, the pH of the wash solution is about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, or about 4.0.

In certain embodiments, the concentration of the salt in the wash solution is greater than about 0.5 M. In certain embodiments, the concentration of the salt is about 0.5 M to about 1.0 M, about 1.0 M to about 1.5 M, about 1.5 M to about 2.0 M, about 2.0 M to about 2.5 M, about 2.5 M to about 3.0 M, about 3.0 M to about 3.5 M. or about 3.5 M to about 4 M.

In certain embodiments, the salt in the wash solution is a sodium salt, a potassium salt, or an ammonium salt.

In certain embodiments, the wash solution further comprises one or more components selected from the group consisting of a polymer, an organic solvent, a detergent, and arginine or an arginine derivative.

In certain embodiments, the method comprises more than one virus-inactivation step, wherein identical or different wash solutions can be used. In certain embodiments, at least one of the wash solutions comprises arginine, an arginine derivative, or a mixture thereof. In certain embodiments, at least one of the wash solutions comprises a detergent.

In certain embodiments, the method further comprises eluting the polypeptide from the chromatography matrix with an elution solution. In certain embodiments, at least about 70% of the polypeptide is recovered in the elution solution. In certain embodiments, at least about 75%, at least about 80%, at least about 85%, at least about 90%, or at least about 95% of the polypeptide is recovered in the elution solution.

BRIEF DESCRIPTION OF THE DRAWINGS/FIGURES

FIG. 1. The chromatogram showing the separation of proteins in a Protein A chromatography column using a wash solution containing 2 M ammonium sulfate at pH 3.5. $UV_{280}$ indicates protein concentration in the collected fractions.

Figure 2:
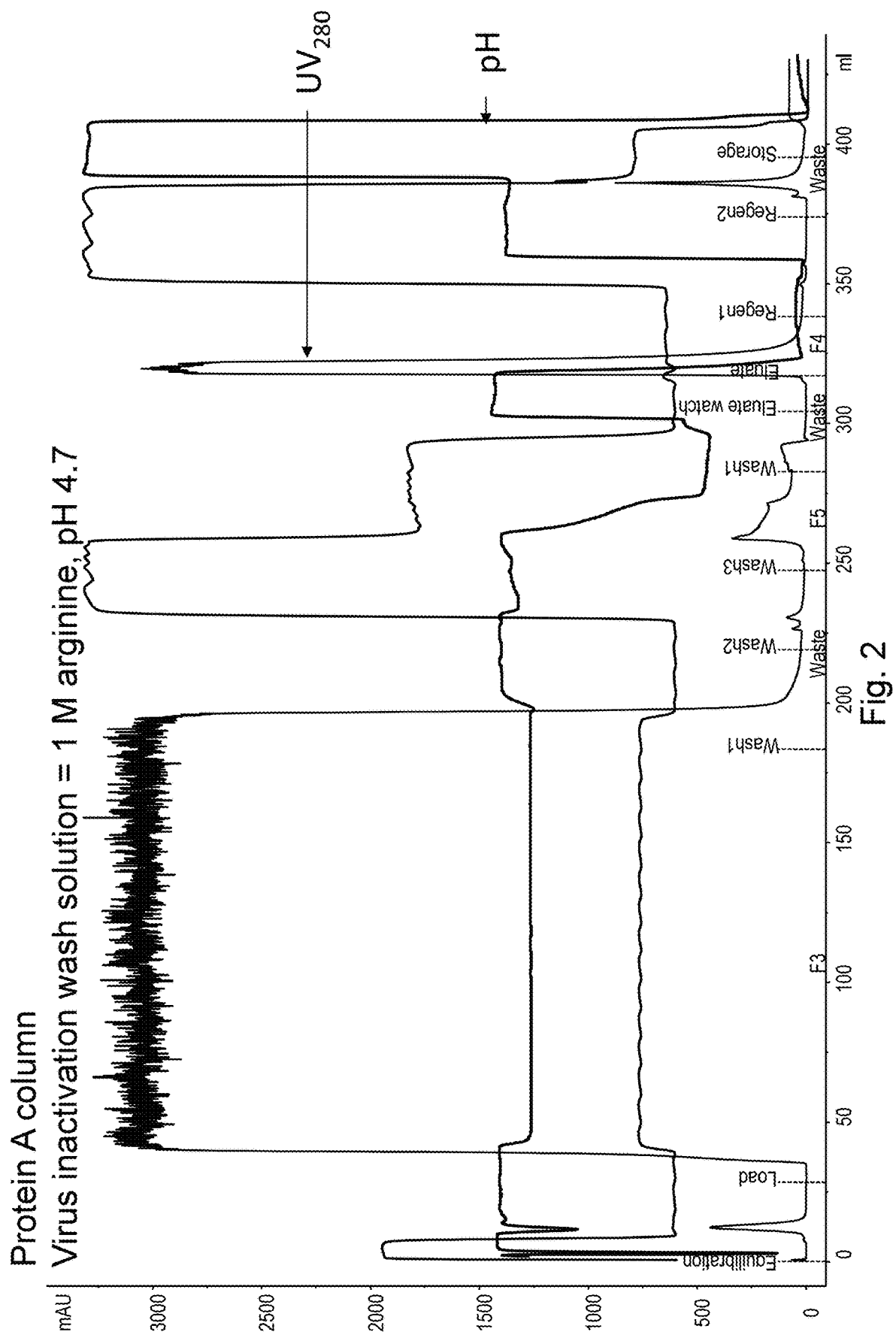

FIG. 2. The chromatogram showing the separation of proteins in a Protein A chromatography column using a wash solution containing 1 M arginine at pH 4.7. $UV_{280}$ indicates protein concentration in the collected fractions.

Figure 3:
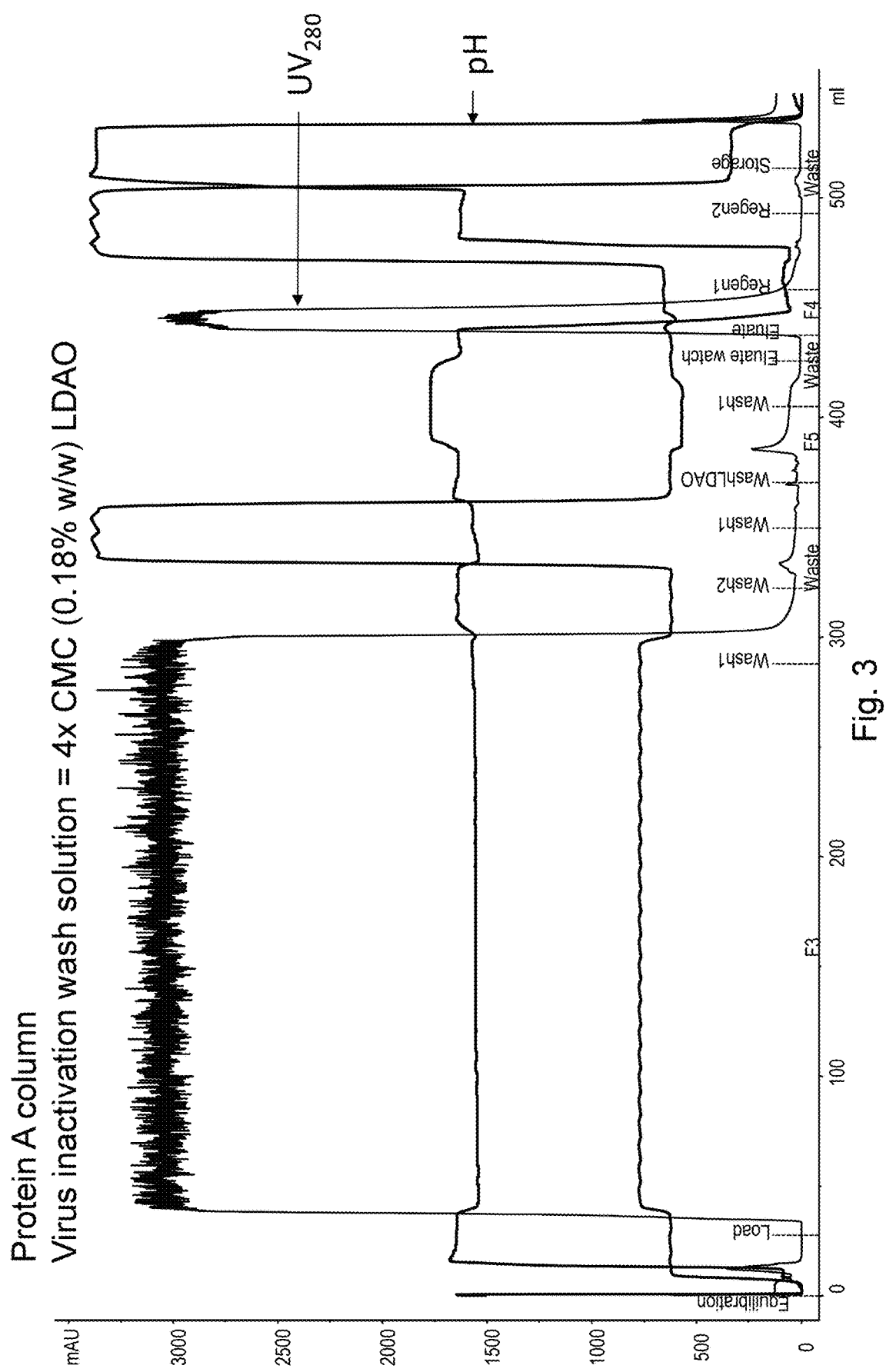

FIG. 3. The chromatogram showing the separation of proteins in a Protein A chromatography column using a wash solution containing 4×CMC (or 0.18% w/w) LDAO. $UV_{280}$ indicates protein concentration in the collected fractions.

Figure 4:
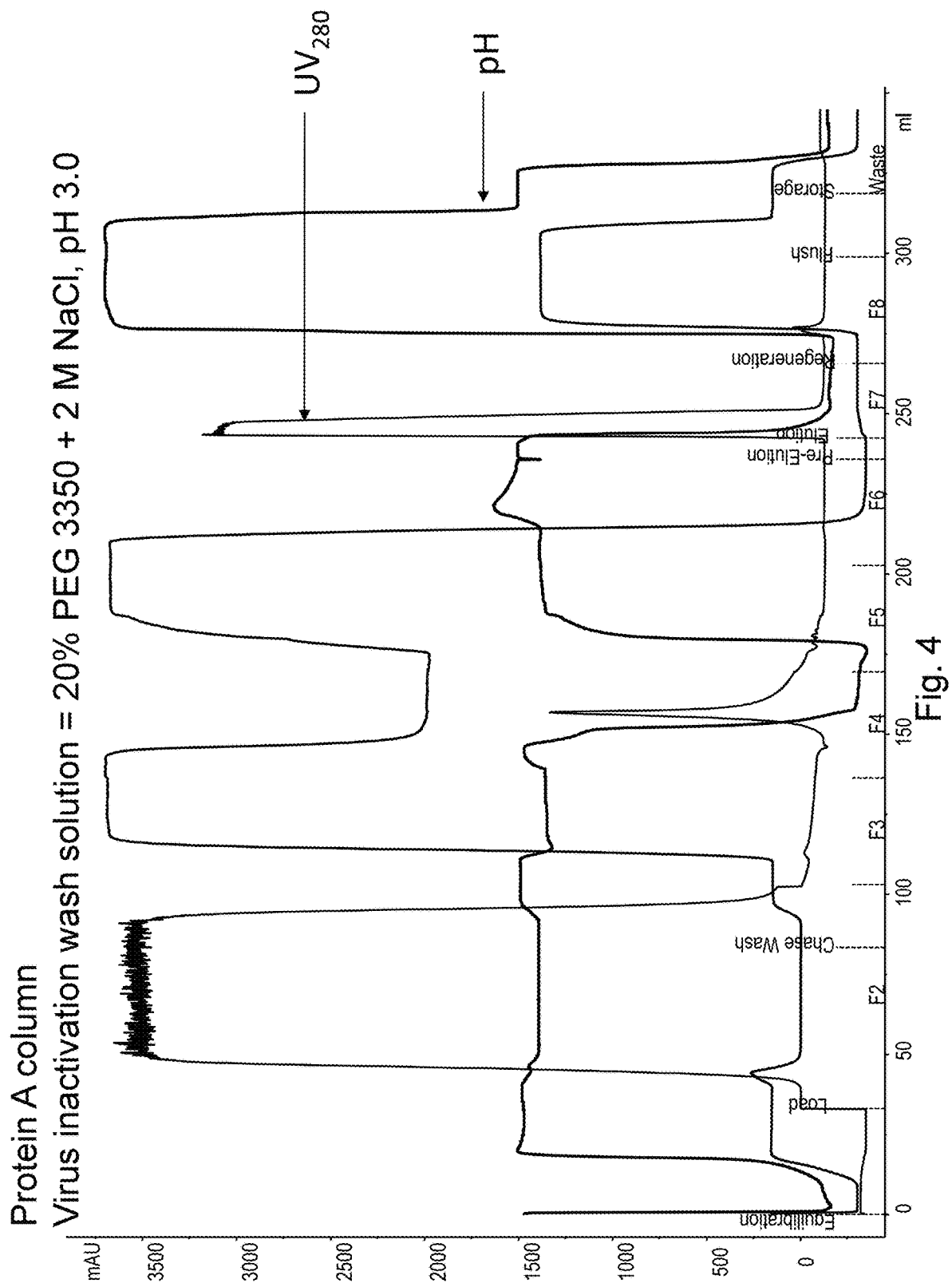

FIG. 4. The chromatogram showing the separation of proteins in a Protein A chromatography column using a wash solution containing 2 M NaCl and 20% PEG at pH 3.0. $UV_{280}$ indicates protein concentration in the collected fractions.

Figure 5:
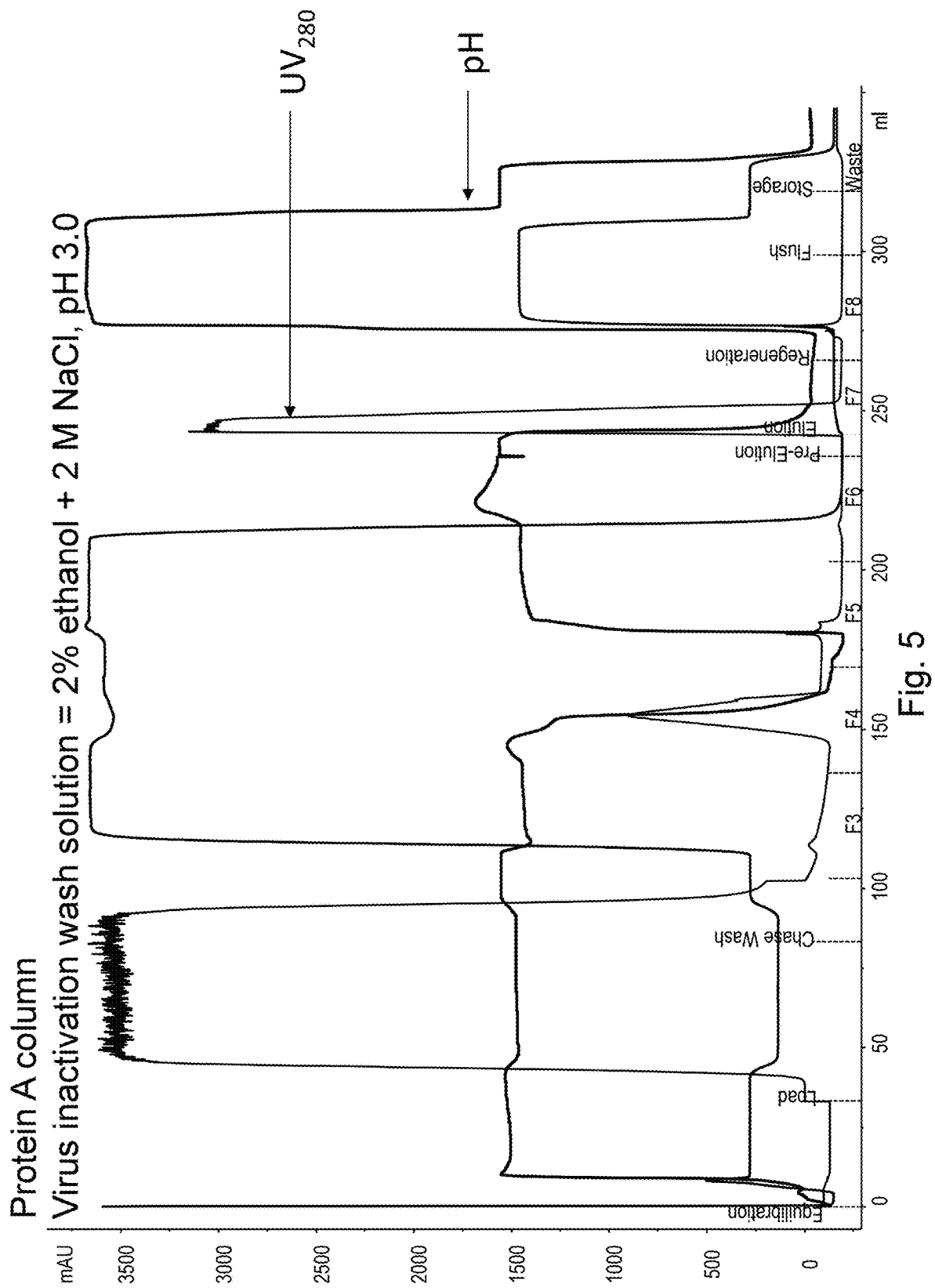

FIG. 5. The chromatogram showing the separation of proteins in a Protein A chromatography column using a wash solution containing 2 M NaCl and 2% ethanol at pH 3.0. $UV_{280}$ indicates protein concentration in the collected fractions.

Figure 6:
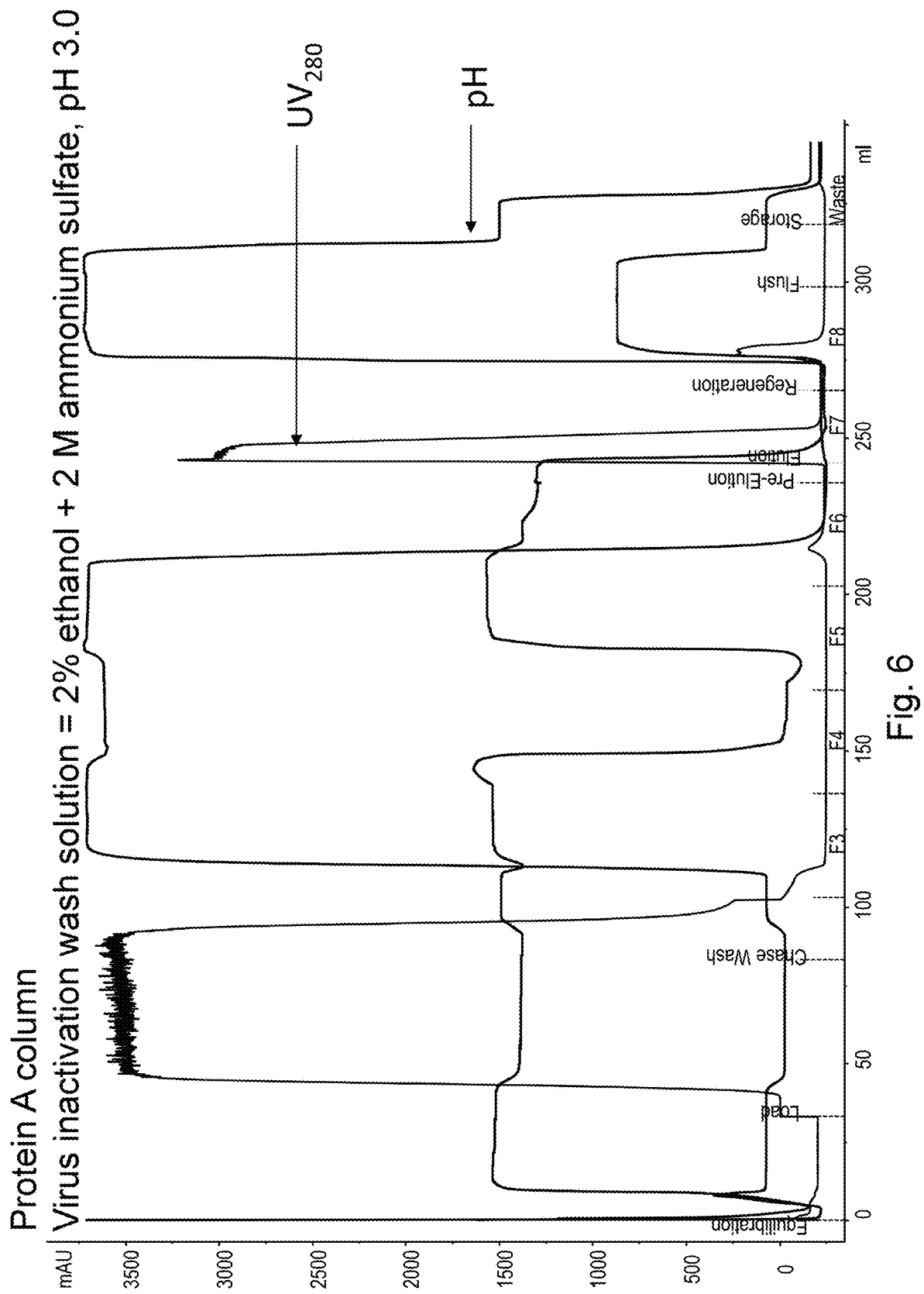

FIG. 6. The chromatogram showing the separation of proteins in a Protein A chromatography column using a wash solution containing 2 M ammonium sulfate and 2% ethanol at pH 3.0. $UV_{280}$ indicates protein concentration in the collected fractions.

Figure 7:
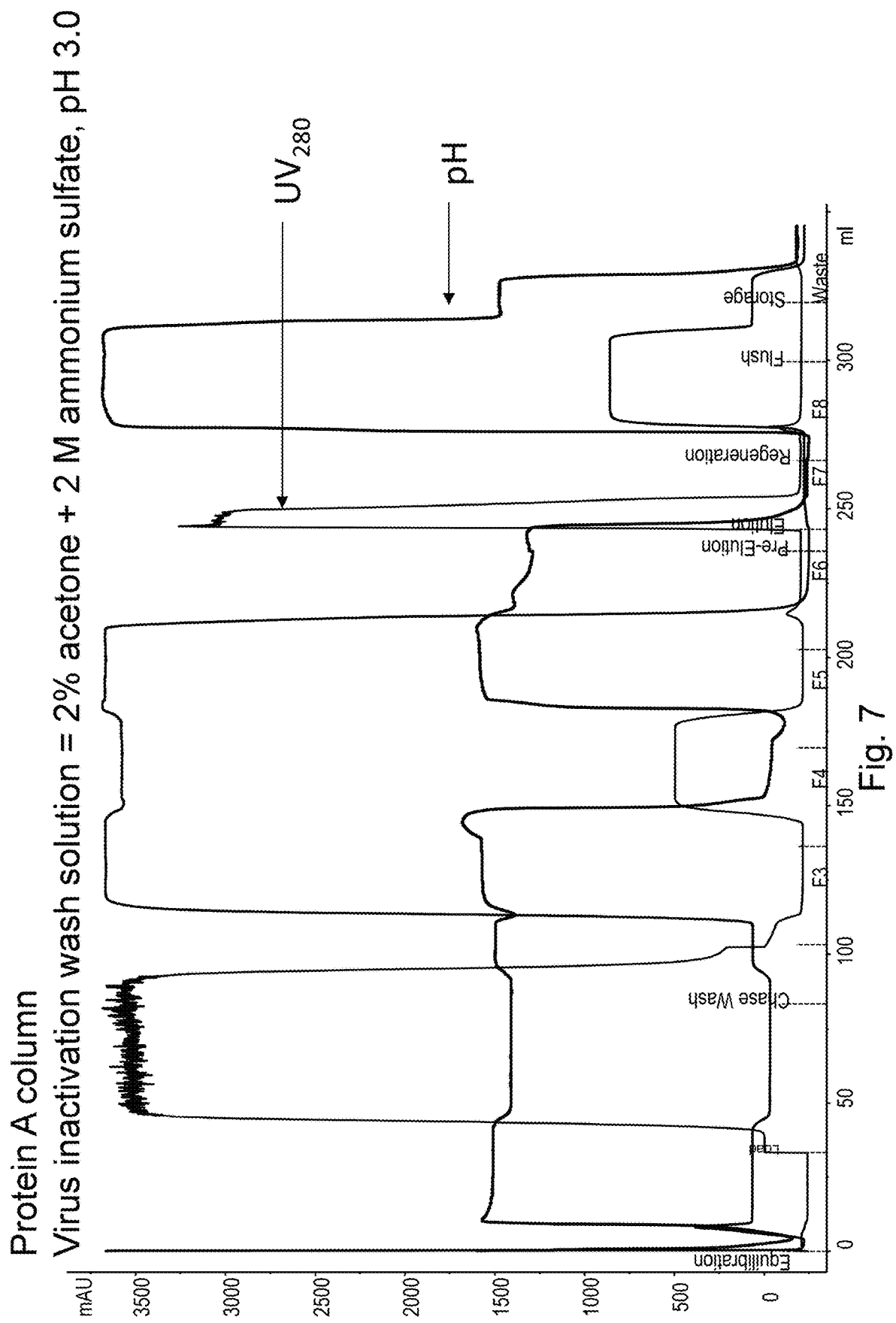

FIG. 7. The chromatogram showing the separation of proteins in a Protein A chromatography column using a wash solution containing 2 M ammonium sulfate and 2% acetone at pH 3.0. $UV_{280}$ indicates protein concentration in the collected fractions.

Figure 8:
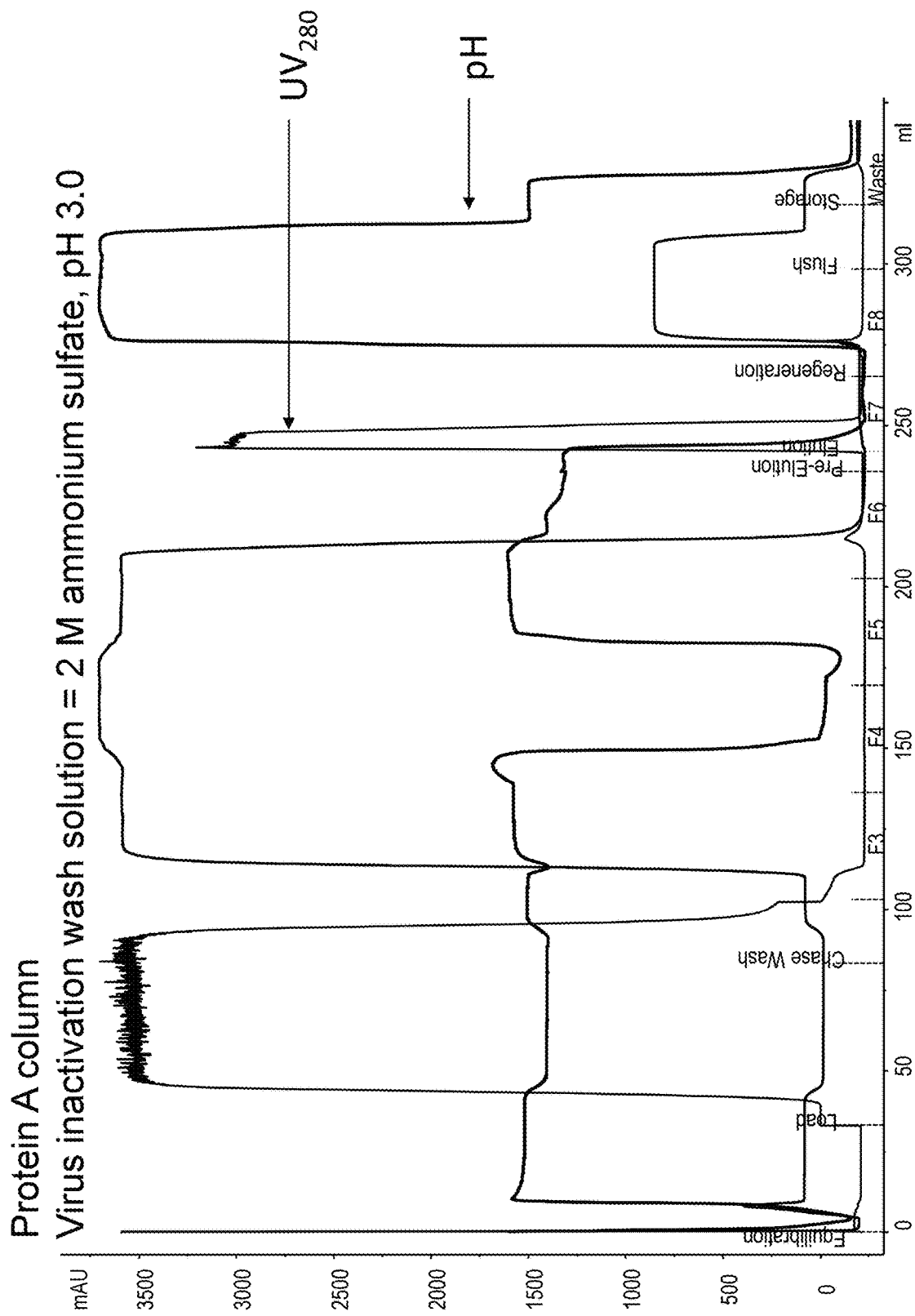

FIG. 8. The chromatogram showing the separation of proteins in a Protein A chromatography column using a wash solution containing 2 M ammonium sulfate at pH 3.0. $UV_{280}$ indicates protein concentration in the collected fractions.

Figure 9:
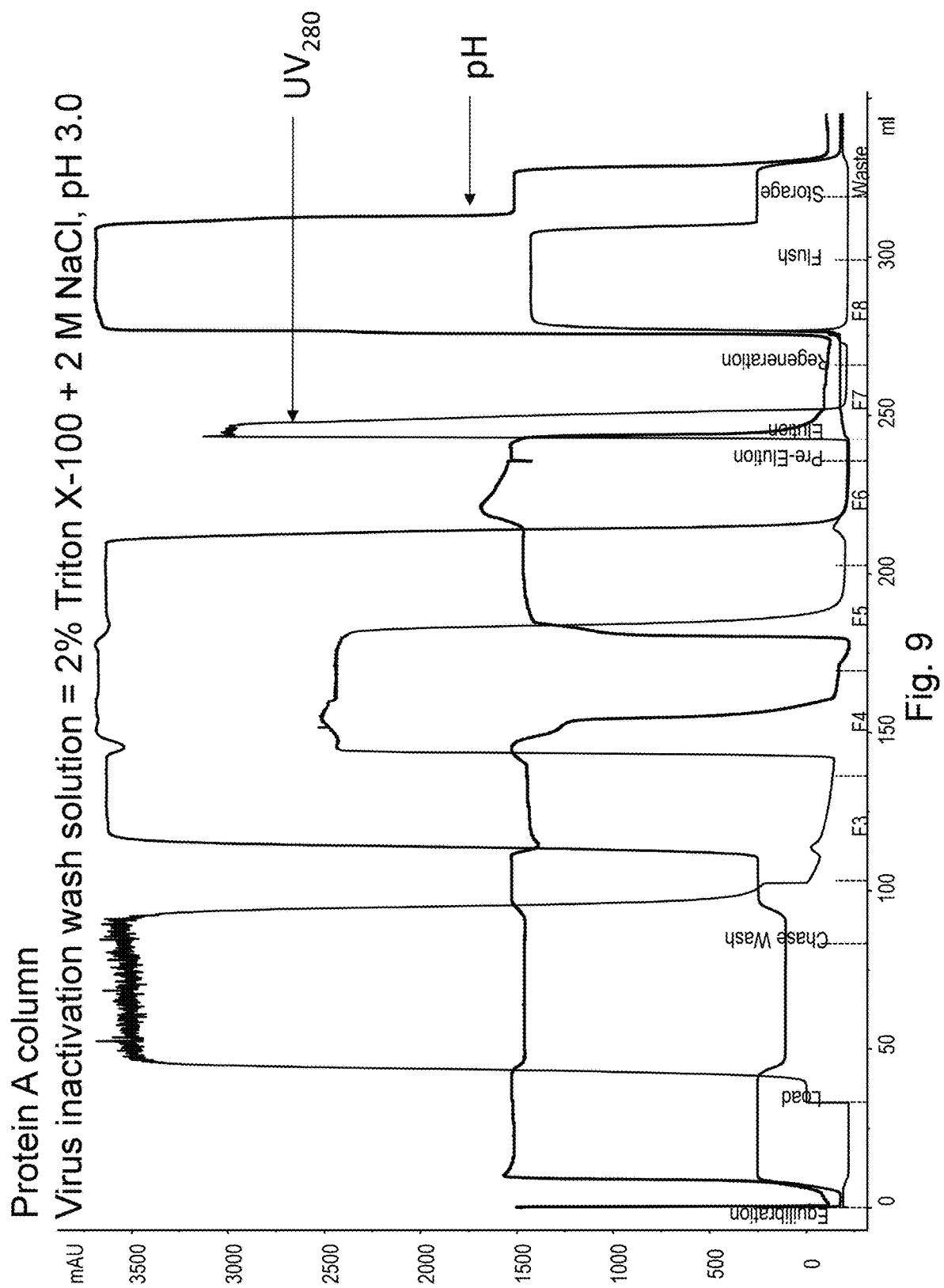

FIG. 9. The chromatogram showing the separation of proteins in a Protein A chromatography column using a wash solution containing 2 M ammonium sulfate and 2% TRITON™ X-100 at pH 3.0. $UV_{280}$ indicates protein concentration in the collected fractions.

Figure 10:
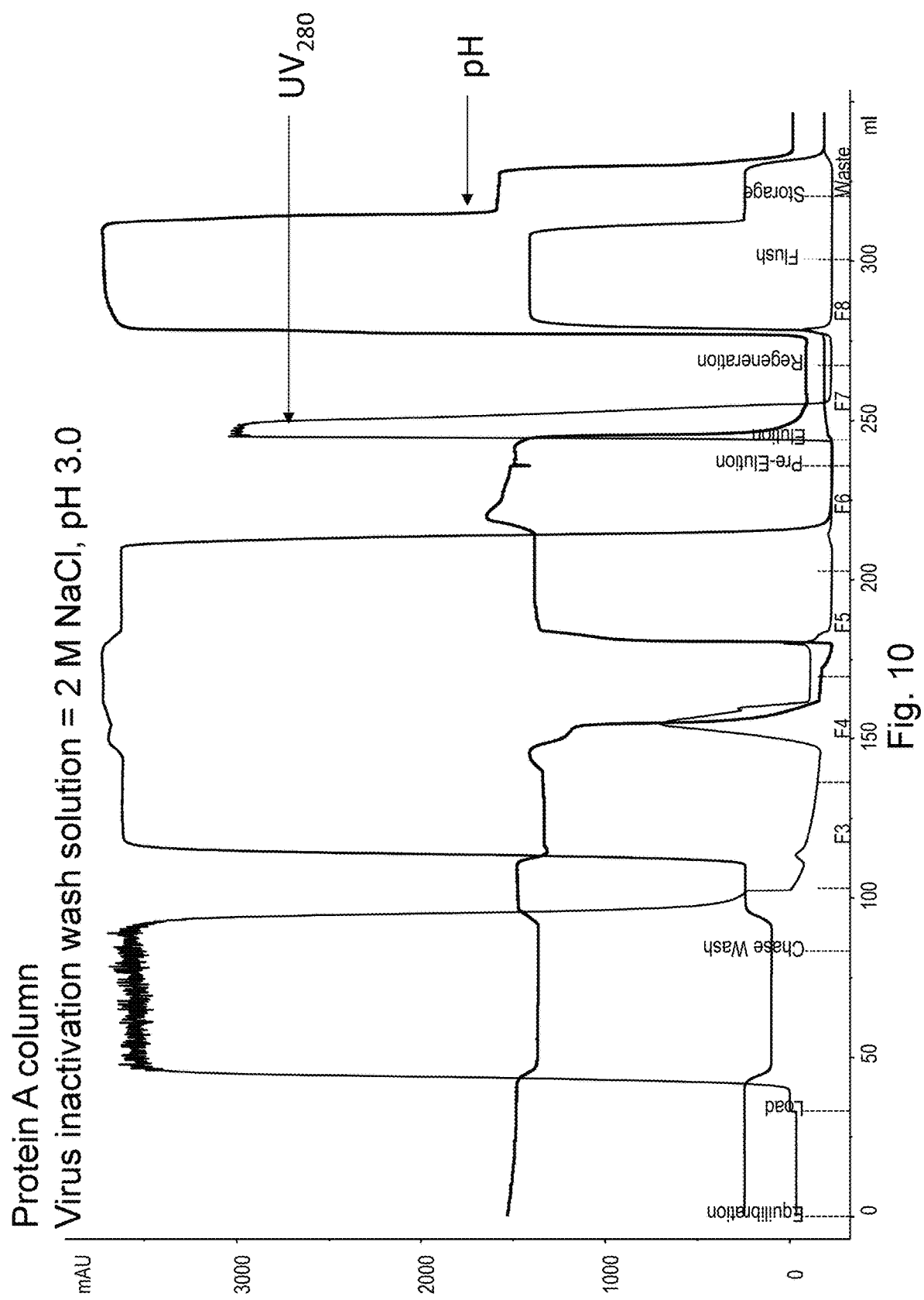

FIG. 10. The chromatogram showing the separation of proteins in a Protein A chromatography column using a wash solution containing 2 M NaCl at pH 3.0. $UV_{280}$ indicates protein concentration in the collected fractions.

Figure 11:
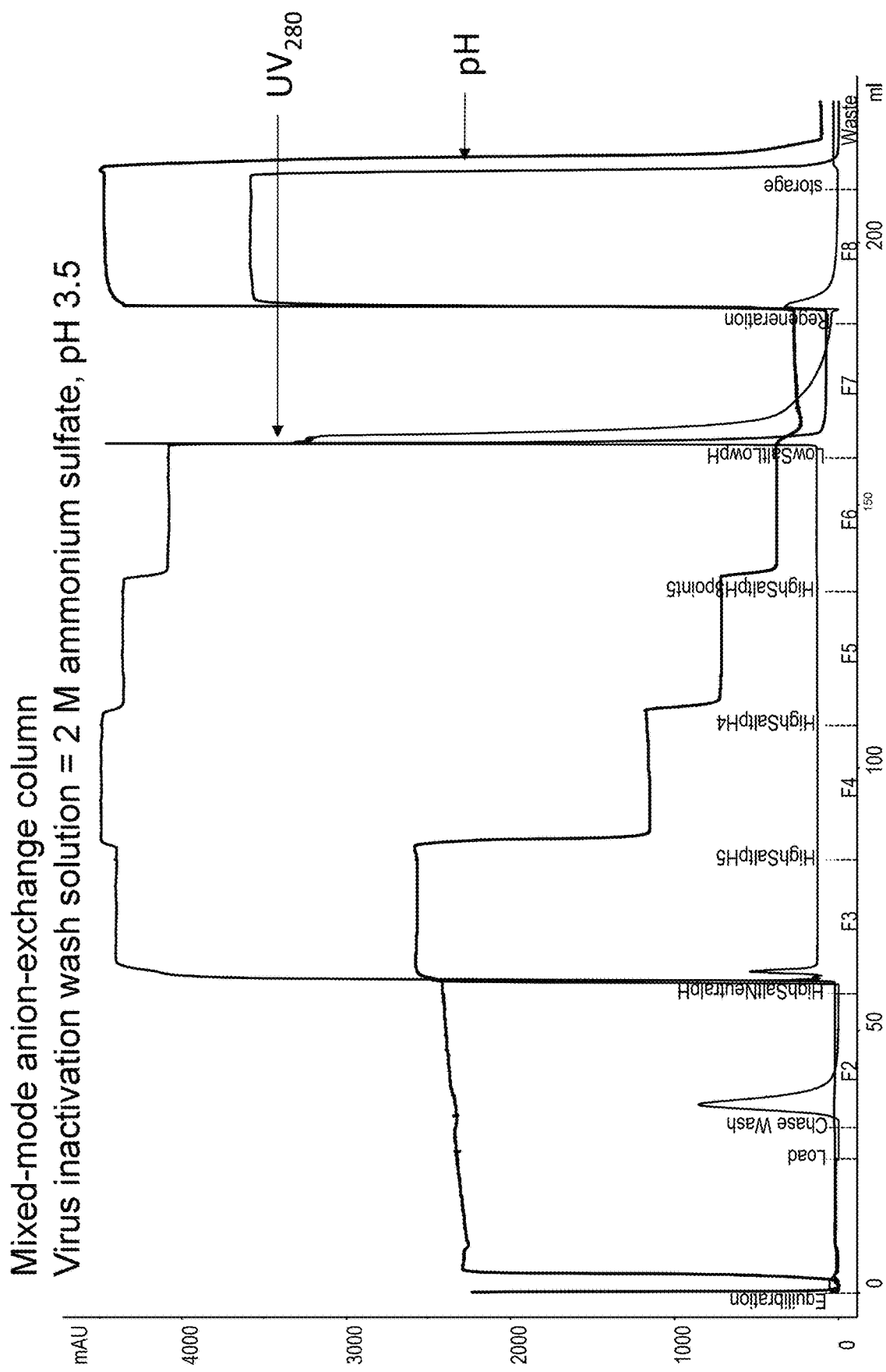

FIG. 11. The chromatogram showing the separation of proteins in a mixed-mode anion-exchange chromatography column using a wash solution containing 2 M ammonium sulfate at pH 3.5 and 4.0. $UV_{280}$ indicates protein concentration in the collected fractions.

Figure 12:
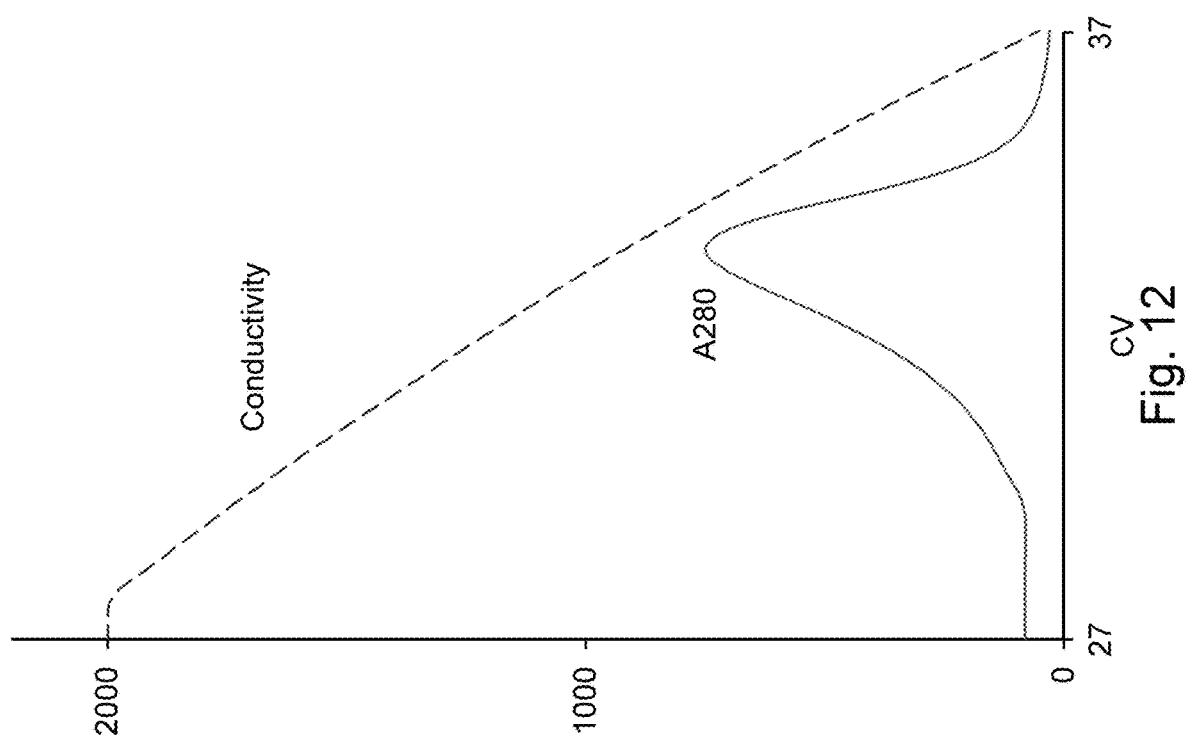

FIG. 12. The concentration of ammonium sulfate was reduced from 2 M to zero over a 9 CV gradient at pH 3.0 to determine the minimum concentration of ammonium sulfate required to keep the antibody bound to the protein A resin at low pH values. At least 1700 mM ammonium sulfate is required to keep the antibody bound to the resin at low pH.

Figure 13:
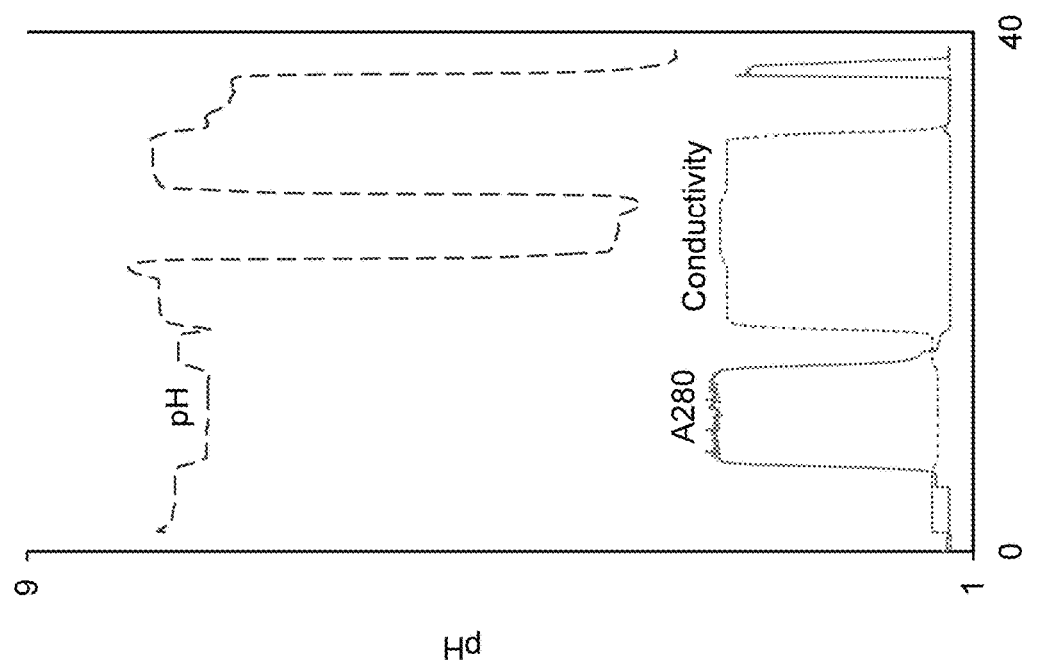

FIG. 13. Protein concentration, conductivity and pH versus column volumes using a pH 3.0, 2 M ammonium sulfate, 100 mM glycine wash. The high level of ammonium sulfate prevented the low pH elution of the antibody, potentially enabling on-column viral inactivation.

Figure 14:
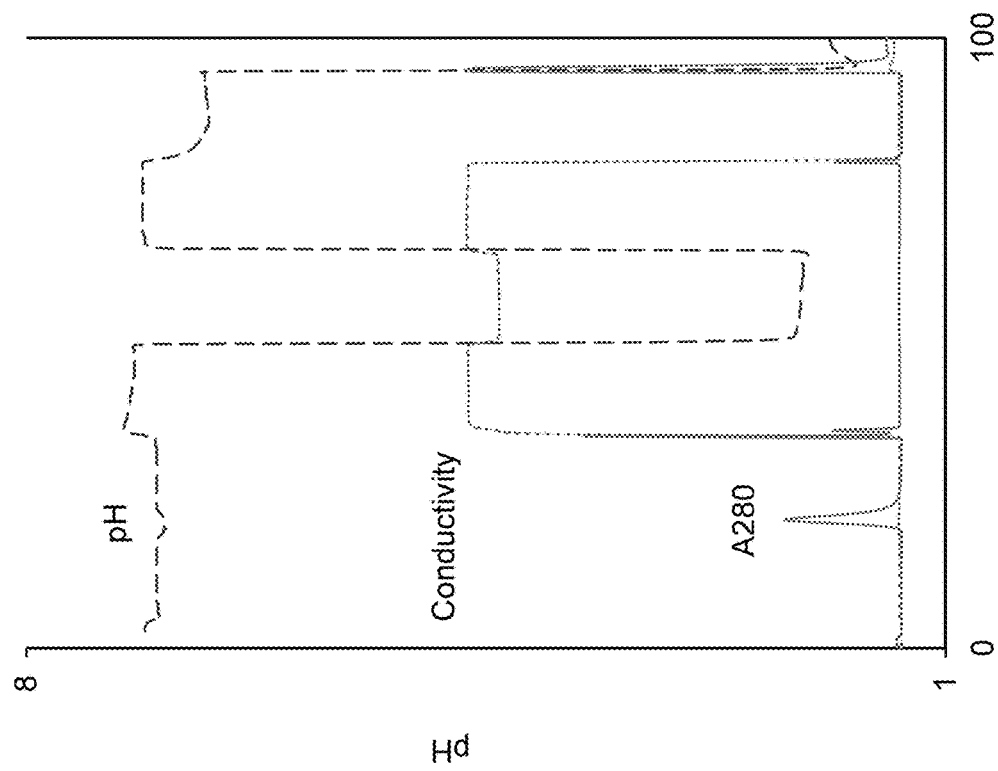

FIG. 14. Protein concentration, conductivity and pH versus column volumes using a pH 3.5, 2 M ammonium sulfate, 100 mM citrate wash to keep the antibody bound to the mixed mode anion exchange resin (Capto Adhere) resin at low pH.

Figure 15:
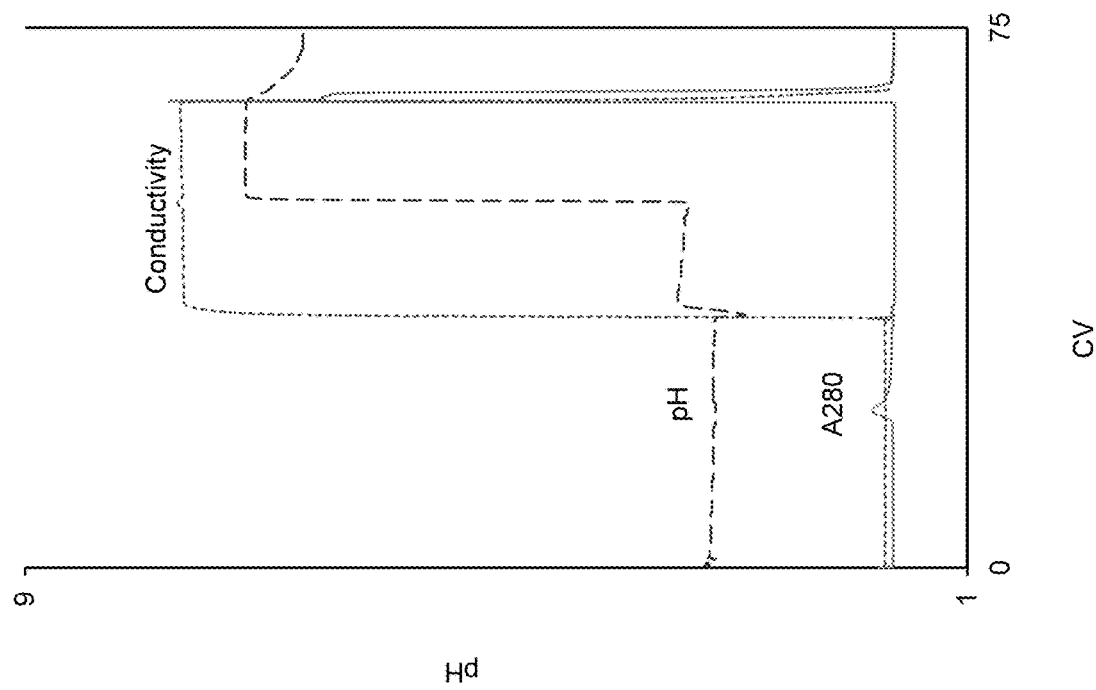

FIG. 15. Protein concentration, conductivity and pH versus column volumes using a pH 8.0, 2 M ammonium sulfate, 50 mM phosphate wash to keep the antibody bound to the mixed mode cation exchange resin (Capto MMC) resin at high pH.

DETAILED DESCRIPTION OF THE INVENTION

I. Definitions

Throughout this disclosure, the term "a" or "an" entity refers to one or more of that entity; for example, "a polypeptide," is understood to represent one or more polypeptides. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

As used herein, the term "about" allows for the degree of variation inherent in the methods and in the instrumentation used for measurement or quantitation. For example, depending on the level of precision of the instrumentation used, standard error based on the number of samples measured, and rounding error, the term "about" includes, without limitation, ±10%.

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "polypeptide" as used herein refers to a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. If a single polypeptide is the discrete functioning unit and does require permanent physical association with other polypeptides in order to form the discrete functioning unit, the terms "polypeptide" and "protein" as used herein are used interchangeably. If discrete functional unit is comprised of more than one polypeptide that physically associate with one another, the term "protein" as used herein refers to the multiple polypeptides that are physically coupled and function together as the discrete unit. Thus, as used herein, a "peptide," a "peptide fragment," a "protein," an "amino acid chain," an "amino acid sequence," or any other term used to refer to a chain or chains of two or more amino acids, are generically included in the definition of a "polypeptide," even though each of these terms can have a more specific meaning. The term "polypeptide" can be used instead of, or interchangeably with any of these terms. The term further includes polypeptides which have undergone post-translational or post-synthesis modifications, for example, glycosylation, acetylation, phosphorylation, amidation, derivatization by known protecting/blocking groups, proteolytic cleavage, or modification by non-naturally occurring amino acids.

"Recombinantly expressed polypeptide" and "recombinant polypeptide" as used herein refer to a polypeptide expressed from a host cell that has been genetically engineered to express that polypeptide. The recombinantly expressed polypeptide can be identical or similar to polypeptides that are normally expressed in the host cell. The recombinantly expressed polypeptide can also be foreign to the host cell, i.e., heterologous to peptides normally expressed in the host cell. Alternatively, the recombinantly expressed polypeptide can be chimeric in that portions of the polypeptide contain amino acid sequences that are identical or similar to polypeptides normally expressed in the host cell, while other portions are foreign to the host cell. Host cells include, but are not limited to, prokaryotic cells, eukaryotic cells, plant cells, yeast cells, animal cells, insect cells, avian cells, and mammalian cells. As used herein, the terms "recombinantly expressed polypeptide" and "recombinant polypeptide" also encompasses an antibody produced by a hybridoma.

The term "expression" or "expresses" are used herein to refer to transcription and translation occurring within a host cell. The level of expression of a product gene in a host cell can be determined on the basis of either the amount of corresponding mRNA that is present in the cell or the amount of the protein encoded by the product gene that is produced by the cell. For example, mRNA transcribed from a product gene is desirably quantitated by northern hybridization. Sambrook et al., Molecular Cloning: A Laboratory Manual, pp. 7.3-7.57 (Cold Spring Harbor Laboratory Press, 1989). Protein encoded by a product gene can be quantitated either by assaying for the biological activity of the protein or by employing assays that are independent of such activity, such as western blotting, ELISA, HPLC, forteBIO, Bradford assay, absorbance at 280 nm, or radioimmunoassay using antibodies that are capable of reacting with the protein. Sambrook et al., Molecular Cloning: A Laboratory Manual, pp. 18.1-18.88 (Cold Spring Harbor Laboratory Press, 1989).

The term "solution" refers to a mixture of one or more liquids (solvents) with one or more solids (solutes), such as a salt, a polymer, or a polypeptide. As used herein, a solution includes a buffer solution.

A "buffer" is a solution that resists changes in pH by the action of its acid-base conjugate components. Various buffers which can be employed depending, for example, on the desired pH of the buffer are described in Buffers. A Guide for the Preparation and Use of Buffers in Biological Systems, Gueffroy, D., ed. Calbiochem Corporation (1975). Many buffers are known in the art for use in buffer solutions and include, but are not limited to, histidine, citrate, phosphate, succinate, tris(hydroxymethyl)aminomethane (Tris), acetate, glycine, aconitate, maleate, phthalate, cacodylate, barbitol, 2-(N-morpholino)ethanesulfonic acid (MES), bis (2-hydroxyethyl)imino-tris-(hydroxymethyl)methane (Bis-tris), N-(2-Acetamido)iminodiacetic acid (ADA), piperazine-N,N'-bis(2-ethanesulfonic acid) (PIPES), 1,3-bis[tris (hydroxymethyl)-methylamino]propane (Bistrispropane). N-(Acetamido)-2-aminoethanesulfonic acid (ACES), 3-(N-morpholino)propanesulfonic acid (MOPS), N,N'-bis(2-hydroxyethyl)-2-amino-ethanesulfonic acid (BES), N-tris(hydroxymethyl)methyl-2-amino-ethanesulfonic acid (TES), N-2-hydroxyethylpiperazine-N'-ethanesulfonic acid (HEPES), N-2-hydroxyethylpiperazine-N'-propanesulfonic acid (HEPPS), N-tris(hydroxymethyl)methylglycine (Tricine), N,N-bis(2-hydroxyethyl)glycine (Bicine), glycylglycine, N-tris(hydroxymethyl)methyl-3-amino-propanesulfonic acid (TAPS), 1,3-bis[tris(hydroxymethyl)-methylamino] propane (Bistrispropane), as well as combinations of these.

The term "loading buffer" refers to the buffer, in which the polypeptide being purified is applied to a purification device, e.g., a chromatography column or a filter cartridge. Typically, the loading buffer is selected so that separation of the polypeptide of interest from unwanted impurities can be accomplished.

The terms "wash solution" and "wash buffer" are used interchangeably herein and refer to the buffer used to remove contaminant(s), such as process-related impurities, from the polypeptide-bound purification device (e.g., a chromatography matrix) without removing significant amounts of the polypeptide of interest. The wash solution can comprise a salt, a detergent, a solvent, a polymer, or any combinations thereof.

The terms "elution solution" and "elution buffer" are used interchangeably herein and refer to the buffer, which is typically used to remove (elute) the polypeptide of interest from the purification device (e.g., a chromatographic column or filter cartridge) to which it was applied earlier. Typically, the elution solution is selected so that separation of the polypeptide of interest from unwanted impurities can be accomplished. Often, the concentration of a particular ingredient, such as a particular salt (e.g. NaCl) in the elution elution is varied during the elution procedure (gradient). The gradient can be continuous or stepwise (interrupted by hold periods). In certain embodiments, low pH, such as a pH value below 4.5, is used in an elution solution.

The term "chromatography" refers to the process by which a solute of interest, typically a polypeptide, in a mixture is separated from other solutes in a mixture as a result of differences in rates at Which the individual solutes of the mixture migrate through a stationary medium under the influence of a moving phase, or in bind and elute processes. The chromatography steps of the present invention can employ any type of chromatographic method. For example, such methods include without limitation: gas chromatography, liquid chromatography (e.g., high performance liquid chromatography); affinity chromatography (such as Protein-A or antibody-antigen affinity chromatography); supercritical fluid chromatography; ion exchange chromatography (such as anion or cation exchange chromatography); size-exclusion chromatography; reversed phase chromatography; two-dimensional chromatography; simulated moving bed chromatography, pyrolysis gas chromatography, fast protein (FPLC) chromatography; countercurrent chromatography; chiral chromatography; aqueous normal phase (ANP) chromatography; mixed mode chromatography; and, pseudo-affinity chromatography.

Any or all chromatographic steps of the invention can be carried out by any mechanical means. Chromatography can be carried out in a column. The column can be run with or without pressure and from top to bottom or bottom to top. The direction of the flow of fluid in the column can be reversed during the chromatography process. Chromatography can also be carried out using a batch process in which the solid support is separated from the liquid used to load, wash, and elute the sample by any suitable means, including gravity, centrifugation, or filtration. Chromatography can also be carried out by contacting the sample with a filter that absorbs or retains some molecules in the sample more strongly than others.

The term "affinity chromatography" refers to a protein separation technique in which a polypeptide of interest is reversibly and specifically bound to a biospecific ligand. Preferably, the biospecific ligand is covalently attached to a chromatographic solid phase material and is accessible to the polypeptide of interest in solution as the solution contacts the chromatographic solid phase material. The polypeptide of interest (e.g., antibody, enzyme, or receptor protein) retains its specific binding affinity for the biospecific ligand (antigen, substrate, cofactor, or hormone, for example) during the chromatographic steps, while other solutes and/or proteins in the mixture do not bind appreciably or specifically to the ligand. Binding of the polypeptide of interest to the immobilized ligand allows contaminating proteins or protein impurities to be passed through the chromatographic medium while the protein of interest remains specifically bound to the immobilized ligand on the solid phase material. The specifically bound polypeptide of interest is then removed in active form from the immobilized ligand with low pH, high pH, high salt, competing ligand, and the like, and passed through the chromatographic column with the elution buffer, free of the contaminating proteins or protein impurities that were earlier allowed to pass through the column. Any component can be used as a ligand for purifying its respective specific binding protein, e.g. antibody.

The terms "Protein A" and "ProA" are used interchangeably herein and encompasses Protein A recovered from a native source thereof, Protein A produced synthetically (e.g. by peptide synthesis or by recombinant techniques), and variants thereof which retain the ability to bind proteins which have a CH2/CH3 region, such as an Fc region. Protein A can be purchased commercially, for example, from Repligen, Pharmacia and Fermatech. Protein A is generally immobilized on a solid phase support material. The term "Prod." also refers to an affinity chromatography resin or column containing chromatographic solid support matrix to which is covalently attached Protein A.

In practice, Protein A chromatography involves using Protein A immobilized to a solid support. Protein G and Protein LG can also be used for affinity chromatography. The solid support is a non-aqueous matrix onto which Protein A adheres. Such supports include agarose, sepharose, class, silica, polystyrene, collodion charcoal, sand, and any other suitable material. Such materials are well known in the art. Any suitable method can be used to affix the second protein to the solid support Methods for affixing proteins to suitable solid supports are well known in the art. Such solid supports, with and without immobilized Protein A, are readily available from many commercial sources including such as Vector Laboratory (Burlingame, Calif.), Santa Cruz Biotechnology (Santa Cruz, Calif.), BioRad (Hercules, Calif.), Amersham Biosciences (part of GE Healthcare, Uppsala, Sweden) and Millipore (Billerica, Mass.). Protein A immobilized to a pore glass matrix is commercially available as PROSEP®-A (Millipore). The solid phase can also be an agarose-based matrix. Protein A immobilized on an agarose matrix is commercially available as MABSELECT™ (GE Healthcare, Uppsala, Sweden).

The term "mixed-mode chromatography" refers to a purification process using mixed mode adsorbents which provide multiple modes of interaction, such as hydrophobic, cation exchange, anion exchange, and hydrogen bonding interaction between the polypeptide of interest and the adsorbent ligands. A mixed-mode anion exchange resin is one that has both anion exchange groups and hydrophobic groups on the ligand. Commercially available mixed mode chromatography resins include, but are not limited to, CAPTO™ MMC, CAPTO™ MMC ImpRes, CAPTO™ Blue, BLUE SEPHAROSE™ 6 Fast Flow, CAPTO™ Adhere, and CAPTO™ Adhere ImpRes from GE Healthcare Life Sciences, or ESHMUNO® HCX from EMD Millipore, or NUVIA™ cPrime, CHT™ Ceramic Hydroxyapatite, and CFT™ Ceramic Fluoroapatite from Bio-Rad.

The terms "anion exchange resin," "anion exchange adsorbent," or "anion exchange matrix" are used herein to refer to a solid phase which is positively charged, e.g. having one or more positively charged ligands, such as quaternary amino groups, attached thereto. Commercially available anion exchange resins include DEAE, SEPHAROSE™ Fast Flow, Q SEPHAROSE™ Fast Flow, Q SEPHAROSE™

High Performance, Q SEPHAROSE™ XL, CAPTO™ DEAE, CAPTO™ Q, and CAPTO™ Q ImpRes from GE Healthcare Life Sciences, or FRACTOGEL® EMD TMAE HiCap, FRACTOGEL® EMD DEAF, and ESHMUNO® from EMD Millipore, or UNOSPHERE™ Q and NUVIA™ Q from Bio-Rad.

The terms "cation exchange resin," "cation exchange adsorbent," or "cation exchange matrix" refer to a solid phase which is negatively charged, and which thus has free cations for exchange with cations in an aqueous solution passed over or through the solid phase. A negatively charged ligand attached to the solid phase to form the cation exchange resin can, e.g., be a carboxylate or sulfonate. Commercially available cation exchange resins include carboxy-methyl-cellulose, sulphopropyl (SP) immobilized on agarose (e.g. SP SEPHAROSE™ XL, SP-SEPHAROSE™ Fast Flow, SP SEPHAROSE™ High Performance, CM SEPHAROSE™ Fast Flow, CM SEPHAROSE™ High Performance, CAPTO™ S, and CAPTO™ SP ImpRes from GE Healthcare Life Sciences, or FRACTOGEL® EMD SE HiCap, FRACTOGEL® EMD SO$^{3-}$, FRACTOGEL® EMD COO$^-$, ESHMUNO® S, and ESHMUNO® CPX from EMD Millipore, or UNOSPHERE™ S and NUVIA™ S from Bio-Rad).

As used herein, the terms "substantially reduce the elution of the polypeptide" or "substantial reduction of the polypeptide elution" are intended to mean that less than 30% of the target polypeptide is eluted from the chromatography matrix in a low pH and high salt wash solution. In one embodiment, less than 25%, less than 20%, less than 15%, less than 10%, or less than 5% of the target polypeptide is eluted from the chromatography matrix in a low pH high salt wash solution.

As used herein, the terms "percent recovery" and "percent purity," are intended to mean the recovery or purity achieved when a target compound (e.g., a protein) is conveyed through a purification step or procedure, compared to the quantity or purity of the target compound in the sample prior to the purification step or procedure. Achieving an increase in percent purity entails obtaining a product with reduced levels of contaminants (in proportion to the target compound) when a sample is compared before and after a purification step or procedure. Preferred percentages within the meaning of percent recovery and percent purity as defined above include, without limitation, at least about 50%, at least about 60%, at least about 70%, at least about 80%, at least about 90%, at least about 95%, at least about 98%, and at least about 99%.

Methods for the determination of yield or purity of a polypeptide are known to those of skill in the art. Yield or purity of a polypeptide can be determined by any suitable, art-recognized method of analysis (e.g., band intensity on a silver stained gel, polyacrylamide gel electrophoresis, ELISA, HPLC and the like). An exemplary method is size-exclusion chromatography (SEC) high-performance liquid chromatography (HPLC), described herein below. Purity can be determined using relative "area under the curve" (AUC) values, which can typically be obtained for peaks in a chromatogram, such as an HPLC chromatogram. Optionally, purifies are determined by chromatographic or other means using a standard curve generated using a reference material of known purity. Purity can also be determined on a weight-by-weight basis.

As used herein, the term "inactivate" or other forms of this word (e.g., inactivation, inactivated, inactivates, etc.) when used in reference to viruses is intended to indicate not only complete virus inactivation (i.e., no detectable infectious virus) but also the detectable reducing or reduction of infectious virus titers (i.e., lowering or lowered levels of detectable infectious virus). Thus, the reducing or reduction of infectious virus titers is included within the meaning of "virus inactivation" (and other forms of this term) whether or not such reducing or reduction is explicitly stated herein. Quantification methods for viral inactivation are well known in the art. Methods such as plaque assays can be used. Plaque assays determine the number of plaque forming units (pfu) in a virus sample, assuming that each plaque formed is representative of one infective virus particle or TCID50 assays, where an endpoint dilution assay quantifies the amount of virus required to kill 50% of infected hosts or to produce a cytopathic effect in 50% of inoculated tissue culture cells.

The term "polymer" refers to a molecule formed by covalent linkage of two or more monomers, where the monomers are not amino acids. Non-limiting examples of polymers include polyethyl glycol, polypropyl glycol, and copolymers of ethylene and propylene glycol.

The term "detergent" refers to nonionic or zwitterionic surfactants such as polysorbates (e.g. polysorbates 20 or 80); poloxamers (e.g. poloxamer 188); octylphenol ethylene oxide condensate (also known as Octoxynol-9, t-octylphenoxypolyethoxyethanol, TRITON™, or TRITON™ X-100); 3-[(3-cholamidopropyl)dimethylammonio]-1-propanesulfonate (CHAPS); 3-[(3-cholamidopropyl)dimethylammonio]-2-hydroxy-1-propanesulfonate (CHAPSO); sodium dodecyl sulfate (SDS), sodium laurel sulfate, sodium octyl glycoside; laurel-, myristyl-, linoleyl- or stearyl-sulfobetaine; lauryl-, myristyl-, linoleyl- or stearyl-sarcosine; linoleyl-, myristyl-, or cetyl-betaine, lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and 1-ethyl-1-(2-hydroxyethyl)-2-isoheptadecylimidazolinium ethylsulfate (e.g., the MONAQUAT® series, Mona Industries, Inc., Paterson, N.J.). Non-limiting examples of commercial products comprising compounds similar to TRITON™ X-100 include CONCO™ NI, DOWFAX™ 9N, IGEPAL™ CO, MAKON™, NEUTRONYX® 600's, NONIPOL™ NO, POLYTERGENT® B, RENEX™ 600's, SOLAR™ NO, STEROX™, SERFONIC™ N, T-DET-N™, TERGITOL™ NP, and TRITON™ N.

The term "antibody" is used to mean an immunoglobulin molecule that recognizes and specifically binds to a target, such as a protein, polypeptide, peptide, carbohydrate, polynucleotide, lipid, or combinations of the foregoing etc., through at least one antigen recognition site within the variable region of the immunoglobulin molecule. As used herein, the term encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, monovalent or monospecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively.

The term "Fc-containing polypeptide" as used herein refers to a protein in which one or more polypeptides are linked to an Fc region or a variant or derivative thereof. The term "Fc" or "Fc region" refers to a C-terminal region of an IgG heavy chain, including any functional variants of IgG Fc that retains the ability of binding to Protein A. One example of an Fc-containing polypeptide is ENBREL® (etanercept) which is a fusion protein fusing a tumor necrosis factor (TNF) receptor to the constant end of the IgG1 antibody.

The term "CH2/CH3-containing polypeptide" as used herein refers to a protein in which one or more polypeptides are linked to the CH2/CH3 domains of an IgG heavy chain, or a functional variant or derivative thereof.

A "fusion" or "chimeric" protein comprises a first amino acid sequence linked to a second amino acid sequence with which it is not naturally linked in nature. The amino acid sequences which normally exist in separate proteins can be brought together in the fusion polypeptide, or the amino acid sequences which normally exist in the same protein can be placed in a new arrangement in the fusion polypeptide, e.g., fusion of a Factor VIII domain of the invention with an immunoglobulin Fc domain. A fusion protein is created, for example, by chemical synthesis, or by creating and translating a polynucleotide in which the peptide regions are encoded in the desired relationship. A chimeric protein can further comprises a second amino acid sequence associated with the first amino acid sequence by a covalent, non-peptide bond or a non-covalent bond.

The term "linked" as used herein refers to a first amino acid sequence covalently or non-covalently joined to a second amino acid sequence. The term "covalently linked" or "covalent linkage" refers to a covalent bond, e.g., a disulfide bond, a peptide bond, or one or more amino acids, e.g., a linker, between the two moieties that are linked together. The first amino acid sequence can be directly joined or juxtaposed to the second amino acid sequence or alternatively an intervening sequence can covalently join the first sequence to the second sequence. The term "linked" means not only a fusion of a first amino acid sequence to a second amino acid sequence at the C-terminus or the N-terminus, but also includes insertion of the whole first amino acid sequence (or the second amino acid sequence) into any two amino acids in the second amino acid sequence (or the first amino acid sequence, respectively).

The term "heterologous moiety" refers to a polypeptide or other moiety which is derived from a distinct entity from that of the entity to which it is being compared. For instance, a heterologous polypeptide can be synthetic, or derived from a different species, different cell type of an individual, or the same or different type of cell of distinct individuals. In one embodiment, a heterologous moiety can be a polypeptide fused to another polypeptide to produce a fusion polypeptide or protein. In another embodiment, a heterologous moiety can be a non-polypeptide such as PEG conjugated to a polypeptide or protein.

The term "monomer-dimer hybrid" used herein refers to a chimeric protein comprising a first polypeptide chain and a second polypeptide chain, which are associated with each other by a covalent bond, wherein the first chain comprises a biologically active molecule, e.g., a clotting factor such as Factor IX, Factor VIII, or Factor VII, and an Fc region, and the second chain comprises, consists essentially of, or consists of an Fc region without the clotting factor. The monomer-dimer hybrid construct thus is a hybrid comprising a monomer aspect having only one biologically active molecule and a dimer aspect having two Fc regions.

As used herein, the term "half-life" refers to a biological half-life of a particular polypeptide in vivo. Half-life can be represented by the time required for half the quantity administered to a subject to be cleared from the circulation and/or other tissues in the animal.

The term "hybridoma" as used herein refers to a cell created by fusion of an immortalized cell derived from an immunologic source and an antibody-producing cell. The resulting hybridoma is an immortalized cell that produces antibodies. The individual cells used to create the hybridoma can be from any mammalian source, including, but not limited to, rat, hamster, pig, rabbit, sheep, pig, goat, and human. The term also encompasses trioma cell lines, which result when progeny of heterohybrid myeloma fusions, which are the product of a fusion between human cells and a murine myeloma cell line, are subsequently fused with a plasma cell. Furthermore, the term is meant to include any immortalized hybrid cell line that produces antibodies such as, for example, quadromas (See, e.g., Milstein et al., *Nature*, 537:3053 (1983)).

II. Production and Purification of Polypeptides of Interest

A. Polypeptides of Interest

The present invention can be used to inactivate virus that is present during production of any polypeptide that is expressed in a host cell. The polypeptide can be expressed from a gene that is endogenous to the host cell, or from a gene that is introduced into the host cell through genetic engineering. The polypeptide can be one that occurs in nature, or can alternatively have a sequence that was engineered or selected by the hand of man. An engineered polypeptide can be assembled from other polypeptide segments that individually occur in nature, or can include one or more segments that are not naturally occurring.

A polypeptide of interest often has a desirable biological or chemical activity. For example, the present invention can be employed to inactivate virus that is present during the production of a pharmaceutically or commercially relevant enzyme, receptor, antibody, hormone, regulatory factor, antigen, binding agent, etc.

The following is a detailed description of some of the polypeptides that can be expressed in a cell culture and purified in accordance with the virus inactivation method of the present invention.

Clotting Factors

In some embodiments, the protein of interest comprises a clotting factor. Clotting factor, as used herein, means any molecule, or analog thereof, which prevents or decreases the duration of a bleeding episode in a subject with a hemostatic disorder. For example, a clotting factor used in the invention can be a full-length clotting factor, a mature clotting factor, or a chimeric clotting factor. In other words, it means any molecule having clotting activity. Clotting activity, as used herein, means the ability to participate in a cascade of biochemical reactions that culminates in the formation of a fibrin clot and/or reduces the severity, duration or frequency of hemorrhage or bleeding episode. Examples of clotting factors can be found in U.S. Pat. No. 7,404,956, which is herein incorporated by reference.

The clotting factor can be a factor that participates in the extrinsic pathway. The clotting factor can be a factor that participates in the intrinsic pathway. Alternatively, the clotting factor can be a factor that participates in both the extrinsic and intrinsic pathway.

Non-limiting examples of clotting factors include factor I (fibrinogen), factor II (prothrombin), Tissue factor, factor V (proaccelerin, labile factor), factor VII (stable factor, proconvertin), factor VIII (Antihemophilic factor A), factor IX (Antihemophilic factor B or Christmas factor), factor X (Stuart-Prower factor), factor XI (plasma thromboplastin antecedent), factor XII (Hageman factor), factor XIII (fibrin-stabilizing factor), von Willebrand Factor (VWF), prekallikrein (Fletcher factor), high-molecular-weight kininogen (HMWK) (Fitzgerald factor), fibronectin, antithrombin III, heparin cofactor II, protein C, protein S, protein Z, plasminogen, alpha 2-anti plasmin, tissue plasminogen activator (tPA), urokinase, plasminogen activator inhibitor-1 (PAI1), and plasminogen activator inhibitor-2 (PAI2).

In one embodiment, the clotting factor can be a human clotting factor or a non-human clotting factor, e.g., derived from a non-human primate, a pig or any mammal. The clotting factor can be chimeric clotting factor, e.g., the clotting factor can comprise a portion of a human clotting factor and a portion of a porcine clotting factor or a portion of a first non-human clotting factor and a portion of a second non-human clotting factor.

In another embodiment, the clotting factor can be an activated clotting factor. Alternatively, the clotting factor can be an inactive form of a clotting factor, e.g., a zymogen. The inactive clotting factor can undergo activation subsequent to being linked to at least a portion of apt immunoglobulin constant region. The inactive clotting factor can be activated subsequent to administration to a subject. Alternatively, the inactive clotting factor can be activated prior to administration.

Factor FIX

"Factor IX protein" or "FIX protein" as used herein, means functional Factor FIX protein in its normal role in coagulation, unless otherwise specified. Thus, the FIX polypeptide includes variant polypeptides that are functional and the polynucleotides that encode such functional variant polypeptides. In one embodiment, the FIX polypeptides are the human, bovine, porcine, canine, feline, and murine FIX polypeptides. The full length polypeptide and polynucleotide sequences of FIX are known, as are many functional variants, e.g., fragments, mutants and modified versions. FIX polypeptides include full-length FIX, full-length FIX minus Met at the N-terminus, full-length FIX minus the signal sequence, mature FIX (minus the signal sequence and propeptide), and mature FIX with an additional Met at the N-terminus. FIX can be made by recombinant means ("recombinant Factor IX" or "rFIX"), it is not naturally occurring or derived from plasma.

A great many functional FIX variants are known. International publication number WO 02/040544 A3, which is herein incorporated by reference in its entirety, discloses mutants that exhibit increased resistance to inhibition by heparin at page 4, lines 9-30 and page 15, lines 6-31. International publication number WO 03/020764 A2, which is herein incorporated by reference in its entirety, discloses FIX mutants with reduced. T cell immunogenicity in Tables 2 and 3 (on pages 14-24), and at page 12, lines 1-27. International publication number WO 2007/149406 A2, which is herein incorporated by reference in its entirety, discloses functional mutant FIX molecules that exhibit increased protein stability, increased in vivo and in vitro half-life, and increased resistance to proteases at page 4, line 1 to page 19, line 11. WO 2007/149406 A2 also discloses chimeric and other variant FIX molecules at page 19, line 12 to page 20, line 9. International publication number WO 08/118507 A2, which is herein incorporated by reference in its entirety, discloses FIX mutants that exhibit increased clotting activity at page 5, line 14 to page 6, line 5. International publication number WO 09/051717 A2, which is herein incorporated by reference in its entirety, discloses FIX mutants having an increased number of N-linked and/or O-linked glycosylation sites, which results in an increased half-life and/or recovery at page 9, line 11 to page 20, line 2. International publication number WO 09/137254 A2, which is herein incorporated by reference in its entirety, also discloses Factor IX mutants with increased numbers of glycosylation sites at page 2, paragraph [006] to page 5, paragraph [011] and page 16, paragraph [044] to page 24, paragraph [057]. International publication number WO 09/130198 A2, which is herein incorporated by reference in its entirely, discloses functional mutant FIX molecules that have an increased number of glycosylation sites, which result in an increased half-life, at page 4, line 26 to page 12, line 6. International publication number WO 09/140015 A2, which is herein incorporated by reference in its entirety, discloses functional FIX mutants that an increased number of Cys residues, which can be used for polymer (e.g., PEG) conjugation, at page 11, paragraph [0043] to page 13, paragraph [0053]. The FIX polypeptides described in International Application No. PCT/US2011/043569 filed Jul. 11, 2011 and published as WO 2012/006624 on Jan. 12, 2012 are also incorporated herein by reference in its entirety.

In one embodiment, the polypeptide of interest is a long-acting or long-lasting FIX polypeptide that is a chimeric polypeptide comprising a FIX polypeptide and an FcRn binding partner. In certain embodiments, the polypeptide of interest is rFIX-Fc which is a fusion protein comprising a single molecule of human recombinant coagulation FIX (rFIX) covalently linked to the dimeric Fc region of immunoglobulin G1 (IgG1) with no intervening sequence. The term "FcRn binding partner" is defined herein.

Factor VIII

"Factor VIII protein" or "FVIII protein" as used herein, means functional Factor VIII protein in its normal role in coagulation, unless otherwise specified. Thus, the term FVIII includes variant proteins that are functional. In one embodiment, the FVIII protein is the human, porcine, canine, rat, or murine FVIII protein. A functional FVIII protein can be a fusion protein, such as, but not limited to, a fusion protein comprising a fully or partially B domain-deleted FVIII, at least a portion of an immunoglobulin constant region, e.g., an Fc domain, or both. Myriad functional FVIII variants have been constructed and can be used as recombinant FVIII proteins as described herein. See PCT Publication Nos. WO 2011/069164 A2, WO 2012/006623 A2, WO 2012/006635 A2, or WO 2012/006633 A2, all of which are incorporated herein by reference in their entirety. FVIII can be a single chain FVIII or a dual chain FVIII.

A great many functional FVIII variants are known. In addition, hundreds of nonfunctional mutations in FVIII have been identified in hemophilia patients. See, e.g., Cutler et al., Hum. Mutat. 19:274-8 (2002), incorporated herein by reference in its entirety. In addition, comparisons between FVIII from humans and other species have identified conserved residues that are likely to be required for function. See, e.g., Cameron et al., Thromb. Haemost. 79:317-22 (1998) and U.S. Pat. No. 6,251,632, incorporated herein by reference in their entirety.

The human FVIII amino acid sequence was deduced from cDNA as shown in U.S. Pat. No. 4,965,199, which is incorporated herein by reference in its entirety. Native mature human FVIII derived from the cDNA sequence (i.e., without the secretory signal peptide but prior to other post-translational processing) can be found as SEQ NO:1 in WO 2013/123457 A1, which is incorporated herein by reference in its entirety. Partially or fully B domain-deleted FVIII is functional and has been used in commercial FVIII therapeutics. See, e.g., EP 506757 B2, which is incorporated herein by reference in its entirety.

In one embodiment, the polypeptide of interest is a long-acting or long-lasting FVIII polypeptide that is a chimeric polypeptide comprising a FVIII polypeptide and an FcRn binding partner. In certain embodiments, the polypeptide of interest is rFVIII-Fc which is a fusion protein comprising a single molecule of human recombinant coagulation FVIII (rFVIII) covalently linked to the dimeric Fc region of immunoglobulin G1 (IgG1) with no intervening sequence.

Factor VII

"Factor VII protein" or "FVII protein" as used herein, means functional Factor VII protein in its normal role in coagulation, unless otherwise specified. It can be a mature form of Factor VII or a variant thereof. Factor VII is a serine protease that is part of the coagulation cascade. FVII includes a Gla domain, two EGF domains (EGF-1 and EGF-2), and a serine protease domain (or peptidase S1 domain) that is highly conserved among all members of the peptidase S1 family of serine proteases, such as for example with chymotrypsin. FVII occurs as a single chain zymogen, an activated zymogen-like two-chain polypeptide (e.g., activatable FVII) and a fully activated two-chain form.

As used herein, a "zymogen-like" protein or polypeptide refers to a protein that has been activated by proteolytic cleavage, but still exhibits properties that are associated with a zymogen, such as, for example, low or no activity, or a conformation that resembles the conformation of the zymogen form of the protein. For example, when it is not bound to tissue factor, the two-chain activated form of FVII is a zymogen-like protein; it retains a conformation similar to the uncleaved FVII zymogen, and, thus, exhibits very low activity. Upon binding to tissue factor, the two-chain activated form of FVII undergoes conformational change and acquires its full activity as a coagulation factor.

Exemplary FVII variants include those with increased specific activity, e.g., mutations that increase the activity of FVII by increasing its enzymatic activity (Kcat or Km). Such variants have been described in the art and include, e.g., mutant forms of the molecule as described for example in Persson et al., Proc. Natl. Acad Sci. USA 98:13583 (2001); Petrovan and Ruf, J. Biol. Chem. 276:6616 (2001); Persson et al., J. Biol. Chem. 276:29195 (2001); Soejima et al., J. Biol. Chem. 276:17229 (2001); Soejima et al, J. Biol. Chem. 247:49027 (2002).

In one embodiment, the polypeptide of interest is a long-acting or long-lasting FVII polypeptide that is a chimeric polypeptide comprising a FVII polypeptide and an FcRn binding partner. In certain embodiments, the polypeptide of interest is rFVII-Fc which is a fusion protein comprising a single molecule of human recombinant coagulation FVII (rFIX) covalently linked to the dimeric Fc region of immunoglobulin G1 (IgG1) with no intervening sequence.

Chimeric Clotting Factors

In certain embodiments, the polypeptide of interest comprises a chimeric clotting factor. In certain embodiments, the chimeric clotting factor comprises a clotting factor and a CH2/CH3 domain. CH2 and CH3 are two constant domains located in the Fc region of an IgG heavy chain. The CH2 domain of a human IgG Fc region usually extends from amino acids 231 to amino acid 341 according to the numbering system as described in Kabat et al. 1991, Sequences of Proteins of immunological Interest, U. S. Department of Public Health, Bethesda; MD, incorporated herein by reference in its entirety. The CH3 domain of a human IgG Fc region usually extends from amino acids 342 to 447 according to the numbering system of Kabat et al., 1991. A CH2/CH3 domain includes any functional derivative or variants of the CH2 and CH3 domains.

In certain embodiments, the chimeric clotting factor comprises a clotting factor and an Fc region. In one embodiment, the chimeric clotting factor is FIX-Fc, FVIII-Fc, or FVII-Fc. Various examples of FIX-Fc, FVIII-Fc, or FVII-Fc chimeric and hybrid polypeptides are described, for example, in U.S. Pub. Nos. 2013/020259.5 A1, 2013/0108629 A1, and U.S. Pat. No. 8,329,182, which are incorporated herein by reference in their entirety.

In one embodiment, the polypeptide of interest is a long-acting or long-lasting clotting factor that is a chimeric polypeptide comprising a clotting factor and an FcRn binding partner. In certain embodiments, the polypeptide of interest is a fusion protein comprising a single molecule of human recombinant clotting factor covalently linked to the dimeric Fc region of immunoglobulin G1 (IgG1) with no intervening sequence.

Heterologous Moieties

In certain embodiments, the polypeptide of interest is a chimeric polypeptide comprising a biologically active molecule and at least one heterologous moiety. In one embodiment, the biologically active molecule is a clotting factor. In one embodiment, the heterologous moiety is capable of extending the half-life of the clotting factor.

In certain embodiments, the heterologous moiety is an IgG or a fragment thereof, an albumin or a fragment thereof, an albumin binding moiety, a PAS sequence, a homo-amino acid polymer (HAP) sequence, transferrin or a fragment thereof, and any combinations thereof, or a non-polypeptide moiety comprising polyethylene glycol (PEG), polysialic acid, hydroxyethyl starch (HES), a derivative thereof, and any combinations thereof.

In one embodiment, the heterologous moiety comprises a first Fc region. In another embodiment, the heterologous moiety comprises a second Fc region.

As used herein, the term "Fc region" is defined as the portion of a polypeptide which corresponds to the Fc region of native immunoglobulin, i.e., as formed by the dimeric association of the respective Fc domains of its two heavy chains. A native Fc region forms a homodimer with another Fc region.

In one embodiment, the "Fc region" refers to the portion of a single immunoglobulin heavy chain beginning in the hinge region just upstream of the papain cleavage site (i.e. residue 216 in IgG, taking the first residue of heavy chain constant region to be 114) and ending at the C-terminus of the antibody. Accordingly, a complete Fc region comprises at least a hinge domain, a CH2 domain, and a CH3 domain.

The Fc region of an immunoglobulin constant region, depending on the immunoglobulin isotype can include the CH2, CH3, and CH4 domains, as well as the hinge region. Chimeric proteins comprising an Fc region of an immunoglobulin bestow several desirable properties on a chimeric protein including increased stability, increased serum half-life (see Capon et al., 1989, Nature 337:525) as well as binding to Fc receptors such as the neonatal Fc receptor (FcRn) (U.S. Pat. Nos. 6,086,875, 6,485,726, 6,030,613; WO 03/077834; US2003-0235536A1), which are incorporated herein by reference in their entirety.

In another embodiment, the "Fc region" includes an amino acid sequence of an Fe domain or derived from an Fe domain. In certain embodiments, an Fc region comprises at least one of: a hinge upper, middle, and/or lower hinge region) domain (about amino acids 216-230 of an antibody Fc region according to EU numbering), a CH2 domain (about amino acids 231-340 of an antibody Fc region according to EU numbering), a CH3 domain (about amino acids 341-438 of an antibody Fc region according to EU numbering), a CH4 domain, or a variant, portion, or fragment thereof. In other embodiments, an Fc region comprises a complete Fe domain (i.e., a hinge domain, a CH2 domain, and a CH3 domain). In some embodiments, an Fe region comprises, consists essentially of, or consists of a hinge domain (or a portion thereof) fused to a CH3 domain (or a portion thereof), a hinge domain (or a portion thereof) fused to a CH2 domain (or a portion thereof), a CH2 domain (or a portion thereof) fused to a CH3 domain (or a portion thereof), a CH2 domain (or a portion thereof) fused to both a hinge domain (or a portion thereof) and a CH3 domain (or a portion thereof). In still other embodiments, an Fc region lacks at least a portion of a CH2 domain (e.g., all or part of a CH2 domain). In a particular embodiment, an Fc region comprises or consists of amino acids corresponding to EU numbers 221 to 447.

The Fc regions of the invention may employ art-recognized Fc variants which are known to impart a change (e.g., an enhancement or reduction) in effector function and/or FcR or FcRn binding. Specifically, a binding molecule of the invention may include, for example, a change (e.g., a substitution) at one or more of the amino acid positions disclosed in International PCT Publications WO88/0708941, WO96/1433941, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/06335142, WO04/074455 A2, WO04/099249A2, WO05/040217A2, WO04/044859, WO05/070963A1, WO05/077981A2, WO05/092925A2, WO05/123780A2, WO06/019447A1, WO06/047350A2; and WO06/085967A2; US Patent Publication Nos. US2007/0231329, US2007/0231329, US2007/0237765, US2007/0237766, US2007/0237767, US2007/0243188, US20070248603, US20070286859, US20080057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; 7,404,956, and 7,317,091, each of which is incorporated by reference herein. In one embodiment, the specific change (e.g., the specific substitution of one or more amino acids disclosed in the art) may be made at one or more of the disclosed amino acid positions. In another embodiment, a different change at one or more of the disclosed amino acid positions (e.g., the different substitution of one or more amino acid position disclosed in the art) can be made.

In certain embodiments, a chimeric polypeptide used in accordance with the invention comprises one or more truncated Fc regions that are nonetheless sufficient to confer Fc receptor (FcR) binding properties to the Fc region. For example, the portion of an Fc region that binds to FcRn (i.e., the FcRn binding portion) comprises from about amino acids 282-438 of IgG1, EU numbering (with the primary contact sites being amino acids 248, 250-257, 272, 285, 288, 290-291, 308-311, and 314 of the CH2 domain and amino acid residues 385-387, 428, and 433-436 of the CH3 domain. Thus, an Fc region of the invention may comprise or consist of an FcRn binding portion. FcRn binding portions may be derived from heavy chains of any isotype, including IgG1, IgG2, IgG3 and IgG4.

FcRn binding partner ("FcRn BP") comprises functional neonatal Fc receptor (FcRn) binding partners, unless otherwise specified. An FcRn binding partner is any molecule that can be specifically bound by the FcRn receptor with consequent active transport by the FcRn receptor of the FcRn binding partner. Thus, the term FcRn BP includes any variants of IgG Fc that are functional. For example, the region of the Fc portion of IgG that binds to the FcRn receptor has been described based on X-ray crystallography (Burmeister et al. 1994, Nature 372:379, incorporated herein by reference in its entirety). The major contact area of the Fe with the FcRn is near the junction of the CH2 and CH3 domains. Fc-FcRn contacts are all within a single Ig heavy chain. FcRn BPs include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of immunological Interest, U. S. Department of Public Health, Bethesda; MD, incorporated herein by reference in its entirety. The FcRn receptor has been isolated from several mammalian species including humans. The sequences of the human FcRn, rat FcRn, and mouse FcRn are known See, e.g., Story et al. 1994, J. Exp. Med. 180: 2377, incorporated herein by reference in its entirety). An FcRn BP can comprise the CH2 and CH3 domains of an immunoglobulin with or without the hinge region of the immunoglobulin. Exemplary FcRn BP variants are provided in WO 2004/101740 and WO 2006/074199, incorporated herein by reference in its entirety.

In certain embodiments, the heterologous moiety is an albumin or a fragment thereof. Human serum albumin (HSA, or HA), a protein of 609 amino acids in its full-length form, is responsible for a significant proportion of the osmotic pressure of serum and also functions as a carrier of endogenous and exogenous ligands. The term "albumin" as used herein includes full-length albumin or a functional fragment, variant, derivative, or analog thereof. Further examples of albumin or the fragments or variants thereof are disclosed in US Pat. Publ. Nos. 2008/0194481 A1, 2008/0004206 A1, 2008/0161243 A1, 2008/0261877 A1, or 2008/0153751 A1 or PCT Appl. Publ. Nos. 2008/033413 A2, 2009/058322 A1, or 2007/021494 A2, which are herein incorporated by reference in their entirety.

In certain embodiments, the heterologous moiety is an albumin binding moiety, which comprises an albumin binding peptide, a bacterial albumin binding domain, an albumin-binding antibody fragment, or any combinations thereof. For example, the albumin binding protein can be a bacterial albumin binding protein, an antibody or an antibody fragment including domain antibodies (see U.S. Pat. No. 6,696,245). An albumin binding protein, for example, can be a bacterial albumin binding domain, such as the one of streptococcal protein G (Konig, T. and Skerra, A. (1998) J. Immunol. Methods 218, 73-83). Other examples of albumin binding peptides that can be used as conjugation partner are, for instance, those having a Cys-Xaa 1-Xaa 2-Xaa 3-Xaa 4-Cys consensus sequence, wherein Xaa 1 is Asp, Asn, Ser, Thr, or Trp; Xaa 2 is Asn, Gin, H is, Ile, Leu, or Lys; Xaa 3 is Ala, Asp, Phe, Trp, or Tyr; and Xaa 4 is Asp, Gly, Leu, Phe, Ser, or Thr as described in US patent application 2003/0069395 or Dennis et al. (Dennis et al. (2002) J. Biol. Chem. 277, 35035-35043).

In other embodiments, the heterologous moiety is a PAS sequence. A PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the chimeric protein. Yet, the skilled person is aware that an amino acid polymer also may form random coil conformation when residues other than alanine, serine, and proline are added as a minor constituent the PAS sequence.

Non-limiting examples of the PAS sequences forming random coil conformation comprise an amino acid sequence selected from the group consisting of ASPAAPA-PASPAAPAPSAPA (SEQ ID NO:17), AAPASPAPAAP-SAPAPAAPS (SEQ ID NO:18), APSSPSP-SAPSSPSPASPSS (SEQ ID NO:19), APSSPSPSAPSSPSPASPS (SEQ ID NO:20), SSP-SAPSPSSPASPSPSSPA (SEQ ID NO:21), AASPAAPSAP-PAAASPAAPSAPPA (SEQ ID NO:22) and ASAAAPAAASAAASAPSAAA (SEQ ID NO:23) or any combinations thereof. Additional examples of PAS sequences are known from, e.g., US Pat. Publ. No. 2010/0292130 A1 and PCT Appl. Publ. No. WO 2008/155134 A1, which are herein incorporated by reference in their entirety.

In yet other embodiments, the heterologous moiety is a glycine-rich homo-amino-acid polymer (HAP). The HAP sequence can comprise a repetitive sequence of glycine, which has at least 50 amino acids in length. In one embodiment, the HAP sequence is capable of extending half-life of a moiety fused to or linked to the HAP sequence. Non-limiting examples of the HAP sequence includes, but are not limited to $(Gly)_n$, $(Gly_4Ser)_n$ or $S(Gly_4Ser)_n$, wherein n is 1 to 20, 20 to 40, or 40 to 200. See, e.g., Schlapschy M et al., Protein Eng. Design Selection, 20: 273-284 (2007).

In certain embodiments, the heterologous moiety is transferrin or a fragment thereof. Any transferrin may be used to make the chimeric proteins used in accordance with the invention. As an example, wild-type human Tf (Tf) is a 679 amino acid protein, of approximately 75 KDa (not accounting for glycosylation), with two main domains, N (about 330 amino acids) and C (about 340 amino acids), which appear to originate from a gene duplication. See GenBank accession numbers NM001063, XM002793, M12530, XM039845, XM 039847 and 595936 (ncbi.nlm.nih.gov/), all of which are herein incorporated by reference in their entirety. Transferrin comprises two domains, N domain and C domain. N domain comprises two subdomains, N1 domain and N2 domain, and C domain comprises two subdomains, C1 domain and C2 domain.

In one embodiment, the transferrin portion of the chimeric protein includes a transferrin splice variant. In one example, a transferrin splice variant can be a splice variant of human transferrin, e.g., Genbank Accession AAA61140. In another embodiment, the transferrin portion of the chimeric protein includes one or more domains of the transferrin sequence, e.g., N domain, C domain, N1 domain, N2 domain. C1 domain, C2 domain or any combinations thereof.

In other embodiments, the heterologous moiety is a soluble polymer known in the art, including, but not limited to, polyethylene glycol, ethylene glycol/propylene glycol copolymers, carboxymethylcellulose, dextran, or polyvinyl alcohol.

The polymer can be of any molecular weight, and can be branched or unbranched. For polyethylene glycol, in one embodiment, the molecular weight is between about 1 kDa and about 100 kDa for ease in handling and manufacturing. Other sizes may be used, depending on the desired profile (e.g., the duration of sustained release desired, the effects, if any on biological activity, the ease in handling, the degree or lack of antigenicity and other known effects of the polyethylene glycol to a protein or analog). For example, the polyethylene glycol may have an average molecular weight of about 200 to about 100,000 kDa.

In some embodiments, the polyethylene glycol may have a branched structure. Branched polyethylene glycols are described, for example, in U.S. Pat. No. 5,643,575; Murpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), each of which is incorporated herein by reference in its entirety.

In certain embodiments, the heterologous moiety is a hydroxyethyl starch (HES) or a derivative thereof. HES is a derivative of naturally occurring amylopectin and is degraded by alpha-amylase in the body. HES is a substituted derivative of the carbohydrate polymer amylopectin, which is present in corn starch at a concentration of up to 95% by weight. HES exhibits advantageous biological properties and is used as a blood volume replacement agent and in hemodilution therapy in the clinics (Sommermeyer et al., *Krankenhauspharmazie*, 8(8), 271-278 (1987); and Weidler et al., *Arzneim.-Forschung/Drug Res.*, 41, 494-498 (1991)).

HES is mainly characterized by the molecular weight distribution and the degree of substitution. The degree of substitution, denoted as DS, relates to the molar substitution, is known to the skilled people. See Sommermeyer et al., *Krankenhauspharmazie*, 8(8), 271-278 (1987), as cited above, in particular p. 273. In one embodiment, HES has a mean molecular weight (weight mean) of from 1 to 300 kD, from 2 to 200 kD, from 3 to 100 kD, or from 4 to 70 kD. HES can further exhibit a molar degree of substitution of from 0.1 to 3, preferably 0.1 to 2, more preferred, 0.1 to 0.9, preferably 0.1 to 0.8, and a ratio between C2:C6 substitution in the range of from 2 to 20 with respect to the hydroxyethyl groups. In certain embodiments, the heterologous moiety can be mixtures of hydroxyethyl starches having different mean molecular weights and/or different degrees of substitution and/or different ratios of C2:C6 substitution.

In still other embodiments, the non-polypeptide heterologous moiety is a polymer, e.g., polysialic acids (PSAs) or a derivative thereof. Polysialic acids (PSAs) are naturally occurring unbranched polymers of sialic acid produced by certain bacterial strains and in mammals in certain cells. Roth J., et al. (1993) in Polysialic Acid: From Microbes to Man, eds. Roth J., Rutishauser U., Troy F. A. (Birkhauser Verlag, Basel, Switzerland), pp 335-348. They can be produced in various degrees of polymerization from n=about 80 or more sialic acid residues down to n=2 by limited acid hydrolysis or by digestion with neuraminidases, or by fractionation of the natural, bacterially derived forms of the polymer. Various methods of attaching or conjugating polysialic acids to a polypeptide have been described (for example, see U.S. Pat. No. 5,846,951; WO-A-0187922, and US 2007/0191597 A1, which are incorporated herein by reference in their entireties.

More detailed description and sequences of the heterologous moieties that can be used in this invention is disclosed, for example, in WO 2013/123457 A1 and WO 2013/106787 A1, which are incorporated herein by reference in their entirety.

In certain embodiments, the polypeptide of interest is a monomer-dimer hybrid comprising a clotting factor. In one embodiment, the monomer-dimer hybrid is a chimeric protein comprising a first polypeptide chain and a second polypeptide chain, which are associated with each other by a disulfide bond, wherein the first chain comprises a clotting factor, e.g., Factor VIII, and an Fc region and the second chain comprises, consists essentially of, or consists of an Fc region without the clotting factor. Various examples of monomer-dimer hybrids comprising one or more clotting factors are described in U.S. Pat. No. 8,329,182, which is incorporated herein by reference in its entirety.

Antibodies

In some embodiments, the polypeptide of interest comprises an antibody or an antibody fragment. Antibodies are proteins that have the ability to specifically bind a particular antigen. Any antibody that can be expressed in a host cell can be used in accordance with the present invention. In one embodiment, the polypeptide of interest is a monoclonal antibody.

Particular antibodies can be made, for example, by preparing and expressing synthetic genes that encode the recited amino acid sequences or by mutating human germline genes to provide a gene that encodes the recited amino acid sequences. Moreover, these antibodies can be produced, e.g., using one or more of the following methods.

Numerous methods are available for obtaining antibodies, particularly human antibodies. One exemplary method includes screening protein expression libraries, e.g., phage or ribosome display libraries. Phage display is described, for example, U.S. Pat. No. 5,223,409; Smith (1985) Science 228:1315-1317; WO 92/18619; WO 91/17271; WO 92/20791; WO 92/15679; WO 93/01288; WO 92/01047; WO 92/09690; and WO 90/02809. The display of Fab's on phage is described, e.g., in U.S. Pat. Nos. 5,658,727; 5,667,988; and 5,885,793.

In addition to the use of display libraries, other methods can be used to obtain an antibody. For example, a protein or a peptide thereof can be used as an antigen in a non-human animal, e.g., a rodent, e.g., a mouse, hamster, or rat.

Humanized antibodies can be generated by replacing sequences of the Fv variable region that are not directly involved in antigen binding with equivalent sequences from human Fv variable regions. General methods for generating humanized antibodies are provided by Morrison, S. L. (1985) Science 229:1202-1207, by Oi et al. (1986) BioTechniques 4:214, and by U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, can be obtained from a hybridoma producing an antibody against a predetermined target, as described above, from germline immunoglobulin genes, or from synthetic constructs. The recombinant DNA encoding the humanized antibody can then be cloned into an appropriate expression vector.

The antibodies can be in the form of full length antibodies, or in the form of fragments of antibodies, e.g., Fab, F(ab')$_2$, Fd, dAb, and scFv fragments. Additional forms include a protein that includes a single variable domain, e.g., a camel or camelized domain. See, e.g., U.S. 2005-0079574 and Davies et al. (1996) Protein Eng. 9(6):531-7.

In certain embodiments, the antibody can be an antigen-binding fragment of a full length antibody, e.g., a Fab, F(ab')2, Fv or a single chain Fv fragment. Typically, the antibody is a full length antibody. The antibody can be a monoclonal antibody or a mono-specific antibody.

In another embodiment, the antibody can be a human, humanized, CDR-grafted, chimeric, mutated, affinity matured, deimmunized, synthetic or otherwise in vitro-generated antibody, and combinations thereof.

The heavy and light chains of the antibody can be substantially full-length. The protein can include at least one, or two, complete heavy chains, and at least one, or two, complete light chains, or can include an antigen-binding fragment (e.g., a Fab. F(ab')2, Fv or a single chain Fv fragment). In yet other embodiments, the antibody has a heavy chain constant region chosen from, e.g., IgG1, IgG2, IgG3, IgG4, IgM, IgA1, IgA2, IgD, and IgE; particularly, chosen from, e.g., IgG1, IgG2, IgG3, and IgG4, more particularly, IgG1 (e.g., human IgG1). Typically, the heavy chain constant region is human or a modified form of a human constant region. In another embodiment, the antibody has a light chain constant region chosen from, e.g., kappa or lambda, particularly, kappa (e.g., human kappa).

The methods of the invention can be used to prepare polypeptides comprising antibodies, human antibodies, humanized antibodies, chimeric antibodies, i.e. antibodies having human constant antibody immunoglobulin domains coupled to one or more murine variable antibody immunoglobulin domain, and/or non-human antibodies, or fragments thereof. Specific examples of antibodies suitable for use in the present invention include commercially available antibodies such as muromonab-CD3 (ORTHOCLONE OKT-3®, Ortho Biotech), abciximab (REOPRO®, Lilly), rituximab (RITUXAN®, Biogen IDEC), natalizumab (TYSABRI®, Biogen IDEC), dacliximab (ZENAPAX®, Roche Laboratories), basiliximab (SIMULECT®, Novartis), infliximab (REMICADE®, Centocor), palivizumab (SYNAGIS®, MedImmune), trastuzumab (HERCEPTIN®, Genentech), gemtuzuman ozogamicin (MYLOTARG™, Wyeth-Ayerst), alemtuzumab (CAMPATH®, Berlex), and any combinations thereof.

Examples of antibodies or antibody/cytotoxin or antibody/luminophore conjugates contemplated for use in the invention include those that recognize one or more of the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-4, IL-5, IL-8, IL-10, IL-2 receptor, IL-4 receptor, IL-6 receptor. IL-13 receptor, PDGF-β, VEGF, TGF, TGF-β2, TGF-β1, EGF receptor, VEGF receptor, C5 complement, IgE, tumor antigen CA125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or polypeptides expressed on breast, colon, squamous cell, prostate, pancreatic, lung, and/or kidney cancer cells and/or on melanoma, glioma, or neuroblastoma cells, TRAIL receptors 1, 2, 3 and 4, the necrotic core of a tumor, integrin alpha 4 beta 7, the integrin VLA-4, B2 integrins, TNF-α, the adhesion molecule VAP-1, epithelial cell adhesion molecule (Ep-CAM), intercellular adhesion molecule-3 (ICAM-3), leukointegrin adhesin, the platelet glycoprotein gp IIb/IIIa, cardiac myosin heavy chain, parathyroid hormone, rNAPc2

(which is an inhibitor of factor Vila-tissue factor), MHC 1, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, L-selectin, IFN-γ, Respiratory Syncitial Virus, human immunodeficiency virus HIV), hepatitis B virus (HBV), *Streptococcus mutans*, and *Staphylococcus aureus*.

The methods of the invention can also be used for anti-idiotypic antibodies, or substantially similar polypeptides, including but not limited to anti-idiotypic antibodies against: an antibody targeted to the tumor antigen gp72; an antibody against the ganglioside GD3; or an antibody against the ganglioside GD2.

Receptors

In some embodiments, the polypeptide of interest comprises a receptor. Receptors are typically trans-membrane glycoproteins that function by recognizing an extra-cellular signaling ligand. Receptors typically have a protein kinase domain in addition to the ligand recognizing domain, which initiates a signaling pathway by phosphorylating target intracellular molecules upon binding the ligand, leading to developmental or metabolic changes within the cell. The receptor can be modified so as to remove the transmembrane and/or intracellular domain(s), in place of which there can optionally be attached an Ig-domain.

One large family of receptors is the receptor tyrosine kinases (RTKs). The RTK family includes receptors that are crucial for a variety of functions numerous cell types (see, e.g., Yarden and Ulrich, *Ann. Rev. Biochem.* 57:433-478, 1988; Ullrich and Schlessinger, *Cell* 61:243-254, 1990, incorporated herein by reference). Non-limiting examples of RTKs include members of the fibroblast growth factor (FGF) receptor family, members of the epidermal growth factor receptor (EGF) family, platelet derived growth factor (PDGF) receptor, tyrosine kinase with immunoglobulin and EGF homology domains-1 (TIE-1) and TIE-2 receptors (Sato et al., *Nature* 376(6535):70-74 (1995), incorporated herein by reference) and c-Met receptor, some of which have been suggested to promote angiogenesis, directly or indirectly (Mustonen and Alitalo, *J. Cell Biol.* 129:895-898, 1995). Other non-limiting examples of RTK's include fetal liver kinase 1 (FLK-1) (sometimes referred to as kinase insert domain-containing receptor (KDR) (Terman et al., *Oncogene* 6:1677-83, 1991) or vascular endothelial cell growth factor receptor 2 (VEGFR-2)), fms-like tyrosine kinase-1 (Flt-1) (DeVries et al. *Science* 255; 989-991, 1992; Shibuya et al., *Oncogene* 5:519-524, 1990), sometimes referred to as vascular endothelial cell growth factor receptor 1 (VEGFR-1), neuropilin-1 endoglin, endosialin, and Ax1.

G-Protein Coupled Receptors

In some embodiments, the polypeptide of interest comprises a G-protein coupled receptor (GPCR). GPCRs are proteins that have seven transmembrane domains. Upon binding of a ligand to a GPCR, a signal is transduced within the cell which results in a change in a biological or physiological property of the cell.

GPCRs, along with G-proteins and effectors (intracellular enzymes and channels which are modulated by G-proteins), are the components of a modular signaling system that connects the state of intracellular second messengers to extracellular inputs. These genes and gene-products are potential causative agents of disease.

The GPCR protein superfamily now contains over 250 types of prologues, receptors that represent variants generated by gene duplications other processes), as opposed to orthologues, the same receptor from different species. The superfamily can be broken down into five families: Family 1, receptors typified by rhodopsin and the beta2-adrenergic receptor and currently represented by over 200 unique members; Family II, the recently characterized parathyroid hormone/calcitonin/secretin receptor family; Family III, the metabotropic glutamate receptor family in mammals; Family IV, the cAMP receptor family, important in the chemotaxis and development of D. discoideum; and Family V, the fungal mating pheromone receptors such as STE2.

Growth Factors and Other Signaling Molecules

In some embodiments, the polypeptide of interests comprises a growth factor or a signaling molecule. Growth factors are typically glycoproteins that are secreted by cells and bind to and activate receptors on other cells, initiating a metabolic or developmental change in the receptor cell.

CH2/CH3-Containing Polypeptides

Any polypeptide containing a CH2/CH3 domain is suitable for use in accordance with the present invention. In one embodiment, the CH2/CH3-containing polypeptide is a soluble form of the TNF receptor fused to an Fc region (TNFR-Fc). A commercially available TNFR-Fc is known as etanercept (ENBREL®, Immunex Corporation), which is a dimeric fusion polypeptide consisting of the extracellular ligand-binding portion of the human 75 kilodalton (p75) tumor necrosis factor receptor (TNFR) linked to the Fc portion of human IgG1. The Fc component of etanercept contains the constant heavy 2 (CH2) domain, the constant heavy 3 (CH3) domain and hinge region, but not the constant heavy 1 (CH1) domain of human IgG1. It is to be understood that an Fc region can contain one or all of the domains described above. Etanercept is produced by recombinant DNA technology in a Chinese hamster ovary (CHO) mammalian cell expression system. It consists of 934 amino acids and has an apparent molecular weight of approximately 150 kilodaltons (Physicians Desk Reference, 2002, Medical Economics Company Inc.).

Other polypeptides that can be purified in accordance with the invention include recombinant fusion polypeptides comprising at least a portion of an Fc region of an antibody. A polypeptide fused to an Fc domain (e.g., a CH2/CH3 domain) and identical to or substantially similar to one of the following polypeptides is suitable for use in the present disclosed method: a flt3 ligand, a CD40 ligand, erythropoietin, thrombopoietin, calcitonin, Fas ligand, ligand for receptor activator of NF-kappa B (RANKL), tumor necrosis factor (TNF)-related apoptosis-inducing ligand (TRAIL), thymic stroma-derived lymphopoietin, granulocyte colony stimulating factor, granulocyte-macrophage colony stimulating factor, mast cell growth factor, stem cell growth factor, epidermal growth factor, RANTES, growth hormone, insulin, insulinotropin, insulin-like growth factors, parathyroid hormone, interferons, nerve growth factors, glucagon, interleukins 1 through 18, colony stimulating factors, lymphotoxin-β, tumor necrosis factor (TNF), leukemia inhibitory factor, oncostatin-M, various ligands for cell surface molecules ELK and Hek (such as the ligands for eph-related kinases or LERKS), and any combinations thereof.

Polypeptides suitable for purification according to the invention also include recombinant fusion polypeptides comprising CH2/CH3 domains of an antibody plus a receptor for any of the above-mentioned polypeptides or polypeptides substantially similar to such receptors. These receptors include: both forms of TNFR (referred to as p55 and p75), interleukin-1 receptors (type 1 and 2). Interleukin-4 receptor, Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK), receptors for TRAIL (TRAIL receptors 1, 3, and 4), and receptors that comprise death domains, such as Fas or Apoptosis-inducing Receptor (AIR), as well as any combinations thereof.

Other polypeptides suitable for use in the present method include differentiation antigens (referred to as CD polypeptides) or their ligands or polypeptides substantially similar to either of these, which are fused to CH2/CH3 domains of an antibody. Such antigens are disclosed in Leukocyte Typing VI (Proceedings of the VIth International Workshop and Conference, Kishimoto, Kikutani et al., eds., Kobe, Japan, 1996). Similar CD polypeptides are disclosed in subsequent workshops and conferences in the above referenced proceedings series. Examples of such antigens include CD27, CD30, CD39, CD40, and ligands thereto (CD27 ligand, CD30 ligand, etc.). Several of the CD antigens are members of the TNF receptor family, which also includes 41BB ligand and OX40. The ligands are often members of the TNF family, as are 41BB ligand and OX40 ligand. Accordingly, members of the TNF and TNFR families can be purified according to the present invention.

Enzymatically active polypeptides or their ligands can also be purified according to the invention. Examples include recombinant fusion polypeptides comprising CH2/C1-13 domains of an antibody fused to all or part of one of the following polypeptides or their ligands or a polypeptide substantially similar to one of these: metalloproteinase-disintegrin family members, various kinases, glucocerebrosidase, superoxide dismutase, tissue plasminogen activator. Factor VIII, Factor IX, apolipoprotein E, apolipoprotein A-I, globins, an IL-2 antagonist, alpha-1 antitrypsin, TNF-alpha Converting Enzyme, ligands for any of the above-mentioned enzymes, numerous other enzymes and their ligands, and any combinations thereof.

B. Production of Polypeptides of Interest in a Cell Culture

Cells

A polypeptide of interest is first expressed and produced in a host cell culture. Host cells include, but are not limited to, prokaryotic cells, eukaryotic cells, plant cells, yeast cells, animal cells, insect cells, avian cells, mammalian cells, and human cells.

Non-limiting examples of prokaryotic cells that can be used in accordance with the present invention include bacterial cells, such as Gram-negative or Gram-positive bacteria, for example, *Escherichia coli*.

Non-limiting examples of mammalian cells that can be used in accordance with the present invention include human embryonic kidney line (293 or 293 cells subcloned for growth in suspension culture. Graham et al., *J. Gen Virol.*, 36:59 (1977)); BALB/c mouse myeloma line (NSO/1, ECACC No: 85110503); human retinoblasts (PER.C6 (Cru-Cell, Leiden, The Netherlands)); monkey kidney CV1 line transformed by SV40 (COS-7, ATCC CRL 1651); baby hamster kidney cells (BHK, ATCC CCL 10); Chinese hamster ovary cells (CHO, Urlaub and Chasin, *Proc. Natl. Acad. Sci. USA*, 77:4216 (1980)); mouse sertoli cells (TM4, Mather, *Biol. Reprod.*, 3:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL5 1); TRI cells (Mather et al., *Annals N.Y. Acad. Sci.*, 383:44-68 (1982)); MRC 5 cells; FS4 cells; and a human hepatoma line (Hep G2).

Additionally, any number of commercially and non-commercially available hybridoma cell lines that express polypeptides or proteins can be utilized in accordance with the present invention.

The host cells can also be selected or engineered to modify its posttranslational modification pathways. For example, the cells can be selected or engineered to modify a protein glycosylation pathway.

Cell Culture Processes for Production of Polypeptide of Interest

Various methods of preparing mammalian cells for production of proteins or polypeptides by batch and fed-batch culture are well known in the art. A nucleic acid sufficient to achieve expression (typically a vector containing the gene encoding the polypeptide or protein of interest and any operably linked genetic control elements) can be introduced into the host cell line by any number of well-known techniques. Typically, cells are screened to determine which of the host cells have actually taken up the vector and express the polypeptide or protein of interest. Traditional methods of detecting a particular polypeptide or protein of interest expressed by mammalian cells include but are not limited to immunohistochemistry, immunoprecipitation, flow cytometry, immunofluorescence microscopy, SDS-PAGE, Western blots, enzyme-linked immunosorbent assay (ELISA), high performance liquid chromatography (HPLC) techniques, biological activity assays and affinity chromatography. One of ordinary skill in the art will be aware of other appropriate techniques for detecting expressed polypeptides or proteins. If multiple host cells express the polypeptide or protein of interest, some or all of the listed techniques can be used to determine which of the cells expresses that polypeptide or protein at the highest levels.

Purification of Polypeptide of Interest

Procedures for purification of proteins from cell culture initially depend on the site of expression of the protein. Some proteins can be caused to be secreted directly from the cell into the surrounding growth media; others are made intracellularly. For the latter proteins, the first step of a purification process involves lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. The same problem arises, although on a smaller scale, with directly secreted proteins due to the natural death of cells and release of intracellular host cell proteins in the course of the protein production run.

Once a clarified solution containing the protein of interest has been obtained, its separation from the other proteins produced by the cell as well as from other impurities is usually attempted using a combination of different chromatography techniques. These techniques separate mixtures of proteins on the basis of their charge, degree of hydrophobicity, size, or specific binding affinity.

III. Inactivation of Virus During the Protein Purification Process

One critical concern during the protein purification process is the inactivation or removal of viral contaminations.

When a polypeptide of interest is recombinantly produced in a cell culture, the recombinant DNA encoding the polypeptide must be transfected into the protein-producing cells. Viruses can remain in the culture after transfection and contaminate the protein samples. Additionally, cells used for expressing proteins of interest can encode viral genomes in their DNA or otherwise contain endogenous viruses, which is another potential source of contamination to a therapeutic product derived from cells. A biologically-derived therapeutic, such as a polypeptide produced in a cell culture, must undergo at least two robust virus purification steps in order to meet the safety requirements of regulatory agencies such as the FDA to ensure no active viruses are administered to a patient.

Several methods are known in the art to inactivate viruses. For example, arginine can be used for virus inactivation, such as the method described in U.S. Publication No. 2012/0015424 A1, which is incorporated herein by reference in its entirety. Each method however has its own disadvantages, and may not be suitable or optimal for some protein products.

When low pH is used to inactivate viruses, it has the potential to precipitate proteins, cause aggregation of the product, and/or alter the conformation of certain proteins which can lead to product loss. In addition, during the protein purification process, the low pH virus inactivation step is typically performed after the protein of interest has been eluted from the chromatography column and held in a tank or vessel, especially if the target protein is known to elute from the matrix under low pH conditions, resulting in significant product loss. For example, a CH2/CH3-containing polypeptide such as a monoclonal antibody or FIX-Fc is eluted from the Protein A column at pH values below 4.5.

The present invention provides a novel method of on-column virus inactivation, comprising washing a polypeptide-bound chromatography matrix with a low pH and high salt wash solution that effectively inactivates viruses and maximizes the recovery of the polypeptide. Carrying out the low pH inactivation step on a polypeptide bound to a chromatography matrix improves stability of the polypeptide because the bound polypeptide tends to remain its natural conformation and is unable to aggregate with each other. In addition, the presence of high salt in the wash solution significantly reduces the elution of the polypeptide under low pH conditions.

The present invention provides a method of inactivating virus that is present during production of a polypeptide of interest, comprising: (a) binding the polypeptide to a chromatography matrix, and (b) performing a virus inactivation step by washing the polypeptide-hound chromatography matrix with a wash solution at a pH of lower than about 4.0. The wash solution used in accordance with the present invention comprises a sufficient concentration of salt to substantially reduce the elution of the polypeptide during the virus inactivation step. The substantial reduction of the polypeptide elution is likely due to enhanced hydrophobic interactions between the polypeptide and the matrix.

The methods of the present invention are useful for inactivating a wide range of enveloped viruses. Viruses that can be inactivated by embodiments of the present invention include, without limitation, enveloped viruses classified such as, for example, mammalian or avian Leukemia viruses, Herpes viruses, Pox viruses, Hepadnaviruses, Flaviviruses, Togaviruses, Coronaviruses, Hepatitis viruses, Retroviruses, Orthomyxoviruses, Paramyxoviruses, Rhadoviruses, Bunyaviruses, Filoviruses, Reoviruses, Encephalitis, Sindbis, Vesicular Stomatitis Virus, Human Immunodeficiency Virus (HIV), Rhinotracheitis, Epstein Barr virus, Cytomegalo Virus, Influenza Virus, Sendai Virus, Vaccinia Virus, or any combinations thereof.

In certain embodiments, the polypeptide of interest is selected from the group consisting of: an antibody, a CH2/CH3-containing polypeptide, a clotting factor, a receptor, and any combinations thereof.

In some embodiments, the polypeptide of interest is an antibody or an antibody fragment. In one embodiment, the antibody is a monoclonal antibody. In another embodiment, the antibody is a chimeric antibody, a human antibody, or a humanized antibody.

In some embodiments, the polypeptide of interest comprises a clotting factor. In certain embodiments, the polypeptide of interest is FIX-Fc, FVIII-Fc, or FVII-Fc. In certain embodiments, the polypeptide is a monomer-dimer hybrid. In certain embodiments, the polypeptide further comprises a heterologous moiety.

Many chromatography techniques known in the art can be used in the present invention. In some embodiments, the chromatography matrix is an affinity chromatography matrix. In one embodiment, the affinity chromatography matrix is a Protein A column. In yet another embodiment, the Protein A column is selected from the group consisting of MABSELECT™, MABSELECT™ SuRe, MABSELECT™ SuRe LX, ESHMUNO® A, AMSPHERE™ JWT203, TOYOPEARL® AF-rProtein A-650F, PROSEP®-vA Ultra, PROSEP® Ultra Plus, PROSEP®-vA High Capacity, and any combinations thereof. Non-limiting examples of chromatography matrix that can be used to immobilize the Protein A ligand include dextran based matrix, agarose based matrix, polystyrene based matrix, hydrophilic polyvinyl ethyl based matrix, rigid polymethacrylate based matrix, porous polymer based matrix, controlled pore glass based matrix, and any combinations thereof.

In some embodiments, the chromatography matrix is a mixed-mode chromatography matrix. In one embodiment, the chromatography matrix is a mixed-mode anion exchange chromatography matrix. In one embodiment, the mixed-mode chromatography matrix is selected from the group consisting of CAPTO™ Adhere, CAPTO™ MMC, ESHMUNO® HCX, CAPTO™ MMC ImpRes, CAPTO™ Blue, NUVIA™ cPrime, BLUE SEPHAROSE® Fast Flow, CAPTO™ Adhere ImpRes, CHT™ Ceramic Hydroxyapatite, CFT™ Ceramic Fluoroapatite, and any combinations thereof. Non-limiting examples of mixed mode chromatography matrix include dextran based matrix, agarose based matrix, polystyrene based matrix, polyvinyl ethyl hydrophilic polymer based matrix, macroporous highly cross-linked polymer based matrix, hydroxyapatite ($(Ca_5(PO_4)_3OH)_2$) based matrix, fluoroapatite ($(Ca_5(PO_4)_3F)_2$) based matrix, and any combinations thereof.

In some embodiments, the polypeptide of interest is first harvested after recombinantly produced in cell culture. In certain embodiments, the polypeptide is loaded to the chromatography matrix at a pH from about 6.0 to about 8.0. In some embodiments, the pH of the loading buffer is about 6.0 to about 7.0 or about 7.0 to about 8.0. In one embodiment, the pH of the loading buffer is about 6.0, about 6.5, about 7.0, about 7.5, or about 8.0.

One or more wash steps can be carried out before the polypeptide is eluted from the chromatography matrix. Same or different wash solutions can be used in these wash steps.

In certain embodiments, the pH of the wash solution is about 2.5 to about 3.0, about 3.0 to about 3.5, or about 3.5 to about 4.0. In certain embodiments, the pH of the wash solution is about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, or about 4.0. In one embodiment, the pH of the wash solution is 3.0. In another embodiment, the pH of the wash solution is 3.5.

Non-limiting examples of salts that can be added into the solution or to any buffer used in accordance with the present invention include sodium salts, potassium salts, calcium salts, magnesium salts, barium salts, zinc salts, aluminum salts, ammonium salts, chloride salts, fluoride salts, bromide salts, iodide salts, carbonate salts, nitrate salts, phosphate salts, sulfate salts, acetate salts, and combination thereof. In one embodiment, the salt is sodium chloride (NaCl). In another embodiment, the salt is ammonium sulfate.

In certain embodiments, the concentration of the salt in the wash solution is greater than about 0.5 M. In some embodiments, the concentration of the salt in the wash solution is about 0.5 M to about 1.0 M, about 1.0 M to about 1.5 M, about 1.5 M to about 2.0 M, about 2.0 M to about 2.5 M, about 2.5 M to about 3.0 M, about 3.0 M to about 3.5 M, or about 3.5 M to about 4 M. In some embodiments, the concentration of the salt in the wash solution is about 0.5 M, about 0.6 M, about 0.7 M, about 0.8 M, about 0.9 M, about 1.0 M, about 1.1 M, about 1.2 M, about 1.3 M, about 1.4 M, about 1.5 M, about 1.6 M, about 1.7 M, about 1.8 M, about 1.9 M, about 2.0 M, about 2.1 M, about 2.2 M, about 2.3 M, about 2.4 M, about 2.5 M, about 2.6 M, about 2.7 M, about 2.8 M, about 2.9 M, about 3.0 M, about 3.1 M, about 3.2 M, about 3.3. M, about 3.4 M, about 3.5 M, about 3.6 M, about 3.7 M, about 3.8 M, about 3.9 M, or about 4.0 M. In a specific embodiment, the salt concentration is about 2 M. In another specific embodiment, the salt concentration is about 3 M.

The wash solution can further comprise one or more other components such as a polymer, an organic solvent, a detergent, arginine, or an arginine derivative.

In certain embodiments, the polymer is a polyethylene glycol (PEG), a polypropylene glycol, or a mixture thereof. In one embodiment, the polymer is PEG. In a specific embodiment, the polymer is PEG 3350. In some embodiments, the concentration of the polymer is from about 0.1% to about 20%. In some embodiments, the concentration of the polymer is from about 0.1% to about 15%, from 0.100 to about 10%, from about 0.1% to about 5%, from about 0.1% to about 2%, from about 10% to about 20%, from about 10% to about 15%, from about 1% to about 10%, from about 1% to about 5%, from about 1% to about 2%, from about 5% to about 20%, from about 5% to about 15%, from about 5% to about 10%, from about 1000 to about 20%, from about 10% to about 15%, or from about 15% to about 20%. In some embodiments, the concentration of the polymer is about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%.

In certain embodiments, the organic solvent is ethanol, methanol, isopropanol, acetone, ethylene glycol, propylene glycol, hexaethylene glycol, or a mixture thereof. In some embodiments, the concentration of the organic solvent is from about 0.1% to about 20%. In some embodiments, the concentration of the organic solvent is from about 0.1% to about 15%, from 0.1% to about 10%, from about 0.1% to about 5%, from about 0.1% to about 2%, from about 1% to about 20%, from about 1% to about 15%, from about 1% to about 10%, from about 1% to about 5%, from about 10% to about 2%, from about 5% to about 20%, from about 5% to about 15%, from about 50 to about 10%, from about 10% to about 20%, from about 10% to about 15%, or from about 15% to about 20%. In some embodiments, the concentration of the organic solvent is about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%.

In certain embodiments, the detergent is selected from the group consisting of octylphenol ethylene oxide condensate (e.g., TRITON™ X-100); 3-[(3-cholamidopropyl)dimethyl-ammonio)]-1-propanesulfonate (CHAPS); 3-[(3-cholami-dopropyl)dimethylammonio]-2-hydroxy-1-propane-sulfonate (CHAPSO); lauryldimethyl amine oxide (LDAO); polysorbates polysorbates 20 or 80); poloxamers (e.g., poloxamer 188); sodium dodecyl sulfate (SDS); sodium laurel sulfate; sodium octyl glycoside; lauryl-, myristyl-, linoleyl- or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopro-pyl-betaine (e.g., lauroamidopropyl); myristamidopropyl-, palmidopropyl-, or isostearamidopropyl-dimethylamine; sodium methyl cocoyl-, or disodium methyl oleyl-taurate; 1-ethyl-1-(2-hydroxyethyl)-2-isoheptadecylimidazolinium ethylsulfate (e.g., the MONAQUAT™ series); and any combinations thereof. Other examples of commercial products comprising compounds similar to TRITON™ X-100 include, but not limited to, CONCO™ NI, DOWFAX™ 9N, IGEPAL™ CO, MAKON™, NEUTRONYX® 600's, NONIPOL™ NO, POLYTERGENT® B, RENEX™ 600's, SOLAR™ NO, STEROX™, SERFONIC™ N, T-DET-N™, TERGITOL™ NP, and TRITON™ N.

In some embodiments, the concentration of the detergent is from about 0.01% to about 8%. In some embodiments, the concentration of the detergent is from about 0.01% to about 7%, from about 0.01% to about 6%, from about 0.01% to about 5%, from about 0.01% to about 4%, from about 0.01% to about 3%, from about 0.01% to about 2%, from about 0.01% to about 1%, from about 0.01% to about 0.5%, from about 0.01% to about 0.1%, from about 0.1% to about 8%, from about 0.1% to about 7%, from about 0.1% to about 6%, from about 0.1% to about 5%, from about 0.1% to about 4%, from about 0.1% to about 3%, from about 0.1% to about 2%, from about 0.1% to about 1%, from about 0.1% to about 0.5%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, from about 0.5% to about 1%, from about 1% to about 8%, from about 1% to about 7%, from about 1% to about 6%, from about 1% to about 5%, from about 1% to about 4%, from about 1% to about 3%, or from about 1% to about 2%. In some embodiments, the concentration of the detergent is about 0.01%, about 0.05%, about 0.1%, about 0.5%, about 1%, about 2%, about 3%, about 4%, about 5%, about 6%, about 7%, or about 8%.

In certain embodiments, more than one on-column virus-inactivation step is carried out during the purification of the polypeptide. In one embodiment, identical wash solutions are used in multiple virus-inactivation steps. In another embodiment, different wash solutions are used in multiple virus-inactivation steps.

In some embodiments, at least one of the wash solutions comprises arginine, an arginine derivative, or a mixture thereof. In some embodiments, the concentration of arginine is from about 0.1 M to about 1 M. In some embodiment, the concentration of arginine is about 0.1 M to about 0.5 M or about 0.5 M to about 1 M. In some embodiments, the concentration of arginine is about 0.1 M, about 0.2 M, about 0.3 M, about 0.4 M, about 0.5 M, about 0.6 M, about 0.7 M, about 0.8 M, about 0.9 M, or about 1 M.

In some embodiments, at least one of the wash solutions comprises detergent. In one embodiment, the detergent is lauryldimethyl amine oxide (LDAO). In another embodiment, the detergent is octylphenol ethylene oxide condensate (e.g., TRITON™ X-100). In other embodiments, the detergent comprises a compound very similar to TRITON™ X-100 (e.g., CONCO™ NI, DOWFAX™ 9N, IGEPAL™ CO, MAKON™, NEUTRONYX® 600's, NONIPOL™ NO, POLYTERGENT® B, RENEX™ 600's, SOLAR™ NO, STEROX™, SERFONIC™ N, T-DET-N™, TERGITOL™ NP, and TRITON™ N).

In certain embodiments, elution of the polypeptide during the low pH wash step for virus inactivation is reduced to less than 30%. In certain embodiments, elution of the polypeptide during the low pH wash step is reduced to less than 25%, less than 20%, less than 15%, less than 10%, or less than 0.5%.

After the wash steps, the polypeptide of interest is eluted from the chromatography matrix with an elution solution. In certain embodiments, the pH of the elution solution is less than 4.5. In one embodiment, the pH of the elution solution is about 3.0. In another embodiment, the pH of the elution solution is about 3.4.

In certain embodiments, at least about 70% of the polypeptide is recovered in the elution solution. In some embodiments, at least about 75%, at least about 80%, at least about 85%, at least about 90%, or at least about 95% of the polypeptide is recovered in the elution solution.

Additional virus inactivation steps can be performed either prior to, or after, the on-column virus inactivation method disclosed herein.

The eluted polypeptide of interest can be subjected to additional purification steps either prior to, or after, the purification method disclosed herein. Standard methods include but not limited to, chromatography (e.g., ion exchange, affinity, size exclusion, and hydroxyapatite chromatography), gel filtration, centrifugation, or differential solubility, ethanol precipitation or by any other available technique for the purification of proteins (See, e.g., Scopes, Protein Purification Principles and Practice 2nd Edition, Springer-Verlag, New York, 1987; Higgins, S. J. and Hames, B. D. (eds), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol 182), Academic Press, 1997, all incorporated herein by reference). Protease inhibitors such as phenyl methyl sulfonyl fluoride (MIST), leupeptin, pepstatin or aprotinin can be added at any or all stages in order to reduce or eliminate degradation of the polypeptide or protein during the purification process. Protease inhibitors are particularly desired when cells must be lysed in order to isolate and purify the expressed polypeptide or protein. One of ordinary skill in the art will appreciate that the exact purification technique will vary depending on the character of the polypeptide or protein to be purified, the character of the cells from which the polypeptide or protein is expressed, and the composition of the medium in which the cells were grown.

The virus inactivation method of present invention can be used to help enable processes that utilize multiple affinity chromatography columns like simulated moving bed or tandem chromatography which generate multiple elution pools. Instead of combining the elution pools to carry out low pH viral inactivation which can result in a long holds at low pH values and a greater product loss, or going through the tedious and time-consuming process of carrying out low pH viral inactivation in the individual pools, the present invention carries out low pH viral inactivation during the individual tandem or simulated moving bed chromatography runs, thus obviating the need for viral inactivation of the elution pools.

The foregoing description is to be understood as being representative only and is not intended to be limiting. Alternative methods and materials for implementing the invention and also additional applications will be apparent to one of skill in the art, and are intended to be included within the accompanying claims.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); *Molecular Cloning: A Laboratory Manual*, Sambrook et al., ed., Cold Springs Harbor Laboratory, New York (1992), DNA Cloning, D. N. Glover ed., Volumes I and II (1985); *Oligonucleotide Synthesis*, M. J. Gait ed., (1984); Mullis et al. U.S. Pat. No. 4,683,195; *Nucleic Acid Hybridization*, B. D. Hames & S. J. Higgins eds. (1984); *Transcription And Translation*, B. D. Hames & S. J. Higgins eds. (1984); *Culture Of Animal Cells*, R. I. Freshney, Alan R. Liss, Inc., (1987); *Immobilized Cells And Enzymes*, IRL Press, (1986); B. Perbal, *A Practical Guide To Molecular Cloning* (1984); the treatise, *Methods In Enzymology*, Academic Press, Inc., N.Y.; *Gene Transfer Vectors For Mammalian Cells*, J. H. Miller and M. P. Calos eds., Cold Spring Harbor Laboratory (1987); *Methods In Enzymology*, Vols. 154 and 155 (Wu et al. eds.); *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds., (1986); *Manipulating the Mouse Embryo*, Cold Spring Harbor Laboratory Press, Cold Spring Harbor, N.Y., (1986); and in Ausubel et al., *Current Protocols in Molecular Biology*, John Wiley and Sons, Baltimore, Md. (1989).

All of the references cited above, as well as all references cited herein, are incorporated herein by reference in their entirety.

The following examples are offered by way of illustration and not by way of limitation.

EXAMPLES

Example 1

On-Column Viral Inactivation Using a Wash Solution Containing 2 M Ammonium Sulfate at pH 3.5

The objective of the experiments shown in Examples 1 to 10 is to demonstrate the feasibility and applicability of an on-column low-pH viral inactivation step using ProA and a target polypeptide. The polypeptide was bound to the ProA under standard conditions before a high salt at neutral pH was applied to the column. A subsequent wash at high salt and low pH was then applied to inactivate virus while the polypeptide remained bound to the adsorbent. A series of washes were performed before the polypeptide was recovered using an elution solution.

The goal of the first experiment was to determine if on-column viral inactivation could be performed with minimal recovery loss using 2 M ammonium sulfate wash at pH 3.5.

In this experiment, a 0.66 cm diameter MABSELECT™ SuRe column (7.2 mL; 21 cm) was first equilibrated (EQ) with 4 column volumes (CVs) of 10 mM sodium phosphate (NaPhosphate). 140 mM NaCl, pH 7.4. 256 nil of filtered (at 0.22 μm) harvested cell culture fluid (HCCF) containing recombinantly produced FIX-Fc was then loaded onto the column (25.5 mg rFIXFc per mL of resin).

The loading was followed by seven wash steps as indicated in Table 1 below. The target polypeptide was subsequently eluted with 25 mM citrate, 150 mM NaCl, pH 3.4. The flow rate of the chromatography was consistent at 300 cm/hr or 1.7 ml/min except that a lower rate (100 cm/hr) was used during the low pH wash step (wash 4),

TABLE 1

Individual buffers used in Example 1.

| Step | Buffer Components | pH | Vol. |
|---|---|---|---|
| EQ | 10 mM NaPhosphate, 140 mM NaCl | 7.4 | 4 CVs |
| Load | Filtered HCCF | | 256 ml |
| Wash 1 | 10 mM NaPhosphate, 140 mM NaCl | 7.4 | 4.5 CVs |
| Wash 2 | 10 mM NaPhosphate, 900 mM NaCl | 7.4 | 4 CVs |
| Wash 3 | 100 mM Bis-Tris, 2M Ammonium Sulfate | 7.0 | 4 CVs |
| Wash 4 | 100 mM Bis-Tris, 2M Ammonium Sulfate | 3.5 | 5 CVs |
| Wash 5 | 100 mM Bis-Tris, 2M Ammonium Sulfate | 7.0 | 4 CVs |
| Wash 6 | 10 mM NaPhosphate, 900 mM NaCl | 7.4 | 4 CVs |
| Wash 7 | 10 mM NaPhosphate, 140 mM NaCl | 7.4 | 3 CVs |
| Elution | 25 mM Citrate, 150 mM NaCl | 3.4 | 3 CVs |
| Strip | 10 mM NaPhosphate, 900 mM NaCl | 7.4 | 5 CVs |
| Regeneration | 0.1N NaOH | | 3 CVs |
| HETP* | 10 mM NaPhosphate, 140 mM NaCl | 7.4 | 4 CVs |
| Storage | 500 mM Acetic Acid, 1% Benzyl Alcohol | 3.2 | 5 CVs |

*HETP stands for Height of an Equivalent Transfer Plate, which is a solution used to measure column integrity.

FIG. 1 is a chromatogram showing the protein concentration and the pH in each fraction during the chromatography steps. The polypeptide recovery was 84% in the eluate, which is surprising given the low pH of wash 4 (pH 3.5) because such low pH wash would usually lead to polypeptide dissociation from the column and cause substantial product loss. The viral removal as measured by PCR was 4.96 $log_{10}$. The combined removal and inactivation provided by the column washes was higher at >6.39 $log_{10}$, indicating the low pH can provide effective inactivation of viruses.

Samples were assayed for infectious virus by plaque assay and for viral nucleic acids by Q-PCR assay. The column loading was 25.5 mg rFIXFc per mL of resin. Tables 2 and 3 summarize the results of X-MLV viral clearance as measured by infectivity and OCR, respectively.

The load was spiked with 8.79 $log_{10}$ X-MLV (PFU) and >6.39 $log_{10}$ retroviral inactivation was calculated. When measured by OCR, the load was spiked with 8.77 $log_{10}$ X-MLV (GC) and a reduction factor of 4.96 $log_{10}$ was calculated. These results show a robust retroviral removal by the MABSELECT™ SuRe column at high loadings and additional low pH/high salt buffer. The infectivity results show total retroviral inactivation after the MABSELECT™ SuRe resin is exposed to one hour of low pH/high salt buffer.

TABLE 2

X-MLV Clearance Data by MABSELECT ™ SuRe Step by Infectivity

| Sample Description | Viral Titer (PFU/mL) | Volume Adjust (mL) | Adjusted Viral Titer (PFU) | $Log_{10}$ Adjusted Titer (PFU) | $Log_{10}$ Reduction |
|---|---|---|---|---|---|
| Stock Virus Control | 4.67E+7 | 263.0 | 6.14E+8 | 8.79 | 9.00 |
| Load | 2.33E+6 | 263.0 | 6.14E+8 | 8.79 | 0.00 |
| Eluate Run 6 | <5.99E+0 | 41.8 | <2.50E+2 | <2.40 | >6.39 |

PFU = Plaque Forming Units

TABLE 3

X-MLV Clearance Data by MABSELECT ™ SuRe Step by qPCR

| Sample Description | Viral Titer by qPCR (GC) | Volume Adjust (mL) | Adjusted Viral Titer (GC) | $Log_{10}$ Adjusted Titer (GC) | $Log_{10}$ Reduction |
|---|---|---|---|---|---|
| Stock Virus Control | 4.53E+7 | 263.0 | 5.96E+8 | 8.77 | 0.00 |
| Load | 2.26E+6 | 263.0 | 5.94E+8 | 8.77 | 0.00 |
| Eluate Run 6 | 1.53E+2 | 41.8 | 6.39E+3 | 3.81 | 4.96 |

GC = Genome Copies

Therefore, the above results demonstrate that a low pH and high salt wash solution can effectively inactivate viruses during a Protein A chromatography purification process without removing the majority of the target polypeptide from the column.

Example 2

On-Column Viral Inactivation Using a Wash Solution Containing 1 M Arginine HCl at pH 4.7

The goal of this experiment was to compare the effects of on-column viral inactivation using a wash solution containing 1 M arginine HCl at pH 4.7.

In this experiment, the Protein A column and the target polypeptide were the same as those in Example 1. A 7.0 mL (20.5 cm) MabSelect SuRe column was first equilibrated, and then 157 ml of HCCF containing Fc-fusion protein was loaded onto the column. Table 4 below summarizes the buffer solutions used in each step. The target polypeptide was bound to the Pro A under standard conditions. A subsequent modified wash 3 containing arginine was then applied to inactivate virus while the polypeptide remained bound to the adsorbent. The flow rate of the chromatography was consistent at 300 cm/hr or 1.7 ml/min except that a lower rate (100 cm/hr or 0.56 ml/min) was used during the arginine wash step (wash 3).

TABLE 4

Individual buffers used in Example 2.

| Step | Buffer Components | pH | Vol. |
|---|---|---|---|
| EQ | 10 mM NaPhosphate, 140 mM NaCl | 7.4 | 4 CVs |
| Load | Filtered HCCF | | 157 ml |
| Wash 1 | 10 mM NaPhosphate, 140 mM NaCl | 7.4 | 4.5 CVs |
| Wash 2 | 10 mM NaPhosphate, 900 mM NaCl | 7.4 | 4 CVs |
| Wash 3 | 1M Arginine HCl | 4.7 | 5 CVs |
| Wash 4 | 10 mM NaPhosphate, 140 mM NaCl | 7.4 | 3 CVs |
| Elution | 25 mM Citrate, 150 mM NaCl | 3.4 | 3 CVs |
| Strip | 10 mM NaPhosphate, 900 mM NaCl | 7.4 | 5 CVs |
| Regeneration | 0.1N NaOH | | 3 CVs |
| HETP | 10 mM NaPhosphate, 140 mM NaCl | 7.4 | 4 CVs |
| Storage | 500 mM Acetic Acid, 1% Benzyl Alcohol | 3.2 | 5 CVs |

FIG. 2 is a chromatogram showing the protein concentration and the pH in each fraction during the chromatography steps. The polypeptide recovery was 83% in the eluate, which is comparable to the recovery percentage using a pH 3.5 and 2 M ammonium sulfate wash solution as shown in Example 1. The viral removal as measured by PCR was >5.54 $\log_{10}$, and the combined removal and inactivation provided by the column washes was higher at >6.39 $\log_{10}$. Both numbers are very similar to those in Example 1.

These results indicate that wash solutions containing either 1 M arginine at pH 4.7 or pH 3.5 with 2 M ammonium sulfate can provide similar level of viral inactivation and protein recovery.

Example 3

On-Column Viral Inactivation Using a Wash Solution Containing 4×CMC Lauryldimethyl Amine Oxide (LDAO)

The goal of this experiment was to compare the effects of on-column viral inactivation using a wash solution containing 4× critical micelle concentration (CMC) lauryldimethyl amine oxide (LDAO).

In this experiment, the Protein A column and the target polypeptide were still the same as those in Example 1. A 7.0 mL (20.5) MABSELECT™ SuRe column was equilibrated and then loaded with 256 ml of HCCF containing Fc-fusion protein. Table 5 below summarizes the buffer solutions used in each step. The target polypeptide was bound to the Pro A under standard conditions. A subsequent modified wash 4 containing 4×CMC LDAO was then applied to inactivate virus while the polypeptide remained bound to the adsorbent. The flow rate of the chromatography was consistent at 300 cm/hr or 1.7 ml/min except that a lower rate (100 cm/hr or 0.56 ml/min) was used during the detergent wash step (wash 4).

TABLE 5

Individual buffers used in Example 3.

| Step | Buffer Components | pH | Vol. |
|---|---|---|---|
| EQ | 10 NaPhosphate, 140 mM NaCl | 7.4 | 4 CVs |
| Load | Filtered HCCF | | 256 ml |
| Wash 1 | 10 mM NaPhosphate, 140 mM NaCl | 7.4 | 4.5 CVs |
| Wash 2 | 10 mM NaPhosphate, 900 mM NaCl | 7.4 | 4 CVs |
| Wash 3 | 10 mM NaPhosphate, 140 mM NaCl | | 3 CVs |
| Wash 4 | 10 mM NaPhosphate, 140 mM NaCl, 4x CMC LDAO | 7.4 | 5 CVs |
| Wash 5 | 10 mM NaPhosphate, 140 mM NaCl | 7.4 | 3 CVs |
| Elution | 25 mM Citrate, 150 mM NaCl | 3.4 | 3 CVs |
| Strip | 10 mM NaPhosphate, 900 mM NaCl | 7.4 | 5 CVs |
| Regeneration | 0.1N NaOH | | 3 CVs |
| HETP | 10 mM NaPhosphate, 140 mM NaCl | 7.4 | 4 CVs |
| Storage | 500 mM Acetic Acid, 1% Benzyl Alcohol | 3.2 | 5 CVs |

FIG. 3 is a chromatogram showing the protein concentration and the pH in each fraction during the chromatography steps. The polypeptide recovery was 85% in the eluate, which is comparable to the recovery percentage using a pH 3.5 and 2 M ammonium sulfate wash solution. The viral removal as measured by PCR was 5.11 $\log_{10}$, and the combined removal and inactivation provided by the column washes was higher at >6.40 $\log_{10}$. Both numbers are similar to those in Example 1.

These results indicate that wash solutions containing either 4×CMC LDAO or pH 3.5 with 2 M ammonium sulfate can provide similar level of viral inactivation.

Example 4

On-Column Viral Inactivation Using a Wash Solution Containing 20% PEG and 2 M NaCl at pH 3.0

Various low pH wash solutions were used in Examples 4 to 10 to further explore the feasibility and applicability of an on-column viral inactivation step. Protein A chromatography and a monoclonal antibody were used in the following experiments. The monoclonal antibody was bound to the ProA under standard conditions before a high salt at neutral pH was applied to the column. A subsequent wash at high salt and low pH (about pH 3.0) was then applied to inactivate virus while the antibody remained bound to the adsorbent. A series of washes were performed before the antibody was recovered using an elution solution.

The goal of this experiment was to determine if on-column viral inactivation could be performed with minimal recovery loss using a pH 3.0, 2 M NaCl, 100 mM glycine wash with 20% PEG.

In this experiment, a 0.6 cm diameter MABSELECT™ SuRe column was first equilibrated (EQ) with 5 column volumes (CVs) of 75 mM sodium phosphate, 100 mM NaCl, pH 7.3. 50 ml of filtered (at 0.22 μm) HCCF containing the polypeptide of interest was then loaded onto the column to ≤35 g/$L_{resin}$. The column was chased with 3 CVs of equilibration buffer.

The loading was followed by 5 CVs wash with 100 mM Bis-Tris, 2 M NaCl, pH 7.0 (wash 1), followed by 5 CVs of low pH wash with 100 mM Glycine, 20% PEG 3350, 2M NaCl, pH 3.0 (wash 2). The column was then washed with 5 CVs of 100 mM Bis-Tris, 2 M NaCl, pH 7.0 (wash 3), followed by 5 CVs wash with 100 mM Bis-Tris, pH 7.0 (wash 4). The target polypeptide was subsequently eluted with 100 mM glycine, pH 3.0 (elution).

FIG. 4 is a chromatogram showing the protein concentration and the pH in each fraction during the chromatography steps. Table 6 below summarizes the condition used in each step. The flow rate of the chromatography was consistent at 250 cm/hr or 1.42 ml/min except that a lower rate (50 cm/hr) was used during the regeneration step. Table 7 summarizes the percentage recovery calculated for each chromatography step.

TABLE 6

Individual buffers used in Example 4.

| Step | Buffer Components | pH | Vol. | Fraction |
|---|---|---|---|---|
| EQ | 75 mM NaPhosphate, 100 mM NaCl | 7.3 | 5 CVs | |
| Load | Filtered HCCF | | 50 ml | F2 |
| Chase | 75 mM NaPhosphate, 100 mM NaCl | 7.3 | 3 CVs | F2 |
| Wash 1 | 100 mM Bis-Tris, 2M NaCl | 7.0 | 5 CVs | F3 |
| Wash 2 | 100 mM Glycine, 20% PEG 3350, 2M NaCl | 3.0 | 5 CVs | F4 |
| Wash 3 | 100 mM Bis-Tris, 2M NaCl | 7.0 | 5 CVs | F5 |
| Wash 4 | 100 mM Bis-Tris | 7.0 | 5 CVs | F6 |
| Elution | 100 mM Glycine | 3.0 | 3.5 CVs | F7 |
| Regeneration | 0.3N NaOH | | 5 CVs | F8 |
| Flush | 75 mM NaPhosphate, 100 mM NaCl | 7.3 | 2 CVs | Waste |
| Storage | 500 mM NaAcetate, 1% Benzyl Alcohol | 3.2 | 4 CVs | Waste |

TABLE 7

Percentage Recovery in Each Chromatography Step Using A Wash Solution Containing 20% PEG and 2M NaCl at pH 3.0

| Step | Volume (ml) | Conc (mg/ml) | Mass (mgs) | % Recovery (calculated from total mass recovered) |
|---|---|---|---|---|
| Load | 50 | | | |
| F3 Wash 1 | 33.15 | 0.2704 | 8.96 | 5.5 |
| F4 Wash 2 | 33.15 | 0.9514 | 31.54 | 19.5 |
| F5 Wash 3 | 33.15 | 0.0125 | 0.41 | 0.3 |
| F6 Wash 4 + pre | 41.44 | 0.0081 | 0.00 | |
| F7 Elution | 23.205 | 5.1370 | 119.20 | 73.8 |
| F8 Regen | 33.15 | 0.0435 | 1.44 | 0.9 |
| Total Mass Recovered (mgs) | | | 161.6 | |
| Recoverable Titer Elution Mass/Load Volume | | | 3.23 | |
| Column Loading (mg/ml resin) | | | 24.5 | |

As shown in FIG. 4 and Table 7, only minor product loss (19.5% of the target polypeptide) was observed during the low pH wash (F4, wash 2) with 20% PEG and 2 M NaCl at pH 3.0. The majority of the product (73.8% of the target polypeptide) was recovered in the elution buffer (F7).

Example 5

On-Column Viral Inactivation Using a Wash Solution Containing 2% Ethanol and 2 M NaCl at pH 3.0

The goal of this experiment was to determine if on-column viral inactivation could be performed with minimal recovery loss using a pH 3.0, 2 M NaCl, 100 mM glycine wash with 2% ethanol.

In this experiment, the Protein A column and the target polypeptide were the same as those in Example 4. All the buffer solutions used in each step were also the same as those listed in Table 6, except that the low pH wash (wash 2) buffer solution was 100 mM glycine, 2% ethanol, 2 M NaCl, pH 3.0. All the flow rates were the same as in Example 4.

FIG. 5 is a chromatogram showing the protein concentration and the pH in each fraction during the chromatography steps. Table 8 summarizes the percentage recovery calculated for each chromatography step.

TABLE 8

Percentage Recovery in Each Chromatography Step Using A Wash Solution Containing 2% Ethanol and 2M NaCl at pH 3.0.

| Step | Volume (ml) | Conc (mg/ml) | Mass (mgs) | % Recovery (calculated from total mass recovered) |
|---|---|---|---|---|
| Load | 50 | | | |
| F3 Wash 1 | 33.15 | 0.4013 | 13.30 | 7.6 |
| F4 Wash 2 | 33.15 | 0.9584 | 31.77 | 18.2 |
| F5 Wash 3 | 33.15 | 0.1419 | 4.71 | 2.7 |
| F6 Wash 4 + pre | 41.44 | 0.0111 | 0.00 | |
| F7 Elution | 23.205 | 5.3128 | 123.28 | 70.7 |
| F8 Regen | 33.15 | 0.0420 | 1.39 | 0.8 |
| Total Mass Recovered (mgs) | | | 174.5 | |
| Recoverable Titer Elution Mass/Load Volume | | | 3.49 | |
| Column Loading (mg/ml resin) | | | 26.4 | |

As shown in FIG. 5 and Table 8, only minor product loss (18.2% of the target polypeptide) was observed during the low pH wash (F4, wash 2) with 20% PEG and 2 M NaCl at pH 3.0. The majority of the product (70.7% of the target polypeptide) was recovered in the elution buffer (F7).

Example 6

On-Column Viral Inactivation Using a Wash Solution Containing 2% Ethanol and 2 M Ammonium Sulfate at pH 3.0

The goal of this experiment was to determine if on-column viral inactivation could be performed with minimal recovery loss using a pH 3.0, 2 M ammonium sulfate, 100 mM glycine wash with 2% ethanol.

In this experiment, the Protein A column and the target polypeptide were the same as those in Example 4. All the buffer solutions used in each step were also the same as those listed in Table 6, except that the low pH wash (wash 2) buffer solution was 100 mM glycine, 2% ethanol, 2 M ammonium sulfate, pH 3.0, and 2 M ammonium sulfate replaced the 2 M NaCl in wash 1 and wash 3 solutions. All the flow rates were the same as in Example 4.

FIG. 6 is a chromatogram showing the protein concentration and the pH in each fraction during the chromatography steps. Table 9 summarizes the percentage recovery calculated for each chromatography step.

TABLE 9

Percentage Recovery in Each Chromatography Step Using A Wash Solution Containing 2% Ethanol and 2M Ammonium Sulfate at pH 3.0.

| Step | Volume (ml) | Conc (mg/ml) | Mass (mgs) | % Recovery (calculated from total mass recovered) |
|---|---|---|---|---|
| Load | 50 | | | |
| F3 Wash 1 | 33.15 | 0.1630 | 5.40 | 3.1 |
| F4 Wash 2 | 33.15 | 0.0100 | 0.33 | 0.2 |
| F5 Wash 3 | 33.15 | 0.0016 | 0.05 | 0.0 |
| F6 Wash 4 + pre | 41.44 | 0.0339 | 0.00 | |
| F7 Elution | 23.205 | 6.9053 | 160.24 | 92.3 |
| F8 Regen | 33.15 | 0.2268 | 7.52 | 4.3 |
| Total Mass Recovered (mgs) | | | 173.5 | |
| Recoverable Titer Elution Mass/Load Volume | | | 3.47 | |
| Column Loading (mg/ml resin) | | | 26.3 | |

As shown in FIG. 6 and Table 9, only insignificant product loss (0.2% of the target polypeptide) was observed during the low pH wash (F4, wash 2) with 2% ethanol and 2 M ammonium sulfate at pH 3.0. The majority of the product (92.3% of the target polypeptide) was recovered in the elution buffer (F7).

Example 7

On-Column-Viral Inactivation Using a Wash Solution Containing 2% Acetone and 2 M Ammonium Sulfate at pH 3.0

The goal of this experiment was to determine if on-column viral inactivation could be performed with minimal recovery loss using a pH 3.0, 2 M ammonium sulfate, 100 mM glycine wash with 2% acetone.

In this experiment, the Protein A column and the target polypeptide were the same as those in Example 4. All the buffer solutions used in each step were also the same as those listed in Table 6, except that the low pH wash (wash 2) buffer solution was 100 mM glycine, 2% acetone, 2 M ammonium sulfate, pH 3.0, and 2 M ammonium sulfate replaced the 2 M NaCl in wash 1 and wash 3 solutions. All the flow rates were the same as in Example 4.

FIG. 7 is a chromatogram showing the protein concentration and the pH in each fraction during the chromatography steps. Table 10 summarizes the percentage recovery calculated for each chromatography step.

TABLE 10

Percentage Recovery in Each Chromatography Step Using A Wash Solution Containing 2% Acetone and 2M Ammonium Sulfate at pH 3.0.

| Step | Volume (ml) | Conc (mg/ml) | Mass (mgs) | % Recovery (calculated from total mass recovered) |
|---|---|---|---|---|
| Load | 50 | | | |
| F3 Wash 1 | 33.15 | 0.1495 | 4.96 | 2.8 |
| F4 Wash 2 | 33.15 | 0.0100 | 0.33 | 0.2 |
| F5 Wash 3 | 33.15 | 0.0016 | 0.05 | 0.0 |
| F6 Wash 4 + pre | 41.44 | 0.0339 | 0.00 | |
| F7 Elution | 23.205 | 7.3562 | 170.70 | 96.3 |
| F8 Regen | 33.15 | 0.0389 | 1.29 | 0.7 |
| Total Mass Recovered (mgs) | | | 177.3 | |
| Recoverable Titer Elution Mass/Load Volume | | | 3.55 | |
| Column Loading (mg/ml resin) | | | 26.9 | |

As shown in FIG. 7 and Table 10, only insignificant product loss (0.2% of the target polypeptide) was observed during the low pH wash (F4, wash 2) with 2% acetone and 2 M ammonium sulfate at pH 3.0. The majority of the product (more than 96.3% of the target polypeptide) was recovered in the elution buffer (F7).

Example 8

On-Column-Viral Inactivation Using a Wash Solution Containing 2 M Ammonium Sulfate at pH 3.0

The goal of this experiment was to determine if on-column viral inactivation could be performed with minimal recovery loss using a pH 3.0, 2 M ammonium sulfate, 100 mM glycine wash with no other modifiers.

In this experiment, the Protein A column and the target polypeptide were still the same as those in Example 4. A 6.6 mL MABSELECT™ SuRe column (19.4 cm) was first equilibrated and then loaded onto 25.8 g/L resin using 50 mL of antibody in HCCF. A flow rate of 250 cm/hr was used except during the regeneration step (50 cm/hr). All the buffer solutions used in each step were also the same as those listed in Table 6, except that the low pH wash wash 2) buffer solution was 100 mM glycine, 2 M ammonium sulfate, pH 3.0, and 2 M ammonium sulfate replaced the 2 M NaCl in wash 1 and wash 3 solutions. All the flow rates were the same as in Example 4. The pH 3.0, 2M ammonium sulfate, 100 mM glycine wash was used to keep the antibody bound to the resin at low pH. The low pH, high ammonium sulfate wash was bracketed by a neutral, high ammonium sulfate wash buffer (pH 7.0, 2 M ammonium sulfate) to ensure that high levels of ammonium sulfate were present as the pH was lowered to 3.0 and also when it was subsequently raised to 7.0. Without this, significant product elution occurred before and after the wash step. Excess wash buffer was used at each step to ensure adequate buffer exchange. FIG. 8 is a chromatogram showing the protein concentration and the pH in each fraction during the chromatography steps. Table 11 summarizes the percentage recovery calculated for each chromatography step.

TABLE 11

Percentage Recovery in Each Chromatography Step Using A Wash Solution Containing 2M Ammonium Sulfate at pH 3.0.

| Step | Volume (ml) | Conc (mg/ml) | Mass (mgs) | % Recovery (calculated from total mass recovered) |
|---|---|---|---|---|
| Load | 50 | | | |
| F3 Wash 1 | 33.15 | 0.1542 | 5.11 | 3.0 |
| F4 Wash 2 | 33.15 | 0.0954 | 3.16 | 1.9 |

TABLE 11-continued

Percentage Recovery in Each Chromatography Step Using A
Wash Solution Containing 2M Ammonium Sulfate at pH 3.0.

| Step | Volume (ml) | Conc (mg/ml) | Mass (mgs) | % Recovery (calculated from total mass recovered) |
|---|---|---|---|---|
| F5 Wash 3 | 33.15 | 0.0000 | 0.00 | 0.0 |
| F6 Wash 4 + pre | 41.44 | 0.0334 | 0.00 | |
| F7 Elution | 23.205 | 6.9315 | 160.85 | 94.4 |
| F8 Regen | 33.15 | 0.0362 | 1.20 | 0.7 |
| Total Mass Recovered (mgs) | | | 170.3 | |
| Recoverable Titer Elution Mass/Load Volume | | | 3.41 | |
| Column Loading (mg/ml resin) | | | 25.8 | |

As shown in FIG. 8 and Table 11, only very minor product loss (1.9% of the target polypeptide) was observed during the low pH wash (F4, wash 2) with 2 M ammonium sulfate at pH 3.0. The majority of the product (94.4% of the target polypeptide) was recovered in the elution buffer (F7). The percentage of the peak that was monomeric antibody, 96.0%, was not altered by the high ammonium sulfate wash.

The high salt, low pH wash buffer did not increase removal of host cell protein (HCP) on the protein A step. The levels of HCP in the eluate were typically the same or higher than those achieved using a simple neutral pH, sodium chloride wash. It is likely that the high levels of ammonium sulfate in the low pH wash enhanced interactions between HCP and antibodies or HCP and protein A resin. It is also possible that the ammonium sulfate decreased the solubility of the HCP, reducing the clearance.

An additional experiment at conditions similar to the previous one was performed but with sodium chloride substituted for ammonium sulfate. The yield loss was higher using a 2 M NaCl, pH 3.0 wash step (17.0%) compared to the 2 M ammonium sulfate pH 3.0 wash step (1.9%). Since ammonium sulfate is a stronger kosmotrope than sodium chloride, a lower concentration is required to prevent antibody elution. It is believed that using a higher concentration of sodium chloride (3 M) would prevent antibody elution and allow on-column viral inactivation.

Example 9

On-Column Viral Inactivation Using a Wash Solution Containing 2% TRITON™ X-100 and 2 M NaCl at pH 3.0

The goal of this experiment was to determine if on-column viral inactivation could be performed with minimal recovery loss using a pH 3.0, 2 M NaCl, 100 mM glycine wash with 2% TRITON™ X-100.

In this experiment, the Protein A column and the target polypeptide were still the same as those in Example 4. All the buffer solutions used in each step were also the same as those listed in Table 6, except that the low pH wash (wash 2) buffer solution was 100 mM glycine, 2% TRITON™ X-100, 2 M NaCl, pH 3.0. All the flow rates were the same as in Example 4.

FIG. 9 is a chromatogram showing the protein concentration and the pH in each fraction during the chromatography steps. Table 12 summarizes the percentage recovery calculated for each chromatography step.

TABLE 12

Percentage Recovery in Each Chromatography Step
Using A Wash Solution Containing 2% TRITON™ χ-100
and 2M NaCl at pH 3.0.

| Step | Volume (ml) | Conc (mg/ml) | Mass (mgs) | % Recovery (calculated from total mass recovered) |
|---|---|---|---|---|
| Load | 50 | | | |
| F3 Wash 1 | 33.15 | 0.4350 | 14.42 | 10.3 |
| F4 Wash 2 | 33.15 | 0.0954 | 3.16 | 2.3 |
| F5 Wash 3 | 33.15 | 0.0000 | 0.00 | 0.0 |
| F6 Wash 4 + pre | 41.44 | 0.0440 | 0.00 | |
| F7 Elution | 23.205 | 5.2009 | 120.69 | 86.2 |
| F8 Regen | 33.15 | 0.0515 | 1.71 | 1.2 |
| Total Mass Recovered (mgs) | | | 140.0 | |
| Recoverable Titer Elution Mass/Load Volume | | | 2.80 | |
| Column Loading (mg/ml resin) | | | 21.2 | |

As shown in FIG. 9 and Table 12, only very minor product loss (2.3% of the target polypeptide) was observed during the low pH wash (F4, wash 2) with 2% TRITON™ X-100 and 2 M NaCl at pH 3.0. The majority of the product (86.2% of the target polypeptide) was recovered in the elution buffer (F7).

Example 10

On-Column Viral Inactivation Using a Wash Solution Containing 2 M NaCl at pH 3.0

The goal of this experiment was to determine if on-column viral inactivation could be performed with minimal recovery loss using a pH 3.0, 2 M NaCl, 100 mM glycine wash with no other modifiers.

In this experiment, the Protein A column and the target polypeptide were still the same as those in Example 4. All the buffer solutions used in each step were also the same as those listed in Table 6, except that the low pH wash (wash 2) buffer solution was 100 mM glycine, 2 M NaCl, pH 3.0. All the flow rates were the same as in Example 4.

FIG. 10 is a chromatogram showing the protein concentration and the pH in each fraction during the chromatography steps. Table 13 summarizes the percentage recovery calculated for each chromatography step.

TABLE 13

Percentage Recovery in Each Chromatography Step Using
A Wash Solution Containing 2M NaCl at pH 3.0.

| Step | Volume (ml) | Conc (mg/ml) | Mass (mgs) | % Recovery (calculated from total mass recovered) |
|---|---|---|---|---|
| Load | 50 | | | |
| F3 Wash 1 | 33.15 | 0.4540 | 15.05 | 8.2 |
| F4 Wash 2 | 33.15 | 0.9881 | 32.75 | 17.9 |
| F5 Wash 3 | 33.15 | 0.1212 | 4.02 | 2.2 |
| F6 Wash 4 + pre | 41.44 | 0.0099 | 0.00 | |
| F7 Elution | 23.205 | 5.6518 | 131.15 | 71.6 |
| F8 Regen | 33.15 | 0.0086 | 0.29 | 0.2 |
| Total Mass Recovered (mgs) | | | 183.3 | |
| Recoverable Titer Elution Mass/Load Volume | | | 3.67 | |
| Column Loading (mg/ml resin) | | | 27.8 | |

As shown in FIG. 10 and Table 13, only minor product loss (17.9% of the target polypeptide) was observed during the low pH wash (F4, wash 2) with 2 M NaCl at pH 3.0. The majority of the product (71.6% of the target polypeptide) was recovered in the elution buffer (F7).

Taken together, the results in Examples 1 to 10 demonstrate that on-column viral inactivation using a low pH and high salt wash solution could be effectively performed with minimal recovery loss.

Example 11

On-Column Viral Inactivation in a Mixed-Mode Anion Exchange Chromatography Column Using a Low pH Wash Solution Containing 2 M Ammonium Sulfate The objective of the following experiment is to demonstrate the potential feasibility and applicability of an on-column viral inactivation step using a low pH and high salt wash solution with other types of chromatography such as a mixed mode anion exchange chromatography.

In this experiment, 6 mL of 0.22 micron filtered product pool containing a monoclonal antibody from an anion exchange purification step at 10 mg/ml mab was loaded onto a 1.7 mL column containing CAPTO™ Adhere resin at pH 8.0. A high salt wash buffer at pH 8.0 was applied to the column (wash 1). A subsequent modified wash (wash 2-4) was then applied to maintain the high salt condition but drop the pH to where is suitable for viral inactivation, while the antibody remained bound to the absorbent.

Table 14 below shows the conditions used in each step. The flow rate of the chromatography was constant at 100 cm/hr.

TABLE 14

Individual buffers used in Example 11.

| Step | Buffer Components | pH | Vol. |
|---|---|---|---|
| EQ | 50 mM Tris | 8.0 | 15 CVs |
| Load | Filtered and concentrated HCCF | | 6 ml |
| Wash 1 | 50 mM Tris, 2M Ammonium Sulfate | 8.0 | 15 CVs |
| Wash 2 | 50 mM Acetate, 2M Ammonium Sulfate | 5.0 | 15 CVs |
| Wash 3 | 50 mM Citrate, 2M Ammonium Sulfate | 4.0 | 15 CVs |
| Wash 4 | 100 mM Citrate, 2M Ammonium Sulfate | 3.5 | 15 CVs |
| Elution | 100 mM Citrate | 3.4 | 15 CVs |
| Regeneration | 1N NaOH | | 15 CVs |
| Storage | 100 mL/L Benzyl Alcohol, 30.3 g/L Acidic Acid, 0.64 g/L NaOH, 965 mL RO/DI | | 10 CVs |

FIG. 11 is a chromatogram showing the protein concentration and the pH in each fraction during the chromatography steps.

The wash solutions used in this experiment resulted in minimal removal of target polypeptide (20.6%) at these low pHs (3.5 and 4.0). The overall recovery was 77.4% in this experiment.

Similar experiment was performed on a standard (not mixed-mode) anion exchange chromatography column using the same low pH and high salt wash solutions. In contrast, the overall recovery of the polypeptide was only 49.8% in this experiment, indicating that a significant amount of the polypeptide was eluted during the low pH wash. This experiment indicates that low pH viral inactivation may not be carried out while product is bound to a standard anion exchange resin by using high salt in the buffer.

Taken together, these results indicate that on-column viral inactivation using a low pH and high salt wash solution could be effectively performed with minimal recovery loss in certain chromatography methods, such as affinity chromatography and mix-mode anion-exchange chromatography.

Example 12

Inactivation of Viruses

Low pH can damage antibodies. An Fc-fusion protein was inactivated by the times and pH values required for viral inactivation. A novel on-column low pH viral inactivation method was developed. The mAb humanized IgG1 was produced in recombinant Chinese hamster ovary (CHO) cells grown in serum free medium. As described in this example, antibodies were retained on protein A and CAPTO ADHERE® at pH 3.0 using 2 M ammonium sulfate to increase hydrophobic interactions. On-column xMuLV inactivation was demonstrated on protein A with 2 M ammonium sulfate pH 3-3.5, 1 M Arginine, and the detergent LDAO. On-column inactivation helps minimize low pH exposure, eliminates added conductivity during pool acidification, and automates low pH inactivation steps. On-column inactivation provides benefit for semi-continuous multi-column chromatography which generates many low pH inactivation pools. As described in this example antibodies were retained on CAPTO MMC® at pH 8.0 using 2 M ammonium sulfate to increase hydrophobic interactions.

The Fc-fusion protein was produced in HEK293 cells grown in serum free medium. Xenotropic murine leukemia virus (X-MLV) was measured with PCR and infectivity based assays. Table 15 shows xMulV virus inactivation and removal provided by protein A wash buffers with an Fc-fusion protein.

TABLE 15 xMulV virus inactivation and removal provided by protein A wash buffers with an Fc-fusion protein.

| Protein A wash buffer | Virus Removal by PCR | Combined Removal andInactivation by Infectivity |
|---|---|---|
| Low pH (pH 3.5, 2M ammonium sulfate) | 4.96 | >6.39 |
| Arginine (1M arginine pH 4.8) | >5.54 | >6.39 |
| Detergent (LDAO 4X CMC) | 5.11 | >6.39 |

The protein A ligand binds the CH2 and CH3 domains of an antibody Fc through hydrophobic, ionic and hydrogen bond interactions. In one part of this example, a 6.6 mL MABSELECT™ SuRe column (19.4 cm) was loaded with 50 mL of HCCF with 2.2 mg/ml antibody. The column was washed with 100 mM BisTris buffer with 2000 mM ammonium sulfate at pH 6.6. A low pH wash buffer with ammonium sulfate was then applied (100 mM sodium citrate, 2000 mM ammonium sulfate at pH 3.0). The ammonium sulfate concentration was then reduced to zero over a 9 CV gradient. The flow rate for all steps was 250 cm/hr.

As shown in FIG. 12, the antibody began to desorb at about 1700 mM and was fully eluted at about 200 mM ammonium sulfate. FIG. 12 shows that at least 1700 mM ammonium sulfate is required to keep the antibody bound to protein A at pH 3.0. Since at least 1700 mM ammonium sulfate was required to keep the antibody bound to the resin at low pH, the solubility of the antibody was measured as a function of pH, antibody and ammonium sulfate concentration. The antibody was found to be soluble in 1000 mM ammonium sulfate but not 1500 mM ammonium sulfate. The precipitation was observed with 1500 mM ammonium sulfate at pH values between 3.5 and 8.0 and with antibody concentrations between 10 and 30 mg/mL.

In one part of this example, a 6.6 mL MABSELECT™ SuRe column (19.4 cm) was first equilibrated and then loaded to 25.8 g/L resin using 50 mL of antibody in HCCF. A flow rate of 250 cm/hr was used except during the regeneration step (50 cm/hr).

A pH 3.0, 2 M ammonium sulfate, 100 mM glycine wash was used to keep the antibody bound to the resin at low pH. The low pH, high ammonium sulfate wash was bracketed by a neutral, high ammonium sulfate wash buffer (pH 7.0, 2 M ammonium sulfate) to ensure that high levels of ammonium sulfate were present as the pH was lowered to 3.0 and also when it was subsequently raised to 7.0. Without this, significant product elution occurred before and after the wash step. Excess wash buffer was used at each step to ensure adequate buffer exchange. The step sequence and buffers used are identical to those used in Example 8. The protein concentration, conductivity, and pH in each step are shown in FIG. 8. FIG. 13 indicates that 2 M ammonium sulfate wash keeps antibody bound to protein A at pH 3.0.

In one part of this example, a 1.7 mL (5.0 cm) CAPTO ADHERE™ column was first equilibrated and then loaded with 6 mL of 11.4 g/L antibody in pH 8.0 50 mM Tris buffer. Subsequently a high salt pH 8.0 wash buffer and then a high salt pH 3.5 wash buffer were applied to the resin. Excess wash buffer was used at each step to ensure adequate buffer exchange. All steps were performed at 100 cm/hr. See Table 16.

TABLE 16

Step sequence and buffers used to produce FIG. 14 of Example 12.

| Step | Buffer | pH | Volume (CV or ml) |
|---|---|---|---|
| Equilibration | 50 mM Tris | 8.0 | 15 |
| Load | 50 mM Tris | 8.0 | 6 mL |
| Wash 1 | 50 mM Tris, 2M Ammonium Sulfate | 8.0 | 15 |
| Wash 2 | 100 mM Citrate 2M Ammonium Sulfate | 3.5 | 15 |
| Wash 3 | 50 mM Tris, 2M Ammonium Sulfate | 8.0 | 15 |
| Wash 4 | 50 mM Tris | 8.0 | 15 |
| Elution | 100 mM Citrate | 3.4 | 15 |
| Regeneration | 1.0 N NaOH | | 15 |

FIG. 14 shows that 2 M ammonium sulfate wash keeps antibody bound to CAPTO ADHERE® at pH 3.5. As shown in FIG. 14, minimal product loss was observed during the 2 M ammonium sulfate, pH 3.5 wash, which is surprising because at this pH both the product and the resin have a positive charge. It is likely that the product remains bound to the resin due to enhanced hydrophobic interactions in this high salt buffer. The majority of the product (79.0%) was recovered in the elution pool. The percentage of the peak that was monomeric antibody (98.4%) was not altered by the high ammonium sulfate wash.

In one part of this example, a 1.7 mL (5.1 cm) column with CAPTO MMC® mixed mode resin was loaded with 6 mL of 12.4 mg/mL antibody in a pH 4.5, 50 mM citrate buffer. Subsequently a high salt pH 4.5 wash and then a high salt pH 8.0 wash were applied. Excess wash buffer was used at each step to ensure adequate buffer exchange. The protein concentration, conductivity, and pH in each step are shown in FIG. 15. The buffers used in each step are shown in Table 17. All steps were performed at 100 cm/hr.

TABLE 17

Step sequence and buffers used to produce FIG. 15 of Example 12.

| Step | Buffer | pH | Volume (CV or ml) |
|---|---|---|---|
| Equilibration | 50 mM Citrate | 4.5 | 15 |
| Load | 50 mM Citrate | 4.5 | 6 mL |
| Wash 1 | 50 mM Citrate, 2M Ammonium Sulfate | 4.5 | 15 |
| Wash 2 | 50 mM Tris, 2M Ammonium Sulfate | 8.0 | 15 |
| Elution | 50 mM Tris | 8.0 | 15 |
| Regeneration | 0.1N NaOH | | 15 |

FIG. 15 shows that 2 M ammonium sulfate wash keeps antibody bound to CAPTO MMC® at pH 8.0. As shown in FIG. 15, minimal product loss was observed during the 2 M ammonium sulfate. pH 8.0 wash, which is surprising because at this pH both the product and the resin have a negative charge and antibody elution would be expected to occur. The percent recovery in the eluate pool was 94.1%. It is likely that the product remains bound to the resin due to enhanced hydrophobic interactions in this high salt buffer.

A similar experiment was performed using TMAE HiCap resin. TMAE HiCap resin is an anion exchange resin that lacks the hydrophobic interaction properties of the CAPTO ADHERE™ resin. Significant product loss occurred during the low pH washes and the overall recovery was 49.8%. The product that eluted during the low pH wash precipitated in the column and in the instrumentation. The TMAE HiCap resin experiment indicates that kosmotropic salts were not capable of preserving adsorption of the mAb to the anion exchange resin at low pH.

The on-column low pH viral inactivation method shows that antibodies were retained on protein A and CAPTO ADHERE® at pH 3.0 using 2 M ammonium sulfate to increase hydrophobic interactions. On-column xMuLV inactivation was demonstrated on protein A with 2 M ammonium sulfate pH 3-3.5, 1 M Arginine, and the detergent LDAO.

These data show that on-column inactivation helps minimize low pH exposure, eliminates added conductivity during pool acidification, automates low pH inactivation step, and helps enable semi-continuous multi-column chromatography.

The present invention is not to be limited in scope by the specific embodiments described which are intended as single illustrations of individual aspects of the invention, and any compositions or methods which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All documents, articles, publications, patents, and patent applications mentioned in this specification are herein incorporated by reference to the same extent as if each individual publication or patent application was specifically and individually indicated to be incorporated by reference.

The present application claims priority to U.S. Provisional Application No. 61/882,488, filed Sep. 25, 2014 and U.S. Provisional Application No. 62/028,657, filed Jul. 24, 2014, which are incorporated herein by reference in their entireties.

TABLE OF SEQUENCES

TABLE 15

Polynucleotide Sequences of FVIII

A. B-Domain Deleted FVIII-Fc
(i) B-Domain Deleted FVIII-Fc Chain DNA Sequence (MB signal peptide
underlined, Fc region in bold) (SEQ ID NO: 1, which encodes SEQ ID NO: 2)

```
   1    atgcaaatag agctctccac ctgcttcttt ctgtgccttt tgcgattctg 51    ctttagtgcc accagaagat actacctggg tgcagtggaa ctgtcatggg 101    actatatgca aagtgatctc ggtgagctgc ctgtggacgc aagatttcct 151    cctagagtgc caaaatcttt tccattcaac acctcagtcg tgtacaaaaa 201    gactctgttt gtagaattca cggatcacct tttcaacatc gctaagccaa 251    ggccaccctg gatgggtctg ctaggtccta ccatccaggc tgaggtttat 301    gatacagtgg tcattacact taagaacatg gcttcccatc ctgtcagtct 351    tcatgctgtt ggtgtatcct actggaaagc ttctgaggga gctgaatatg 401    atgatcagac cagtcaaagg gagaaagaag atgataaagt cttccctggt 451    ggaagccata catatgtctg gcaggtcctg aaagagaatg gtccaatggc 501    ctctgaccca ctgtgcctta cctactcata tctttctcat gtggacctgg 551    taaaagactt gaattcaggc ctcattggag ccctactagt atgtagagaa 601    gggagtctgg ccaaggaaaa gacacagacc ttgcacaaat ttatactact 651    ttttgctgta tttgatgaag ggaaaagttg gcactcagaa acaaagaact 701    ccttgatgca ggatagggat gctgcatctg ctcgggcctg gcctaaaatg 751    cacacagtca atggttatgt aaacaggtct ctgccaggtc tgattggatg 801    ccacaggaaa tcagtctatt ggcatgtgat tggaatgggc accactcctg 851    aagtgcactc aatattcctc gaaggtcaca catttcttgt gaggaaccat 901    cgccaggcgt ccttggaaat ctcgccaata actttcctta ctgctcaaac 951    actcttgatg gaccttggac agtttctact gttttgtcat atctcttccc 1001    accaacatga tggcatggaa gcttatgtca aagtagacag ctgtccagag 1051    gaaccccaac tacgaatgaa aaataatgaa gaagcggaag actatgatga 1101    tgatcttact gattctgaaa tggatgtggt caggtttgat gatgacaact 1151    ctccttcctt tatccaaatt cgctcagttg ccaagaagca tcctaaaact 1201    tgggtacatt acattgctgc tgaagaggag gactgggact atgctccctt 1251    agtcctcgcc cccgatgaca aagttataaa agtcaatatt tgaacaatg 1301    gccctcagcg gattggtagg aagtacaaaa aagtccgatt tatggcatac 1351    acagatgaaa cctttaagac tcgtgaagct attcagcatg aatcaggaat 1401    cttgggacct ttactttatg gggaagttgg agacacactg ttgattatat 1451    ttaagaatca agcaagcaga ccatataaca tctaccctca cggaatcact 1501    gatgtccgtc ctttgtattc aaggagatta ccaaaaggtg taaaacattt 1551    gaaggatttt ccaattctgc caggagaaat attcaaatat aaatggacag
```

TABLE 15-continued

Polynucleotide Sequences of FVIII

```
1601  tgactgtaga agatgggcca actaaatcag atcctcggtg cctgacccgc
1651  tattactcta gtttcgttaa tatggagaga gatctagctt caggactcat
1701  tggccctctc ctcatctgct acaaagaatc tgtagatcaa agaggaaacc
1751  agataatgtc agacaagagg aatgtcatcc tgttttctgt atttgatgag
1801  aaccgaagct ggtacctcac agagaatata caacgctttc tccccaatcc
1851  agctggagtg cagcttgagg atccagagtt ccaagcctcc aacatcatgc
1901  acagcatcaa tggctatgtt tttgatagtt tgcagttgtc agtttgtttg
1951  catgaggtgg catactggta cattctaagc attggagcac agactgactt
2001  cctttctgtc ttcttctctg gatataccct caaacacaaa atggtctatg
2051  aagacacact caccctattc ccattctcag gagaaactgt cttcatgtcg
2101  atggaaaacc caggtctatg gattctgggg tgccacaact cagactttcg
2151  gaacagaggc atgaccgcct tactgaaggt ttctagttgt gacaagaaca
2201  ctggtgatta ttacgaggac agttatgaag atatttcagc atacttgctg
2251  agtaaaaaca atgccattga accaagaagc ttctctcaaa acccaccagt
2301  cttgaaacgc catcaacggg aaataactcg tactactctt cagtcagatc
2351  aagaggaaat tgactatgat gataccatat cagttgaaat gaagaaggaa
2401  gattttgaca tttatgatga ggatgaaaat cagagccccc gcagctttca
2451  aaagaaaaca cgacactatt ttattgctgc agtggagagg ctctgggatt
2501  atgggatgag tagctcccca catgttctaa gaaacagggc tcagagtggc
2551  agtgtccctc agttcaagaa agttgttttc caggaattta ctgatggctc
2601  ctttactcag cccttatacc gtggagaact aaatgaacat ttgggactcc
2651  tggggccata tataagagca gaagttgaag ataatatcat ggtaactttc
2701  agaaatcagg cctctcgtcc ctattccttc tattctagcc ttatttctta
2751  tgaggaagat cagaggcaag gagcagaacc tagaaaaaac tttgtcaagc
2801  ctaatgaaac caaaacttac ttttggaaag tgcaacatca tatggcaccc
2851  actaaagatg agtttgactg caaagcctgg gcttatttct ctgatgttga
2901  cctggaaaaa gatgtgcact caggcctgat tggacccctt ctggtctgcc
2951  acactaacac actgaaccct gctcatggga gacaagtgac agtacaggaa
3001  tttgctctgt ttttcaccat ctttgatgag accaaaagct ggtacttcac
3051  tgaaaatatg gaaagaaact gcagggctcc ctgcaatatc cagatggaag
3101  atcccacttt taaagagaat atcgcttcc atgcaatcaa tggctacata
3151  atggatacac tacctggctt agtaatggct caggatcaaa ggattcgatg
3201  gtatctgctc agcatgggca gcaatgaaaa catccattct attcatttca
3251  gtggacatgt gttcactgta cgaaaaaaag aggagtataa aatggcactg
3301  tacaatctct atccaggtgt ttttgagaca gtggaaatgt taccatccaa
3351  agctggaatt tggcgggtgg aatgccttat tggcgagcat ctacatgctg
3401  ggatgagcac acttttttctg gtgtacagca ataagtgtca gactcccctg
3451  ggaatggctt ctggacacat tagagatttt cagattacag cttcaggaca
3501  atatggacag tgggcccaa agctggccag acttcattat tccggatcaa
```

TABLE 15-continued

Polynucleotide Sequences of FVIII

```
3551  tcaatgcctg agcaccaag gagcccttt cttggatcaa ggtggatctg
3601  ttggcaccaa tgattattca cggcatcaag acccagggtg cccgtcagaa
3651  gttctccagc ctctacatct ctcagtttat catcatgtat agtcttgatg
3701  ggaagaagtg gcagacttat cgaggaaatt ccactggaac cttaatggtc
3751  ttctttggca atgtggattc atctgggata aaacacaata ttttttaaccc
3801  tccaattatt gctcgataca tccgtttgca cccaactcat tatagcattc
3851  gcagcactct tcgcatggaa ttgatgggct gtgatttaaa tagttgcagc
3901  atgccattgg gaatggagag taaagcaata tcagatgcac agattactgc
3951  ttcatcctac tttaccaata tgtttgccac ctggtctcct tcaaaagctc
4001  gacttcacct ccaagggagg agtaatgcct ggagacctca ggtgaataat
4051  ccaaaagagt ggctgcaagt ggacttccag aagacaatga agtcacagg
4101  agtaactact cagggagtaa aatctctgct taccagcatg tatgtgaagg
4151  agttcctcat ctccagcagt caagatggca atcagtggac tctcttttt
4201  cagaatggca aagtaaaggt ttttcaggga aatcaagact ccttcacacc
4251  tgtggtgaac tctctagacc caccgttact gactcgctac cttcgaattc
4301  accccagag ttgggtgcac caaattgccc tgaggatgga ggttctgggc
4351  tgcgaggcac aggacctcta cgacaaaact cacacatgcc caccgtgccc
4401  agctccagaa ctcctgggcg gaccgtcagt cttcctcttc cccccaaaac
4451  ccaaggacac cctcatgatc tcccggaccc ctgaggtcac atgcgtggtg
4501  gtggacgtga gccacgaaga ccctgaggtc aagttcaact ggtacgtgga
4551  cggcgtggag gtgcataatg ccaagacaaa gccgcgggag gagcagtaca
4601  acagcacgta ccgtgtggtc agcgtcctca ccgtcctgca ccaggactgg
4651  ctgaatggca aggagtacaa gtgcaaggtc tccaacaaag ccctcccagc
4701  ccccatcgag aaaaccatct ccaaagccaa agggcagccc cgagaaccac
4751  aggtgtacac cctgccccca tcccgggatg agctgaccaa gaaccaggtc
4801  agcctgacct gcctggtcaa aggcttctat cccagcgaca tcgccgtgga
4851  gtgggagagc aatgggcagc cggagaacaa ctacaagacc acgcctcccg
4901  tgttggactc cgacggctcc ttcttcctct acagcaagct caccgtggac
4951  aagagcaggt ggcagcaggg gaacgtcttc tcatgctccg tgatgcatga
5001  ggctctgcac aaccactaca cgcagaagag cctctccctg tctccgggta
5051  aa
```

(ii) Fc DNA sequence (mouse Igκ signal peptide underlined) (SEQ ID NO: 3, which encodes SEQ ID NO: 4)

```
  1  atggagacag acacactcct gctatgggta ctgctgctct gggttccagg
 51  ttccactggt gacaaaactc acacatgccc accgtgccca gcacctgaac
101  tcctgggagg accgtcagtc ttcctcttcc ccccaaaacc caaggacacc
151  ctcatgatct cccggacccc tgaggtcaca tgcgtggtgg tggacgtgag
201  ccacgaagac cctgaggtca agttcaactg gtacgtggac ggcgtggagg
251  tgcataatgc caagacaaag ccgcgggagg agcagtacaa cagcacgtac
301  cgtgtggtca gcgtcctcac cgtcctgcac caggactggc tgaatggcaa
```

TABLE 15-continued

Polynucleotide Sequences of FVIII

| | |
|---|---|
| 351 | ggagtacaag tgcaaggtct ccaacaaagc cctcccagcc cccatcgaga |
| 401 | aaaccatctc caaagccaaa gggcagcccc gagaaccaca ggtgtacacc |
| 451 | ctgcccccat cccgcgatga gctgaccaag aaccaggtca gcctgacctg |
| 501 | cctggtcaaa ggcttctatc ccagcgacat cgccgtggag tgggagagca |
| 551 | atgggcagcc ggagaacaac tacaagacca cgcctcccgt gttggactcc |
| 601 | gacggctcct tcttcctcta cagcaagctc accgtggaca gagcaggtg |
| 651 | gcagcagggg aacgtcttct catgctccgt gatgcatgag gctctgcaca |
| 701 | accactacac gcagaagagc ctctccctgt ctccgggtaa a |

B. Full Length FVIII-Fc
(i) Full Length FVIII-Fc DNA Sequence (FVIII signal peptide underlined, Fc region in bold) (SEQ ID NO: 5, which encodes SEQ ID NO: 6)

| | |
|---|---|
| 1 | <u>atgcaaatag agctctccac ctgcttcttt ctgtgccttt tgcgattctg</u> |
| 51 | <u>ctttagt</u>gcc accagaagat actacctggg tgcagtggaa ctgtcatggg |
| 101 | actatatgca agtgatctc ggtgagctgc ctgtggacgc aagatttcct |
| 151 | cctagagtgc caaaatcttt tccattcaac acctcagtcg tgtacaaaaa |
| 201 | gactctgttt gtagaattca cggatcacct tttcaacatc gctaagccaa |
| 251 | ggccaccctg gatgggtctg ctaggtccta ccatccaggc tgaggtttat |
| 301 | gatacagtgg tcattacact taagaacatg gcttcccatc ctgtcagtct |
| 351 | tcatgctgtt ggtgtatcct actggaaagc ttctgaggga gctgaatatg |
| 401 | atgatcagac cagtcaaagg gagaaagaag atgataaagt cttccctggt |
| 451 | ggaagccata catatgtctg gcaggtcctg aaagagaatg gtccaatggc |
| 501 | ctctgaccca ctgtgcctta cctactcata tctttctcat gtggacctgg |
| 551 | taaaagactt gaattcaggc ctcattggag ccctactagt atgtagagaa |
| 601 | gggagtctgg ccaaggaaaa gacacagacc ttgcacaaat ttatactact |
| 651 | ttttgctgta tttgatgaag ggaaaagttg gcactcagaa acaaagaact |
| 701 | ccttgatgca ggataggat gctgcatctg ctcgggcctg gcctaaaatg |
| 751 | cacacagtca atggttatgt aaacaggtct ctgccaggtc tgattggatg |
| 801 | ccacaggaaa tcagtctatt ggcatgtgat tggaatgggc accactcctg |
| 851 | aagtgcactc aatattcctc gaaggtcaca catttcttgt gaggaaccat |
| 901 | cgccaggcgt ccttggaaat ctcgccaata acttttcctta ctgctcaaac |
| 951 | actcttgatg gaccttggac agtttctact gttttgtcat atctcttccc |
| 1001 | accaacatga tggcatgaa gcttatgtca agtagacag ctgtccagag |
| 1051 | gaaccccaac tacgaatgaa aaataatgaa gaagcggaag actatgatga |
| 1101 | tgatcttact gattctgaaa tggatgtggt caggtttgat gatgacaact |
| 1151 | ctccttcctt tatccaaatt cgctcagtta ccaagaagca tcctaaaact |
| 1201 | tgggtacatt acattgctgc tgaagaggaa gactgggact atgctccctt |
| 1251 | agtcctcgcc cccgatgaca aagttataa aagtcaatat ttgaacaatg |
| 1301 | gccctcagcg gattggtagg aagtacaaaa aagtccgatt tatggcatac |
| 1351 | acagatgaaa cctttaagac tcgtgaagct attcagcatg aatcaggaat |
| 1401 | cttgggacct ttactttatg ggaagttga agacacactg ttgattatat |

TABLE 15-continued

Polynucleotide Sequences of FVIII

```
1451  ttaagaatca agcaagcaga ccatataaca tctaccctca cggaatcact
1501  gatgtccgtc ctttgtattc aaggagatta ccaaaaggtg taaaacattt
1551  gaaggatttt ccaattctgc aggagaaat attcaaatat aaatggacag
1601  tgactgtaga agatgggcca actaaatcag atcctcggtg cctgacccac
1651  tattactcta gtttcgttaa tatggagaga gatctagctt caggactcat
1701  tggccctctc ctcatctgct acaaagaatc tgtagatcaa agaggaaacc
1751  agataatgtc agacaagagg aatgtcatcc tgttttctgt atttgatgag
1801  aaccgaagct ggtacctcac agagaatata caacgctttc tccccaatcc
1851  agctggagtg cagcttgagg atccagagtt ccaagcctcc aacatcatgc
1901  acagcatcaa tggctatgtt tttgatagtt tgcagttgtc agtttgtttg
1951  catgaggtgg catactggta cattctaagc attggagcac agactgactt
2001  cctttctgtc ttcttctctg atatacctt caaacacaaa atggtctatg
2051  aagacacact caccctattc ccattctcag gagaaactgt cttcatgtcg
2101  atggaaaacc caggtctatg gattctgggg tgccacaact cagactttcg
2151  gaacagagc atgaccgcct tactgaaggt ttctagttgt gacaagaaca
2201  ctggtgatta ttacgaggac agttatgaag atatttcagc atacttgctg
2251  agtaaaaaca atgccattga accaagaagc ttctcccaga attcaagaca
2301  ccctagcact aggcaaaagc aatttaatgc caccacaatt ccagaaaatg
2351  acatagagaa gactgacct tggtttgcac acagaacacc tatgcctaaa
2401  atacaaaatg tctcctctag tgatttgttg atgctcttgc gacagagtcc
2451  tactccacat gggctatcct tatctgatct ccaagaagcc aaatatgaga
2501  cttttctga tgatccatca cctggagcaa tagacagtaa taacagcctg
2551  tctgaaataa cacacttcag gccacagctc catcacagtg gggacatggt
2601  atttacccct gagtcaggcc tccaattaag attaaatgag aaactgggga
2651  caactgcagc aacagagttg aagaaacttg atttcaaagt ttctagtaca
2701  tcaaataatc tgattcaac aattccatca gacaatttgg cagcaggtac
2751  tgataataca agttccttag acccccaag tatgccagtt cattatgata
2801  gtcaattaga taccactcta tttggcaaaa agtcatctcc ccttactgag
2851  tctggtggac ctctgagctt gagtgaagaa aataatgatt caaagttgtt
2901  agaatcaggt ttaatgaata gccaagaaag ttcatgggga aaaaatgtat
2951  cgtcaacaga gagtggtagg ttatttaaag ggaaaagagc tcatggacct
3001  gctttgttga ctaaagataa tgccttattc aaagttagca tctctttgtt
3051  aaagacaaac aaaacttcca ataattcagc aactaataga aagactcaca
3101  ttgatggccc atcattatta attgagaata gtccatcagt ctggcaaaat
3151  atattagaaa gtgacactga gtttaaaaaa gtgacacctt tgattcatga
3201  cagaatgctt atggacaaaa atgctacagc tttgaggcta aatcatatgt
3251  caaataaaac tacttcatca aaaaacatgg aaatggtcca acagaaaaaa
3301  gagggcccca ttccaccaga tgcacaaaat ccagatatgt cgttctttaa
3351  gatgctattc ttgccagaat cagcaaggtg gatacaaagg actccatggaa
```

TABLE 15-continued

Polynucleotide Sequences of FVIII

```
3401  agaactctct gaactctggg caaggcccca gtccaaagca attagtatcc
3451  ttaggaccag aaaaatctgt ggaaggtcag aatttcttgt ctgagaaaaa
3501  caaagtggta gtaggaaagg gtgaatttac aaaggacgta ggactcaaag
3551  agatggtttt tccaagcagc agaaacctat ttcttactaa cttggataat
3601  ttacatgaaa ataatacaca caatcaagaa aaaaaaattc aggaagaaat
3651  agaaaagaag gaaacattaa tccaagagaa tgtagttttg cctcagatac
3701  atacagtgac tggcactaag aatttcatga agaacctttt cttactgagc
3751  actaggcaaa atgtagaagg ttcatatgac ggggcatatg ctccagtact
3801  tcaagatttt aggtcattaa atgattcaac aaatagaaca agaaacacac
3851  cagctcattt ctcaaaaaaa ggggaggaag aaaacttgga aggcttggga
3901  aatcaaacca agcaaattgt agagaaatat gcatgcacca caaggatatc
3951  tcctaataca agccagcaga attttgtcac gcaacgtagt aagagagctt
4001  tgaaacaatt cagactccca ctagaagaaa cagaacttga aaaaggata
4051  attgtggatg acacctcaac ccagtggtcc aaaaacatga acatttgac
4101  cccgagcacc ctcacacaga tagactacaa tgagaaggag aaaggggcca
4151  ttactcagtc tcccttatca gattgcctta cgaggagtca tagcatccct
4201  caagcaaata gatctccatt acccattgca aaggtatcat catttccatc
4251  tattagacct atatatctga ccagggtcct attccaagac aactcttctc
4301  atcttccagc agcatcttat agaaagaaag attctggggt ccaagaaagc
4351  agtcatttct tacaaggagc aaaaaaaat aaccttttctt tagccattct
4401  aaccttggag atgactggtg atcaaagaga ggttggctcc ctggggacaa
4451  gtgccacaaa ttcagtcaca tacaagaaag ttgagaacac tgttctcccg
4501  aaaccagact tgcccaaaac atctggcaaa gttgaattgc ttccaaaagt
4551  tcacatttat cagaaggacc tattccctac ggaaactagc aatgggtctc
4601  ctggccatct ggatctcgtg aagggagcc ttcttcaggg aacagaggga
4651  gcgattaagt ggaatgaagc aaacagacct agaaaagttc cctttctgag
4701  agtagcaaca gaaagctctg caaagactcc ctccaagcta ttggatcctc
4751  ttgcttggga taaccactat ggtactcaga taccaaaaga agagtggaaa
4801  tcccaagaga agtcaccaga aaaacagct tttaagaaaa aggataccat
4851  tttgtccctg aacgcttgtg aaagcaatca tgcaatagca gcaataaatg
4501  agggacaaaa taagcccgaa atagaagtca cctgggcaaa gcaaggtagg
4551  actgaaaggc tgtgctctca aaacccacca gtcttgaaac gccatcaacg
5001  ggaaataact cgtactactc ttcagtcaga tcaagaggaa attgactatg
5051  atgataccat atcagttgaa atgaagaagg aagattttga catttatgat
5101  gaggatgaaa atcagagccc ccgcagcttt caaaagaaaa cacgacacta
5151  ttttattgct gcagtggaga ggctctggga ttatgggatg agtagctccc
5201  cacatgttct aagaaacagg gctcagagtg gcagtgtccc tcagttcaag
5251  aaagttgttt tccaggaatt tactgatggc tcctttactc agcccttata
5301  ccgtggagaa ctaaatgaac atttgggact cctggggcca tatataagag
```

TABLE 15-continued

Polynucleotide Sequences of FVIII

```
5351  cagaagttga agataatatc atggtaactt tcagaaatca ggcctctcgt
5401  ccctattcct tctattctag ccttatttct tatgaggaag atcagaggca
5451  aggagcagaa cctagaaaaa actttgtcaa gcctaatgaa accaaaactt
5501  acttttggaa agtgcaacat catatggcac ccactaaaga tgagtttgac
5551  tgcaaagcct gggcttattt ctctgatgtt gacctagaaa agatgtgca
5601  ctcaggcctg attggacccc ttctggtctg ccacactaac acactgaacc
5651  ctgctcatgg gagacaagtg acagtacagg aatttgctct gttttttcacc
5701  atctttgatg agaccaaaag ctggtacttc actgaaaata tggaaagaaa
5751  ctgcagggct ccctgcaata tccagatgga agatcccact tttaaagaga
5801  attatcgctt ccatgcaatc aatggctaca ataatggatac actacctggc
5851  ttagtaatgg ctcaggatca aaggattcga tggtatctgc tcagcatggg
5901  cagcaatgaa acatccatt ctattcattt cagtggacat gtgttcactg
5951  tacgaaaaaa agaggagtat aaaatggcac tgtacaatct ctatccaggt
6001  gttttttgaga cagtggaaat gttaccatcc aaagctggaa tttggcgggt
6051  ggaatgcctt attggcgagc atctacatgc tgggatgagc acttttttc
6101  tggtgtacag caataagtgt cagactcccc tgggaatggc ttctggacac
6151  attagagatt tcagattac agcttcagga caatatggac agtgggcccc
6201  aaagctggcc agacttcatt attccggatc aatcaatgcc tggagcacca
6251  aggagccctt tcttggatc aaggtggatc tgttggcacc aatgattatt
6301  cacggcatca agacccaggg tgcccgtcag aagttctcca gcctctacat
6351  ctctcagttt atcatcatgt atagtcttga tgggaagaag tggcagactt
6401  atcgaggaaa ttccactgga accttaatgg tcttctttgg caatgtggat
6451  tcatctggga taaaacacaa tattttttaac cctccaatta ttgctcgata
6501  catccgtttg cacccaactc attatagcat tcgcagcact cttcgcatgg
6551  agttgatggg ctgtgattta aatagttgca gcatgccatt gggaatggag
6601  agtaaagcaa tatcagatgc acagattact gcttcatcct actttaccaa
6651  tatgtttgcc acctggtctc cttcaaaagc tcgacttcac ctccaaggga
6701  ggagtaatgc ctggagacct caggtgaata atccaaaaga gtggctgcaa
6751  gtggacttcc agaagacaat gaaagtcaca ggagtaacta tcagggagt
6801  aaaatctctg cttaccagca tgtatgtgaa ggaattcctc atctccagca
6851  gtcaagatgg ccatcagtgg actctctttt ttcagaatgg caaagtaaag
6901  gttttttcagg gaaatcaaga ctccttcaca cctgtggtga actctctaga
6951  cccaccgtta ctgactcgct accttcgaat tcaccccag agttgggtgc
7001  accagattgc cctgaggatg gaggttctgg gctgcgaggc acaggacctc
7051  tacgacaaaa ctcacacatg cccaccgtgc ccagctccag aactcctggg
7101  cggaccgtca gtcttcctct tccccccaaa acccaaggac accctcatga
7151  tctcccggac ccctgaggtc acatgcgtgg tggtggacgt gagccacgaa
7201  gaccctgagg tcaagttcaa ctggtacgtg gacggcgtgg aggtgcataa
7251  tgccaagaoa aagccgcggg aggagcagta caacagcacg taccgtgtgg
```

TABLE 15-continued

Polynucleotide Sequences of FVIII

| | |
|---|---|
| 7301 | tcagcgtcct caccgtcctg caccaggact ggctgaatgg caaggagtac |
| 7351 | aagtgcaagg tctccaacaa agccctccca gcccccatcg agaaaaccat |
| 7401 | ctccaaagcc aaagggcagc ccgagaacc acaggtgtac accctgcccc |
| 7451 | catcccggga tgagctgacc aagaaccagg tcagcctgaa ctgcctggtc |
| 7501 | aaaggcttct atcccagcga catcgccgtg gagtgggaga gcaatgggca |
| 7551 | gccggagaac aactacaaga ccacgcctcc cgtgttggac tccgacggct |
| 7601 | ccttcttcct ctacagcaag ctcaccgtgg acaagagcag gtggcagcag |
| 7651 | gggaacgtct tctcatgctc cgtgatgcat gaggctctgc acaaccacta |
| 7701 | cacgcagaag agcctctccc tgtctccggg taaa |

C. FVIII-Fc Heterodimer Hybrid
(i) FVIII Heavy Chain (HC)-Fc DNA sequence (no linker between HC and Fc) (signal peptide underlined, Fc region in bold) (SEQ ID NO: 7, which encodes SEQ ID NO: 8)

| | |
|---|---|
| 1 | <u>atgcaaatag agctctccac ctgcttcttt ctgtgccttt tgcgattctg</u> |
| 51 | <u>ctttagt</u>gcc accagaagat actacctggg tgcagtggaa ctgtcatggg |
| 101 | actatatgca aagtgatctc ggtgagctgc ctatggacgc aagatttcct |
| 151 | cctagagtgc caaatctttt ccattcaac acctcagtcg tgtacaaaaa |
| 201 | gactctgttt gtagaattca cgaatcacct tttcaacatc gctaagccaa |
| 251 | ggccaccctg atgggtctg ctaggtccta ccatccaggc tgaggtttat |
| 301 | gatacagtgg tcattacact taagaacata gcttcccatc ctgtcagtct |
| 351 | tcatgctgtt ggtgtatcct actggaaagc ttctgaggga ctgaatatg |
| 401 | atgatcagac cagtcaaagg gagaaagaag atgataaagt cttccctggt |
| 451 | ggaagccata catatgtctg gcaggtcctg aaagagaatg gtccaatggc |
| 501 | ctctgaccca ctgtgcctta cctactcata tctttctcat gtggacctgg |
| 551 | taaaagactt gaattcaggc ctcattggag ccctactagt atgtagagaa |
| 601 | gggagtctgg ccaaggaaaa gacacagacc ttgcacaaat ttatactact |
| 651 | ttttgctgta tttgatgaag ggaaaagttg gcactcagaa acaaagaact |
| 701 | ccttgatgca ggatagggat gctgcatctg ctcgggcctg gcctaaaatg |
| 751 | ccacaggaaa tcagtctatt ggcatgtgat tggaatgggc accactcctg |
| 851 | aagtgcactc aatattcctc gaaggtcaca catttcttgt gaggaaccat |
| 901 | cgccaggcgt ccttggaaat ctcgccaata actttcctta ctgctcaaac |
| 951 | actcttgatg gaccttggac agtttctact gttttgtcat atctcttccc |
| 1001 | accaacatga tggcatggaa gcttatgtca agtagacag ctgtccagag |
| 1051 | gaaccccaac tacgaatgaa aaataatgaa gaagcggaag actatgatga |
| 1101 | tgatcttact gattctgaaa tggatgtggt caggtttgat gatgacaact |
| 1151 | ctccttcctt tatccaaatt cgctcagttg ccaagaagca tcctaaaact |
| 1201 | tgggtacatt acattgctgc tgaagaggag gactgggact atgctccctt |
| 1251 | agtcctcgcc cccgatgaca aagttataa aagtcaatat ttgaacaatg |
| 1301 | gccctcagcg gattggtagg aagtacaaaa aagtccgatt tatggcatac |
| 1351 | acagatgaaa cctttaagac tcgtgaagct attcagcatg aatcaggaat |
| 1401 | cttgggacct ttactttatg ggaagttgg agacacactg ttgattatat |

TABLE 15-continued

Polynucleotide Sequences of FVIII

| | |
|---|---|
| 1451 | ttaagaatca agcaagcaga ccatataaca tctaccctca cggaatcact |
| 1501 | gatgtccgtc ctttgtattc aaggagatta ccaaaaggtg taaaacattt |
| 1551 | gaaggatttt ccaattctgc caggagaaat attcaaatat aaatggacag |
| 1601 | tgactgtaga aaatgggcca actaaatcag atcctcggtg cctgacccgc |
| 1651 | tattactcta gtttcgttaa tatggagaga gatctagctt caggactcat |
| 1701 | tggccctctc ctcatctgct acaaagaatc tgtagatcaa agaggaaacc |
| 1751 | agataatgtc agacaagagg aatgtcatcc tgttttctgt atttgatgag |
| 1801 | aaccgaagct ggtacctcac agagaatata caacgctttc tccccaatcc |
| 1851 | agctggagtg cagcttgagg atccagagtt ccaagcctcc aacatcatgc |
| 1S01 | acagcatcaa tggctatgtt tttgatagtt tgcagttgtc agtttgtttg |
| 1951 | catgaggtgg catactggta cattctaagc attggagcac agactgactt |
| 2001 | cctttctgtc ttcttctctg gatataccct caaacacaaa atggtctatg |
| 2051 | aagacacact caccctattc ccattctcag agaaactgt cttcatgtcg |
| 2101 | atggaaaacc caggtctatg gattctgggg tgccacaact cagactttcg |
| 2151 | gaacagaggc atgaccgcct tactgaaggt ttctagttgt gacaagaaca |
| 2201 | ctggtgatta ttacgaggac agttatgaag atatttcagc atacttgctg |
| 2251 | agtaaaaaca atgccattga accaagagac aaaactcaca catgcccacc |
| 2301 | gtgcccagct ccagaactcc tgggcggacc gtcagtcttc ctcttccccc |
| 2351 | caaaacccaa ggacaccctc atgatctccc ggacccctga ggtcacatgc |
| 2401 | gtggtggtgg acgtgagcca cgaagaccct gaggtcaagt tcaactggta |
| 2451 | cgtggacggc gtggaggtgc ataatgccaa gacaaagccg cgggaggagc |
| 2501 | agtacaacag cacgtaccgt gtggtcagcg tcctcaccgt cctgcaccag |
| 2551 | gactggctga atggcaagga gtacaagtgc aaggtctcca acaaagccct |
| 2601 | cccagccccc atcgagaaaa ccatctccaa agccaagggg cagccccgag |
| 2651 | aaccacaggt gtacaccctg cccccatccc gggatgagct gaccaagaac |
| 2701 | caggtcagcc tgacctgcct ggtcaaaggc ttctatccca gcgacatcgc |
| 2751 | cgtggagtgg gagagcaatg ggcagccgga gaacaactac aagaccacgc |
| 2801 | ctcccgtgtt ggactccgac ggctccttct tcctctacag caagctcacc |
| 2851 | gtggacaaga gcaggtggca gcaggggaac gtcttctcat gctccgtgat |
| 2901 | gcatgaggct ctgcacaacc actacacgca gaagagcctc tccctgtctc |
| 2951 | cgggtaaa |

(ii) FVIII Heavy Chain (HC)-Fc DNA sequence (5 amino acid linker between HC and Fc) (signal peptide underlined, Fc region in bold, 5 amino acid linker is double-underlined) (SEQ ID NO: 9, which encodes SEQ ID NO: 10)

| | |
|---|---|
| 1 | <u>atgcaaatag agctctccac ctgcttcttt ctgtgccttt tgcgattctg</u> |
| 51 | <u>ctttagtgcc</u> accagaagat actacctggg tgcagtggaa ctgtcatggg |
| 101 | actatatgca aagtgatctc ggtgagctgc ctgtggacgc aagatttcct |
| 151 | cctagagtgc caaaatcttt tccattcaac acctcagtcg tgtacaaaaa |
| 201 | gactctgttt gtagaattca cggatcacct tttcaacatc gctaagccaa |
| 251 | ggccaccctg gatgggtctg ctaggtccta ccatccaggc tgaggtttat |

TABLE 15-continued

Polynucleotide Sequences of FVIII

```
 301   gatacagtgg tcattacact taagaacatg gcttcccatc ctgtcagtct
 351   tcatgctgtt ggtgtatcct actggaaagc ttctgaggga gctgaatatg
 401   atgatcagac cagtcaaagg gagaaagaag atgataaagt cttccctggt
 451   ggaagccata catatgtctg gcaggtcctg aaagagaatg gtccaatggc
 501   ctctgaccca ctgtgcctta cctactcata tctttctcat gtggacctgg
 551   taaaagactt gaattcaggc ctcattggag ccctactagt atgtagagaa
 601   gggagtctgg ccaaggaaaa gacacagacc ttgcacaaat ttatactact
 651   ttttgctgta tttgatgaag ggaaaagttg gcactcagaa acaaagaact
 701   ccttgatgca ggataggggat gctgcatctg ctcgggcctg gcctaaaatg
 751   cacacagtca atggttatgt aaacaggtct ctgccaggtc tgattggatg
 801   ccacaggaaa tcaatctatt ggcatgtgat tgaaatgggc accactcctg
 851   aagtgcactc aatattcctc gaaggtcaca catttcttgt gaggaaccat
 901   cgccaggcgt ccttggaaat ctcgccaata actttcctta ctgctcaaac
 951   actcttgatg gaccttggac agtttctact gttttgtcat atctcttccc
1001   accaacatga tggcatgaa gcttatgtca aagtagacag ctgtccagag
1051   gaaccccaac tacgaatgaa aaataatgaa gaagcggaag actatgatga
1101   tgatcttact gattctgaaa tggatgtggt caggtttgat gatgacaact
1151   ctccttcctt tatccaaatt cgctcagttg ccaagaagca tcctaaaact
1201   tgggtacatt acattgctgc tgaagaggag gactgggact atgctccctt
1251   agtcctcgcc cccgatgaca gaagttataa aagtcaatat ttgaacaatg
1301   gccctcagcg gattggtagg aagtacaaaa aagtccgatt tatggcatac
1351   acagatgaaa cctttaagac tcgtgaagct attcagcatg aatcaggaat
1401   cttgggacct ttactttatg gggaagttgg agacacactg ttgattatat
1451   ttaagaatca agcaagcaga ccatataaca tctaccctca cggaatcact
1501   gatgtccgtc ctttgtattc aaggagatta ccaaaaggtg taaaacattt
1551   gaaggatttt ccaattctgc caggagaaat attcaaatat aaatggacag
1601   tgactgtaga agatgggcca actaaatcag atcctcggtg cctgacccgc
1651   tattactcta gtttcgttaa tatggagaga gatctagctt caggactcat
1701   tggccctctc ctcatctgct acaaagaatc tgtagatcaa agaggaaacc
1751   agataatgtc agacaagagg aatgtcatcc tgttttctgt atttgatgag
1801   aaccgaagct ggtacctcac agagaatata caacgctttc tccccaatcc
1851   agctggagtg cagcttgagg atccagagtt ccaagcctcc aacatcatgc
1901   acagcatcaa tggctatgtt tttgatagtt tgcagttgtc agtttgtttg
1951   catgaggtgg catactggta cattctaagc attggagcac agactgactt
2001   cctttctgtc ttcttctctg gatataccct caaacacaaa atggtctatg
2051   aagacacact caccctattc ccattctcag gagaaactgt cttcatgtcg
2101   atggaaaacc caggtctatg gattctgggg tgccacaact cagactttcg
2151   gaacagaggc atgaccgcct tactgaaggt ttctagttgt gacaagaaca
2201   ctggtgatta ttacgaggac agttatgaag atatttcagc atacttgctg
```

TABLE 15-continued

Polynucleotide Sequences of FVIII

```
2251   agtaaaaaca atgccattga accaagaagc ttctcccaga atgacaaaac 2301   tcacacatgc ccaccgtgcc cagctccaga actcctgggc ggaccgtcag 2351   tcttcctctt ccccccaaaa cccaaggaca ccctcatgat ctcccggacc 2401   cctgaggtca catgcgtggt ggtggacgtg agccacgaag accctgaggt 2451   caagttcaac tggtacgtgg acggcgtgga ggtgcataat gccaagacaa 2501   agccgcggga ggagcagtac aacagcacgt accgtgtggt cagcgtcctc 2551   accgtcctgc accaggactg gctgaatggc aaggagtaca agtgcaaggt 2601   ctccaacaaa gccctcccag cccccatcga gaaaaccatc tccaaagcca 2651   aagggcagcc ccgagaacca caggtgtaca ccctgccccc atcccgggat 2701   gagctgacca agaaccaggt cagcctgacc tgcctggtca aaggcttcta 2751   tcccagcgac atcgccgtgg agtgggagag caatgggcag ccggagaaca 2801   actacaagac cacgcctccc gtgttggact ccgacggctc cttcttcctc 2851   tacagcaagc tcaccgtgga caagagcagg tggcagcagg ggaacgtctt 2901   ctcatgctcc gtgatgcatg aggctctgca caaccactac acgcagaaga 2951   gcctctccct gtctccgggt aaa
```

(iii) FVIII Light Chain (LC)-Fc DNA sequence (signal peptide underlined, Fc region in bold) (SEQ ID NO: 11, which encodes SEQ ID NO: 12)

```
   1   atggagacag acacactcct gctatgggta ctgctgctct gggttccagg 51   ttccactggt gaaataactc gtactactct tcagtcagat caagaggaaa 101   ttgactatga tgataccata tcagttgaaa tgaagaagga agattttgac 151   atttatgatg aggatgaaaa tcagagcccc cgcagctttc aaaagaaaac 201   acgacactat tttattgctg cagtggagag gctctgggat tatgggatga 251   gtagctcccc acatgttcta agaaacaggg ctcagagtgg cagtgtccct 301   cagttcaaga agttgttttt ccaggaattt actgatggct cctttactca 351   gcccttatac cgtggagaac taaatgaaca tttgggactc ctggggccat 401   atataagagc agaagttgaa gataatatca tggtaacttt cagaaatcag 451   gcctctcgtc cctattcctt ctattctagc cttatttctt atgaggaaga 501   tcagaggcaa ggagcagaac ctagaaaaaa ctttgtcaag cctaatgaaa 551   ccaaaactta cttttggaaa gtgcaacatc atatggcacc cactaaagat 601   gagtttgact gcaaagcctg gcttatttc tctgatgttg acctggaaaa 651   agatgtgcac tcaggcctga ttggacccct tctggtctgc cacactaaca 701   cactgaaccc tgctcatggg agacaagtga cagtacagga atttgctctg 751   tttttcacca tctttgatga gaccaaaagc tggtacttca ctgaaaatat 801   ggaaagaaac tgcagggctc cctgcaatat ccagatggaa gatcccactt 851   ttaaagaaaa ttatcgcttc catgcaatca atggctacat aatggataca 901   ctacctggct tagtaatggc tcaggatcaa aggattcgat ggtatctgct 951   cagcatgggc agcaatgaaa acatccattc tattcatttc agtggacatg 1001   tgttcactgt acgaaaaaaa gaggagtata aaatggcact gtacaatctc 1051   tatccaggtg tttttgagac agtggaaatg ttaccatcca aagctggaat
```

TABLE 15-continued

Polynucleotide Sequences of FVIII

```
1101  ttggcgggtg gaatgccttg

TABLE 16-continued

Polypeptide Sequences of FVIII generate the BDD FVIIIFc monomer-. For the BDD FVIIIFc chain, the Fc sequence is shown in bold; HC sequence is shown in double underline; remaining B domain sequence is shown in italics. Signal peptides are underlined.
i) B domain deleted FVIII-Fc chain (19 amino acid signal sequence underlined)(SEQ ID NO: 2)

```
   1 MQIELSTCFF LCLLRFCFSA TRRYYLGAVE LSWDYMQSDL GELPVDARFP

51 PRVPKSFPFN TSVVYKKTLF VEFTDHLFNI AKPRPPWMGL LGPTIQAEVY

101 DTVVITLKNM ASHPVSLHAV GVSYWKASEG AEYDDQTSQR EKEDDKVFPG

151 GSHTYVWQVL KENGPMASDP LCLTYSYLSH VDLVKDLNSG LIGALLVCRE

201 GSLAKENTQT LHKFILLFAV FDEGKSWHSE TKNSLMQDRD AASARAWPKM

251 HTVNGYVNRS LPGLIGCHRK SVYWHVIGMG TTPEVHSIFL EGHTFLVRNH

301 RQASLEISPI TFLTAQTLLM DLGQFLLFCH ISSHQHDGME AYVKVDSCPE

351 EPQLRMKNNE EAEDYDDDLT DSEMDVVRFD DDNSPSFIQI RSVAKKHPKT

401 WVHYIAAEEE DWDYAPLVLA PDDRSYKSQY LNNGPQRIGR KYKKVRFMAY

451 TDETFKTREA IQHESGILGP LLYGEVGDTL LIIFKNQASR PYNIYPHGIT

501 DVRPLYSRRL PKGVKHLKDF PILPGEIFKY KWTVTVEDGP TKSDPRCLTR

551 YYSSFVNMER DLASGLIGPL LICYKESVDQ RGNQIMSDKR NVILFSVFDE

601 NRSMYLTENI QRFLPNPAGV QLEDPEFQAS NIMHSINGYV FDSLQLSVCL

651 HEVAYWYILS IGAQTDFLSV FFSGYTFKHK MVYEDTLTLF PFSGETVFMS

701 MENPGLWILG CHNSDFRNRG MTALLKVSSC DKNTGDYYED SYEDISAYLL

751 SKNNAIEPRS FSQNPPVLKR HQREITRTTL QSDQEEIDYD DTISVEMKKE

801 DFDIYDEDEN QSPRSFQKKT RHYFIAAVER LWDYGMSSSP HVLRNRAQSG

851 SVPQFKKVVF QEFTDGSFTQ PLYRGELNEH LGLLGPYIRA EVEDNIMVTF

901 RNQASRPYSF YSSLISYEED QRQGAEPRKN FVKPNETKTY FWKVQHHMAP

951 TKDEFDCKAW AYFSDVDLEK DVHSGLIGPL LVCHTNTLNP AHGRQVTVQE

1001 FALFFTIFDE TKSWYFTENM ERNCRAPCNI QMEDPTFKEN YRFHAINGYI

1051 MDTLPGLVMA QDQPIRWYLL SMGSNENIHS IHFSGHVFTV RKKEEYKMAL

1101 YNLYPGVFET VEMLPSKAGI WRVECLIGEH LHAGMSTLFL VYSNKCQTPL

1151 GMASGHIRDF QITASGQYGQ WAPKLARLHY SGSINAWSTK EPFSWIKVDL

1201 LAPMIIHGIK TQGARQKFSS LYISQFIIMY SLDGKKWQTY RGNSTGTLMV

1251 FFGNVDSSGI KHNIFNPPII ARYIRLHPTH YSIRSTLRME LMGCDLNSCS

1301 MPLGMESKAI SDAQITASSY FTNMFATWSP SKARLHLQGR SNAWRPQVNN

1351 PKEWLQVDFQ KTMKVTGVTT QGVKSLLTSM YVKEFLISSS QDGHQWTLFF

1401 QNGKVKVFQG NQDSFTPVVN SLDPPLLTRY LRIHPQSWVH QIAIRMEVLG

1451 CEADDLYDKT HTCPPCPAPE LLGGPSVFLF PPKPKDTLMI SRTPEVTCVV

1501 VDVSHEDPEV KFNWYVDGVE VHNAKTKPRE EQYNSTYRVV SVLTVLHQDW

1551 LNGKEYKCKV SNKALPAPIE KTISKAKGQP REPQVYTLPP SRDELTKNQV

1601 SLTCLVKGFY PSDIAVEWES NGQPENNYKT TPPVLDSDGS FFLYSKLTVD

1651 KSRWQQGNVF SCSVMHEALH NHYTQKSLSL SPGK
``` ii) Fc chain 20 amino acid heterologous signal peptide from mouse Igκ chain underlined) (SEQ ID NO: 4)

```
   1 METDTLLLWV LLWVPGSTG DKTHTCPPCP APELLGGPSV FLFTPKPKDT

51 LMISRTPEVT CVVVDVSHED PEVKFNWYVD GVEVHNAKTK PREEQYNSTY
```

TABLE 16-continued

Polypeptide Sequences of FVIII

101 RVVSVLTVLH QDWLNGKEYK CKVSNKALPA PIEKTISKAK GQPREPQVYT

151 LPPSRDELTK NQVSLTCLVK GFYPSDIAVE WESNGQPENN YKTTPPVLDS

201 DGSFFLYSKL TVDKSRWQQG NVFSCSVMHE ALHNHYTQKS LSLSPGK

B. Full length FVIIIFc monomer hybrid (Full length FVIIIFc monomer dimer): created by coexpressing FVIIIFc and Fc chains.
Construct = HC-B-LC-Fc fusion. An Fc expression cassette is cotransfected with full length FVIII-Fc to generate the full length FVIIIFc monomer. For the FVIIIFc chain, the Fc sequence is shown in bold; HC sequence is shown in double underline; B domain sequence is shown in italics. Signal peptides are underlined.
i) Full length FVIIIFc chain (FVIII signal peptide underlined (SEQ ID NO: 6)

1 MQIELSTCFF LCLLRFCFSA TRRYYLGAVE LSWDYMQSDL GELPVDARFP

51 PRVPKSFPFN TSVVYKKTLF VEFTDHLFNI AKPRPPWMGL LGPTIQAEVY

101 DTVVITLKNM ASHPVSLHAV GVSYWKASEG AEYDDQTSQR EKEDDKVFPG

151 GSHTYVWQVL KENGPMASDP LCLTYSYLSH VDLVKDLNSG LIGALLVCRE

201 GSLAKEKTQT LHKFILLFAV FDEGKSWHSE TKNSLMQDRD AASARAWPKM

251 HTVNGYVNRS LPGLIGCHRK SVYWHVIGMG TTPEVHSIFL EGHTFLVRNH

301 RQASLEISPI TFLTAQTLLM DLGQFLLFCH ISSHQHDGME AYVKVDSCPE

351 EPQLRMKNNE EAEDYDDDLT DSEMDVVRFD DDNSPSFIQI RSVAKKHPKT

401 WVHYIAAEEE DWDYAPLVLA PDDRSYKSQY LNNGPQRIGR KYKKVRFMAY

451 TDETFKTREA ICHESGILGP LLYGEVGDTL LIIFKNQASR PYNIYPHGIT

501 DVRPLYSRRL PKGVKHLKDF PILPGEIFKY KWTVTVEDGP TKSDPRCLTR

551 YYSSFVNMER DLASGLIGPL LICYKESVDQ RGNQIMSDKR NVILFSVFDE

601 NRSWYLTENI QRFLPNPAGV QLEDPEFQAS NIMHSINGYV FDSLQLSVCL

651 HEVAYWYILS IGAQTDFLSV FFSGYTFKHK MVYEDTLTLF PFSGETVFMS

701 MENPGLWILG CHNSDFRNRG MTALLKVSSC DKNTGDYYED SYEDISAYLL

731 SKNNAIEPRS FSQNSRHPST RQKQFNATTI PENDIEKTDP WFAHRTPMPK

801 IQNVSSSDLL MLLRQSPTPH GLSLSDLQEA KYETFSDDPS PGAIDSNNSL

851 SEMTHFRPQL HHSGDMVFTP ESGLQLRLNE KLGTTAATEL KKLDFKVSST

901 SNNLISTIPS DNLAAGTDNT SSLGPPSMPV HYDSQLDTTL FGKKSSPLTE

951 SGGPLSLSEE NNDSKLLESG LMWSQESSWG KNVSSTESGR LFKGKRAHGP

1001 ALLTKDNALF KVSISLLKTN KTSNNSATNR KTHIDGPSLL IENSPSVWQN

1051 ILESDTEFKK VTPLIHDRML MDKNATALRL NHMSNKTTSS KNMEMVQQKK

1101 EGPIPPDAQN PDMSFFKMLF LPESARWIQR THGKNSLNSG QGPSPKQLVS

1131 LGPEKSVEGQ NFLSEKNKVV VGKGEFTKDV GLKEMVFPSS RNLFLTNLDN

1201 LHENNTHNQE KKIQEEIEKK ETLIQENVVL PQIHTVTGTK NFMKNLFLLS

1251 TRQNVEGSYD GAYAPVLQDF RSLNDSTNRT KKHTAHFSKK GEEENLEGLG

1301 NQTKQIVEKY ACTTRISPNT SQQNFVTQRS KRALKQFRLP LEETELEKRI

1351 IVDDTSTQWS KNMKHLTPST LTQIDYNEKE KGAITQSPLS DCLTRSHSIP

1401 QANRSPLPIA KVSSFPSIRP IYLTRVLFQD NSSHLPAASY RKKDSGVQES

1451 SHFLQGAKKN NLSLAILTLE MTGDQREVGS LGTSATNSVT YKKVENTVLP

1501 KTDLPKTSGK VELLPKVHIY QKDLFPTETS NGSPGHLDLV EGSLLQGTEG

1551 AIKWNEANRP GKVPFLRVAT ESSAKTPSKL LDPLAWDNHY GTQIPKEEWK

1601 SQEKSPEKTA FKKKDTILSL NACESNHAIA AINEGQNKPE IEVTWAKQGR

TABLE 16-continued

Polypeptide Sequences of FVIII

```
1651 TERLCSQNPP VLKRHQREIT RTTLQSDQEE IDYDDTISVE MKKEDFDIYD

1701 EDENQSPRSF QKKTRHYFIA AVERLMDYGM SSSPHVLRNR AQSGSVPQFK

1751 KVVFQEFTDG SFTQPLYRGE LNEHLGLLGP YIRAEVEDNI MVTFRNQASR

1801 PYSFYSSLIS YEEDQRQGAE PRKNFVKPNE TKTYFWKVQH HMAPTKDEFD

1851 CKAWAYFSDV DLEKDVHSGL IGPLLVCHTN TLNPAHGRQV TVQEFALFFT

1901 IFDETKSWYF TENMERNCRA PCNIQMEDPT FKENYRFHAI NGYIMDTLPG

1951 LVMAQDQRIR WYLLSMGSNE NIHSIHFSGH VFTVRKKEEY KMALYNLYPG

2001 VFETVEMLPS KAGIWRVECL IGEHLHAGMS TLFLVYSNKC QTPLGMASGH

2051 IRDFQITASG QYGQWAPKLA RLHYSGSINA WSTKEPFSWI KVDLLAPMII

2101 HGIKTQGARQ KFSSLYISQF IIMYSLDGKK WQTYRGNSTG TLMVFFGNVD

2151 SSGIKHNIFN PPIIARYIRL HPTHYSIRST LRMELMGCDL NSCSMPLGME

2201 SKAISDAQIT ASSYFTNMFA TWSPSKARLH LQGRSNAWRP QVNNPKEWLQ

2251 VDFQKTMKVT GVTTQGVKSL LTSMYVKEFL ISSSQDGHQW TLFFQNGKVK

2301 VFQGNQDSFT PVVNSLDPPL LTRYLRIHPQ SWVHQIALRM EVLGCEAQDL

2351 YDKTHTCPPC PAPELLGGPS VFLFPPKPKD TLMISRTPEV TCVVVDVSHE

2101 DPEVKFNWYV DGVEVHNAKT KPREEQYNST YRVVSVLTVL HQDWLNGKEY

2151 KCKVSNKALP APIEKTISKA KGQPREPQVY TLPPSRDELT KNQVSLTCLV

2501 KGFYPSDIAV EWESNGQPEN NYKTTPPVLD SDGSFFLYSK LTVDKSRWQQ

2551 GNVFSCSVMH EALHNHYTQK SLSLSPGK
```

C. FVIII-Fc Heterodimer Hybrid
This is made by cotransfecting HC-Fc and LC-Fc constructs. Two HC-Fc constructs have been made. One has no linker between HC and Fc (HC-Fc) while the other has a 5 amino acid linker between HC and Fc (HC + 5-Fc). The FVIII signal peptide was used for the HC-Fc constructs, while the mouse Igκ signal sequence was used for the LC-Fc construct.
(i) HC-Fc (Fc sequence is shown in bold, signal peptide underlined)(SEQ ID NO: 8)

```
  1 MQIELSTCFF LCLLRFCFSA TRRYYLGAVE LSWDYMQSDL GELPVDARFP

51 PRVPKSFPFN TSVVYKKTLK VEFTDHLFNI AKRRPPWMGL LGPTIQAEVY

101 DTVVITLKNM ASHPVSLHAV GVSYWKASEG AEYDDQTSQR EKEDDKVFPG

151 GSHTYVWQVL KENGPMASDP LCLTYSYLSH VDLVKDLNSG LIGALLVCRE

201 GSLAKEKTQT LHNFILLFAV FDEGKSWHSE TKNSLMQDRD AASARAWPKM

251 HTVNGYVNRS LPGLIGCHRK SVYWHVIGMG TTPEVHSIFL EGHTFLVRNH

301 RQASLEISPI TFLTAQTLLM DLGQFLLFCH ISSHQHDGME AYVKVDSCPE

351 EPQLRMKNNE EAEDYDDDLT DSEMDVVRFD DDNSPSFIQI RSVAKKHPKT

401 WVHYIAAEEE DWDYAPLVLA PDDRSYKSQY LNNGPQRIGR KYKKVRFMAY

451 TDETFKTREA IQHESGILGP LLYGEVGDTL LIIFKNQASR PYNIYPHGIT

501 DVRPLYSRRL PKGVKHLKDF PILPGEIFKY KWTVTVEDGP TKSDPRCLTR

551 YYSSFVNMER DLASGLIGPL LICYKESVDQ RGNQIMSDKR NVILFSVFDE

601 NRSWYLTENI QRFLPNPAGV QLEDPEFQAS NIMHSINGYV FDSLQLSVCL

651 HEVAYWYILS IGAQTDFLSV FFSGYTFKHK MVYEDTLTLF PFSGETVFMS

701 MENPGLWILG CHNSDFRNRG MTALLKVSSC DKNTGDYYED SYEDISAYLL

751 SKNNAIEPRD KTHTCPPCPA PELLGGPSVF LFPPKPKDTL MISRTPEVTC

801 VVVDVSHEDP EVKFNWYVDG VEVHNAKTKP REEQYNSTYR VVSVLTVLHQ
```

TABLE 16-continued

Polypeptide Sequences of FVIII

851 DWLNGKEYKC KVSNKALPAP IEKTISKAKG QPREPQVYTL PPSRDELTKN

901 QVSLTCLVKG FYPSDIAVEW ESNGQPENNY KTTPPVLDSD GSFFLYSKLT

951 VDKSRWQQGN VFSCSVMHEA LHNHYTQKSL SLSPGK

(ii) HC + 5-Fc (Fc sequence is shown in bold, 5 amino acid linker sequence (from the B domain of FVIII) is shown in italics, signal peptide underlined:)(SEQ ID NO: 10)

```
  1 MQIELSTCFF LCLLRFCFSA TRRYYLGAVE LSWDYMQSDL GELPVDARFP
 51 PRVPKSFPFN TSVVYKKTLF VEFTDHLFNI AKPRPPWMGL LGPTIQAEVY
101 DTVVITLKNM ASHPVSLHAV GVSYWKASEG AEYDDQTSQR EKEDDKVFPG
151 GSHTYVWQVL KENGPMASDP LCLTYSYLSH VDLVKDLNSG LIGALLVCRE
201 GSLAKEKTQT LHKFILLFAV FDEGKSWHSE TKNSLMQDRD AASARAWPKM
251 HTVNGYVNRS LPGLIGCHRK SVYWHVIGMG TTPEVHSIFL EGHTYLVRNH
301 RQASLEISPI TFLTAQTLLM DLGQFLLFCH ISSHQHDGME AYVKVDSCPE
351 EPQLRMKNNE EAEDYDDDLT DSEMDVVRFD DDNSPSFIQI RSVAKKHPKT
401 WVHYIAAEEE DWDYAPLVLA PDDRSYKSQY LNNGPQRIGR KYKKVRFMAY
451 TDETFKTREA IQHESGILGP LLYGEVGDTL LIIFKNQASR PYNIYPHGIT
501 DVRPLYSRRL PKGVKHLKDF PILPGEIFKY KWTVTVEDGP TKSDPRCLTR
551 YYSSFVNMER DLASGLIGPL LICYKESVDQ RGNQIMSDKR NVILFSVFDE
601 NRSWYLTENI QRFLPNPAGV QLEDPEFQAS NIMHSINGYV FDSLQLSVCL
651 HEVAYWYILS IGAQTDFLSV FFSGYTFKHK MVYEDTLTLF PFSGETVFMS
701 MENPGLWILG CHNSDFRNRG MTALLKVSSC DKNTGDYYED SYEDISAYLL
751 SKNNAIEPR*S FSQN*DKTHTC PPCPAPELLG GPSVFLFPPK PKDTLMISRT
801 PEVTCVVVDV SHEDPEVKFN WYVDGVEVHN AKTKPREEQY NSTYRVVSVL
851 TVLHQDWLNG KEYKCKVSNK ALPAPIEKTI SKAKGQPREP QVYTLPPSRD
901 ELTKNQVSLT CLVKGFYPSD IAVEWESNGQ PENNYKTTPP VLDSDGSFFL
951 YSKLTVDKSR WQQGNVFSCS VMHEALHNHY TQKSLSLSPG K
```

(iii) LC-Fc6His (Fc sequence is shown in bold, signal peptide underlined.)(SEQ ID NO: 12)

```
  1 METDTLLLWV LLLWVPGSTG EITRTTLQSD QEEIDYDDTI SVEMKKEDFD
 51 IYDEDENQSP RSFQKKTRHY FIAAVERLWD YGMSSSPHVL RNRAQSGSVP
101 QFKKVVFQEF TDGSFTQPLY RGELNEHLGL LGPYIRAEVE DNIMVTFRNQ
151 ASRPYSFYSS LISYEEDQRQ GAEPRKNFVK PNETKTYFWK VQHHMAPTKD
201 EFDCKAWAYF SDVDLEKDVH SGLIGPLLVC HTNTLNPAHG RQVTVQEFAL
251 FFTIFDETKS WYFTENMERN CRAPCNIQME DPTFKENYRF HAINGYIMDT
301 LPGLVMAQDQ RIRWYLLSMG SNENIHSIHF SGHVFTVRKK EEYKMALYNL
351 YPGVFETVEM LPSKAGIWRV ECLIGEHLHA GMSTLFLVYS NKCQTPLGMA
401 SGHIRDFQIT ASGQYGQWAP KLARLHYSGS INAWSTKEPF SWIKVDLLAP
451 MIIHGIKTQG AFQKFSSLYI SQFIIMYSLD GKKWQTYRGN STGTLMVFFG
501 NVDSSGIKHN IFNPPIIARY IRLHPTHYSI RSTLRMELMG CDLNSCSMPL
551 GMESKAISDA QITASSYFTN MFATWSPSKA RLHLQGRSNA WRPQVNNPKE
601 WLQVDFQKTM KVTGVTTQGV KSLLTSMYVK EFLISSSQDG HQWTLFFQNG
651 KVKVFQGNQD SFTPVVNSLD PPLLTRYLRI HPQSWVHQIA LRMEVLGCEA
```

TABLE 16-continued

Polypeptide Sequences of FVIII

```
701 QDLYDKTHTC PPCPAPELLG GPSVFLFPPK PKDTLMISRT PEVTCVVVDV

751 SHEDPEVKFN WYVDGVEVHN AKTKPREEQY NSTYRVVSVL TVLHQDWLNG

801 KEYKCKVSNK ALPAPIEKTI SKAKGQPREP QVYTLPPSRD ELTKNQVSLT

851 CLVYGFYPSD IAVEWESNGQ PENNYKTTPP VLDSDGSFFL YSKLTVDKSR

901 WQQGNVFSCS VMHEALHNHY TQKSLSLSPG K
```

TABLE 17

Polynucleotide Sequences of FIX

FIX-Fc Chain DNA Sequence (FIX signal peptide underlined, FIX sequence double underlined, Fc region in bold)(SEQ ID NO: 13, which encodes SEQ ID NO: 14)
pSYN-FIX-030 Nucleotide sequence (nt 1 to 7583):
FIX exon 1 (signal peptide, 1st amino acid propeptide): nt 690-777
FIX mini intron: nt 778-1076
FIX sequence: nt 1077-2371
Fc: nt 2372-3052

```
   1 gcgcgcgttg acattgatta ttgactagtt attaatagta atcaattacg 51 gggtcattag ttcatagccc atatatggag ttccgcgtta cataacttac 101 ggtaaatggc ccgcctggct gaccgcccaa cgacccccgc ccattgacgt 151 caataatgac gtatgttccc atagtaacgc caatagggac tttccattga 201 cgtcaatggg tggagtattt acggtaaact gcccacttgg cagtacatca 251 agtgtatcat atgccaagta cgccccctat tgacgtcaat gacggtaaat 301 ggcccgcctg gcattatgcc cagtacatga ccttatggga ctttcctact 351 tggcagtaca tctacgtatt agtcatcgct attaccatgg tgatgcggtt 401 ttggcagtac atcaatgggc gtggatagcg gtttgactca cggggatttc 451 caagtctcca ccccattgac gtcaatggga gtttgttttg gcaccaaaat 501 caacgggact ttccaaaatg tcgtaacaac tccgccccat tgacgcaaat 551 gggcaatagg cgtgtacggt gggaggtcta taagcaga gctctctggc 601 taactagaga acccactgct tactggctta tcgaaattaa tacgactcac 651 tataggaaga cccaagcttc gcgacgtacg gccgccacca tgcagcgcgt 701 gaacatgatc atggcagaat caccaggcct catcaccatc tgccttttag 751 gatatctact cagtgctgaa tgtacaggtt tatttccttt tttaaaatac 801 attgagtatg cttgccttt agatatgaa atatctgatg ctgtcttctt 851 cactaaattt tgattacatg atttgacaac aatattgaag agtctaacag 901 ccagcacgca ggttggtaag tactgtggga acatcacaga ttttggctcc 951 atgccctaaa gagaaattgg ctttcagatt atttggatta aaacaaaga 1001 ctttcttaag agatgtaaaa ttttcatgat gttttctttt ttgctaaaac 1051 taaagaatta ttcttttaca tttcagtttt tcttgatcat gaaaacgcca 1101 acaaattct gaatcggcca aagaggtata attcaggtaa attggaagag 1151 tttgttcaag ggaatctaga gagagaatgt atggaaagaa agtgtagttt 1201 tgaagaagca cgagaagttt ttgaaaacac tgaaagaaca actgaatttt 1251 ggaagcagta tgttgatgga gatcagtgtg agtccaatcc atgtttaaat 1301 ggcggcagtt gcaaggatga cattaattcc tatgaatgtt ggtgtccctt
```

TABLE 17-continued

Polynucleotide Sequences of FIX

```
1351 tggatttgaa ggaaagaact gtgaattaga tgtaacatgt aacattaaga 1401 atggcagatg cgagcagttt tgtaaaaata gtgctgataa caaggtggtt 1451 tgctcctgta ctgagggata tcgacttgca gaaaaccaga agtcctgtga 1501 accagcagtg ccatttccat gtggaagagt ttctgtttca caaacttcta 1551 agctcacccg tgctgagact gttttcctg atgtggacta tgtaaattct 1601 actgaagctg aaaccatttt ggataacatc actcaaagca cccaatcatt 1651 taatgacttc actcgggttg ttggtggaga agatgccaaa ccaggtcaat 1701 tcccttggca ggttgttttg aatggtaaag ttgatgcatt ctgtggaggc 1751 tctatcgtta atgaaaaatg gattgtaact gctgccact gtgttgaaac 1801 tggtgttaaa attacagttg tcgcaggtga acataatatt gaggagacag 1851 aacatacaga gcaaaagcga aatgtgattc gaattattcc tcaccacaac 1901 tacaatgcag ctattaataa gtacaaccat gacattgccc ttctggaact 1951 ggacgaaccc ttagtgctaa acagctacgt tacacctatt tgcattgctg 2001 acaaggaata cacgaacatc ttcctcaaat ttggatctgg ctatgtaagt 2051 ggctggggaa gagtcttcca caaagggaga tcagctttag ttcttcagta 2101 ccttagagtt ccacttgttg accgagccac atgtcttcga tctacaaagt 2151 tcaccatcta taacaacatg ttctgtgctg gcttccatga aggaggtaga 2201 gattcatgtc aaggagatag tgggggaccc catgttactg aagtggaagg 2251 gaccagtttc ttaactggaa ttattagctg gggtgaagag tgtgcaatga 2301 aaggcaaata tggaatatat accaaggtgt cccggtatgt caactggatt 2351 aaggaaaaaa caaagctcac tgacaaaact cacacatgcc caccgtgccc 2401 agctccggaa ctcctgggcg gaccgtcagt cttcctcttc ccccaaaac 2451 ccaaggacac cctcatgatc tcccggaccc ctgaggtcac atgcgtggtg 2501 gtggacgtga gccacgaaga ccctgaggtc aagttcaact ggtacgtgga 2551 cggcgtggag gtgcataatg ccaagacaaa gccgcgggag gagcagtaca 2601 acagcacgta ccgtgtggtc agcgtcctca ccgtcctgca ccaggactgg 2651 ctgaatggca aggagtacaa gtgcaaggtc tccaacaaag ccctcccagc 2701 ccccatcgag aaaaccatct ccaaagccaa agggcagccc cgagaaccac 2751 aggtgtacac cctgccccca tcccgggatg agctgaccaa gaaccaggtc 2801 agcctgacct gcctggtcaa aggcttctat cccagcgaca tcgccgtgga 2851 gtgggagagc aatgggcagc cggagaacaa ctacaagacc acgcctcccg 2901 tgttggactc cgacggctcc ttcttcctct acagcaagct caccgtggac 2951 aagagcaggt ggcagcaggg gaacgtcttc tcatgctccg tgatgcatga 3001 ggctctgcac aaccactaca cgcagaagag cctctccctg tctccgggta 3051 aatgagaatt cagacatgat aagatacatt gatgagtttg gacaaaccac 3101 aactagaatg cagtgaaaaa aatgctttat ttgtgaaatt tgtgatgcta 3151 ttgctttatt tgtaaccatt ataagctgca ataaacaagt tggggtgggc 3201 gaagaactcc agcatgagat ccccgcgctg gaggatcatc cagccggcgt 3251 cccggaaaac gattccgaag cccaacctt catagaaggc ggcggtggaa
```

TABLE 17-continued

Polynucleotide Sequences of FIX

```
3301 tcgaaatctc gtagcacgtg tcagtcctgc tcctcggcca cgaagtgcac
3351 gcagttgccg gccgggtcgc gcagggcgaa ctcccgcccc cacggctgct
3401 cgccgatctc ggtcatggcc ggcccgaagg cgtcccggaa gttcgtggac
3451 acgacctccg accactcggc gtacagctcg tccaggccgc gcacccacac
3501 ccaggccagg gtgttgtccg gcaccacctg gtcctggacc gcgctgatga
3551 acagggtcac gtcgtcccgg accacaccgg cgaagtcgtc ctccacgaag
3601 tcccgggaga acccgagccg gtcggtccag aactcgaccg ctccggcgac
3651 gtcgcgcgcg gtgagcaccg gaacggcact ggtcaacttg gccatggttt
3701 agttcctcac cttgtcgtat tatactatgc cgatatacta tgccgatgat
3751 taattgtcaa cacgtgctga tcagatccga aaatggatat acaagctccc
3801 gggagctttt tgcaaaagcc taggcctcca aaaaagcctc ctcactactt
3851 ctggaatagc tcagaggcag aggcggcctc ggcctctgca taaataaaaa
3901 aaattagtca gccatggggc ggagaatggg cggaactggg cggagttagg
3951 ggcgggatgg gcggagttag gggcgggact atggttgctg actaattgag
4001 atgcatgctt tgcatacttc tgcctgctgg ggagcctggg gactttccac
4051 acctggttgc tgactaattg agatgcatgc tttgcatact tctgcctgct
4101 ggggagcctg gggactttcc acccctcgt cgagctagct cgtgaggct
4151 ccggtgcccg tcagtgggca gagcgcacat cgcccacagt ccccgagaag
4201 ttgggggggag gggtcggcaa ttgaaccggt gcctagagaa ggtggcgcgg
4251 ggtaaactgg gaaagtgatg tcgtgtactg gctccgcctt tttcccgagg
4301 gtgggggaga accgtatata agtgcagtag tcgccgtgaa cgttctttt
4351 cgcaacgggt ttgccgccag aacacaggta agtgccgtgt gtggttcccg
4401 cgggcctggc ctctttacgg gttatggccc ttgcgtgcct tgaattactt
4451 ccacctggct ccagtacgtg attcttgatc ccgagctgga gccaggggcg
4501 ggccttgcgc tttaggagcc ccttcgcctc gtgcttgagt tgaggcctgg
4551 cctgggcgct ggggccgccg cgtgcgaatc tggtggcacc ttcgcgcctg
4601 tctcgctgct ttcgataagt ctctagccat ttaaaatttt tgatgacctg
4651 ctgcgacgct ttttttctgg caagatagtc ttgtaaatgc gggccaggat
4701 ctgcacactg gtatttcggt ttttgggggcc gcgggcggcg acgggccccg
4731 tgcgtcccag cgcacatgtt cggcgaggcg gggcctgcga gcgcggccac
4801 cgagaatcgg acgggggtag tctcaagctg gccggcctgc tctggtgcct
4851 ggcctcgcgc cgccgtgtat cgccccgccc tgggcggcaa ggctggcccg
4901 gtcggcacca gttgcgtgag cggaaagatg gccgcttccc ggccctgctc
4951 caggggggctc aaaatggagg acgcggcgct cgggagagcg ggcgggtgag
5001 tcacccacac aaaggaaagg ggcctttccg tcctcagccg tcgcttcatg
5051 tgactccacg gagtaccggg cgccgtccag gcacctcgat tagttctgga
5101 gcttttggag tacgtcgtct ttaggttggg gggagggggtt ttatgcgatg
5131 gagtttcccc acactgagtg ggtggagact gaagttaggc cagcttggca
5201 cttgatgtaa ttctccttgg aatttgccct ttttgagttt ggatcttggt
```

TABLE 17-continued

Polynucleotide Sequences of FIX

```
5251 tcattctcaa gcctcagaca gtggttcaaa gttttttttct tccatttcag
5301 gtgtcgtgaa cacgtggtcg cggccgcgcc gccaccatgg agacagacac
5351 actcctgcta tgggtactgc tgctctgggt tccaggttcc actggtgaca
5401 aaactcacac atgcccaccg tgcccagcac ctgaactcct gggaggaccg
5451 tcagtcttcc tcttcccccc aaaacccaag gacaccctca tgatctcccg
5501 gacccctgag gtcacatgcg tggtggtgga cgtgagccac gaagaccctg
5531 aggtcaagtt caactggtac gtggacggcg tggaggtgca taatgccaag
5601 acaaagccgc gggaggagca gtacaacagc acgtaccgtg tggtcagcgt
5651 cctcaccgtc ctgcaccagg actggctgaa tggcaaggag tacaagtgca
5701 aggtctccaa caaagccctc ccagccccca tcgagaaaac catctccaaa
5751 gccaaagggc agccccgaga accacaggtg tacaccctgc ccccatcccg
5801 cgatgagctg accaagaacc aggtcagcct gacctgcctg gtcaaaggct
5851 tctatcccag cgacatcgcc gtggagtggg agagcaatgg gcagccggag
5901 aacaactaca agaccacgcc tcccgtgttg gactccgacg gctccttctt
5951 cctctacagc aagctcaccg tggacaagag caggtggcag caggggaacg
6001 tcttctcatg ctccgtgatg catgaggctc tgcacaacca ctacacgcag
6051 aagagcctct ccctgtctcc gggtaaatga ctcgagagat ctggccggct
6101 gggcccgttt cgaaggtaag cctatcccta accctctcct cggtctcgat
6151 tctacgcgta ccggtcatca tcaccatcac cattgagttt aaacccgctg
6201 atcagcctcg actgtgcctt ctagttgcca gccatctgtt gtttgcccct
6251 cccccgtgcc ttccttgacc ctggaaggtg ccactcccac tgtcctttcc
6301 taataaaatg aggaaattgc atcgcattgt ctgagtaggt gtcattctat
6351 tctggggggt ggggtggggc aggacagcaa ggggaggat tgggaagaca
6401 atagcaggca tgctggggat gcggtgggct ctatggcttc tgaggcggaa
6451 agaaccagtg gcggtaatac ggttatccac agaatcaggg gataacgcag
6501 gaaagaacat gtgagcaaaa ggccagcaaa aggccaggaa ccgtaaaaag
6551 gccgcgttgc tggcgttttt ccataggctc cgcccccctg acgagcatca
6601 caaaaatcga cgctcaagtc agaggtggcg aaacccgaca ggactataaa
6651 gataccaggc gtttccccct agaagctccc tcgtgcgctc tcctgttccg
6701 accctgccgc ttaccggata cctgtccgcc tttctccctt cgggaagcgt
6751 ggcgctttct catagctcac gctgtaggta tctcagttcg gtgtaggtcg
6801 ttcgctccaa gctgggctgt gtgcacgaac cccccgttca gcccgaccgc
6851 tgcgccttat ccggtaacta tcgtcttgag tccaacccgg taagacacga
6901 cttatcgcca ctggcagcag ccactggtaa caggattagc agagcgaggt
6951 atgtaggcgg tgctacagag ttcttgaagt ggtggcctaa ctacggctac
7001 actagaagaa cagtatttgg tatctgcgct ctgctgaagc cagttacctt
7051 cggaaaaaga gttggtagct cttgatccgg caaacaaacc accgctggta
7101 gcggtggttt ttttgtttgc aagcagcaga ttacgcgcag aaaaaaagga
7151 tctcaagaag atcctttgat cttttctacg gggtctgacg ctcagtggaa
```

TABLE 17-continued

Polynucleotide Sequences of FIX

```
7201 cgaaaactca cgttaaggga ttttggtcat gacattaacc tataaaaata 7251 ggcgtatcac gaggcccttt cgtctcgcgc gtttcggtga tgacggtgaa 7301 aacctctgac acatgcagct cccggagacg gtcacagctt gtctgtaagc 7351 ggatgccggg agcagacaag cccgtcaggg cgcgtcagcg ggtgttggcg 7401 ggtgtcgggg ctggcttaac tatgcggcat cagagcagat tgtactgaga 7451 gtgcaccata tatgcggtgt gaaataccgc acagatgcgt aaggagaaaa 7501 taccgcatca ggcgccattc gccattcagg ctgcgcaact gttgggaagg 7551 gcgatcggtg cgggcctctt cgctattacg cca
```

TABLE 18

Polypeptide Sequences of FIX

FIX-Fc Monomer Hybrid: created by coexpressing FIX-Fc and Fc chains.
A. FIX-Fc chain (46 amino acid signal sequence underlined) (SEQ ID NO: 14)
The c-terminal lysine is not present in either subunit; this processing is often observed in recombinant proteins produced in mammalian cell culture, as well as with plasma derived proteins.
FIX-FC-SC Subunit (the Fc part of FIX-Fc is in bold):

```
  1  MQRVNMIMAE SPSLITICLL GYLLSAECTV FLDHENANKI LNRPKRYNSG

51  KLEEFVQGNL ERECMEMKCS FEEAREVFEN TERTTEFWKQ YVDGDQCESN

101  PCLNGGSCKD DINSYECWCP FGFEGKNCEL DVTCNIKNGR CEQFCKNSAD

151  NKVVCSCTEG YRLAENQKSC EPAVPFPCGR VSVSQTSKLT RAETVFPDVD

201  YVNSTEAETI LDNITQSTQS FNDFTRVVGG EDAKPGQFPW QVVLNGKVDA

251  FCGGSIVNEK WIVTAAHCVE TGVKITVVAG EHNIEETEHT EQKRNVIRII

301  PHHNMNAAIN KYNHDIALLE LDEPLVLNSY VTPICIADKE YTNIFLKFGS

351  GYVSGWGRVF HKGRSALVLQ YLRVPLVDRA TCLRSTKFTI YNNMFCAGFH

401  EGGRDSCQGD SGGPHVTEVE GTSFLTGIIS WGEECAMKGK YGIYTKVSRY

451  VNWIKEKTKL TDKTHTCPPC PAPELLGGPS VFLFPPKPKD TLMISRTPEV

501  TCVVVDVSHE DPEVKFNWYV DGVEVHNAKT KPREEQYNST YRVVSVLTVL

551  HQDWLNGKEY KCKVSNKALP APIEKTISKA KGQPREPQVY TLPPSRDELT

601  KNQVSLTCLV KGFYPSDIAV EWESNGQPEN NYKTTPPVLD SDGSFFLYSK

651  LTVDKSRWQQ GNVFSCSVMH EALHNHYTQK SLSLSPGK
```

TABLE 19

Polynucleotide sequences of FVII

A. Full Length FVII-Fc
Full Length FVII-Fc DNA Sequence (FVII signal peptide underlined, Fc region in bold)(SEQ ID NO: 15, which encodes SEQ ID NO: 16)

```
  1  atggtctccc aggccctcag gctcctctgc cttctgcttg ggcttcaggg 51  ctgcctggct gcaggcgggg tcgctaaggc ctcaggagga gaaacacggg 101  acatgccgtg gaagccgggg cctcacagag tcttcgtaac ccaggaggaa 151  gcccacggcg tcctgcaccg gcgccggcgc gccaacgcgt tcctggagga
```

TABLE 19-continued

Polynucleotide sequences of FVII

```
 201 gctgcggccg ggctccctgg agagggagtg caaggaggag cagtgctcct
 251 tcgaggaggc ccggggagatc ttcaaggacg cggagaggac gaagctgttc
 301 tggatttctt acagtgatgg ggaccagtgt gcctcaagtc catgccagaa
 351 tggggggctcc tgcaaggacc agctccagtc ctatatctgc ttctgcctcc
 401 ctgccttcga gggccggaac tgtgagacgc acaaggatga ccagctgatc
 151 tgtgtgaacg agaacggcgg ctgtgagcag tactgcagtg accacacggg
 501 caccaagcgc tcctgtcggt gccacgaggg gtactctctg ctggcagacg
 551 gggtgtcctg cacacccaca gttgaatatc catgtggaaa aatacctatt
 601 ctagaaaaaa gaaatgccag caaaccccaa ggccgaattg tgggggcaa
 651 ggtgtgcccc aaggggagt gtccatggca ggtcctgttg ttggtgaatg
 701 gagctcagtt gtgtgggggg accctgatca acaccatctg ggtggtctcc
 751 gcggcccact gtttcgacaa aatcaagaac tggaggaacc tgatcgcggt
 801 gctgggcgag cacgacctca gcgagcacga cggggatgag cagagccggc
 851 gggtggcgca ggtcatcatc cccagcacgt acgtcccggg caccaccaac
 901 cacgacatcg cgctgctccg cctgcaccag cccgtggtcc tcactgacca
 951 tgtggtgccc ctctgcctgc ccgaacggac gttctctgag aggacgctgg
1001 ccttcgtgcg cttctcattg gtcagcaact ggggccagct gctggaccgt
1051 ggcgccacgg ccctggagct catggtcctc aacgtgcccc ggctgatgac
1101 ccaggactgc ctgcagcagt cacggaaggt gggagactcc ccaaatatca
1151 cggagtacat gttctgtgcc ggctactcgg atggcagcaa ggactcctgc
1201 aagggggaca gtggaggccc acatgccacc cactaccggg gcacgtggta
1251 cctgacgggc atcgtcagct ggggccaggg ctgcgcaacc gtgggccact
1301 ttggggtgta caccagggtc tcccagtaca tcgagtggct gcaaaagctc
1351 atgcgctcag agccacgccc aggagtcctc ctgcgagccc catttcccta
1401 ggacaaaact cacacatgcc caccgtgccc agctccagaa ctcctgggcg
1151 gaccgtcagt cttcctcttc cccccaaaac ccaaggacac cctcatgatc
1501 tcccggaccc ctgaggtcac atgcgtggtg gtggacgtga gccacgaaga
1551 ccctgaggtc aagttcaact ggtacgtgga cggcgtggag gtgcataatg
1501 ccaagacaaa gccgcgggag gagcagtaca acagcacgta ccgtgtggtc
1651 agcgtcctca ccgtcctgca ccaggactgg ctgaatggca aggagtacaa
1701 gtgcaaggtc tccaacaaag ccctcccagc ccccatcgag aaaaccatct
1751 ccaaagccaa agggcagccc cgagaaccac aggtgtacac cctgccccca
1801 tcccgggatg agctgaccaa gaaccaggtc agcctgacct gcctggtcaa
1851 aggcttctat cccagcgaca tcgccgtgga gtgggagagc aatgggcagc
1901 cggagaacaa ctacaagacc acgcctcccg tgttggactc cgacggctcc
1951 ttcttcctct acagcaagct caccgtggac aagagcaggt ggcagcaggg
2001 gaacgtcttc tcatgctccg tgatgcatga ggctctgcac aaccactaca
2051 cgcagaagag cctctccctg tctccgggta aa
```

TABLE 20

Polypeptide Sequences of FVII

FIVII-Fc Monomer Hybrid: created by coexpressing FVII-Fc and Fc chains.
A. FVII-Fc chain (signal sequence underlined, Fc region is in bold)
(SEQ ID NO: 16) FVII-Fc-Sc Subunit:

```
  1 MVSQALRLLC LLLGLQGCLA AGGVAKASGG ETRDMPWKPG PHRVFVTQEE

51 AHGVLHRRRR ANAFLEELRP GSLERECKEE QCSFEEAREI FKDAERTKLF

101 WISYSDGDQC ASSPCQNGGS CKDQLQSYIC FCLPAFEGRN CETHKDDQLI

151 CVNENGGCEQ YCSDHTGTKR SCRCHEGYSL LADGVSCTPT VEYPCGKIPI

201 LEKRNASKPQ GRIVGGKVCP KGECPWQVLL LVNGAQLCGG TLINTIWVVS

251 AAHCFDKIKN WRNLIAVLGE HDLSEHDGDE QSRRVAQVII PSTYVPGTTN

301 HDIALLRLHQ PVVLTDHVVP LCLPERTFSE RTLAFVRFSL VSGWGQLLDR

351 GATALELMVL MVPRLMTQDC LQQSRKVGDS PNITEYMFCA GYSDGSKDSC

401 KGDSGGPHAT HYRGTWYLTG IVSWGQGCAT VGHFGVYTRV SQYIEWLQKL

451 MRSEPRPGVL LRAPFPDKTH TCPPCPAPEL LGGPSVFLFP PKPKDTLMIS

501 RTPEVTCVVV DVSHEDPEVK FNWYVDGVEV HNAKTKPREE QYNSTYRVVS

551 VLTVLHQDWL NGKEYKCKVS NKALPAPIEK TISKAKGQPR EPQVYTLPPS

601 RDELTKNQVS LTCLVKGFYP SDIAVEWESN GQPENNYKTT PPVLDSDGSF

651 FLYSKLTVDK SRWQQGNVFS CSVMHEALHN HYTQKSLSLS PGK

What is claimed is:

1. A method of producing a purified polypeptide of interest, comprising:
   (a) recombinantly producing the polypeptide of interest in a cell culture, wherein the cell culture is a human cell culture, wherein the human cell is a Human Embryonic Kidney (HEK) 293 cell;
   (b) binding the polypeptide to a chromatography matrix; washing the polypeptide-bound chromatography matrix with a wash solution a pH above 6.5, and
   (c) washing the polypeptide-bound chromatography matrix with a wash solution at a pH of lower than about 4.0,
      wherein the wash solution comprises a sufficient concentration of salt to substantially reduce elution of the polypeptide during step (c).

2. The method of claim 1, wherein the chromatography matrix is a Protein A column.

3. The method of claim 1, wherein the chromatography matrix is a mixed-mode anion-exchange chromatography matrix.

4. The method of claim 3, wherein the mixed-mode chromatography matrix comprises dextran based matrix, agarose based matrix, polystyrene based matrix, polyvinyl ethyl hydrophilic polymer based matrix, macroporous highly crosslinked polymer based matrix, hydroxyapatite $((Ca_5(PO_4)_3OH)_2)$ based matrix, fluoroapatite $((Ca_5(PO_4)_3F)_2)$ based matrix, or any combinations thereof.

5. The method of claim 1, wherein the pH of the wash solution is about 2.5 to about 4.0, about 2.5 to about 3.0, about 3.0 to about 3.5, or about 3.5 to about 4.0.

6. The method of claim 1, wherein the salt is a sodium salt, a potassium salt, or an ammonium salt.

7. The method of claim 6, wherein the sodium salt is NaCl.

8. The method of claim 1, wherein the polypeptide is bound to the chromatography matrix at a pH from about 6.0 to about 8.0.

9. The method of claim 1, wherein the method further comprises eluting the polypeptide from the chromatography matrix with an elution solution.

10. The method of claim 9, wherein at least about 70% of the polypeptide is recovered in the elution solution.

11. The method of claim 1, wherein the polypeptide is FIX-Fc or FVII-Fc.

12. The method of claim 1, wherein the polypeptide is a monomer-dimer hybrid.

13. The method of claim 1, wherein the polypeptide further comprises a heterologous moiety.

14. The method of claim 13, wherein the heterologous moiety is selected from the group consisting of albumin, albumin-binding polypeptide, Fc, PAS, the C-terminal peptide (CTP) of the β subunit of human chorionic gonadotropin, polyethylene glycol (PEG), hydroxyethyl starch (HES), albumin-binding small molecules, or any combinations thereof.

15. A method of producing a purified polypeptide of interest, the method comprising the following sequential steps:
   (a) recombinantly producing the polypeptide of interest in a cell culture, wherein the cell culture is a human cell culture, wherein the human cell is a Human Embryonic Kidney (HEK) 293 cell;
   (b) binding the polypeptide to a chromatography matrix;
   (c) washing the polypeptide-bound chromatography matrix of step (b) with a first wash solution comprising a salt at a pH above 6.5;
   (d) washing the polypeptide-bound chromatography matrix of (c) with a second wash solution comprising a salt at a concentration greater than about 0.5M and a pH of lower than about 4.0, and
   (e) washing the polypeptide-bound chromatography matrix of step (d) with a third wash solution comprising a salt at a pH above 6.5.

16. The method of claim 15, wherein the concentration of the salt in the first or third wash solution is about 0.5 M to about 1.0 M, about 1.0 M to about 1.5 M, about 1.5 M to about 2.0 M, about 2.0 M to about 2.5 M, about 2.5 M to about 3.0 M, about 3.0 M to about 3.5 M, or about 3.5 M to about 4 M.

17. The method of claim 15, wherein the second wash solution further comprises one or more components selected from the group consisting of a polymer, an organic solvent, a detergent, arginine, an arginine derivative, and any combination thereof.

18. The method of claim 15, wherein the second wash solution further comprises any one or more of PEG, ethanol, acetone, or octylphenol ethylene oxide condensate.

19. The method of claim 15, wherein the second wash solution comprises a detergent.

20. The method of claim 19, wherein the detergent is selected from the group consisting of: octylphenol ethylene oxide condensate; 3-[(3-cholamidopropyl)dimethylammonio]-1-propanesulfonate (CHAPS); 3-[(3-cholamidopropyl)dimethylammonio]-2-hydroxy-1-propanesulfonate (CHAPSO); lauryldimethyl amine oxide (LDAO); polysorbates; poloxamers; sodium dodecyl sulfate (SDS); sodium laurel sulfate; sodium octyl glycoside; lauryl-, myristyl-, linoleyl- or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine; myristamidopropyl-, palmidopropyl-, or isostearamidopropyl-dimethylamine; sodium methyl cocoyl-, or disodium methyl oleyl-taurate; 1-ethyl-1-(2-hydroxyethyl)-2-isoheptadecylimidazolinium ethyl sulfate; and any combination thereof.

* * * * *